US012709769B2

(12) United States Patent
Dalgaard Mikkelsen et al.

(10) Patent No.: US 12,709,769 B2
(45) **Date of Patent: *Aug. 18, 2026**

(54) METHODS FOR IMPROVED PRODUCTION OF REBAUDIOSIDE D AND REBAUDIOSIDE M

(71) Applicant: EVOLVA SA, Reinach (CH)

(72) Inventors: Michael Dalgaard Mikkelsen, Vaerlose (DK); Jorgen Hansen, Frederiksberg (DK); Ernesto Simon, Copenhagen (DK); Federico Brianza, Riehen (CH); Angelika Semmler, Copenhagen (DK); Kim Olsson, Søborg (DK); Simon Carlsen, Copenhagen (DK); Louis Düring, Copenhagen (DK); Alexei Ouspenski, Mulhouse (FR); Paula Hicks, Bend, OR (US)

(73) Assignee: Danstar Ferment AG, Schweiz (CH)

( * ) Notice: Subject to any disclaimer, the term of this patent is extended or adjusted under 35 U.S.C. 154(b) by 787 days.

This patent is subject to a terminal disclaimer.

(21) Appl. No.: 18/052,477

(22) Filed: Nov. 3, 2022

(65) Prior Publication Data

US 2023/0279459 A1 Sep. 7, 2023

Related U.S. Application Data

(60) Continuation of application No. 16/799,541, filed on Feb. 24, 2020, now Pat. No. 11,530,431, which is a continuation of application No. 15/908,214, filed on Feb. 28, 2018, now Pat. No. 10,612,066, which is a division of application No. 14/761,629, filed as application No. PCT/EP2014/052363 on Feb. 6, 2014, now Pat. No. 9,957,540.

(60) Provisional application No. 61/761,490, filed on Feb. 6, 2013, provisional application No. 61/886,442, filed on Oct. 3, 2013.

(51) Int. Cl.

| | |
|---|---|
| ***C12P 19/56*** | (2006.01) |
| ***A23L 2/60*** | (2006.01) |
| ***A23L 27/30*** | (2016.01) |
| ***C12N 9/02*** | (2006.01) |
| ***C12N 9/10*** | (2006.01) |
| ***C12N 9/90*** | (2006.01) |
| ***C12N 15/81*** | (2006.01) |

(52) U.S. Cl.

CPC ................. *C12P 19/56* (2013.01); *A23L 2/60* (2013.01); *A23L 27/36* (2016.08); *C12N 9/0071* (2013.01); *C12N 9/1051* (2013.01); *C12N 9/1081* (2013.01); *C12N 9/1085* (2013.01); *C12N 9/90* (2013.01); *C12N 15/81* (2013.01); *C12Y 204/01* (2013.01); *C12Y 204/99* (2013.01)

(58) Field of Classification Search

CPC . C12P 19/56; A23L 2/60; A23L 27/36; C12N 9/0071; C12N 9/1051; C12N 9/1081; C12N 9/1085; C12N 9/90; C12N 15/81; C12Y 204/01; C12Y 204/99

See application file for complete search history.

(56) References Cited

U.S. PATENT DOCUMENTS

| | | | |
|---|---|---|---|
| 4,590,160 | A | 5/1986 | Nishihashi et al. |
| 5,204,253 | A | 4/1993 | Sanford et al. |
| 5,306,862 | A | 4/1994 | Chappell et al. |
| 5,460,949 | A | 10/1995 | Saunders et al. |
| 5,538,880 | A | 7/1996 | Lundquist et al. |
| 6,013,863 | A | 1/2000 | Lundquist et al. |
| 6,215,051 | B1 | 4/2001 | Yu et al. |
| 6,255,557 | B1 | 7/2001 | Brandle |
| 6,284,493 | B1 | 9/2001 | Roth |
| 6,284,506 | B1 | 9/2001 | Hoshino et al. |
| 6,329,571 | B1 | 12/2001 | Hiei |
| 6,586,202 | B2 | 7/2003 | Hoshino et al. |
| 6,660,507 | B2 | 12/2003 | Cheng et al. |
| 6,806,076 | B1 | 10/2004 | Miyake et al. |
| 6,969,595 | B2 | 11/2005 | Brzostowicz et al. |
| 7,034,140 | B2 | 4/2006 | Bramucci et al. |
| 7,056,717 | B2 | 6/2006 | Cheng et al. |
| 7,098,000 | B2 | 8/2006 | Cheng et al. |
| 7,129,392 | B2 | 10/2006 | Hahn et al. |
| 7,132,268 | B2 | 11/2006 | Miyake et al. |
| 7,172,886 | B2 | 2/2007 | Keasling et al. |
| 7,183,089 | B2 | 2/2007 | Keasling et al. |
| 7,186,891 | B1 | 3/2007 | Chappell et al. |
| 7,208,298 | B2 | 4/2007 | Miyake et al. |
| 7,335,815 | B2 | 2/2008 | Boronat et al. |
| 7,364,885 | B2 | 4/2008 | Miyake et al. |
| 7,422,884 | B2 | 9/2008 | Bai et al. |
| 7,514,597 | B2 | 4/2009 | Nakamura et al. |

(Continued)

FOREIGN PATENT DOCUMENTS

| | | |
|---|---|---|
| CN | 101720910 | 6/2010 |
| CN | 103397064 | 11/2013 |

(Continued)

OTHER PUBLICATIONS

Banerjee et al., Improving enzymes for biomass conversion: A basic research perspective. Bioenerg. Res., 2010, vol. 3: 82-92. (Year: 2010).*

(Continued)

*Primary Examiner* — Ganapathirama Raghu

(74) *Attorney, Agent, or Firm* — McDonnell Boehnen Hulbert & Berghoff LLP

(57) ABSTRACT

Methods for recombinant production of steviol glycoside and compositions containing steviol glycosides are provided by this invention.

12 Claims, 24 Drawing Sheets

Specification includes a Sequence Listing.

(56) References Cited

U.S. PATENT DOCUMENTS

| | | | |
|---|---|---|---|
| 7,569,389 | B2 | 8/2009 | Feldmann et al. |
| 7,692,065 | B2 | 4/2010 | Harper et al. |
| 7,838,287 | B2 | 11/2010 | Goldsmith et al. |
| 7,923,541 | B2 | 4/2011 | Yang et al. |
| 7,927,851 | B2 | 4/2011 | Brandle et al. |
| 9,562,251 | B2 | 2/2017 | Kishore et al. |
| 9,957,540 | B2 * | 5/2018 | Mikkelsen ........... C12Y 204/01 |
| 10,612,066 | B2 * | 4/2020 | Mikkelsen ........... C12N 9/1081 |
| 10,947,515 | B2 | 3/2021 | Boer et al. |
| 11,530,431 | B2 * | 12/2022 | Mikkelsen ........... C12N 9/1051 |
| 2002/0142408 | A1 | 10/2002 | DiCosimo et al. |
| 2003/0033626 | A1 | 2/2003 | Hahn et al. |
| 2003/0148416 | A1 | 8/2003 | Berry et al. |
| 2003/0148479 | A1 | 8/2003 | Keasling et al. |
| 2003/0190734 | A1 | 10/2003 | Hoshino et al. |
| 2003/0219798 | A1 | 11/2003 | Gokarn et al. |
| 2004/0010815 | A1 | 1/2004 | Lange et al. |
| 2004/0072311 | A1 | 4/2004 | DiCosimo et al. |
| 2004/0078846 | A1 | 4/2004 | Desouza et al. |
| 2004/0176570 | A1 | 9/2004 | Bacher et al. |
| 2004/0194162 | A1 | 9/2004 | Hahn et al. |
| 2005/0003474 | A1 | 1/2005 | Desouza et al. |
| 2005/0032169 | A1 | 2/2005 | Miyake et al. |
| 2006/0014264 | A1 | 1/2006 | Sauer et al. |
| 2006/0079476 | A1 | 4/2006 | Keasling et al. |
| 2006/0083838 | A1 | 4/2006 | Jackson et al. |
| 2007/0004000 | A1 | 1/2007 | Miyake et al. |
| 2007/0077616 | A1 | 4/2007 | Keasling et al. |
| 2007/0099261 | A1 | 5/2007 | Keasling et al. |
| 2007/0118916 | A1 | 5/2007 | Puzio et al. |
| 2007/0128311 | A1 | 6/2007 | Prakash et al. |
| 2007/0166782 | A1 | 7/2007 | Keasling et al. |
| 2007/0202579 | A1 | 8/2007 | Berry et al. |
| 2007/0238157 | A1 | 10/2007 | Millis et al. |
| 2007/0238159 | A1 | 10/2007 | Millis et al. |
| 2007/0238160 | A1 | 10/2007 | Millis et al. |
| 2007/0254354 | A1 | 11/2007 | Millis et al. |
| 2007/0269857 | A1 | 11/2007 | Miyake et al. |
| 2007/0286850 | A1 | 12/2007 | Bai et al. |
| 2008/0064063 | A1 | 3/2008 | Brandle et al. |
| 2008/0081358 | A1 | 4/2008 | Vittanen et al. |
| 2008/0131926 | A1 | 6/2008 | Miyake et al. |
| 2008/0261280 | A1 | 10/2008 | Hahn et al. |
| 2008/0271205 | A1 | 10/2008 | Yamaguchi et al. |
| 2008/0286870 | A1 | 11/2008 | Vittanen et al. |
| 2008/0292775 | A1 | 11/2008 | Prakash et al. |
| 2008/0318227 | A1 | 12/2008 | Bacher et al. |
| 2009/0004724 | A1 | 1/2009 | Keasling et al. |
| 2009/0047718 | A1 | 2/2009 | Blaschek et al. |
| 2009/0055974 | A1 | 2/2009 | Tanksley et al. |
| 2009/0074935 | A1 | 3/2009 | Lee |
| 2009/0143308 | A1 | 6/2009 | Monk et al. |
| 2009/0286262 | A1 | 11/2009 | Slack |
| 2009/0298706 | A1 | 12/2009 | Lee et al. |
| 2010/0112156 | A1 | 5/2010 | Abelyan et al. |
| 2010/0120096 | A1 | 5/2010 | Kitaoka et al. |
| 2010/0221801 | A1 | 9/2010 | Van Dyk |
| 2010/0297722 | A1 | 11/2010 | Anterola et al. |
| 2011/0087011 | A1 | 4/2011 | Chiang et al. |
| 2011/0092684 | A1 | 4/2011 | Abelyan et al. |
| 2011/0126318 | A1 | 5/2011 | Allen et al. |
| 2011/0160311 | A1 | 6/2011 | Prakash et al. |
| 2012/0021111 | A1 | 1/2012 | Pfister et al. |
| 2012/0083593 | A1 | 4/2012 | Liu et al. |
| 2012/0164678 | A1 | 6/2012 | Stephanopoulos et al. |
| 2012/0178169 | A1 | 7/2012 | Voytas et al. |
| 2013/0137138 | A1 | 5/2013 | Hansen |
| 2013/0171328 | A1 | 7/2013 | Kishore et al. |
| 2015/0159188 | A1 | 6/2015 | Ono et al. |
| 2015/0342234 | A1 | 12/2015 | Hicks et al. |
| 2018/0230504 | A1 | 8/2018 | Anderson et al. |
| 2021/0147815 | A1 | 5/2021 | Boer et al. |

FOREIGN PATENT DOCUMENTS

| | | |
|---|---|---|
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2902410 | 8/2015 |
| EP | 3034614 | 6/2016 |
| JP | 3-277275 | 12/1991 |
| JP | 05-115298 | 5/1993 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/140394 | 11/2009 |
| WO | WO 2010/021001 | 2/2010 |
| WO | WO 2010/038911 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/060057 | 5/2011 |
| WO | WO 2011/153378 | 8/2011 |
| WO | 2011/140329 | 11/2011 |
| WO | WO 2011/151326 | 12/2011 |
| WO | WO 2011/153144 | 12/2011 |
| WO | WO 2012/075030 | 6/2012 |
| WO | WO 2013/019050 | 2/2013 |
| WO | WO 2013/022989 | 2/2013 |
| WO | WO 2013/021261 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122328 | 8/2014 |
| WO | 2014/191580 | 12/2014 |
| WO | 2014/191581 | 12/2014 |
| WO | 2015/011209 | 1/2015 |
| WO | 2015/014959 | 2/2015 |
| WO | 2015/016393 | 2/2015 |
| WO | WO 2015/014969 | 2/2015 |
| WO | WO 2016/023844 | 2/2016 |
| WO | WO 2016/038095 | 3/2016 |

(56) References Cited

FOREIGN PATENT DOCUMENTS

WO WO2016054544 A1 4/2016
WO WO-2016120486 A1 * 8/2016 .......... C07H 15/256

OTHER PUBLICATIONS

Sen et al., Developments in directed evolution for enzyme functions. Appl. Biochem. Biotechnol., 2007, vol. 143: 212-223. (Year: 2007).*
Bowles et al., Glycosyltransferases of Lipophilic Small Molecules. Annu. Rev. Plant Biol., 2006, vol. 57: 67-97 (Year: 2006).*
Guo et al., Protein tolerance to random amino acid change. PNAS., 2004, vol. 101 (25): 9205-9210. (Year: 2004).*
Kubo et al., Alteration of sugar donor specificities of plant glycosyltransferases by a single point mutation. Arch. Biochem. Biophys., 2004, vol. 249: 198-203 (Year: 2004).*
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3): 179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for pligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," EMBO J. 11(13):4705-13 (Dec. 1992).
Rodríguez-Concepción & Boronat, "Elucidation of the methylerythritol phosphate pathway for isoprenoid biosynthesis in bacteria and plastids. A metabolic milestone achieved through genomics," Plant Physiol. 130(3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
Abraham & Bhat, "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the Arabidopsis DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen & Geuns, "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in *Saccharomyces cerevisiae*," Microb Cell Fact. 5:20 (2006).

(56) References Cited

OTHER PUBLICATIONS

Chen et al., "MolProbity: all-atom structure validation for macromolecular crystallography." Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol. 16(4):378-84 (2005).
Chow & Palecek, "Enzyme encapsulation in permeabilized *Saccharomyces cerevisiae* cells," Biotechnol Prog. 20(2):449- 56 (2004).
Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "*Arabidopsis* ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
Emboss Needle results for Pairwise Sequence Alignment of UGT91D1 and UGT91D2; dated Apr. 4, 2016, 2 pages.
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant acking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in Escherichia coli," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Gietz & Schiestl, "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast Schizosaccharomyces Pombe," Biotechnol. & Biotechnol. Eq. 20(3):76-82 (2006).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mot Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Written Opinion issued by the Intellectual Property Office of Singapore for Singaporean Application No. 201208854-8, dated Nov. 3, 2014.
Non-Final Office Action for U.S. Appl. No. 14/237,540, mailed Dec. 30, 2015 (pp. 1-19).
Final Office Action issued in U.S. Appl. No. 14/237,540; mailed Jul. 8, 2016, pp. 1-19.
International Preliminary Report on Patentability issued by the International Bureau for International Application No. PCT/US2012/050021, dated Feb. 11, 2014.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Examination Report issued by the European Patent Office for European Application No. 12750513.9, dated Nov. 26, 2014.
Response to Examination Report issued by the European Patent Office for European Application No. 12750513.9, dated Mar. 25, 2015.
Extended European Search Report issued in EP 15193074.0; dated Feb. 12, 2016, pp. 1-9.
Statement of Facts and Arguments In Support Of Opposition for EP Application No. 12750513.9; mailed Feb. 28, 2017 pp. 1-24.

(56) References Cited

OTHER PUBLICATIONS

Communication of Notice of Opposition against EP Application No. 12750513.9; mailed Mar. 6, 2017 pp. 1-8.
Sequence alignment between the sequence of Uniprot database entry Q75183 version 31, updated Jul. 22, 2008 and SEQ ID No: 152 (from European Patent No. 2742142) as cited in Notice of Opposition against EP Application No. 12750513.9; mailed Mar. 6, 2017; pp. 1-2.
International Search Report from the International Searching Authority for International Application No. PCT/ EP2014/052363, mailed Sep. 22, 2014 (12 pages).
Written Opinion of the International Searching Authority for International Application No. PCT/EP2014/052363, mailed Sep. 22, 2014 (10 pages).
International Preliminary Report on Patentability issued by the Intemational Bureau for International Application No. PCT/EP2014/052363, dated Aug. 11, 2015. (11 pages).
Communication pursuant to Rules 161(1) and 162 EPC for European Application No. 14702889.8, dated Oct. 14, 2015 (2 pages).
International Search Report by the International Searching Authority for International Application No. PCT/EP2014/052675, mailed Apr. 23, 2014 (5 pages).
Written Opinion of the International Searching Authority for International Application No. PCT/EP2014/052675, mailed Apr. 23, 2014 (7 pages).
International Preliminary Report on Patentability issued by the International Bureau for International Application No. PCT/EP2014/052675, dated Aug. 11, 2015 (8 pages).
Communication pursuant to Rules 161(1) and 162 EPC for European Application No. 14704558.7, dated Sep. 18, 2015 (2 pages).
International Search Report of the International Searching Authority for International Application No. PCT/EP2013/075587, mailed Feb. 20, 2014 (pp. 1-5).
Written Opinion of the International Searching Authority for International Application No. PCT/EP2013/075587, mailed Feb. 20, 2014 (pp. 1-9).
International Preliminary Report on Patentability from the International Bureau for International Application No. PCT/EP2013/075587, dated Jun. 9, 2015 (pp. 1-10).
Communication pursuant to Rules 161(1) and 162 EPC for European Application No. 13801569.8, dated Jul. 14, 2015 2 pages).
Response to Communication pursuant to Rules 161(1) and 162 EPC for European Application No. 13801569.8, Jan. 13, 2016 (9 pages).
Third Party Submission in U.S. Appl. No. 14/648,747; dated Mar. 28, 2016, pp. 1-231.
Non-Final Office Action for U.S. Appl. No. 14/648,747, mailed Mar. 23, 2017, pp. 1-20.
Third Party Observation in EP Application No. 13801569.8; mailed Apr. 26, 2017. pp. 1-5.
Invitation to Pay Additional Fees and, Where Applicable, Protest Fee by the International Searching Authority for International Application No. PCT/EP2015/070620, mailed Nov. 27, 2015 (pp. 1-14).
International Search Report by the International Searching Authority for International Application No. PCT/EP2015/070620; mailed Mar. 29, 2016, pp. 1-10.
Written Opinion of the International Searching Authority for International Application No. PCT/EP2015/070620; mailed Mar. 29, 2016, pp. 1-24.
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
International Preliminary Report on Patentability from the International Bureau for International Application PCTEP2015/068314; mailed Feb. 14, 2017 (pp. 1-10).
International Search Report and Written Opinion of the International Searching Authority for International Application No. PCT/EP2015/052007; mailed Jul. 4, 2016, pp. 1-24.
International Search Report and Written Opinion of the International Searching Authority for International Application No. PCT/EP2016/068259; mailed Jan. 24, 2017, pp. 1-18.
International Search Report and Written Opinion of International Search Authority for International Application No. PCTEP2016/080516; mailed Mar. 15, 2017, pp. 1-22.
International Search Report and Written Opinion of International Search Authority for International Application No. PCTEP2017/059028; mailed Jun. 27, 2017, pp. 1-15.
Saier, "Families of transmembrane sugar transport proteins," Mol Microbiol., 35(4):699-710 (2000).
Uniprot Accession No. Q75183, dated Jul. 5, 2004 (pp. 1-2).
Uniprot Accession No. Q75183, dated Jul. 22, 2008 (pp. 1-4).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Extended European Search Report and Opinion issued by the European Patent Office for European Application No. 11790428.4, dated Dec. 20, 2013.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
English Translation of First Office Action issued by the State Intellectual Property Office of People's Republic of China for CN Application No. 201180038475.4, dated Nov. 21, 2013.
First Examination Report issued by the Intellectual Property Office of New Zealand for New Zealand Application No. 604915, dated Sep. 2, 2013.
Ju et al., "Functional and Biochemical Characterization of *Escherichia coli* Sugar Efflux Transporters," JBC, 274 (33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
Broun et al., "Catalytic plasticity of fatty acid modification enzymes underlying chemical diversity of plant lipids," Science, vol. 282: 1315-1317 (1998).
Cheng, "Food Biotechnology," Inner Mongolia Science and Technology Press (2008).
Devos et al., "Practical limits of function prediction," Proteins: Structure, Function, and Genetics, vol. 41: 98-107 (2000).
Pearson & Lipman, "Improved tools for biological sequence comparison," Proc Natl Acad Sci. 85(8):2444-8 (1988).
Seffernick et al., "Melamine deaminase and Atrazine chlorohydrolase: 98 percent identical but functionally different," J. Bacterial., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Duetz, "Microtiter plates as mini-bioreactors: miniaturization of fermentation methods," Trends Microbiol 15(10):469-75 (2007).
François et al., "Reserve carbohydrates metabolism in the yeast Saccharomyces cerevisiae," FEMS Microbiol Rev., 25(1):125-45 (2001).

(56) References Cited

OTHER PUBLICATIONS

Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of entKaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of entkaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin *Stevia rebaudiana* (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1 (3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10): 1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of entcopalyl diphosphate synthase from Scoparia dulcis L.," Plant Sci. 169:760-7 (2005).
Nelson et al., "P450 superfamily: update on new sequences, gene mapping, accession Nos. and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Schwab et al., Poster, "Watchmaker®-Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143(3):212-23 (2007).
GenBank Accession No. AAS07253.1, dated Jan. 31, 2004 (3 pages).
Guo et al., "Protein tolerance to random amino acid change", Proceedings of the National Academy of Sciences USA, vol. 101, No. 25, pp. 9205-9210 (2004).
Ni et al., "Outer membrane mutation effects on UDP-glucose permeability and whole-cell catalysis rate," Appl Microbiol Biotechnol. 73(2):384-93 (2006).
Prisic et al, "Synergistic substrate inhibition of ent-copalyl diphosphate synthase: a potential feed-forward inhibition mechanism limiting gibberellin metabolism," Plant Physiol. 144(1):445-54 (2007).

(56) References Cited

OTHER PUBLICATIONS

Ünligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6 (3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment-63rd JECFA, pp. 1-5 (2004).
Wallin, "Steviol Glycosides," Chem. Tech Assessment-69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20):3303-9 (2009).
UniProt Accession No. Q7FPQ4, 2004 (pp. 1-6).
Yadav et al., "A review on the improvement of stevia [Stevia rebaudiana (Bertoni)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
UniProt Accession No. F2DG34, May 2011 (pp. 1-4).
UniProt Accession No. Q6VAA8, 2004 (pp. 1-6).
Bateman et al., "Pfam 3.1: 1313 multiple alignments and profile HMMs match the majority of proteins," Nucleic Acids Res. 27(1):260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31(13):3497-500 (Jul. 2003).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. NP_195399, dated Jan. 22, 2014 (3 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).

(56) References Cited

OTHER PUBLICATIONS

GenBank Accession No. CAA76703, dated Nov. 14, 2006 (1 page).
GenBank Accession No. CAE09055, dated Nov. 14, 2006 (2 pages).
GenBank Accession No. NP_197872.1, dated Jan. 22, 2014 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. NM_116512, dated Jan. 22, 2014 (3 pages).
GenBank Accession No. NP_194183, dated Jan. 22, 2014 (4 pages).
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Chen, "Summary on Study of Stevioside," China Pharmacist, vol. 10, No. 6, p. 598-599 (2007).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Giaever & Nislow, "The yeast deletion collection: a decade of functional genomics," Genetics 197(2):451-65 (Jun. 2014).
Piirainen et al., "Glycoengineering of yeasts from the perspective of glycosylation efficiency," N Biotechnol. 31(6):532-7 (Dec. 2014).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Xu et al., "Generation of hepatitis B virus PreS2-S antigen in Hansenula polymorpha," Virol Sin. 29(6):403-9 (Dec. 2014).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
GenBank Accession No. AEE36246, dated Oct. 6, 2014 (3 pages).
GenBank Accession No. AZF53544, dated Apr. 14, 2011 (2 pages).
GenBank Accession No. CAG41604, dated Feb. 6, 2015 (2 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. Q9UVY5.1, dated Apr. 1, 2015 (3 pages).
UniProt Accession No. B5MEX6, Nov. 4, 2008 (1 page).
UniProt Accession No. E4MVV7, Feb. 8, 2011 (1 page).
UniProt Accession No. F6KWJ2, Jul. 27, 2011 (1 page).
UniProt Accession No. H9BYK3, May 16, 2012 (1 page).
Third-Party Submission under 37 CFR 1.290 for U.S. Appl. No. 13/701,406, dated Mar. 7, 2014 (238 pages).
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, mailed Dec. 15, 2015 (pp. 1-5).
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.
Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
English Translation of Notification of Reasons for Refusal of Japanese Application No. 2013-513355, dated Aug. 4, 2015 (pp. 1-10).
Examination Report issued by the Intellectual Property Corporation of Malaysia for Malaysian Application No. PI 2012005201, dated Jul. 31, 2014.
Response to Examination Report issued by the Intellectual Property Corporation of Malaysian for MY Application No. PI 2012005201, dated Sep. 18, 2014.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 604915, dated Feb. 3, 2014.
Response to Further Examination Report issued by the Intellectual Property Office of New Zealand for New Zealand Application No. 604915, dated May 27, 2014.
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).

* cited by examiner

FIG.1

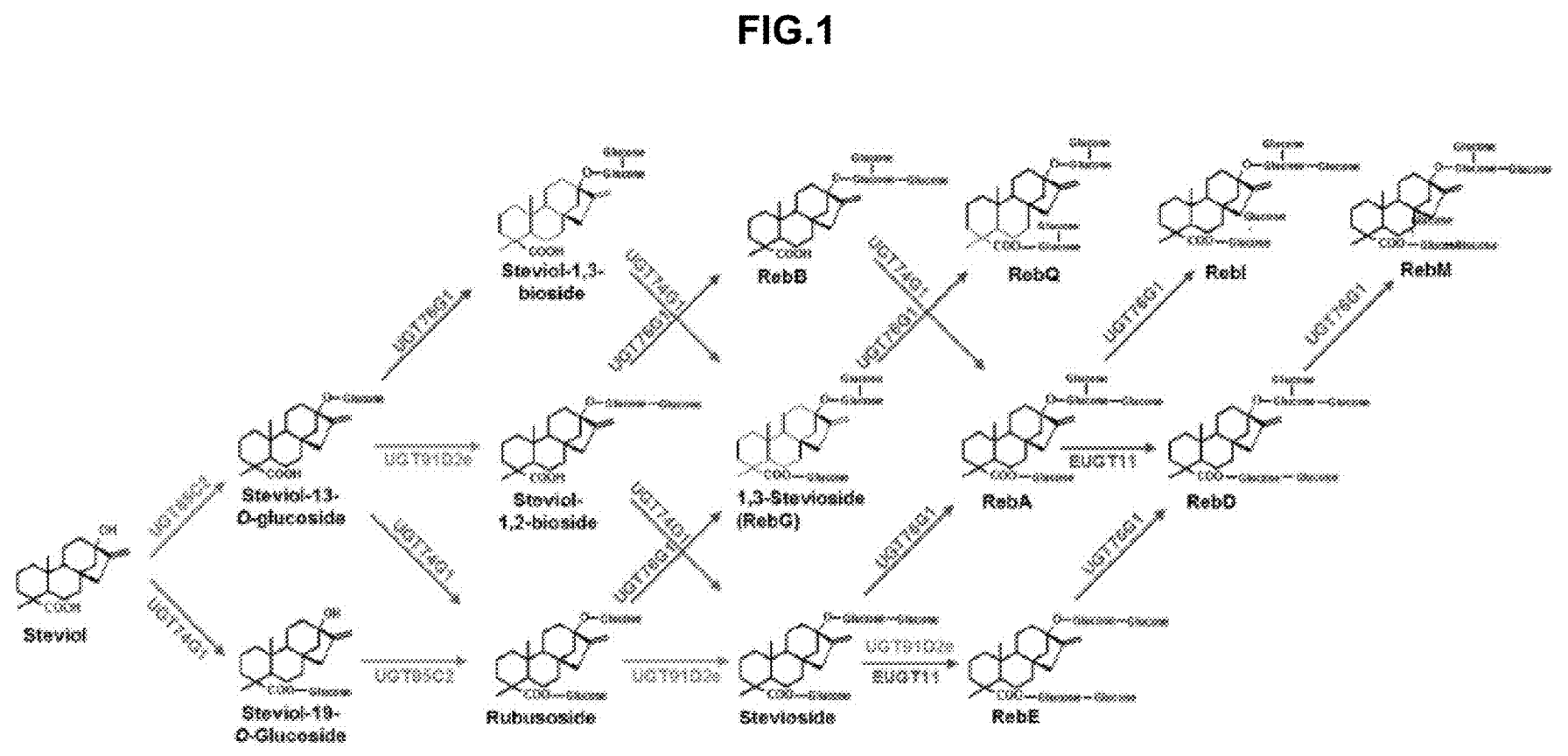

Steviol

Steviol-13-O-glucoside

Steviol-19-O-Glucoside

Steviol-1,3-bioside

Steviol-1,2-bioside

Rubusoside

RebB 1,3-Stevioside (RebG)

Stevioside

RebQ

RebA

RebE

RebI

RebD

RebM

FIG.2

| *Rebaudioside M* | *Notation* |
| --- | --- |
| | Glc-(1->2)Glc<br>\|<br>(1->3)Glc<br><br>Glc-(1->2)Glc<br>(1->3)Glc |
| ChemAxon IUPAC name from structure [JCIUPACName() function]:<br>(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl(1R,5R,9S,13R)-13-{[(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl]oxy}-5,9-dimethyl-14-methylidenetetracyclo[11.2.1.0$^{1,10}$.0$^{4,9}$]hexadecane-5-carboxylate | |
| CambridgeSoft name from structure [CFW_CHEMICAL_NAME() function]:<br>(4R,6aR,9S,11bS)-(3R,4S,5R,6R)-5-hydroxy-6-(hydroxymethyl)-3-(((2S,3R,4S,5S,6R)-3,4,5-trihydroxy-6-(hydroxymethyl)tetrahydro-2H-pyran-2-yl)oxy)-4-(((3R,4S,5S,6R)-3,4,5-trihydroxy-6-(hydroxymethyl)tetrahydro-2H-pyran-2-yl)oxy)tetrahydro-2H-pyran-2-yl 9-(((3R,4S,5R,6R)-5-hydroxy-6-(hydroxymethyl)-3,4-bis(((3R,4S,5S,6R)-3,4,5-trihydroxy-6-(hydroxymethyl)tetrahydro-2H-pyran-2-yl)oxy)tetrahydro-2H-pyran-2-yl)oxy)-4,11b-dimethyl-8-methylenetetradecahydro-6a,9-methanocyclohepta[a]naphthalene-4-carboxylate | |

FIG.3

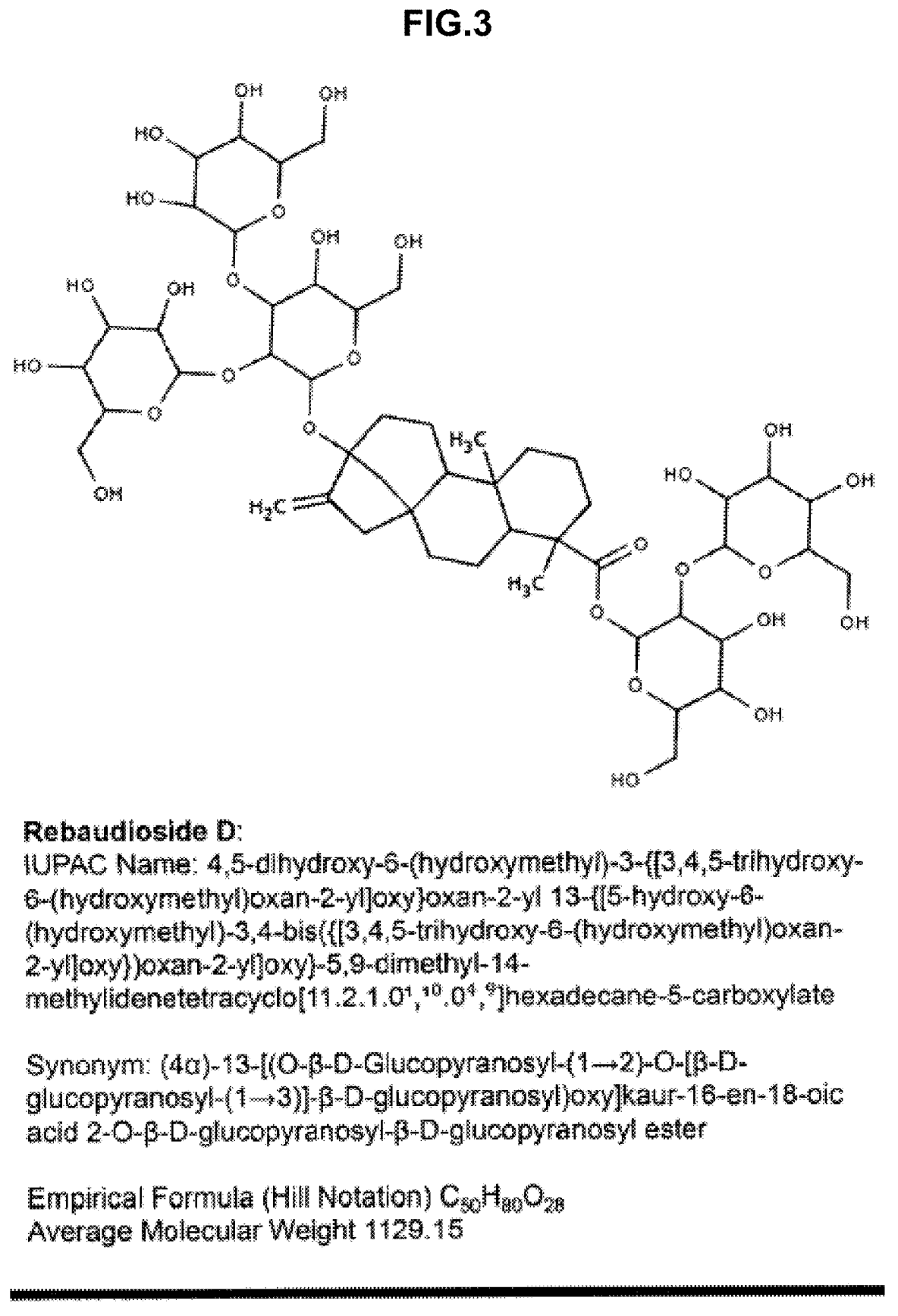

Rebaudioside D:

IUPAC Name: 4,5-dihydroxy-6-(hydroxymethyl)-3-{[3,4,5-trihydroxy-6-(hydroxymethyl)oxan-2-yl]oxy}oxan-2-yl 13-{[5-hydroxy-6-(hydroxymethyl)-3,4-bis({[3,4,5-trihydroxy-6-(hydroxymethyl)oxan-2-yl]oxy})oxan-2-yl]oxy}-5,9-dimethyl-14-methylidenetetracyclo[11.2.1.0$^{1}$,$^{10}$.0$^{4}$,$^{9}$]hexadecane-5-carboxylate Synonym: (4α)-13-[(O-β-D-Glucopyranosyl-(1→2)-O-[β-D-glucopyranosyl-(1→3)]-β-D-glucopyranosyl)oxy]kaur-16-en-18-oic acid 2-O-β-D-glucopyranosyl-β-D-glucopyranosyl ester Empirical Formula (Hill Notation) $C_{50}H_{80}O_{28}$
Average Molecular Weight 1129.15

```
                1         11        21        31        41
76G1_1    --IILFPVPFQGHINPILQLANVLYSKGFSITIFHTNFNKPKTSNYPHFT
76G1_2    RRIILFPVPFQGHINPILQLANVLYSKGFSITIFHTNFNKPKTSNYPHFT
76G1_3    RRIILFPVPFQGHINPILQLANVLYSKGFSITIFHTNFNKPKTSNYPHFT

                51        61        71        81        91
76G1_1    FRFILDNDPQDERISNLPTHGPLAGMRIPIINEHGADELRRELELLMLAS
76G1_2    FRFILDNDPQDERISNLPTHGPLAGMRIPIINEHGADELRRELELLMLAS
76G1_3    FRFILDNDPQDERISNLPTHGPLAGMRIPIINEHGADELRRELELLMLAS

                101       111       121       131       141
76G1_1    EEDEEVSCLITDALWYFAQSVADSLNLRRLVLMTSSLFNFHAHVSLPQFD
76G1_2    EEDEEVSCLITDALWYFAQSVADSLNLRRLVLMTSSLFNFHAHVSLPQFD
76G1_3    EEDEEVSCLITDALWYFAQSVADSLNLRRLVLMTSSLFNFHAHVSLPQFD

                151       161       171       181       191
76G1_1    ELGYLDPDDKTRLEEQASGFPMLKVKDIKSAYSNWQILKEILGKMIKQTK
76G1_2    ELGYLDPDDKTRLEEQASGFPMLKVKDIKSAYSNWQILKEILGKMIKQTK
76G1_3    ELGYLDPDDKTRLEEQASGFPMLKVKDIKSAYSNWQILKEILGKMIKQTK

                201       211       221       231       241
76G1_1    ASSGVIWNSFKELEESELETVIREIPAPSFLIPLPKHLTASSSSLLDHDR
76G1_2    ASSGVIWNSFKELEESELETVIREIPAPSFLIPLPKHLTASSSSLLDHDR
76G1_3    ASSGVIWNSFKELEESELETVIREIPAPSFLIPLPKHLTASSSSLLDHDR

                251       261       271       281       291
76G1_1    TVFQWLDQQPPSSVLYVSFGSTSEVDEKDFLEIARGLVDSKQSFLWVVRP
76G1_2    TVFQWLDQQPPSSVLYVSFGSTSEVDEKDFLEIARGLVDSKQSFLWVVRP
76G1_3    TVFQWLDQQPPSSVLYVSFGSTSEVDEKDFLEIARGLVDSKQSFLWVVRP

                301       311       321       331       341
76G1_1    GFVKGSTWVEPLPDGFLGERGRIVKWVPQQEVLAHGAIGAFWTHSGWNST
76G1_2    GFVKGSTWVEPLPDGFLGERGRIVKWVPQQEVLAHGAIGAFWTHSGWNST
76G1_3    GFVKGSTWVEPLPDGFLGERGRIVKWVPQQEVLAHGAIGAFWTHSGWNST

                351       361       371       381       391
76G1_1    LESVCEGVPMIFSDFGLDQPLNARYMSDVLKV------------------
76G1_2    LESVCEGVPMIFSDFGLDQPLNARYMSDVLKVGVYLENGWERGEIANAIR
76G1_3    LESVCEGVPMIFSDFGLDQPLNARYMSDVLKVGVYLENGWERGEIANAIR
```

FIG.14 continued

| | 401 411 421 431 441 |
|---|---|
| 76G1_1 | -------------------------LMKGGSSYESLESLVSYISS- |
| 76G1_2 | RVMVDEEGEYIRQNARVLKQKADVSLMKGGSSYESLESLVSYISSL |
| 76G1_3 | RVMVDEEGEYIRQNARVLKQKADVSLMKGGSSYESLESLVSYISSL |

<1 2 3 4 >4 Å variance between models

SEQUENCE LISTING

```
Sequence total quantity: 138
SEQ ID NO: 1            moltype = DNA  length = 1616
FEATURE                 Location/Qualifiers
misc_feature            1..1616
                        note = Synthetic oligonucleotide
source                  1..1616
                        mol_type = other DNA
                        organism = synthetic construct
SEQUENCE: 1
cttgcgtgta aacgtcagtc aaacccaatg gaaaataaaa cggagaccac cgttcgccgg  60
cgccggagaa taatattatt cccggtacca tttcaaggcc acattaaccc aattcttcag  120
ctagccaatg tgttgtactc taaaggattc agtatcacca tctttcacac caacttcaac  180
aaacccaaaa catctaatta ccctcacttc actttcagat tcatcctcga caacgaccca  240
caagacgaac gcatttccaa tctaccgact catggtccgc tcgctggtat gcggattccg  300
attatcaacg aacacggagc tgacgaatta cgacgcgaac tggaactgtt gatgttagct  360
tctgaagaag atgaagaggt atcgtgttta atcacggatg ctctttggta cttcgcgcaa  420
tctgttgctg acagtcttaa cctccgacgg cttgttttga tgacaagcag cttgtttaat  480
tttcatgcac atgtttcact tcctcagttt gatgagcttg gttacctcga tcctgatgac  540
aaaacccgtt tggaagaaca agcgagtggg tttcctatgc taaaagtgaa agacatcaag  600
tctgcgtatt cgaactggca aatactcaaa gagatattag ggaagatgat aaaacaaaca  660
aaagcatctt caggagtcat ctggaactca tttaaggaac tcgaagagtc tgagctcgaa  720
actgttatcc gtgagatccc ggctccaagt ttcttgatac cactccccaa gcatttgaca  780
gcctcttcca gcagcttact agaccacgat cgaaccgttt ttcaatggtt agaccaacaa  840
ccgccaagtt cggtactgta tgttagtttt ggtagtacta gtgaagtgga tgagaaagat  900
ttcttggaaa tagctcgtgg gttggttgat agcaagcagt cgtttttatg ggtggttcga  960
cctgggtttg tcaagggttc gacgtgggtc gaaccgttgc cagatgggtt cttgggtgaa  1020
agaggacgta ttgtgaaatg ggttccacag caagaagtgc tagctcatgg agcaataggc  1080
gcattctgga ctcatagcgg atggaactct acgttggaaa gcgtttgtga aggtgttcct  1140
atgattttct cggattttgg gctcgatcaa ccgttgaatg ctagatacat gagtgatgtt  1200
ttgaaggtag ggtgtatttt ggaaaatggg tgggaaagag gagagatagc aaatgcaata  1260
agaagagtta tggtggatga agaaggagaa tacattagac agaatgcaag agttttgaaa  1320
caaaaggcag atgtttcttt gatgaagggt ggttcgtctt acgaatcatt agagtctcta  1380
gtttcttaca tttcatcgtt gtaaataaca cgatgattaa tcaagcactt ggattgcatg  1440
ctagctgagt agctggtaat ttgagttatt agaagcaaag actacttggt ttaaattaaa  1500
taaaggatgg ttgttggtta tgtgagctag tttatgttat gttttgtagg ctataaaagc  1560
cttcatatgt ttcttattgt ttctgtttct aaggtgaaaa aaatgctcgt ttttat      1616

SEQ ID NO: 2            moltype = AA  length = 458
```

```
FEATURE                Location/Qualifiers
source                 1..458
                       mol_type = protein
                       organism = Stevia rebaudiana
SEQUENCE: 2
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVDEK DFLEIARGLV  300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                        458

SEQ ID NO: 3           moltype = DNA  length = 1446
FEATURE                Location/Qualifiers
misc_feature           1..1446
                       note = Synthetic oligonucleotide
source                 1..1446
                       mol_type = other DNA
                       organism = synthetic construct
SEQUENCE: 3
atggatgcaa tggcaactac tgagaaaaag cctcatgtga tcttcattcc atttcctgca  60
caatctcaca taaaggcaat gctaaagtta gcacaactat tacaccataa gggattacag  120
ataactttcg tgaataccga cttcatccat aatcaatttc tggaatctag tggccctcat  180
tgtttggacg gagccccagg gtttagattc gaaacaattc ctgacggtgt ttcacattcc  240
ccagaggcct ccatcccaat aagagagagt ttactgaggt caatagaaac caactttttg  300
gatcgtttca ttgacttggt cacaaaactt ccagacccac caacttgcat aatctctgat  360
ggctttctgt cagtgtttac tatcgacgct gccaaaaagt tgggtatccc agttatgatg  420
tactggactc ttgctgcatg cggtttcatg ggtttctatc acatccattc tcttatcgaa  480
aagggttttg ctccactgaa agatgcatca tacttaacca acggctacct ggatactgtt  540
attgactggg taccaggtat ggaaggtata agacttaaag attttccttt ggattggtct  600
acagacctta atgataaagt attgatgttt actacagaag ctccacaaag atctcataag  660
gtttcacatc atatctttca cacctttgat gaattggaac catcaatcat caaaaccttg  720
tctctaagat acaatcatat ctacactatt ggtccattac aattacttct agatcaaatt  780
cctgaagaga aaaagcaaac tggtattaca tccttacacg gctactcttt agtgaaagag  840
gaaccagaat gttttcaatg gctacaaagt aaagagccta attctgtggt ctacgtcaac  900
ttcggaagta caacagtcat gtccttggaa gatatgactg aatttggttg gggccttgct  960
aattcaaatc attactttct atggattatc aggtccaatt tggtaatagg ggaaaacgcc  1020
gtattacctc cagaattgga ggaacacatc aaaaagagag gtttcattgc ttcctggtgt  1080
tctcaggaaa aggtattgaa acatccttct gttggtggtt tccttactca ttgcggttgg  1140
ggctctacaa tcgaatcact aagtgcagga gttccaatga tttgttggcc atattcatgg  1200
gaccaactta caaattgtag gtatatctgt aaagagtggg aagttggatt agaaatggga  1260
acaaaggtta aacgtgatga agtgaaaaga ttggttcagg agttgatggg ggaaggtggc  1320
cacaagatga gaaacaaggc caaagattgg aaggaaaaag ccagaattgc tattgctcct  1380
aacgggtcat cctctctaaa cattgataag atggtcaaag agattacagt cttagccaga  1440
aactaa                                                           1446

SEQ ID NO: 4           moltype = AA  length = 707
FEATURE                Location/Qualifiers
source                 1..707
                       mol_type = protein
                       organism = Stevia rebaudiana
SEQUENCE: 4
MQSNSVKISP LDLVTALFSG KVLDTSNASE SGESAMLPTI AMIMENRELL MILTTSVAVL  60
IGCVVVLVWR RSSTKKSALE PPVIVVPKRV QEEEVDDGKK KVTVFFGTQT GTAEGFAKAL  120
VEEAKARYEK AVFKVIDLDD YAADDDEYEE KLKKESLAFF FLATYGDGEP TDNAARFYKW  180
FTEGDAKGEW LNKLQYGVFG LGNRQYEHFN KIAKVVDDGL VEQGAKRLVP VGLGDDDQCI  240
EDDFTAWKEL VWPELDQLLR DEDDTTVATP YTAAVAEYRV VFHEKPDALS EDYSYTNGHA  300
VHDAQHPCRS NVAVKKELHS PESDRSCTHL EFDISNTGLS YETGDHVGVY CENLSEVVND  360
AERLVGLPPD TYSSIHTDSE DGSPLGGASL PPPFPPCTLR KALTCYADVL SSPKKSALLA  420
LAAHATDPSE ADRLKFLASP AGKDEYSQWI VASQRSLLEV MEAFPSAKPS LGVFFASVAP  480
RLQPRYYSIS SSPKMAPDRI HVTCALVYEK TPAGRIHKGV CSTWMKNAVP MTESQDCSWA  540
PIYVRTSNFR LPSDPKVPVI MIGPGTGLAP FRGFLQERLA LKEAGTDLGL SILFFGCRNR  600
KVDFIYENEL NNFVETGALS ELIVAFSREG PTKEYVQHKM SEKASDIWNL LSEGAYLYVC  660
GDAKGMAKDV HRTLHTIVQE QGSLDSSKAE LYVKNLQMSG RYLRDVW                707

SEQ ID NO: 5           moltype = DNA  length = 2124
FEATURE                Location/Qualifiers
misc_feature           1..2124
                       note = Synthetic oligonucleotide
source                 1..2124
                       mol_type = other DNA
                       organism = synthetic construct
SEQUENCE: 5
atgcaatcta actccgtgaa gatttcgccg cttgatctgg taactgcgct gtttagcggc  60
aaggttttgg acacatcgaa cgcatcggaa tcgggagaat ctgctatgct gccgactata  120
gcgatgatta tggagaatcg tgagctgttg atgatactca caacgtcggt tgctgtattg  180
atcggatgcg ttgtcgtttt ggtgtggcgg agatcgtcta cgaagaagtc ggcgttggag  240
```

-continued

```
ccaccggtga ttgtggttcc gaagagagtg caagaggagg aagttgatga tggtaagaag  300
aaagttacgg ttttcttcgg cacccaaact ggaacagctg aaggcttcgc taaggcactt  360
gttgaggaag ctaaagctcg atatgaaaag gctgtctta aagtaattga tttggatgat  420
tatgctgctg atgacgatga gtatgaggag aaactaaaga aagaatcttt ggcctttttc  480
tttttggcta cgtatggaga tggtgagcca acagataatg ctgccagatt ttataaatgg  540
tttactgagg gagatgcgaa aggagaatgg cttaataagc ttcaatatgg agtatttggt  600
ttgggtaaca gacaatatga acattttaac aagatcgcaa aagtggttga tgatggtctt  660
gtagaacagg gtgcaaagcg tcttgttcct gttggacttg gagatgatga tcaatgtatt  720
gaagatgact tcaccgcatg gaaagagtta gtatggccgg agttggatca attacttcgt  780
gatgaggatg acacaactgt tgctactcca tacacagctg ctgttgcaga atatcgcgtt  840
gtttttcatg aaaaaccaga cgcgctttct gaagattata gttatacaaa tggccatgct  900
gttcatgatg ctcaacatcc atgcagatcc aacgtggctg tcaaaaagga acttcatagt  960
cctgaatctg accggtcttg cactcatctt gaatttgaca tctcgaacac cggactatca  1020
tatgaaactg ggaccatgt tggagtttac tgtgaaaact tgagtgaagt tgtgaatgat  1080
gctgaaagat tagtaggatt accaccagac acttactcct ccatccacac tgatagtgaa  1140
gacgggtcgc cacttggcgg agcctcattg ccgcctcctt tcccgccatg cactttaagg  1200
aaagcattga cgtgttatgc tgatgttttg agttctccca agaagtcggc tttgcttgca  1260
ctagctgctc atgccaccga tcccagtgaa gctgatagat tgaaatttct tgcatccccc  1320
gccggaaagg atgaatattc tcaatggata gttgcaagcc aaagaagtct ccttgaagtc  1380
atggaagcat tcccgtcagc taagccttca cttggtgttt tctttgcatc tgttgccccg  1440
cgcttacaac caagatacta ctctatttct tcctcaccca agatggcacc ggataggatt  1500
catgttacat gtgcattagt ctatgagaaa acacctgcag gccgcatcca caaaggagtt  1560
tgttcaactt ggatgaagaa cgcagtgcct atgaccgaga gtcaagattg cagttgggcc  1620
ccaatatacg tccgaacatc caatttcaga ctaccatctg accctaaggt cccggttatc  1680
atgattggac ctggcactgg tttggctcct tttagaggtt tccttcaaga gcggttagct  1740
ttaaaggaag ccggaactga cctcggttta tccattttat tcttcggatg taggaatcgc  1800
aaagtggatt tcatatatga aaacgagctt aacaactttg tggagactgg tgctctttct  1860
gagcttattg ttgctttctc ccgtgaaggc ccgactaagg aatatgtgca acacaagatg  1920
agtgagaagg cttcggatat ctggaacttg ctttctgaag gagcatattt atacgtatgt  1980
ggtgatgcca aaggcatggc caaagatgta catcgaaccc tccacacaat tgtgcaagaa  2040
cagggatctc ttgactcgtc aaaggcagaa ctctacgtga agaatctaca aatgtcagga  2100
agatacctcc gtgacgtttg gtaa                                          2124
```

```
SEQ ID NO: 6            moltype = DNA  length = 2358
FEATURE                 Location/Qualifiers
misc_feature            1..2358
                        note = Synthetic oligonucleotide
source                  1..2358
                        mol_type = other DNA
                        organism = synthetic construct
SEQUENCE: 6
atgtctatta atttgagatc ttccggttgt agctccccaa taagcgcaac tttggaaagg  60
ggtctagact ctgaagttca aacaagagca aacaatgtat cttttgagca gaccaaagag  120
aagatcagga aaatgcttga gaaggtcgag ttgagcgtga gtgcctatga cactagttgg  180
gtagctatgg tcccatcacc atccagtcaa aacgcacctc ttttcccaca gtgcgtcaaa  240
tggctacttg ataatcaaca tgaggacggc tcttggggat tggataacca cgaccatcag  300
agcttaaaga aagatgtgtt gtcatccaca ttagcctcta tcctagctct taagaaatgg  360
ggaataggcg aaagacagat caataagggt ctacagttca ttgaattaaa ctctgcacta  420
gttaccgatg aaactataca aaaacctaca ggtttcgaca tcatttttcc aggaatgatt  480
aagtacgcca gggaccttaa tttgaccata cctcttggct cagaagtagt cgacgatatg  540
atcaggaaaa gagatctaga cttaaagtgt gatagcgaga aattcagcaa aggtagagag  600
gcttatcttg cctatgttct tgaaggaact aggaacttga aggactggga cttaattgtg  660
aaatatcaga gaaagaacgg tagtctattt gatagtccag ctacaaccgc cgcagctttc  720
actcaatttg gcaatgacgg ttgcttgagg tacttatgtt cactttaca gaaattcgag  780
gccgcagtgc ctagtgtata tccatttgat caatacgcta gattaagcat aatcgtcact  840
ttagaatcat tgggaattga cagagatttc aagactgaga taaaaagcat attggatgag  900
acctataggt actggcttag aggtgacgaa gaaatttgcc tagatttggc cacatgtgca  960
cttgctttta ggttgctttt agcccacggc tatgacgtgt catacgatcc tctaaagcca  1020
tttgcagagg aatctggttt cagcgatacc cttgagggat atgttaaaaa caccttttcc  1080
gtattagagc ttttcaaggc tgcccaaagt taccctcatg agagtgcttt gaaaaagcag  1140
tgttgctgga caaaacaata tctagaaatg gaactaagtt catgggttaa aacaagcgtt  1200
agggacaagt acttgaaaaa ggaagtggag gatgctttgg catttccatc atatgcctct  1260
ttagaaagaa gtgaccacag aaggaaaatt cttaatggct cagcagttga aaacacaaga  1320
gtaaccaaga cctcttacag gttgcataat atatgtacat cagatatctt aaaacttgct  1380
gtcgacgatt tcaactttttg ccaatctatt catagagagg aaatggaaag attggataga  1440
tggatagtgg agaatagact acaggaatta aagttcgcca gacaaaaatt ggcttactgt  1500
tactttagtg gcgctgccac actattctct ccagaattgt ctgacgcaag gatctcatgg  1560
gctaagggag gtgttctaac cacagtagtc gatgactttt ttgatgttgg cggtagtaaa  1620
gaagagcttg agaacttaat tcacttggtg gaaaagtggg atcttaatgg agttcctgaa  1680
tactcttcag agcatgtaga aataattttc tctgtcctaa gagacactat cttagaaacc  1740
ggtgataaag cctttacata tcagggcaga aacgttactc accatattgt gaaaatatgg  1800
ttggacttac ttaagagcat gctaagggag gctgaatggt ccagtgacaa atcaacccca  1860
tctttggaag attacatgga gaatgcctat atcagcttcg cattaggtcc tattgtattg  1920
ccagctacat accttatagg acctccacta cctgaaaaga ctgtcgactc ccaccaatat  1980
aatcaattat acaaattggt tagtaccatg ggtagactat taaacgatat ccagggcttt  2040
aagagggaat cagccgaggg aaaacttaat gcagtgtctc tacatatgaa gcatgaaaga  2100
gacaacagaa gcaaagaggt tattatagaa tccatgaaag gattggctga aaggaaaaga  2160
gaggaattac acaaacttgt actagaagag aaaggtagtg tcgttccaag agaatgcaag  2220
gaagccttct taaaaatgtc aaaagtgttg aacctttttt ataggaagga tgatggcttc  2280
```

```
acatctaacg acttgatgag ccttgtgaaa tccgtcatct acgagcctgt ttcacttcaa  2340
aaggagagtc taacttga                                                2358

SEQ ID NO: 7            moltype = AA  length = 785
FEATURE                 Location/Qualifiers
source                  1..785
                        mol_type = protein
                        organism = Arabidopsis thaliana
SEQUENCE: 7
MSINLRSSGC SSPISATLER RLDSEVQTRA NNVSFEQTKE KIRKMLEKVE LSVSAYDTSW  60
VAMVPSPSSQ NAPLFPQCVK WLLDNQHEDG SWGLDNHDHQ SLKKDVLSST LASILALKKW  120
GIGERQINKG LQFIELNSAL VTDETIQKPT GFDIIFPGMI KYARDLNLTI PLGSEVVDDM  180
IRKRDLDLKC DSEKFSKGRE AYLAYVLEGT RNLKDWDLIV KYQRKNGSLF DSPATTAAAF  240
TQFGNDGCLR YLCSLLQKFE AAVPSVYPFD QYARLSIIVT LESLGIDRDF KTEIKSILDE  300
TYRYWLRGDE EICLDLATCA LAFRLLLAHG YDVSYDPLKP FAEESGFSDT LEGYVKNTFS  360
VLELFKAAQS YPHESALKKQ CCWTKQYLEM ELSSWVKTSV RDKYLKKEVE DALAFPSYAS  420
LERSDHRRKI LNGSAVENTR VTKTSYRLHN ICTSDILKLA VDDFNFCQSI HREEMERLDR  480
WIVENRLQEL KFARQKLAYC YFSGAATLFS PELSDARISW AKGGVLTTVV DDFFDVGGSK  540
EELENLIHLV EKWDLNGVPE YSSEHVEIIF SVLRDTILET GDKAFTYQGR NVTHHIVKIW  600
LDLLKSMLRE AEWSSDKSTP SLEDYMENAY ISFALGPIVL PATYLIGPPL PEKTVDSHQY  660
NQLYKLVSTM GRLLNDIQGF KRESAEGKLN AVSLHMKHER DNRSKEVIIE SMKGLAERKR  720
EELHKLVLEE KGSVVPRECK EAFLKMSKVL NLFYRKDDGF TSNDLMSLVK SVIYEPVSLQ  780
EESLT                                                              785

SEQ ID NO: 8            moltype = DNA  length = 1503
FEATURE                 Location/Qualifiers
misc_feature            1..1503
                        note = Synthetic oligonucleotide
source                  1..1503
                        mol_type = other DNA
                        organism = synthetic construct
SEQUENCE: 8
atggaagcct cttacctata catttctatt ttgcttttac tggcatcata cctgttcacc  60
actcaactta gaaggaagag cgctaatcta ccaccaaccg tgtttccatc aataccaatc  120
attggacact tatacttact caaaaagcct ctttatagaa ctttagcaaa aattgccgct  180
aagtacggac caatactgca attacaactc ggctacagac gtgttctggt gatttcctca  240
ccatcagcag cagaagagtg ctttaccaat aacgatgtaa tcttcgcaaa tagacctaag  300
acattgtttg gcaaaatagt gggtggaaca tcccttggca gtttatccta cggcgatcaa  360
tggcgtaatc taaggagagt agcttctatc gaaatcctat cagttcatag gttgaacgaa  420
tttcatgata tcagagtgga tgagaacaga ttgttaatta gaaaacttag aagttcatct  480
tctcctgtta ctcttataac agtcttttat gctctaacat tgaacgtcat tatgagaatg  540
atctctggca aaagatattt cgacagtggg gatagagaat tggaggagga aggtaagaga  600
tttcgagaaa tcttagacga aacgttgctt ctagccggtg cttctaatgt tggcgactac  660
ttaccaatat tgaactggtt gggagttaag tctcttgaaa agaaattgat cgctttgcag  720
aaaaagagag atgacttttt ccagggtttg attgaacagg ttagaaaatc tcgtggtgct  780
aaagtaggca aaggtagaaa aacgatgatc gaactcttat tatctttgca agagtcagaa  840
cctgagtact atacagatgc tatgataaga tcttttgtcc taggtctgct ggctgcaggt  900
agtgatactt cagcgggcac tatggaatgg gccatgagct tactggtcaa tcacccacat  960
gtattgaaga aagctcaagc tgaaatcgat agagttatcg gtaataacag attgattgac  1020
gagtcagaca ttggaaatat cccttacatc gggtgtatta tcaatgaaac tctaagactc  1080
tatccagcag ggccattgtt gttcccacat gaaagttctg ccgactgcgt tatttccggt  1140
tacaatatac ctagaggtac aatgttaatc gtaaaccaat gggcgattca tcacgatcct  1200
aaagtctggg atgatcctga aacctttaaa cctgaaagat ttcaaggatt agaaggaact  1260
agagatggtt tcaaacttat gccattcggt tctgggagaa gaggatgtcc aggtgaaggt  1320
ttggcaataa ggctgttagg gatgacacta ggctcagtga tccaatgttt tgattgggag  1380
agagtaggag atgagatggt tgacatgaca gaaggtttgg gtgtcacact tcctaaggcc  1440
gttccattag ttgccaaatg taagccacgt tccgaaatga ctaatctcct atccgaactt  1500
taa                                                                1503

SEQ ID NO: 9            moltype = AA  length = 712
FEATURE                 Location/Qualifiers
source                  1..712
                        mol_type = protein
                        organism = Arabidopsis thaliana
SEQUENCE: 9
MSSSSSSTS MIDLMAAIIK GEPVIVSDPA NASAYESVAA ELSSMLIENR QFAMIVTTSI  60
AVLIGCIVML VWRRSGSGNS KRVEPLKPLV IKPREEEIDD GRKKVTIFFG TQTGTAEGFA  120
KALGEEAKAR YEKTRFKIVD LDDYAADDDE YEEKLKKEDV AFFFLATYGD GEPTDNAARF  180
YKWFTEGNDR GEWLKNLKYG VFGLGNRQYE HFNKVAKVVD DILVEQGAQR LVQVGLGDDD  240
QCIEDDFTAW REALWPELDT ILREEGDTAV ATPYTAAVLE YRVSIHDSED AKFNDITLAN  300
GNGYTVFDAQ HPYKANVAVK RELHTPESDR SCIHLEFDIA GSGLTMKLGD HVGVLCDNLS  360
ETVDEALRLL DMSPDTYFSL HAEKEDGTPI SSSLPPPFPP CNLRTALTRY ACLLSSPKKS  420
ALVALAAHAS DPTEAERLKH LASPAGKDEY SKWVVESQRS LLEVMAEFPS AKPPLGVFFA  480
GVAPRLQPRF YSISSSPKIA ETRIHVTCAL VYEKMPTGRI HKGVCSTWMK NAVPYEKSEK  540
LFLGRPIFVR QSNFKLPSDS KVPIIMIGPG TGLAPFRGFL QERLALVESG VELGPSVLFF  600
GCRNRRMDFI YEEELQRFVE SGALAELSVA FSREGPTKEY VQHKMMDKAS DIWNMISQGA  660
YLYVCGDAKG MARDVHRSLH TIAQEQGSMD STKAEGFVKN LQTSGRYLRD VW          712

SEQ ID NO: 10           moltype = DNA  length = 2139
```

```
FEATURE                Location/Qualifiers
misc_feature           1..2139
                       note = Synthetic oligonucleotide
source                 1..2139
                       mol_type = other DNA
                       organism = synthetic construct
SEQUENCE: 10
atgtcttcct cttcctcttc cagtacctct atgattgatt tgatggctgc tattattaaa  60
ggtgaaccag ttatcgtctc cgacccagca aatgcctctg cttatgaatc agttgctgca  120
gaattgtctt caatgttgat cgaaaacaga caattcgcca tgatcgtaac tacatcaatc  180
gctgttttga tcggttgtat tgtcatgttg gtatggagaa gatccggtag tggtaattct  240
aaaagagtcg aacctttgaa accattagta attaagccaa gagaagaaga aatagatgac  300
ggtagaaaga aagttacaat atttttcggt acccaaactg gtacagctga aggttttgca  360
aaagccttag gtgaagaagc taaggcaaga tacgaaaaga ctagattcaa gatagtcgat  420
ttggatgact atgccgctga tgacgatgaa tacgaagaaa agttgaagaa agaagatgtt  480
gcatttttct tttggcaac ctatggtgac ggtgaaccaa ctgacaatgc agccagattc  540
tacaaatggt ttacagaggg taatgatcgt ggtgaatggt tgaaaaactt aaagtacggt  600
gttttcggtt tgggtaacag acaatacgaa catttcaaca aagttgcaaa ggttgtcgac  660
gatattttgg tcgaacaagg tgctcaaaga ttagtccaag taggtttggg tgacgatgac  720
caatgtatag aagatgactt tactgcctgg agagaagctt tgtggcctga attagacaca  780
atcttgagag aagaaggtga caccgccgtt gctaccccat atactgctgc agtattagaa  840
tacagagttt ccatccatga tagtgaagac gcaaagttta atgatatcac tttggccaat  900
ggtaacggtt atacagtttt cgatgcacaa cacccttaca aagctaacgt tgcagtcaag  960
agagaattac atacaccaga atccgacaga agttgtatac acttggaatt tgatatcgct  1020
ggttccggtt taaccatgaa gttgggtgac catgtaggtg ttttatgcga caatttgtct  1080
gaaactgttg atgaagcatt gagattgttg gatatgtccc ctgacactta ttttagtttg  1140
cacgctgaaa aagaagatgg tacaccaatt tccagttctt taccacctcc attccctcca  1200
tgtaacttaa gaacagcctt gaccagatac gcttgcttgt tatcatcccc taaaaagtcc  1260
gccttggttg ctttagccgc tcatgctagt gatcctactg aagcagaaag attgaaacac  1320
ttagcatctc cagccggtaa agatgaatat tcaaagtggg tagttgaatc tcaaagatca  1380
ttgttagaag ttatggcaga atttccatct gccaagcctc cattaggtgt cttctttgct  1440
ggtgtagcac ctagattgca accaagattc tactcaatca gttcttcacc taagatcgct  1500
gaaactagaa ttcatgttac atgtgcatta gtctacgaaa agatgccaac cggtagaatt  1560
cacaagggtg tatgctctac ttggatgaaa aatgctgttc cttacgaaaa atcagaaaag  1620
ttgttcttag gtagaccaat cttcgtaaga caatcaaact tcaagttgcc ttctgattca  1680
aaggttccaa taatcatgat aggtcctggt acaggtttag ccccattcag aggtttcttg  1740
caagaaagat tggctttagt tgaatctggt gtcgaattag gtccttcagt tttgttcttt  1800
ggttgtagaa acagaagaat ggatttcatc tatgaagaag aattgcaaag attcgtcgaa  1860
tctggtgcat tggccgaatt atctgtagct tttcaagag aaggtccaac taaggaatac  1920
gttcaacata agatgatgga taaggcatcc gacatatgga acatgatcag tcaaggtgct  1980
tatttgtacg tttgcggtga cgcaaagggt atggccagag atgtccatag atctttgcac  2040
acaattgctc aagaacaagg ttccatggat agtaccaaag ctgaaggttt cgtaaagaac  2100
ttacaaactt ccggtagata cttgagagat gtctggtga                         2139

SEQ ID NO: 11          moltype = AA  length = 500
FEATURE                Location/Qualifiers
source                 1..500
                       mol_type = protein
                       organism = Stevia rebaudiana
SEQUENCE: 11
MEASYLYISI LLLLASYLFT TQLRRKSANL PPTVFPSIPI IGHLYLLKKP LYRTLAKIAA  60
KYGPILQLQL GYRRVLVISS PSAAEECFTN NDVIFANRPK TLFGKIVGGT SLGSLSYGDQ  120
WRNLRRVASI EILSVHRLNE FHDIRVDENR LLIRKLRSSS SPVTLITVFY ALTLNVIMRM  180
ISGKRYFDSG DRELEEEGKR FREILDETLL LAGASNVGDY LPILNWLGVK SLEKKLIALQ  240
KKRDDFFQGL IEQVRKSRGA KVGKGRKTMI ELLLSLQESE PEYYTDAMIR SFVLGLLAAG  300
SDTSAGTMEW AMSLLVNHPH VLKKAQAEID RVIGNNRLID ESDIGNIPYI GCIINETLRL  360
YPAGPLLFPH ESSADCVISG YNIPRGTMLI VNQWAIHHDP KVWDDPETFK PERFQGLEGT  420
RDGFKLMPFG SGRRGCPGEG LAIRLLGMTL GSVIQCFDWE RVGDEMVDMT EGLGVTLPKA  480
VPLVAKCKPR SEMTNLLSEL                                              500

SEQ ID NO: 12          moltype = DNA  length = 2490
FEATURE                Location/Qualifiers
misc_feature           1..2490
                       note = Synthetic oligonucleotide
source                 1..2490
                       mol_type = other DNA
                       organism = synthetic construct
SEQUENCE: 12
atggttttgt cttcttcttg tactacagta ccacacttat cttcattagc tgtcgtgcaa  60
cttggtcctt ggagcagtag gattaaaaag aaaaccgata ctgttgcagt accagccgct  120
gcaggaaggt ggagaagggc cttggctaga gcacagcaca catcagaatc cgcagctgtc  180
gcaaagggca gcagtttgac ccctatagtg agaactgacg ctgagtcaag gagaacaaga  240
tggccaaccg atgacgatga cgccgaacct ttagtggatg agatcagggc aatgcttact  300
tccatgtctg atggtgacat ttccgtgagc gcatacgata cagcctgggt cggattggtt  360
ccaagattag acggcggtga aggtcctcaa tttccagcag ctgtgagatg gataagaaat  420
aaccagttgc ctgacggaag ttggggcgat gccgcattat tctctgccta tgacaggctt  480
atcaataccc ttgcctgcgt tgtaactttg acaaggtggt ccctagaacc agagatgaga  540
ggtagaggac tatctttttt gggtaggaac atgtggaaat tagcaactga agatgaagag  600
tcaatgccta ttggcttcga attagcattt ccatctttga tagagcttgc taagagccta  660
```

```
ggtgtccatg acttccctta tgatcaccag gccctacaag gaatctactc ttcaagagag  720
atcaaaatga agaggattcc aaaagaagtg atgcataccg ttccaacatc aatattgcac  780
agtttggagg gtatgcctgg cctagattgg gctaaactac ttaaactaca gagcagcgac  840
ggaagttttt tgttctcacc agctgccact gcatatgctt taatgaatac cggagatgac  900
aggtgtttta gctacatcga tagaacagta aagaaattca acggcggcgt ccctaatgtt  960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttggattt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
ttggcaagaa tggatttcaa ccactgccag gctttgcatc agttagagtg gcaaggacta  1620
aaaagatggt atactgaaaa taggttgatg gactttggtg tcgcccaaga agatgccctt  1680
agagcttatt ttcttgcagc cgcatctgtt tacgagcctt gtagagctgc cgagaggctt  1740
gcatgggcta gagccgcaat actagctaac gccgtgagca cccacttaag aaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaatttctg ccggtagggc agctggtgaa  2160
gcagccagtg aggacggcga tagaagaata attcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                   2490

SEQ ID NO: 13          moltype = AA  length = 827
FEATURE                Location/Qualifiers
source                 1..827
                       mol_type = protein
                       organism = Zea mays
SEQUENCE: 13
MVLSSSCTTV PHLSSLAVVQ LGPWSSRIKK KTDTVAVPAA AGRWRRALAR AQHTSESAAV  60
AKGSSLTPIV RTDAESRRTR WPTDDDDAEP LVDEIRAMLT SMSDGDISVS AYDTAWVGLV  120
PRLDGGEGPQ FPAAVRWIRN NQLPDGSWGD AALFSAYDRL INTLACVVTL TRWSLEPEMR  180
GRGLSFLGRN MWKLATEDEE SMPIGFELAF PSLIELAKSL GVHDFPYDHQ ALQGIYSSRE  240
IKMKRIPKEV MHTVPTSILH SLEGMPGLDW AKLLKLQSSD GSFLFSPAAT AYALMNTGDD  300
RCFSYIDRTV KKFNGGVPNV YPVDLFEHIW AVDRLERLGI SRYFQKEIEQ CMDYVNRHWT  360
EDGICWARNS DVKEVDDTAM AFRLLRLHGY SVSPDVFKNF EKDGEFFAFV GQSNQAVTGM  420
YNLNRASQIS FPGEDVLHRA GAFSYEFLRR KEAEGALRDK WIISKDLPGE VVYTLDFPWY  480
GNLPRVEARD YLEQYGGGDD VWIGKTLYRM PLVNNDVYLE LARMDFNHCQ ALHQLEWQGL  540
KRWYTENRLM DFGVAQEDAL RAYFLAAASV YEPCRAAERL AWARAAILAN AVSTHLRNSP  600
SFRERLEHSL RCRPSEETDG SWFNSSSGSD AVLVKAVLRL TDSLAREAQP IHGGDPEDII  660
HKLLRSAWAE WVREKADAAD SVCNGSSAVE QEGSRMVHDK QTCLLLARMI EISAGRAAGE  720
AASEDGDRRI IQLTGSICDS LKQKMLVSQD PEKNEEMMSH VDDELKLRIR EFVQYLLRLG  780
EKKTGSSETR QTFLSIVKSC YYAAHCPPHV VDRHISRVIF EPVSAAK                827

SEQ ID NO: 14          moltype = DNA  length = 1377
FEATURE                Location/Qualifiers
misc_feature           1..1377
                       note = Synthetic oligonucleotide
source                 1..1377
                       mol_type = other DNA
                       organism = synthetic construct
SEQUENCE: 14
atggaaaaca agaccgaaac aacagttaga cgtaggcgta gaatcattct gtttccagta  60
ccttttcaag ggcacatcaa tccaatacta caactagcca acgttttgta ctctaaaggt  120
ttttctatta caatctttca caccaatttc aacaaaccaa aaacatccaa ttacccacat  180
ttcacattca gattcatact tgataatgat ccacaagatg aacgtatttc aaacttacct  240
acccacggtc ctttagctgg aatgagaatt ccaatcatca atgaacatgg tgccgatgag  300
cttagaagag aattagagtt acttatgttg gcatccgaag aggacgagga agtctcttgt  360
ctgattactg acgctctatg gtactttgcc caatctgtgg ctgatagttt gaatttgagg  420
agattggtac taatgacatc cagtctgttt aactttcacg ctcatgttag tttaccacaa  480
tttgacgaat tgggatactt ggaccctgat gacaagacta ggttagagga acaggcctct  540
ggttttccta tgttgaaagt caaagatatc aagtctgcct attctaattg gcaaatcttg  600
aaagagatct taggaaagat gatcaaacag acaaaggctt catctggagt gatttggaac  660
agtttcaaag agttagaaga gtctgaattg gagactgtaa tcagagaaat tccagcacct  720
tcattcctga taccattacc aaaacatttg actgcttcct cttcctcttt gttggatcat  780
gacagaacag tttttcaatg gttggaccaa caaccaccta gttctgtttt gtacgtgtca  840
tttggtagta cttctgaagt cgatgaaaag gacttccttg aaatcgcaag aggcttagtc  900
gatagtaagc agtcattcct ttgggtcgtg cgtccaggtt tcgtgaaagg ctcaacatgg  960
gtcgaaccac ttccagatgg ttttctaggc gaaagaggta gaatagtcaa atgggttcct  1020
caacaggaag ttttagctca tggcgctatt ggggcattct ggactcattc cggatggaat  1080
```

```
tcaactttag aatcagtatg cgaaggggta cctatgatct tttcagattt tggtcttgat  1140
caaccactga acgcaagata catgtctgat gttttgaaag tgggtgtata tctagaaaat  1200
ggctgggaaa ggggtgaaat agctaatgca ataagacgtg ttatggttga tgaagagggg  1260
gagtatatca gacaaaacgc aagagtgctg aagcaaaagg ccgacgtttc tctaatgaag  1320
ggaggctctt catacgaatc cttagaatct cttgtttcct acatttcatc actgtaa     1377

SEQ ID NO: 15          moltype = AA  length = 473
FEATURE                Location/Qualifiers
source                 1..473
                       mol_type = protein
                       organism = Stevia rebaudiana
SEQUENCE: 15
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG LVLKGSDCLL SKCYHEFGTQ WLPLLETLHQ  240
VPVVPVGLLP PEIPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNARAVAID HES         473

SEQ ID NO: 16          moltype = AA  length = 462
FEATURE                Location/Qualifiers
source                 1..462
                       mol_type = protein
                       organism = Oryza sativa
SEQUENCE: 16
MDSGYSSSYA AAAGMHVVIC PWLAFGHLLP CLDLAQRLAS RGHRVSFVST PRNISRLPPV  60
RPALAPLVAF VALPLPRVEG LPDGAESTND VPHDRPDMVE LHRRAFDGLA APFSEFLGTA  120
CADWVIVDVF HHWAAAAALE HKVPCAMMLL GSAHMIASIA DRRLERAETE SPAAAGQGRP  180
AAAPTFEVAR MKLIRTKGSS GMSLAERFSL TLSRSSLVVG RSCVEFEPET VPLLSTLRGK  240
PITFLGLMPP LHEGRREDGE DATVRWLDAQ PAKSVVYVAL GSEVPLGVEK VHELALGLEL  300
AGTRFLWALR KPTGVSDADL LPAGFEERTR GRGVVATRWV PQMSILAHAA VGAFLTHCGW  360
NSTIEGLMFG HPLIMLPIFG DQGPNARLIE AKNAGLQVAR NDGDGSFDRE GVAAAIRAVA  420
VEEESSKVFQ AKAKKLQEIV ADMACHERYI DGFIQQLRSY KD                     462

SEQ ID NO: 17          moltype = DNA  length = 1389
FEATURE                Location/Qualifiers
misc_feature           1..1389
                       note = Synthetic oligonucleotide
source                 1..1389
                       mol_type = other DNA
                       organism = synthetic construct
SEQUENCE: 17
atggactccg gctactcctc ctcctacgcc gccgccgccg ggatgcacgt cgtgatctgc  60
ccgtggctcg ccttcggcca cctgctcccg tgcctcgacc tcgcccagcg cctcgcgtcg  120
cggggccacc gcgtgtcgtt cgtctccacg ccgcggaaca tatcccgcct cccgccggtg  180
cgccccgcgc tcgcgccgct cgtcgccttc gtggcgctgc cgctcccgcg cgtcgagggg  240
ctccccgacg gcgccgagtc caccaacgac gtcccccacg acaggccgga catggtcgag  300
ctccaccgga gggccttcga cgggctcgcc gcgcccttct cggagttctt gggcaccgcg  360
tgcgccgact gggtcatcgt cgacgtcttc caccactggg ccgcagccgc cgctctcgag  420
cacaaggtgc catgtgcaat gatgttgttg ggctctgcac atatgatcgc ttccatagca  480
gacagacggc tcgagcgcgc ggagacagag tcgcctgcgg ctgccgggca gggacgccca  540
gcggcggcgc caacgttcga ggtggcgagg atgaagttga tacgaaccaa aggctcatcg  600
ggaatgtccc tcgccgagcg cttctccttg acgctctcga ggagcagcct cgtcgtcggg  660
cggagctgcg tggagttcga gccggagacc gtcccgctcc tgtcgacgct ccgcggtaag  720
cctattacct tccttggcct tatgccgccg ttgcatgaag gccgccgcga ggacggcgag  780
gatgccaccg tccgctggct cgacgcgcag ccggccaagt ccgtcgtgta cgtcgcgcta  840
ggcagcgagg tgccactggg agtggagaag gtccacgagc tcgcgctcgg gctggagctc  900
gccgggacgc gcttcctctg ggctcttagg aagcccactg gcgtctccga cgccgacctc  960
ctccccgccg gcttcgagga gcgcacgcgc ggccgcggcg tcgtggcgac gagatgggtt  1020
cctcagatga gcatactggc gcacgccgcc gtgggcgcgt tcctgaccca ctgcggctgg  1080
aactcgacca tcgagggggct catgttcggc cacccgctta tcatgctgcc gatcttcggc  1140
gaccagggac cgaacgcgcg gctaatcgag gcgaagaacg ccggattgca ggtggcaaga  1200
aacgacggcg atggatcgtt cgaccgagaa ggcgtcgcgg cggcgattcg tgcagtcgcg  1260
gtggaggaag aaagcagcaa agtgtttcaa gccaaagcca agaagctgca ggagatcgtc  1320
gcggacatgg cctgccatga gaggtacatc gacggattca ttcagcaatt gagatcttac  1380
aaggattga                                                          1389

SEQ ID NO: 18          moltype = DNA  length = 1389
FEATURE                Location/Qualifiers
misc_feature           1..1389
                       note = Synthetic oligonucleotide
source                 1..1389
                       mol_type = other DNA
                       organism = synthetic construct
SEQUENCE: 18
atggatagtg gctactcctc atcttatgct gctgccgctg gtatgcacgt tgtgatctgc  60
ccttggttgg cctttggtca cctgttacca tgtctggatt tagcccaaag actggcctca  120
```

```
agaggccata gagtatcatt tgtgtctact cctagaaata tctctcgttt accaccagtc  180
agacctgctc tagctcctct agttgcattc gttgctcttc cacttccaag agtagaagga  240
ttgccagacg gcgctgaatc tactaatgac gtaccacatg atagacctga catggtcgaa  300
ttgcatagaa gagcctttga tggattggca gctccatttt ctgagttcct gggcacagca  360
tgtgcagact gggttatagt cgatgtattt catcactggg ctgctgcagc cgcattggaa  420
cataaggtgc cttgtgctat gatgttgtta gggtcagcac acatgatcgc atccatagct  480
gatagaagat tggaaagagc tgaaacagaa tccccagccg cagcaggaca aggtaggcca  540
gctgccgccc caacctttga agtggctaga atgaaattga ttcgtactaa aggtagttca  600
gggatgagtc ttgctgaaag gttttctctg acattatcta gatcatcatt agttgtaggt  660
agatcctgcg tcgagttcga acctgaaaca gtacctttac tatctacttt gagaggcaaa  720
cctattactt tccttggtct aatgcctcca ttacatgaag gaaggagaga agatggtgaa  780
gatgctactg ttaggtggtt agatgcccaa cctgctaagt ctgttgttta cgttgcattg  840
ggttctgagg taccactagg ggtggaaaag gtgcatgaat tagcattagg acttgagctg  900
gccggaacaa gattcctttg ggctttgaga aaaccaaccg gtgtttctga cgccgacttg  960
ctaccagctg ggttcgaaga gagaacaaga ggccgtggtg tcgttgctac tagatgggtc  1020
ccacaaatga gtattctagc tcatgcagct gtaggggcct ttctaaccca ttgcggttgg  1080
aactcaacaa tagaaggact gatgtttggt catccactta ttatgttacc aatctttggc  1140
gatcagggac ctaacgcaag attgattgag gcaaagaacg caggtctgca ggttgcacgt  1200
aatgatggtg atggttcctt tgatagagaa ggcgttgcag ctgccatcag agcagtcgcc  1260
gttgaggaag agtcatctaa agttttccaa gctaaggcca aaaaattaca agagattgtg  1320
gctgacatgg cttgtcacga aagatacatc gatggtttca tccaacaatt gagaagttat  1380
aaagactaa                                                         1389

SEQ ID NO: 19          moltype = AA  length = 460
FEATURE                Location/Qualifiers
source                 1..460
                       mol_type = protein
                       organism = Stevia rebaudiana
SEQUENCE: 19
MAEQQKIKKS PHVLLIPFPL QGHINPFIQF GKRLISKGVK TTLVTTIHTL NSTLNHSNTT  60
TTSIEIQAIS DGCDEGGFMS AGESYLETFK QVGSKSLADL IKKLQSEGTT IDAIIYDSMT  120
EWVLDVAIEF GIDGGSFFTQ ACVVNSLYYH VHKGLISLPL GETVSVPGFP VLQRWETPLI  180
LQNHEQIQSP WSQMLFGQFA NIDQARWVFT NSFYKLEEEV IEWTRKIWNL KVIGPTLPSM  240
YLDKRLDDDK DNGFNLYKAN HHECMNWLDD KPKESVVYVA FGSLVKHGPE QVEEITRALI  300
DSDVNFLWVI KHKEEGKLPE NLSEVIKTGK GLIVAWCKQL DVLAHESVGC FVTHCGFNST  360
LEAISLGVPV VAMPQFSDQT TNAKLLDEIL GVGVRVKADE NGIVRRGNLA SCIKMIMEEE  420
RGVIIRKNAV KWKDLAKVAV HEGGSSDNDI VEFVSELIKA                       460

SEQ ID NO: 20          moltype = AA  length = 481
FEATURE                Location/Qualifiers
source                 1..481
                       mol_type = protein
                       organism = Stevia rebaudiana
SEQUENCE: 20
MDAMATTEKK PHVIFIPFPA QSHIKAMLKL AQLLHHKGLQ ITFVNTDFIH NQFLESSGPH  60
CLDGAPGFRF ETIPDGVSHS PEASIPIRES LLRSIETNFL DRFIDLVTKL PDPPTCIISD  120
GFLSVFTIDA AKKLGIPVMM YWTLAACGFM GFYHIHSLIE KGFAPLKDAS YLTNGYLDTV  180
IDWVPGMEGI RLKDFPLDWS TDLNDKVLMF TTEAPQRSHK VSHHIFHTFD ELEPSIIKTL  240
SLRYNHIYTI GPLQLLLDQI PEEKKQTGIT SLHGYSLVKE EPECFQWLQS KEPNSVVYVN  300
FGSTTVMSLE DMTEFGWGLA NSNHYFLWII RSNLVIGENA VLPPELEEHI KKRGFIASWC  360
SQEKVLKHPS VGGFLTHCGW GSTIESLSAG VPMICWPYSW DQLTNCRYIC KEWEVGLEMG  420
TKVKRDEVKR LVQELMGEGG HKMRNKAKDW KEKARIAIAP NGSSSLNIDK MVKEITVLAR  480
N                                                                 481

SEQ ID NO: 21          moltype = AA  length = 785
FEATURE                Location/Qualifiers
source                 1..785
                       mol_type = protein
                       organism = Arabidopsis thaliana
SEQUENCE: 21
MSINLRSSGC SSPISATLER GLDSEVQTRA NNVSFEQTKE KIRKMLEKVE LSVSAYDTSW  60
VAMVPSPSSQ NAPLFPQCVK WLLDNQHEDG SWGLDNHDHQ SLKKDVLSST LASILALKKW  120
GIGERQINKG LQFIELNSAL VTDETIQKPT GFDIIFPGMI KYARDLNLTI PLGSEVVDDM  180
IRKRDLDLKC DSEKFSKGRE AYLAYVLEGT RNLKDWDLIV KYQRKNGSLF DSPATTAAAF  240
TQFGNDGCLR YLCSLLQKFE AAVPSVYPFD QYARLSIIVT LESLGIDRDF KTEIKSILDE  300
TYRYWLRGDE EICLDLATCA LAFRLLLAHG YDVSYDPLKP FAEESGFSDT LEGYVKNTFS  360
VLELFKAAQS YPHESALKKQ CCWTKQYLEM ELSSWVKTSV RDKYLKKEVE DALAFPSYAS  420
LERSDHRRKI LNGSAVENTR VTKTSYRLHN ICTSDILKLA VDDFNFCQSI HREEMERLDR  480
WIVENRLQEL KFARQKLAYC YFSGAATLFS PELSDARISW AKGGVLTTVV DDFFDVGGSK  540
EELENLIHLV EKWDLNGVPE YSSEHVEIIF SVLRDTILET GDKAFTYQGR NVTHHIVKIW  600
LDLLKSMLRE AEWSSDKSTP SLEDYMENAY ISFALGPIVL PATYLIGPPL PEKTVDSHQY  660
NQLYKLVSTM GRLLNDIQGF KRESAEGKLN AVSLHMKHER DNRSKEVIIE SMKGLAERKR  720
EELHKLVLEE KGSVVPRECK EAFLKMSKVL NLFYRKDDGF TSNDLMSLVK SVIYEPVSLQ  780
KESLT                                                             785

SEQ ID NO: 22          moltype = DNA  length = 894
FEATURE                Location/Qualifiers
misc_feature           1..894
                       note = Synthetic oligonucleotide
```

```
source                  1..894
                        mol_type = other DNA
                        organism = synthetic construct
SEQUENCE: 22
atggtcgcac aaactttcaa cctggatacc tacttatccc aaagacaaca acaagttgaa  60
gaggccctaa gtgctgctct tgtgccagct tatcctgaga gaatatacga agctatgaga  120
tactccctcc tggcaggtgg caaaagatta agacctatct tatgtttagc tgcttgcgaa  180
ttggcaggtg gttctgttga acaagccatg ccaactgcgt gtgcacttga aatgatccat  240
acaatgtcac taattcatga tgacctgcca gccatggata acgatgattt cagaagagga  300
aagccaacta atcacaaggt gttcggggaa gatatagcca tcttagcggg tgatgcgctt  360
ttagcttacg cttttgaaca tattgcttct caaacaagag gagtaccacc tcaattggtg  420
ctacaagtta ttgctagaat cggacacgcc gttgctgcaa caggcctcgt tggaggccaa  480
gtcgtagacc ttgaatctga aggtaaagct atttccttag aaacattgga gtatattcac  540
tcacataaga ctggagcctt gctggaagca tcagttgtct caggcggtat tctcgcaggg  600
gcagatgaag agcttttggc cagattgtct cattacgcta gagatatagg cttggctttt  660
caaatcgtcg atgatatcct ggatgttact gctacatctg aacagttggg gaaaaccgct  720
ggtaaagacc aggcagccgc aaaggcaact tatccaagtc tattgggttt agaagcctct  780
agacagaaag cggaagagtt gattcaatct gctaaggaag ccttaagacc ttacggttca  840
caagcagagc cactcctagc gctggcagac ttcatcacac gtcgtcagca ttaa        894

SEQ ID NO: 23           moltype = DNA  length = 1542
FEATURE                 Location/Qualifiers
misc_feature            1..1542
                        note = Synthetic oligonucleotide
source                  1..1542
                        mol_type = other DNA
                        organism = synthetic construct
SEQUENCE: 23
atggatgctg tgacgggttt gttaactgtc ccagcaaccg ctataactat tggtggaact  60
gctgtagcat tggcggtagc gctaatcttt tggtacctga aatcctacac atcagctaga  120
agatcccaat caaatcatct tccaagagtg cctgaagtcc caggtgttcc attgttagga  180
aatctgttac aattgaagga gaaaaagcca tacatgactt ttacgagatg ggcagcgaca  240
tatggaccta tctatagtat caaaactggg gctacaagta tggttgtggt atcatctaat  300
gagatagcca aggaggcatt ggtgaccaga ttccaatcca tatctacaag gaacttatct  360
aaagccctga aagtacttac agcagataag acaatggtcg caatgtcaga ttatgatgat  420
tatcataaaa cagttaagag acacatactg accgccgtct tgggtcctaa tgcacagaaa  480
aagcatagaa ttcacagaga tatcatgatg gataacatat ctactcaact tcatgaattc  540
gtgaaaaaca acccagaaca ggaagaggta gaccttagaa aaatctttca atctgagtta  600
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatcg atgttgattg gagagacttc tttccatacc taaagtgggt cccaaacaaa  780
aagttcgaaa atactattca acaaatgtac atcagaagag aagctgttat gaaatcttta  840
atcaaagagc acaaaaagag aatagcgtca ggcgaaaagc taaatagtta tatcgattac  900
cttttatctg aagctcaaac tttaaccgat cagcaactat tgatgtcctt gtgggaacca  960
atcattgaat cttcagatac aacaatggtc acaacagaat gggcaatgta cgaattagct  1020
aaaaacccta aattgcaaga taggttgtac agagacatta agtccgtctg tggatctgaa  1080
aagataaccg aagagcatct atcacagctg ccttacatta cagctatttt ccacgaaaca  1140
ctgagaagac actcaccagt tcctatcatt cctctaagac atgtacatga agataccgtt  1200
ctaggcggct accatgttcc tgctggcaca gaacttgccg ttaacatcta cggttgcaac  1260
atggacaaaa acgtttggga aaatccagag gaatggaacc cagaaagatt catgaaagag  1320
aatgagacaa ttgattttca aaagacgatg gccttcggtg gtggtaagag agtttgtgct  1380
ggttccttgc aagccctttt aactgcatct attgggattg ggagaatggt tcaagagttc  1440
gaatggaaac tgaaggatat gactcaagag gaagtgaaca cgataggcct aactacacaa  1500
atgttaagac cattgagagc tattatcaaa cctaggatct aa                     1542

SEQ ID NO: 24           moltype = AA  length = 297
FEATURE                 Location/Qualifiers
source                  1..297
                        mol_type = protein
                        organism = Synechococcus sp.
SEQUENCE: 24
MVAQTFNLDT YLSQRQQQVE EALSAALVPA YPERIYEAMR YSLLAGGKRL RPILCLAACE  60
LAGGSVEQAM PTACALEMIH TMSLIHDDLP AMDNDDFRRG KPTNHKVFGE DIAILAGDAL  120
LAYAFEHIAS QTRGVPPQLV LQVIARIGHA VAATGLVGGQ VVDLESEGKA ISLETLEYIH  180
SHKTGALLEA SVVSGGILAG ADEELLARLS HYARDIGLAF QIVDDILDVT ATSEQLGKTA  240
GKDQAAAKAT YPSLLGLEAS RQKAEELIQS AKEALRPYGS QAEPLLALAD FITRRQH     297

SEQ ID NO: 25           moltype = AA  length = 513
FEATURE                 Location/Qualifiers
source                  1..513
                        mol_type = protein
                        organism = Stevia rebaudiana
SEQUENCE: 25
MDAVTGLLTV PATAITIGGT AVALAVALIF WYLKSYTSAR RSQSNHLPRV PEVPGVPLLG  60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
```

```
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRI                               513

SEQ ID NO: 26          moltype = AA  length = 480
FEATURE                Location/Qualifiers
source                 1..480
                       mol_type = protein
                       organism = Stevia rebaudiana
SEQUENCE: 26
MDAMATTEKK PHVIFIPFPA QSHIKAMLKL AQLLHHKGLQ ITFVNTDFIH NQFLESSGPH  60
CLDGAPGFRF ETIPDGVSHS PEASIPIRES LLRSIETNFL DRFIDLVTKL PDPPTCIISD  120
GFLSVFTIDA AKKLGIPVMM YWTLAACGFM GFYHIHSLIE KGFAPLKDAS YLTNGYLDTV  180
IDWVPGMEGI RLKDFPLDWS TDLNDKVLMF TTEAPQRSHK VSHHIFHTFD ELEPSIIKTL  240
SLRYNHIYTI GPLQLLLDQI PEEKKQTGIT SLHGYSLVKE EPECFQWLQS KEPNSVVYVN  300
FGSTTVMSLE DMTEFGWGLA NSNHYFLWII RSNLVIGENA VLPPELEEHI KKRGFIASWC  360
SQEKVLKHPS VGGFLTHCGW GSTIESLSAG VPMICWPYSW DQLTNCRYIC KEWEVGLEMG  420
TKVKRDEVKR LVQELMGEGG HKMRNKAKDW KEKARIAIAP NGSSSLNIDK MVKEITVLAR  480

SEQ ID NO: 27          moltype = AA  length = 784
FEATURE                Location/Qualifiers
source                 1..784
                       mol_type = protein
                       organism = Stevia rebaudiana
SEQUENCE: 27
MNLSLCIASP LLTKSNRPAA LSAIHTASTS HGGQTNPTNL IIDTTKERIQ KQFKNVEISV  60
SSYDTAWVAM VPSPNSPKSP CFPECLNWLI NNQLNDGSWG LVNHTHNHNH PLLKDSLSST  120
LACIVALKRW NVGEDQINKG LSFIESNLAS ATEKSQPSPI GFDIIFPGLL EYAKNLDINL  180
LSKQTDFSLM LHKRELEQKR CHSNEMDGYL AYISEGLGNL YDWNMVKKYQ MKNGSVFNSP  240
SATAAAFINH QNPGCLNYLN SLLDKFGNAV PTVYPHDLFI RLSMVDTIER LGISHHFRVE  300
IKNVLDETYR CWVERDEQIF MDVVTCALAF RLLRINGYEV SPDPLAEITN ELALKDEYAA  360
LETYHASHIL YQEDLSSGKQ ILKSADFLKE IISTDSNRLS KLIHKEVENA LKFPINTGLE  420
RINTRRNIQL YNVDNTRILK TTYHSSNISN TDYLRLAVED FYTCQSIYRE ELKGLERWVV  480
ENKLDQLKFA RQKTAYCYFS VAATLSSPEL SDARISWAKN GILTTVVDDF FDIGGTIDEL  540
TNLIQCVEKW NVDVDKDCCS EHVRILFLAL KDAICWIGDE AFKWQARDVT SHVIQTWLEL  600
MNSMLREAIW TRDAYVPTLN EYMENAYVSF ALGPIVKPAI YFVGPKLSEE IVESSEYHNL  660
FKLMSTQGRL LNDIHSFKRE FKEGKLNAVA LHLSNGESGK VEEEVVEEMM MMIKNKRKEL  720
MKLIFEENGS IVPRACKDAF WNMCHVLNFF YANDDGFTGN TILDTVKDII YNPLVLVNEN  780
EEQR                                                               784

SEQ ID NO: 28          moltype = AA  length = 784
FEATURE                Location/Qualifiers
source                 1..784
                       mol_type = protein
                       organism = Stevia rebaudiana
SEQUENCE: 28
MNLSLCIASP LLTKSSRPTA LSAIHTASTS HGGQTNPTNL IIDTTKERIQ KLFKNVEISV  60
SSYDTAWVAM VPSPNSPKSP CFPECLNWLI NNQLNDGSWG LVNHTHNHNH PLLKDSLSST  120
LACIVALKRW NVGEDQINKG LSFIESNLAS ATDKSQPSPI GFDIIFPGLL EYAKNLDINL  180
LSKQTDFSLM LHKRELEQKR CHSNEIDGYL AYISEGLGNL YDWNMVKKYQ MKNGSVFNSP  240
SATAAAFINH QNPGCLNYLN SLLDKFGNAV PTVYPLDLYI RLSMVDTIER LGISHHFRVE  300
IKNVLDETYR CWVERDEQIF MDVVTCALAF RLLRIHGYKV SPDQLAEITN ELAFKDEYAA  360
LETYHASQIL YQEDLSSGKQ ILKSADFLKG ILSTDSNRLS KLIHKEVENA LKFPINTGLE  420
RINTRRNIQL YNVDNTRILK TTYHSSNISN TYYLRLAVED FYTCQSIYRE ELKGLERWVV  480
QNKLDQLKFA RQKTAYCYFS VAATLSSPEL SDARISWAKN GILTTVVDDF FDIGGTIDEL  540
TNLIQCVEKW NVDVDKDCCS EHVRILFLAL KDAICWIGDE AFKWQARDVT SHVIQTWLEL  600
MNSMLREAIW TRDAYVPTLN EYMENAYVSF ALGPIVKPAI YFVGPKLSEE IVESSEYHNL  660
FKLMSTQGRL LNDIHSFKRE FKEGKLNAVA LHLSNGESGK VEEEVVEEMM MMIKNKRKEL  720
MKLIFEENGS IVPRACKDAF WNMCHVLNFF YANDDGFTGN TILDTVKDII YNPLVLVNEN  780
EEQR                                                               784

SEQ ID NO: 29          moltype = AA  length = 590
FEATURE                Location/Qualifiers
source                 1..590
                       mol_type = protein
                       organism = Zea mays
SEQUENCE: 29
MAMPVKLTPA SLSLKAVCCR FSSGGHALRF GSSLPCWRRT PTQRSTSSST TRPAAEVSSG  60
KSKQHDQEAS EATIRQQLQL VDVLENMGIS RHFAAEIKCI LDRTYRSWLQ RHEEIMLDTM  120
TCAMAFRILR LNGYNVSSDE LYHVVEASGL HNSLGGYLND TRTLLELHKA STVSISEDES  180
ILDSIGSRSR TLLREQLESG GALRKPSLFK EVEHALDGPF YTTLDRLHHR WNIENFNIIE  240
QHMLETPYLS NQHTSRDILA LSIRDFSSSQ FTYQQELQHL ESWVKECRLD QLQFARQKLA  300
YFYLSAAGTM FSPELSDART LWAKNGVLTT IVDDFFDVAG SKEELENLVM LVEMWDEHHK  360
VEFYSEQVEI IFSSIYDSVN QLGEKASLVQ DRSITKHLVE IWLDLLKSMM TEVEWRLSKY  420
VPTEKEYMIN ASLIFGLGPI VLPALYFVGP KISESIVKDP EYDELFKLMS TCGRLLNDVQ  480
TFEREYNEGK LNSVSLLVLH GGPMSISDAK RKLQKPIDTC RRDLLSLVLR EESVVPRPCK  540
ELFWKMCKVC YFFYSTTDGF SSQVERAKEV DAVINEPLKL QGSHTLVSDV              590

SEQ ID NO: 30          moltype = AA  length = 775
```

```
FEATURE              Location/Qualifiers
source               1..775
                     mol_type = protein
                     organism = Populus trichocarpa
SEQUENCE: 30
MSCIRPWFCP SSISATLTDP ASKLVTGEFK TTSLNFHGTK ERIKKMFDKI ELSVSSYDTA  60
WVAMVPSPDC PETPCFPECT KWILENQLGD GSWSLPHGNP LLVKDALSST LACILALKRW  120
GIGEEQINKG LRFIELNSAS VTDNEQHKPI GFDIIFPGMI EYAKDLDLNL PLKPTDINSM  180
LHRRALELTS GGGKNLEGRR AYLAYVSEGI GKLQDWEMAM KYQRKNGSLF NSPSTTAAAF  240
IHIQDAECLH YIRSLLQKFG NAVPTIYPLD IYARLSMVDA LERLGIDRHF RKERKFVLDE  300
TYRFWLQGEE EIFSDNATCA LAFRILRLNG YDVSLEDHFS NSLGGYLKDS GAALELYRAL  360
QLSYPDESLL EKQNSRTSYF LKQGLSNVSL CGDRLRKNII GEVHDALNFP DHANLQRLAI  420
RRRIKHYATD DTRILKTSYR CSTIGNQDFL KLAVEDFNIC QSIQREEFKH IERWVVERRL  480
DKLKFARQKE AYCYFSAAAT LFAPELSDAR MSWAKNGVLT TVVDDFFDVG GSEEELVNLI  540
ELIERWDVNG SADFCSEEVE IIYSAIHSTI SEIGDKSFGW QGRDVKSHVI KIWLDLLKSM  600
LTEAQWSSNK SVPTLDEYMT TAHVSFALGP IVLPALYFVG PKLSEEVAGH PELLNLYKVM  660
STCGRLLNDW RSFKRESEEG KLNAISLYMI HSGGASTEEE TIEHFKGLID SQRRQLLQLV  720
LQEKDSIIPR PCKDLFWNMI KLLHTFYMKD DGFTSNEMRN VVKAIINEPI SLDEL       775

SEQ ID NO: 31        moltype = DNA  length = 2358
FEATURE              Location/Qualifiers
misc_feature         1..2358
                     note = Synthetic oligonucleotide
source               1..2358
                     mol_type = other DNA
                     organism = synthetic construct
SEQUENCE: 31
atgtctatca accttcgctc ctccggttgt tcgtctccga tctcagctac tttggaacga  60
ggattggact cagaagtaca gacaagagct aacaatgtga gctttgagca aacaaaggag  120
aagattagga agatgttgga gaaagtggag ctttctgttt cggcctacga tactagttgg  180
gtagcaatgg ttccatcacc gagctcccaa aatgctccac ttttcccaca gtgtgtgaaa  240
tggttattgg ataatcaaca tgaagatgga tcttggggac ttgataacca tgaccatcaa  300
tctcttaaga aggatgtgtt atcatctaca ctggctagta tcctcgcgtt aaagaagtgg  360
ggaattggtg aaagacaaat aaacaagggt ctccagttta ttgagctgaa ttctgcatta  420
gtcactgatg aaaccataca gaaaccaaca gggtttgata ttatatttcc tgggatgatt  480
aaatatgcta gagatttgaa tctgacgatt ccattgggct cagaagtggt ggatgacatg  540
atacgaaaaa gagatctgga tcttaaatgt gatagtgaaa agttttcaaa gggaagagaa  600
gcatatctgg cctatgtttt agaggggaca agaaacctaa aagattggga tttgatagtc  660
aaatatcaaa ggaaaaatgg gtcactgttt gattctccag ccacaacagc agctgctttt  720
actcagtttg ggaatgatgg ttgtctccgt tatctctgtt ctctccttca gaaattcgag  780
gctgcagttc cttcagttta tccatttgat caatatgcac gccttagtat aattgtcact  840
cttgaaagct taggaattga tagagatttc aaaaccgaaa tcaaaagcat attggatgaa  900
acctatagat attggcttcg tggggatgaa gaaatatgtt tggacttggc cacttgtgct  960
ttggctttcc gattattgct tgctcatggc tatgatgtgt cttacgatcc gctaaaacca  1020
tttgcagaag aatctggttt ctctgatact ttggaaggat atgttaagaa tacgttttct  1080
gtgttagaat tatttaaggc tgctcaaagt tatccacatg aatcagcttt gaagaagcag  1140
tgttgttgga ctaaacaata tctggagatg gaattgtcca gctgggttaa gacctctgtt  1200
cgagataaat acctcaagaa agaggtcgag gatgctcttg cttttccctc ctatgcaagc  1260
ctagaaagat cagatcacag gagaaaaata ctcaatggtt ctgctgtgga aaacaccaga  1320
gttacaaaaa cctcatatcg tttgcacaat atttgcacct ctgatatcct gaagttagct  1380
gtggatgact tcaatttctg ccagtccata caccgtgaag aaatggaacg tcttgatagg  1440
tggattgtgg agaatagatt gcaggaactg aaatttgcca gacagaagct ggcttactgt  1500
tatttctctg ggctgcaac tttattttct ccagaactat ctgatgctcg tatatcgtgg  1560
gccaaaggtg gagtacttac aacggttgta gacgacttct ttgatgttgg agggtccaaa  1620
gaagaactgg aaaacctcat acacttggtc gaaaagtggg atttgaacgg tgttcctgag  1680
tacagctcag aacatgttga gatcatattc tcagttctaa gggacaccat tctcgaaaca  1740
ggagacaaag cattcaccta tcaaggacgc aatgtgacac accacattgt gaaaatttgg  1800
ttggatctgc tcaagtctat gttgagagaa gccgagtggt ccagtgacaa gtcaacacca  1860
agcttggagg attacatgga aaatgcgtac atatcatttg cattaggacc aattgtcctc  1920
ccagctacct atctgatcgg acctccactt ccagagaaga cagtcgatag ccaccaatat  1980
aatcagctct acaagctcgt gagcactatg ggtcgtcttc taaatgacat acaaggtttt  2040
aagagagaaa gcgcggaagg gaagctgaat gcggtttcat tgcacatgaa acacgagaga  2100
gacaatcgca gcaaagaagt gatcatagaa tcgatgaaag gtttagcaga gagaaagagg  2160
gaagaattgc ataagctagt tttggaggag aaaggaagtg tggttccaag ggaatgcaaa  2220
gaagcgttct tgaaaatgag caaagtgttg aacttatttt acaggaagga cgatggattc  2280
acatcaaatg atctgatgag tcttgttaaa tcagtgatct acgagcctgt tagcttacag  2340
aaagaatctt taacttga                                                2358

SEQ ID NO: 32        moltype = AA  length = 785
FEATURE              Location/Qualifiers
source               1..785
                     mol_type = protein
                     organism = Arabidopsis thaliana
SEQUENCE: 32
MSINLRSSGC SSPISATLER GLDSEVQTRA NNVSFEQTKE KIRKMLEKVE LSVSAYDTSW  60
VAMVPSPSSQ NAPLFPQCVK WLLDNQHEDG SWGLDNHDHQ SLKKDVLSST LASILALKKW  120
GIGERQINKG LQFIELNSAL VTDETIQKPT GFDIIFPGMI KYARDLNLTI PLGSEVVDDM  180
IRKRDLDLKC DSEKFSKGRE AYLAYVLEGT RNLKDWDLIV KYQRKNGSLF DSPATTAAAF  240
TQFGNDGCLR YLCSLLQKFE AAVPSVYPFD QYARLSIIVT LESLGIDRDF KTEIKSILDE  300
```

```
TYRYWLRGDE EICLDLATCA LAFRLLLAHG YDVSYDPLKP FAEESGFSDT LEGYVKNTFS  360
VLELFKAAQS YPHESALKKQ CCWTKQYLEM ELSSWVKTSV RDKYLKKEVE DALAFPSYAS  420
LERSDHRRKI LNGSAVENTR VTKTSYRLHN ICTSDILKLA VDDFNFCQSI HREEMERLDR  480
WIVENRLQEL KFARQKLAYC YFSGAATLFS PELSDARISW AKGGVLTTVV DDFFDVGGSK  540
EELENLIHLV EKWDLNGVPE YSSEHVEIIF SVLRDTILET GDKAFTYQGR NVTHHIVKIW  600
LDLLKSMLRE AEWSSDKSTP SLEDYMENAY ISFALGPIVL PATYLIGPPL PEKTVDSHQY  660
NQLYKLVSTM GRLLNDIQGF KRESAEGKLN AVSLHMKHER DNRSKEVIIE SMKGLAERKR  720
EELHKLVLEE KGSVVPRECK EAFLKMSKVL NLFYRKDDGF TSNDLMSLVK SVIYEPVSLQ  780
KESLT                                                              785

SEQ ID NO: 33           moltype = AA  length = 513
FEATURE                 Location/Qualifiers
source                  1..513
                        mol_type = protein
                        organism = Stevia rebaudiana
SEQUENCE: 33
MDAVTGLLTV PATAITIGGT AVALAVALIF WYLKSYTSAR RSQSNHLPRV PEVPGVPLLG  60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRI                               513

SEQ ID NO: 34           moltype = AA  length = 509
FEATURE                 Location/Qualifiers
source                  1..509
                        mol_type = protein
                        organism = Arabidopsis thaliana
SEQUENCE: 34
MAFFSMISIL LGFVISSFIF IFFFKKLLSF SRKNMSEVST LPSVPVVPGF PVIGNLLQLK  60
EKKPHKTFTR WSEIYGPIYS IKMGSSSLIV LNSTETAKEA MVTRFSSIST RKLSNALTVL  120
TCDKSMVATS DYDDFHKLVK RCLLNGLLGA NAQKRKRHYR DALIENVSSK LHAHARDHPQ  180
EPVNFRAIFE HELFGVALKQ AFGKDVESIY VKELGVTLSK DEIFKVLVHD MMEGAIDVDW  240
RDFFPYLKWI PNKSFEARIQ QKHKRRLAVM NALIQDRLKQ NGSESDDDCY LNFLMSEAKT  300
LTKEQIAILV WETIIETADT TLVTTEWAIY ELAKHPSVQD RLCKEIQNVC GGEKFKEEQL  360
SQVPYLNGVF HETLRKYSPA PLVPIRYAHE DTQIGGYHVP AGSEIAINIY GCNMDKKRWE  420
RPEDWWPERF LDDGKYETSD LHKTMAFGAG KRVCAGALQA SLMAGIAIGR LVQEFEWKLR  480
DGEEENVDTY GLTSQKLYPL MAIINPRRS                                   509

SEQ ID NO: 35           moltype = AA  length = 525
FEATURE                 Location/Qualifiers
source                  1..525
                        mol_type = protein
                        organism = Gibberella fujikuroi
SEQUENCE: 35
MSKSNSMNST SHETLFQQLV LGLDRMPLMD VHWLIYVAFG AWLCSYVIHV LSSSSTVKVP  60
VVGYRSVFEP TWLLRLRFVW EGGSIIGQGY NKFKDSIFQV RKLGTDIVII PPNYIDEVRK  120
LSQDKTRSVE PFINDFAGQY TRGMVFLQSD LQNRVIQQRL TPKLVSLTKV MKEELDYALT  180
KEMPDMKNDE WVEVDISSIM VRLISRISAR VFLGPEHCRN QEWLTTTAEY SESLFITGFI  240
LRVVPHILRP FIAPLLPSYR TLLRNVSSGR RVIGDIIRSQ QGDGNEDILS WMRDAATGEE  300
KQIDNIAQRM LILSLASIHT TAMTMTHAMY DLCACPEYIE PLRDEVKSVV GASGWDKTAL  360
NRFHKLDSFL KESQRFNPVF LLTFNRIYHQ SMTLSDGTNI PSGTRIAVPS HAMLQDSAHV  420
PGPTPPTEFD GFRYSKIRSD SNYAQKYLFS MTDSSNMAFG YGKYACPGRF YASNEMKLTL  480
AILLLQFEFK LPDGKGRPRN ITIDSDMIPD PRARLCVRKR SLRDE                  525

SEQ ID NO: 36           moltype = AA  length = 499
FEATURE                 Location/Qualifiers
source                  1..499
                        mol_type = protein
                        organism = Trametes versicolor
SEQUENCE: 36
MEDPTVLYAC LAIAVATFVV RWYRDPLRSI PTVGGSDLPI LSYIGALRWT RRGREILQEG  60
YDGYRGSTFK IAMLDRWIVI ANGPKLADEV RRRPDEELNF MDGLGAFVQT KYTLGEAIHN  120
DPYHVDIIRE KLTRGLPAVL PDVIEELTLA VRQYIPTEGD EWVSVNCSKA ARDIVARASN  180
RVFVGLPACR NQGYLDLAID FTLSVVKDRA IINMFPELLK PIVGRVVGNA TRNVRRAVPF  240
VAPLVEERRR LMEEYGEDWS EKPNDMLQWI MDEAASRDSS VKAIAERLLM VNFAAIHTSS  300
NTITHALYHL AEMPETLQPL REEIEPLVKE EGWTKAAMGK MWWLDSFLRE SQRYNGINIV  360
SLTRMADKDI TLSDGTFLPK GTLVAVPAYS THRDDAVYAD ALVFDPFRFS RMRAREGEGT  420
KHQFVNTSVE YVPFGHGKHA CPGRFFAANE LKAMLAYIVL NYDVKLPGDG KRPLNMYWGP  480
TVLPAPAGQV LFRKRQVSL                                               499

SEQ ID NO: 37           moltype = DNA  length = 1678
FEATURE                 Location/Qualifiers
misc_feature            1..1678
                        note = Synthetic oligonucleotide
source                  1..1678
```

```
                        mol_type = other DNA
                        organism = synthetic construct
SEQUENCE: 37
aaacaaagaa tgattcaagt tctaacaccg atccttctct tcctcatttt cttcgttttc  60
tggaaggttt acaagcacca gaaaaccaaa atcaatcttc caccgggaag cttcggatgg  120
ccatttctgg gcgaaactct ggcactccta cgtgcaggtt gggactcaga gccggagaga  180
tttgttcgtg aacggatcaa gaaacacgga agtcctctag tgtttaagac gtcgttgttt  240
ggcgaccgtt ttgcggtgtt gtgtggacct gccggaaaca agttcctgtt ctgcaacgag  300
aacaagctgg tggcgtcgtg gtggccggtt ccggtgagga agcttttcgg caagtctctg  360
ctcacgattc gtggtgatga agctaagtgg atgaggaaga tgttgttatc gtatctcggt  420
cctgatgctt tcgcaactca ttatgccgtc accatggacg tcgtcacccg tcggcatatc  480
gacgttcatt ggcgagggaa ggaagaggtg aacgtattcc aaaccgttaa gttatatgcc  540
tttgagcttg catgtcgttt attcatgaac ctagacgacc caaaccacat tgcaaaactc  600
ggttccttgt tcaacatttt cttgaaaggc atcattgagc ttccaatcga cgtcccaggg  660
acacgatttt atagctccaa aaaagcagca gcagctatca ggattgaact aaaaaaattg  720
attaaagcaa gaaaactgga actgaaagaa gggaaggcat catcttcaca agacctctta  780
tcacatttgc ttacatctcc agatgaaaat ggtatgtttc taaccgaaga agagattgta  840
gacaacatct tgttactact ctttgcgggt catgatacct cggctctttc aatcactttg  900
ctcatgaaga ctcttggcga acattctgat gtttatgaca aggtgttaaa agagcaacta  960
gagatatcga agacgaaaga agcatgggag tccctgaaat gggaggacat acaaaagatg  1020
aaatactcct ggagtgttat atgtgaagtc atgagactaa atccacctgt tataggaacc  1080
tatagagagg cccttgtgga tattgattat gcgggttata ccatccccaa aggatggaag  1140
ctgcactgga gtgctgtatc gacacaaagg gacgaggcta actttgaaga cgtaacacgt  1200
tttgacccat cacggtttga aggcgcagga ccgactccat tcacctttgt tccgtttgga  1260
ggggggccta gaatgtgttt agggaaagaa tttgctcgat tggaagtact tgcgtttctt  1320
cacaatattg tcaccaattt caaatgggac ctgttgatac ctgatgagaa aatagaatat  1380
gatcccatgg ctaccccagc aaaggggctt ccaattcgtc ttcatcccca tcaagtttga  1440
ttacttcaag catgaatcag tgatgtgaag gtaaaccata atggatctta ttggtagtta  1500
cagattatgt gtttttatgg catgaagaag ttatgataaa taaaattgtg ttattctaca  1560
acttatgtaa tttgtgcctg taagtaactg aatctattaa tgttttatgt gacatgaaac  1620
ataaatgtat aattagtaaa ttttctgctc aaaaaaaaaa aaaaaaaaaa aaaaaaa    1678

SEQ ID NO: 38           moltype = AA  length = 476
FEATURE                 Location/Qualifiers
source                  1..476
                        mol_type = protein
                        organism = Stevia rebaudiana
SEQUENCE: 38
MIQVLTPILL FLIFFVFWKV YKHQKTKINL PPGSFGWPFL GETLALLRAG WDSEPERFVR  60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
TLGEHSDVYD KVLKEQLEIS KTKEAWESLK WEDIQKMKYS WSVICEVMRL NPPVIGTYRE  360
ALVDIDYAGY TIPKGWKLHW SAVSTQRDEA NFEDVTRFDP SRFEGAGPTP FTFVPFGGGP  420
RMCLGKEFAR LEVLAFLHNI VTNFKWDLLI PDEKIEYDPM ATPAKGLPIR LHPHQV      476

SEQ ID NO: 39           moltype = AA  length = 476
FEATURE                 Location/Qualifiers
source                  1..476
                        mol_type = protein
                        organism = Stevia rebaudiana
SEQUENCE: 39
MIQVLTPILL FLIFFVFWKV YKHQKTKINL PPGSFGWPFL GETLALLRAG WDSEPERFVR  60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
TLGEHSDVYD KVLKEQLEIS KTKEAWESLK WEDIQKMKYS WSVICEVMRL NPPVIGTYRE  360
ALVDIDYAGY TIPKGWKLHW SAVSTQRDEA NFEDVTRFDP SRFEGAGPTP FTFVPFGGGP  420
RMCLGKEFAR LEVLAFLHNI VTNFKWDLLI PDEKIEYDPM ATPAKGLPIR LHPHQV      476

SEQ ID NO: 40           moltype = AA  length = 525
FEATURE                 Location/Qualifiers
source                  1..525
                        mol_type = protein
                        organism = Arabidopsis thaliana
SEQUENCE: 40
MESLVVHTVN AIWCIVIVGI FSVGYHVYGR AVVEQWRMRR SLKLQGVKGP PPSIFNGNVS  60
EMQRIQSEAK HCSGDNIISH DYSSSLFPHF DHWRKQYGRI YTYSTGLKQH LYINHPEMVK  120
ELSQTNTLNL GRITHITKRL NPILGNGIIT SNGPHWAHQR RIIAYEFTHD KIKGMVGLMV  180
ESAMPMLNKW EEMVKRGGEM GCDIRVDEDL KDVSADVIAK ACFGSSFSKG KAIFSMIRDL  240
LTAITKRSVL FRFNGFTDMV FGSKKHGDVD IDALEMELES SIWETVKERE IECKDTHKKD  300
LMQLILEGAM RSCDGNLWDK SAYRRFVVDN CKSIYFAGHD STAVSVSWCL MLLALNPSWQ  360
VKIRDEILSS CKNGIPDAES IPNLKTVTMV IQETMRLYPP APIVGREASK DIRLGDLVVP  420
KGVCIWTLIP ALHRDPEIWG PDANDFKPER FSEGISKACK YPQSYIPFGL GPRTCVGKNF  480
GMMEVKVLVS LIVSKFSFTL SPTYQHSPSH KLLVEPQHGV VIRVV                 525

SEQ ID NO: 41           moltype = AA  length = 526
```

```
FEATURE               Location/Qualifiers
source                1..526
                      mol_type = protein
                      organism = Vitis vinifera
SEQUENCE: 41
MYFLLQYLNI TTVGVFATLF LSYCLLLWRS RAGNKKIAPE AAAAWPIIGH LHLLAGGSHQ  60
LPHITLGNMA DKYGPVFTIR IGLHRAVVVS SWEMAKECST ANDQVSSSRP ELLASKLLGY  120
NYAMFGFSPY GSYWREMRKI ISLELLSNSR LELLKDVRAS EVVTSIKELY KLWAEKKNES  180
GLVSVEMKQW FGDLTLNVIL RMVAGKRYFS ASDASENKQA QRCRRVFREF FHLSGLFVVA  240
DAIPFLGWLD WGRHEKTLKK TAIEMDSIAQ EWLEEHRRRK DSGDDNSTQD FMDVMQSVLD  300
GKNLGGYDAD TINKATCLTL ISGGSDTTVV SLTWALSLVL NNRDTLKKAQ EELDIQVGKE  360
RLVNEQDISK LVYLQAIVKE TLRLYPPGPL GGLRQFTEDC TLGGYHVSKG TRLIMNLSKI  420
QKDPRIWSDP TEFQPERFLT THKDVDPRGK HFEFIPFGAG RRACPGITFG LQVLHLTLAS  480
FLHAFEFSTP SNEQVNMRES LGLTNMKSTP LEVLISPRLS SCSLYN                 526

SEQ ID NO: 42         moltype = AA  length = 479
FEATURE               Location/Qualifiers
source                1..479
                      mol_type = protein
                      organism = Medicago truncatula
SEQUENCE: 42
MEPNFYLSLL LLFVTFISLS LFFIFYKQKS PLNLPPGKMG YPIIGESLEF LSTGWKGHPE  60
KFIFDRMRKY SSELFKTSIV GESTVVCCGA ASNKFLFSNE NKLVTAWWPD SVNKIFPTTS  120
LDSNLKEESI KMRKLLPQFF KPEALQRYVG VMDVIAQRHF VTHWDNKNEI TVYPLAKRYT  180
FLLACRLFMS VEDENHVAKF SDPFQLIAAG IISLPIDLPG TPFNKAIKAS NFIRKELIKI  240
IKQRRVDLAE GTASPTQDIL SHMLLTSDEN GKSMNELNIA DKILGLLIGG HDTASVACTF  300
LVKYLGELPH IYDKVYQEQM EIAKSKPAGE LLNWDDLKKM KYSWNVACEV MRLSPPLQGG  360
FREAITDFMF NGFSIPKGWK LYWSANSTHK NAECFPMPEK FDPTRFEGNG PAPYTFVPFG  420
GGPRMCPGKE YARLEILVFM HNLVKRFKWE KVIPDEKIIV DPFPIPAKDL PIRLYPHKA   479

SEQ ID NO: 43         moltype = AA  length = 522
FEATURE               Location/Qualifiers
source                1..522
                      mol_type = protein
                      organism = Stevia rebaudiana
SEQUENCE: 43
MGLFPLEDSY ALVFEGLAIT LALYYLLSFI YKTSKKTCTP PKASGEHPIT GHLNLLSGSS  60
GLPHLALASL ADRCGPIFTI RLGIRRVLVV SNWEIAKEIF TTHDLIVSNR PKYLAAKILG  120
FNYVSFSFAP YGPYWVGIRK IIATKLMSSS RLQKLQFVRV FELENSMKSI RESWKEKKDE  180
EGKVLVEMKK WFWELNMNIV LRTVAGKQYT GTVDDADAKR ISELFREWFH YTGRFVVGDA  240
FPFLGWLDLG GYKKTMELVA SRLDSMVSKW LDEHRKKQAN DDKKEDMDFM DIMISMTEAN  300
SPLEGYGTDT IIKTTCMTLI VSGVDTTSIV LTWALSLLLN NRDTLKKAQE ELDMCVGKGR  360
QVNESDLVNL IYLEAVLKEA LRLYPAAFLG GPRAFLEDCT VAGYRIPKGT CLLINMWKLH  420
RDPNIWSDPC EFKPERFLTP NQKDVDVIGM DFELIPFGAG RRYCPGTRLA LQMLHIVLAT  480
LLQNFEMSTP NDAPVDMTAS VGMTNAKASP LEVLLSPRVK WS                     522

SEQ ID NO: 44         moltype = AA  length = 710
FEATURE               Location/Qualifiers
source                1..710
                      mol_type = protein
                      organism = Stevia rebaudiana
SEQUENCE: 44
MQSDSVKVSP FDLVSAAMNG KAMEKLNASE SEDPTTLPAL KMLVENRELL TLFTTSFAVL  60
IGCLVFLMWR RSSSKKLVQD PVPQVIVVKK KEKESEVDDG KKKVSIFYGT QTGTAEGFAK  120
ALVEEAKVRY EKTSFKVIDL DDYAADDDEY EEKLKKESLA FFFLATYGDG EPTDNAANFY  180
KWFTEGDDKG EWLKKLQYGV FGLGNRQYEH FNKIAIVVDD KLTEMGAKRL VPVGLGDDDQ  240
CIEDDFTAWK ELVWPELDQL LRDEDDTSVT TPYTAAVLEY RVVYHDKPAD SYAEDQTHTN  300
GHVVHDAQHP SRSNVAFKKE LHTSQSDRSC THLEFDISHT GLSYETGDHV GVYSENLSEV  360
VDEALKLLGL SPDTYFSVHA DKEDGTPIGG ASLPPPFPPC TLRDALTRYA DVLSSPKKVA  420
LLALAAHASD PSEADRLKFL ASPAGKDEYA QWIVANQRSL LEVMQSFPSA KPPLGVFFAA  480
VAPRLQPRYY SISSSPKMSP NRIHVTCALV YETTPAGRIH RGLCSTWMKN AVPLTESPDC  540
SQASIFVRTS NFRLPVDPKV PVIMIGPGTG LAPFRGFLQE RLALKESGTE LGSSIFFFGC  600
RNRKVDFIYE DELNNFVETG ALSELIVAFS REGTAKEYVQ HKMSQKASDI WKLLSEGAYL  660
YVCGDAKGMA KDVHRTLHTI VQEQGSLDSS KAELYVKNLQ MSGRYLRDVW             710

SEQ ID NO: 45         moltype = AA  length = 692
FEATURE               Location/Qualifiers
source                1..692
                      mol_type = protein
                      organism = Arabidopsis thaliana
SEQUENCE: 45
MTSALYASDL FKQLKSIMGT DSLSDDVVLV IATTSLALVA GFVVLLWKKT TADRSGELKP  60
LMIPKSLMAK DEDDDLDLGS GKTRVSIFFG TQTGTAEGFA KALSEEIKAR YEKAAVKVID  120
LDDYAADDDQ YEEKLKKETL AFFCVATYGD GEPTDNAARF YKWFTEENER DIKLQQLAYG  180
VFALGNRQYE HFNKIGIVLD EELCKKGAKR LIEVGLGDDD QSIEDDFNAW KESLWSELDK  240
LLKDEDDKSV ATPYTAVIPE YRVVTHDPRF TTQKSMESNV ANGNTTIDIH HPCRVDVAVQ  300
KELHTHESDR SCIHLEFDIS RTGITYETGD HVGVYAENHV EIVEEAGKLL GHSLDLVFSI  360
HADKEDGSPL ESAVPPPFPG PCTLGTGLAR YADLLNPPRK SALVALAAYA TEPSEAEKLK  420
HLTSPDGKDE YSQWIVASQR SLLEVMAAFP SAKPPLGVFF AAIAPRLQPR YYSISSSPRL  480
```

-continued

```
APSRVHVTSA LVYGPTPTGR IHKGVCSTWM KNAVPAEKSH ECSGAPIFIR ASNFKLPSNP  540
STPIVMVGPG TGLAPFRGFL QERMALKEDG EELGSSLLFF GCRNRQMDFI YEDELNNFVD  600
QGVISELIMA FSREGAQKEY VQHKMMEKAA QVWDLIKEEG YLYVCGDAKG MARDVHRTLH  660
TIVQEQEGVS SSEAEAIVKK LQTEGRYLRD VW                               692

SEQ ID NO: 46           moltype = AA  length = 713
FEATURE                 Location/Qualifiers
source                  1..713
                        mol_type = protein
                        organism = Gibberella fujikuroi
SEQUENCE: 46
MAELDTLDIV VLGVIFLGTV AYFTKGKLWG VTKDPYANGF AAGGASKPGR TRNIVEAMEE  60
SGKNCVVFYG SQTGTAEDYA SRLAKEGKSR FGLNTMIADL EDYDFDNLDT VPSDNIVMFV  120
LATYGEGEPT DNAVDFYEFI TGEDASFNEG NDPPLGNLNY VAFGLGNNTY EHYNSMVRNV  180
NKALEKLGAH RIGEAGEGDD GAGTMEEDFL AWKDPMWEAL AKKMGLEERE AVYEPIFAIN  240
ERDDLTPEAN EVYLGEPNKL HLEGTAKGPF NSHNPYIAPI AESYELFSAK DRNCLHMEID  300
ISGSNLKYET GDHIAIWPTN PGEEVNKFLD ILDLSGKQHS VVTVKALEPT AKVPFPNPTT  360
YDAILRYHLE ICAPVSRQFV STLAAFAPND DIKAEMNRLG SDKDYFHEKT GPHYYNIARF  420
LASVSKGEKW TKIPFSAFIE GLTKLQPRYY SISSSSLVQP KKISITAVVE SQQIPGRDDP  480
FRGVATNYLF ALKQKQNGDP NPAPFGQSYE LTGPRNKYDG IHVPVHVRHS NFKLPSDPGK  540
PIIMIGPGTG VAPFRGFVQE RAKQARDGVE VGKTLLFFGC RKSTEDFMYQ KEWQEYKEAL  600
GDKFEMITAF SREGSKKVYV QHRLKERSKE VSDLLSQKAY FYVCGDAAHM AREVNTVLAQ  660
IIAEGRGVSE AKGEEIVKNM RSANQYQVCS DFVTLHCKET TYANSELQED VWS          713

SEQ ID NO: 47           moltype = AA  length = 480
FEATURE                 Location/Qualifiers
source                  1..480
                        mol_type = protein
                        organism = Stevia rebaudiana
SEQUENCE: 47
MDAMATTEKK PHVIFIPFPA QSHIKAMLKL AQLLHHKGLQ ITFVNTDFIH NQFLESSGPH  60
CLDGAPGFRF ETIPDGVSHS PEASIPIRES LLRSIETNFL DRFIDLVTKL PDPPTCIISD  120
GFLSVFTIDA AKKLGIPVMM YWTLAACGFM GFYHIHSLIE KGFAPLKDAS YLTNGYLDTV  180
IDWVPGMEGI RLKDFPLDWS TDLNDKVLMF TTEAPQRSHK VSHHIFHTFD ELEPSIIKTL  240
SLRYNHIYTI GPLQLLLDQI PEEKKQTGIT SLHGYSLVKE EPECFQWLQS KEPNSVVYVN  300
FGSTTVMSLE DMTEFGWGLA NSNHYFLWII RSNLVIGENA VLPPELEEHI KKRGFIASWC  360
SQEKVLKHPS VGGFLTHCGW GSTIESLSAG VPMICWPYSW DQLTNCRYIC KEWEVGLEMG  420
TKVKRDEVKR LVQELMGEGG HKMRNKAKDW KEKARIAIAP NGSSSLNIDK MVKEITVLAR  480

SEQ ID NO: 48           moltype = AA  length = 787
FEATURE                 Location/Qualifiers
source                  1..787
                        mol_type = protein
                        organism = Stevia rebaudiana
SEQUENCE: 48
MKTGFISPAT VFHHRISPAT TFRHHLSPAT TNSTGIVALR DINFRCKAVS KEYSDLLQKD  60
EASFTKWDDD KVKDHLDTNK NLYPNDEIKE FVESVKAMFG SMNDGEINVS AYDTAWVALV  120
QDVDGSGSPQ FPSSLEWIAN NQLSDGSWGD HLLFSAHDRI INTLACVIAL TSWNVHPSKC  180
EKGLNFLREN ICKLEDENAE HMPIGFEVTF PSLIDIAKKL NIEVPEDTPA LKEIYARRDI  240
KLTKIPMEVL HKVPTTLLHS LEGMPDLEWE KLLKLQCKDG SFLFSPSSTA FALMQTKDEK  300
CLQYLTNIVT KFNGGVPNVY PVDLFEHIWV VDRLQRLGIA RYFKSEIKDC VEYINKYWTK  360
NGICWARNTH VQDIDDTAMG FRVLRAHGYD VTPDVFRQFE KDGKFVCFAG QSTQAVTGMF  420
NVYRASQMLF PGERILEDAK KFSYNYLKEK QSTNELLDKW IIAKDLPGEV GYALDIPWYA  480
SLPRLETRYY LEQYGGEDDV WIGKTLYRMG YVSNNTYLEM AKLDYNNYVA VLQLEWYTIQ  540
QWYVDIGIEK FESDNIKSVL VSYYLAAASI FEPERSKERI AWAKTTILVD KITSIFDSSQ  600
SSKEDITAFI DKFRNKSSSK KHSINGEPWH EVMVALKKTL HGFALDALMT HSQDIHPQLH  660
QAWEMWLTKL QDGVDVTAEL MVQMINMTAG RWVSKELLTH PQYQRLSTVT NSVCHDITKL  720
HNFKENSTTV DSKVQELVQL VFSDTPDDLD QDMKQTFLTV MKTFYYKAWC DPNTINDHIS  780
KVFEIVI                                                           787

SEQ ID NO: 49           moltype = AA  length = 527
FEATURE                 Location/Qualifiers
source                  1..527
                        mol_type = protein
                        organism = Streptomyces clavuligerus
SEQUENCE: 49
MPDAHDAPPP QIRQRTLVDE ATQLLTESAE DAWGEVSVSE YETARLVAHA TWLGGHATRV  60
AFLLERQHED GSWGPPGGYR LVPTLSAVHA LLTCLASPAQ DHGVPHDRLL RAVDAGLTAL  120
RRLGTSDSPP DTIAVELVIP SLLEGIQHLL DPAHPHSRPA FSQHRGSLVC PGGLDGRTLG  180
ALRSHAAAGT PVPGKVWHAS ETLGLSTEAA SHLQPAQGII GGSAAATATW LTRVAPSQQS  240
DSARRYLEEL QHRYSGPVPS ITPITYFERA WLLNNFAAAG VPCEAPAALL DSLEAALTPQ  300
GAPAGAGLPP DADDTAAVLL ALATHGRGRR PEVLMDYRTD GYFQCFIGER TPSISTNAHV  360
LETLGHHVAQ HPQDRARYGS AMDTASAWLL AAQKQDGSWL DKWHASPYYA TVCCTQALAA  420
HASPATAPAR QRAVRWVLAT QRSDGGWGLW HSTVEETAYA LQILAPPSGG GNIPVQQALT  480
RGRARLCGAL PLTPLWHDKD LYTPVRVVRA ARAAALYTTR DLLLPPL               527

SEQ ID NO: 50           moltype = AA  length = 516
FEATURE                 Location/Qualifiers
source                  1..516
```

```
                         mol_type = protein
                         organism = Bradyrhizobium diazoefficiens
SEQUENCE: 50
MNALSEHILS ELRRLLSEMS DGGSVGPSVY DTAQALRFHG NVTGRQDAYA WLIAQQQADG  60
GWGSADFPLF RHAPTWAALL ALQRADPLPG AADAVQTATR FLQRQPDPYA HAVPEDAPIG  120
AELILPQFCG EAAWLLGGVA FPRHPALLPL RQACLVKLGA VAMLPSGHPL LHSWEAWGTS  180
PTTACPDDDG SIGISPAATA AWRAQAVTRG STPQVGRADA YLQMASRATR SGIEGVFPNV  240
WPINVFEPCW SLYTLHLAGL FAHPALAEAV RVIVAQLEAR LGVHGLGPAL HFAADADDTA  300
VALCVLHLAG RDPAVDALRH FEIGELFVTF PGERNASVST NIHALHALRL LGKPAAGASA  360
YVEANRNPHG LWDNEKWHVS WLYPTAHAVA ALAQGKPQWR DERALAALLQ AQRDDGGWGA  420
GRGSTFEETA YALFALHVMD GSEEATGRRR IAQVVARALE WMLARHAAHG LPQTPLWIGK  480
ELYCPTRVVR VAELAGLWLA LRWGRRVLAE GAGAAP                           516

SEQ ID NO: 51            moltype = DNA  length = 2490
FEATURE                  Location/Qualifiers
misc_feature             1..2490
                         note = Synthetic oligonucleotide
source                   1..2490
                         mol_type = other DNA
                         organism = synthetic construct
SEQUENCE: 51
atggttttgt cttcttcttg tactacagta ccacacttat cttcattagc tgtcgtgcaa  60
cttggtcctt ggagcagtag gattaaaaag aaaaccgata ctgttgcagt accagccgct  120
gcaggaaggt ggagaagggc cttggctaga gcacagcaca catcagaatc cgcagctgtc  180
gcaaagggca gcagtttgac ccctatagtg agaactgacg ctgagtcaag gagaacaaga  240
tggccaaccg atgacgatga cgccgaacct ttagtggatg agatcagggc aatgcttact  300
tccatgtctg atggtgacat ttccgtgagc gcatacgata cagcctgggt cggattggtt  360
ccaagattag acggcggtga aggtcctcaa tttccagcag ctgtgagatg gataagaaat  420
aaccagttgc ctgacggaag ttggggcgat gccgcattat tctctgccta tgacaggctt  480
atcaataccc ttgcctgcgt tgtaactttg acaaggtggt ccctagaacc agagatgaga  540
ggtagaggac tatctttttt gggtaggaac atgtggaaat tagcaactga agatgaagag  600
tcaatgccta ttggcttcga attagcattt ccatctttga tagagcttgc taagagccta  660
ggtgtccatg acttccctta tgatcaccag gccctacaag gaatctactc ttcaagagag  720
atcaaaatga agaggattcc aaaagaagtg atgcataccg ttccaacatc aatattgcac  780
agtttggagg gtatgcctgg cctagattgg gctaaactac ttaaactaca gagcagcgac  840
ggaagttttt tgttctcacc agctgccact gcatatgctt taatgaatac cggagatgac  900
aggtgtttta gctacatcga tagaacagta aagaaattca acggcggcgt ccctaatgtt  960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttggattt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
ttggcaagaa tggatttcaa ccactgccag gctttgcatc agttagagtg gcaaggacta  1620
aaaagatggt atactgaaaa taggttgatg gactttggtg tcgcccaaga agatgccctt  1680
agagcttatt ttcttgcagc cgcatctgtt tacgagcctt gtagagctgc cgagaggctt  1740
gcatgggcta gagccgcaat actagctaac gccgtgagca cccacttaag aaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaatttctg ccggtagggc agctggtgaa  2160
gcagccagtg aggacggcga tagaagaata attcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                  2490

SEQ ID NO: 52            moltype = AA  length = 827
FEATURE                  Location/Qualifiers
source                   1..827
                         mol_type = protein
                         organism = Zea mays
SEQUENCE: 52
MVLSSSCTTV PHLSSLAVVQ LGPWSSRIKK KTDTVAVPAA AGRWRRALAR AQHTSESAAV  60
AKGSSLTPIV RTDAESRRTR WPTDDDDAEP LVDEIRAMLT SMSDGDISVS AYDTAWVGLV  120
PRLDGGEGPQ FPAAVRWIRN NQLPDGSWGD AALFSAYDRL INTLACVVTL TRWSLEPEMR  180
GRGLSFLGRN MWKLATEDEE SMPIGFELAF PSLIELAKSL GVHDFPYDHQ ALQGIYSSRE  240
IKMKRIPKEV MHTVPTSILH SLEGMPGLDW AKLLKLQSSD GSFLFSPAAT AYALMNTGDD  300
RCFSYIDRTV KKFNGGVPNV YPVDLFEHIW AVDRLERLGI SRYFQKEIEQ CMDYVNRHWT  360
EDGICWARNS DVKEVDDTAM AFRLLRLHGY SVSPDVFKNF EKDGEFFAFV GQSNQAVTGM  420
YNLNRASQIS FPGEDVLHRA GAFSYEFLRR KEAEGALRDK WIISKDLPGE VVYTLDFPWY  480
GNLPRVEARD YLEQYGGGDD VWIGKTLYRM PLVNNDVYLE LARMDFNHCQ ALHQLEWQGL  540
```

```
KRWYTENRLM DFGVAQEDAL RAYFLAAASV YEPCRAAERL AWARAAILAN AVSTHLRNSP  600
SFRERLEHSL RCRPSEETDG SWFNSSSGSD AVLVKAVLRL TDSLAREAQP IHGGDPEDII  660
HKLLRSAWAE WVREKADAAD SVCNGSSAVE QEGSRMVHDK QTCLLLARMI EISAGRAAGE  720
AASEDGDRRI IQLTGSICDS LKQKMLVSQD PEKNEEMMSH VDDELKLRIR EFVQYLLRLG  780
EKKTGSSETR QTFLSIVKSC YYAAHCPPHV VDRHISRVIF EPVSAAK                827

SEQ ID NO: 53          moltype = DNA  length = 2570
FEATURE                Location/Qualifiers
misc_feature           1..2570
                       note = Synthetic oligonucleotide
source                 1..2570
                       mol_type = other DNA
                       organism = synthetic construct
SEQUENCE: 53
cttcttcact aaatacttag acagagaaaa cagagctttt taaagccatg tctcttcagt  60
atcatgttct aaactccatt ccaagtacaa cctttctcag ttctactaaa acaacaatat  120
cttcttcttt ccttaccatc tcaggatctc ctctcaatgt cgctagagac aaatccagaa  180
gcggttccat acattgttca aagcttcgaa ctcaagaata cattaattct caagaggttc  240
aacatgattt gcctctaata catgagtggc aacagcttca aggagaagat gctcctcaga  300
ttagtgttgg aagtaatagt aatgcattca aagaagcagt gaagagtgtg aaaacgatct  360
tgagaaacct aacggacggg gaaattacga tatcggctta cgatacagct tgggttgcat  420
tgatcgatgc cggagataaa actccggcgt ttccctccgc cgtgaaatgg atcgccgaga  480
accaactttc cgatggttct tggggagatg cgtatctctt ctcttatcat gatcgtctca  540
tcaataccct tgcatgcgtc gttgctctaa gatcatggaa tctctttcct catcaatgca  600
acaaaggaat cacgtttttc cgggaaaata ttgggaagct agaagacgaa aatgatgagc  660
atatgccaat cggattcgaa gtagcattcc catcgttgct tgagatagct cgaggaataa  720
acattgatgt accgtacgat tctccggtct taaaagatat atacgccaag aaagagctaa  780
agcttacaag gataccaaaa gagataatgc acaagatacc aacaacattg ttgcatagtt  840
tggaggggat gcgtgattta gattgggaaa agctcttgaa acttcaatct caagacggat  900
ctttcctctt ctctccttcc tctaccgctt ttgcattcat gcagacccga gacagtaact  960
gcctcgagta tttgcgaaat gccgtcaaac gtttcaatgg aggagttccc aatgtctttc  1020
ccgtggatct tttcgagcac atatggatag tggatcggtt acaacgttta gggatatcga  1080
gatactttga agaagagatt aaagagtgtc ttgactatgt ccacagatat tggaccgaca  1140
atggcatatg ttgggctaga tgttcccatg tccaagacat cgatgataca gccatggcat  1200
ttaggctctt aagacaacat ggataccaag tgtccgcaga tgtattcaag aactttgaga  1260
aagagggaga gtttttctgc tttgtggggc aatcaaacca agcagtaacc ggtatgttca  1320
acctataccg ggcatcacaa ttggcgtttc caagggaaga gatattgaaa aacgccaaag  1380
agtttctta taattatctg ctagaaaaac gggagagaga ggagttgatt gataagtgga  1440
ttataatgaa agacttacct ggcgagattg ggtttgcgtt agagattcca tggtacgcaa  1500
gcttgcctcg agtagagacg agattctata ttgatcaata tggtggagaa aacgacgttt  1560
ggattggcaa gactctttat aggatgccat acgtgaacaa taatggatat ctggaattag  1620
caaaacaaga ttacaacaat tgccaagctc agcatcagct cgaatgggac atattccaaa  1680
agtggtatga agaaaatagg ttaagtgagt ggggtgtgcg cagaagtgag cttctcgagt  1740
gttactactt agcggctgca actatatttg aatcagaaag gtcacatgag agaatggttt  1800
gggctaagtc aagtgtattg gttaaagcca tttcttcttc ttttggggaa tcctctgact  1860
ccagaagaag cttctccgat cagtttcatg aatacattgc caatgctcga cgaagtgatc  1920
atcactttaa tgacaggaac atgagattgg accgaccagg atcggttcag gccagtcggc  1980
ttgccggagt gttaatcggg actttgaatc aaatgtcttt tgaccttttc atgtctcatg  2040
gccgtgacgt taacaatctc ctctatctat cgtggggaga ttggatggaa aaatggaaac  2100
tatatggaga tgaaggagaa ggagagctca tggtgaagat gataattcta atgaagaaca  2160
atgacctaac taacttcttc acccacactc acttcgttcg tctcgcggaa atcatcaatc  2220
gaatctgtct tcctcgccaa tacttaaagg caaggagaaa cgatgagaag gagaagacaa  2280
taaagagtat ggagaaggag atggggaaaa tggttgagtt agcattgtcg gagagtgaca  2340
catttcgtga cgtcagcatc acgtttcttg atgtagcaaa agcattttac tactttgctt  2400
tatgtggcga tcatctccaa actcacatct ccaaagtctt gtttcaaaaa gtctagtaac  2460
ctcatcatca tcatcgatcc attaacaatc agtggatcga tgtatccata gatgcgtgaa  2520
taatatttca tgtagagaag gagaacaaat tagatcatgt agggttatca             2570

SEQ ID NO: 54          moltype = AA  length = 802
FEATURE                Location/Qualifiers
source                 1..802
                       mol_type = protein
                       organism = Arabidopsis thaliana
SEQUENCE: 54
MSLQYHVLNS IPSTTFLSST KTTISSSFLT ISGSPLNVAR DKSRSGSIHC SKLRTQEYIN  60
SQEVQHDLPL IHEWQQLQGE DAPQISVGSN SNAFKEAVKS VKTILRNLTD GEITISAYDT  120
AWVALIDAGD KTPAFPSAVK WIAENQLSDG SWGDAYLFSY HDRLINTLAC VVALRSWNLF  180
PHQCNKGITF FRENIGKLED ENDEHMPIGF EVAFPSLLEI ARGINIDVPY DSPVLKDIYA  240
KKELKLTRIP KEIMHKIPTT LLHSLEGMRD LDWEKLLKLQ SQDGSFLFSP SSTAFAFMQT  300
RDSNCLEYLR NAVKRFNGGV PNVFPVDLFE HIWIVDRLQR LGISRYFEEE IKECLDYVHR  360
YWTDNGICWA RCSHVQDIDD TAMAFRLLRQ HGYQVSADVF KNFEKEGEFF CFVGQSNQAV  420
TGMFNLYRAS QLAFPREEIL KNAKEFSYNY LLEKREREEL IDKWIIMKDL PGEIGFALEI  480
PWYASLPRVE TRFYIDQYGG ENDVWIGKTL YRMPYVNNNG YLELAKQDYN NCQAQHQLEW  540
DIFQKWYEEN RLSEWGVRRS ELLECYYLAA ATIFESERSH ERMVWAKSSV LVKAISSSFG  600
ESSDSRRSFS DQFHEYIANA RRSDHHFNDR NMRLDRPGSV QASRLAGVLI GTLNQMSFDL  660
FMSHGRDVNN LLYLSWGDWM EKWKLYGDEG EGELMVKMII LMKNNDLTNF FTHTHFVRLA  720
EIINRICLPR QYLKARRNDE KEKTIKSMEK EMGKMVELAL SESDTFRDVS ITFLDVAKAF  780
YYFALCGDHL QTHISKVLFQ KV                                           802
```

```
SEQ ID NO: 55          moltype = AA  length = 983
FEATURE                Location/Qualifiers
source                 1..983
                       mol_type = protein
                       organism = Diaporthe amygdali
SEQUENCE: 55
MEFDEPLVDE ARSLVQRTLQ DYDDRYGFGT MSCAAYDTAW VSLVTKTVDG RKQWLFPECF  60
EFLLETQSDA GGWEIGNSAP IDGILNTAAS LLALKRHVQT EQIIQPQHDH KDLAGRAERA  120
AASLRAQLAA LDVSTTEHVG FEIIVPAMLD PLEAEDPSLV FDFPARKPLM KIHDAKMSRF  180
RPEYLYGKQP MTALHSLEAF IGKIDFDKVR HHRTHGSMMG SPSSTAAYLM HASQWDGDSE  240
AYLRHVIKHA AGQGTGAVPS AFPSTHFESS WILTTLFRAG FSASHLACDE LNKLVEILEG  300
SFEKEGGAIG YAPGFQADVD DTAKTISTLA VLGRDATPRQ MIKVFEANTH FRTYPGERDP  360
SLTANCNALS ALLHQPDAAM YGSQIQKITK FVCDYWWKSD GKIKDKWNTC YLYPSVLLVE  420
VLVDLVSLLE QGKLPDVLDQ ELQYRVAITL FQACLRPLLD QDAEGSWNKS IEATAYGILI  480
LTEARRVCFF DRLSEPLNEA IRRGIAFADS MSGTEAQLNY IWIEKVSYAP ALLTKSYLLA  540
ARWAAKSPLG ASVGSSLWTP PREGLDKHVR LFHQAELFRS LPEWELRASM IEAALFTPLL  600
RAHRLDVFPR QDVGEDKYLD VVPFFWTAAN NRDRTYASTL FLYDMCFIAM LNFQLDEFME  660
ATAGILFRDH MDDLRQLIHD LLAEKTSPKS SGRSSQGTKD ADSGIEEDVS MSDSASDSQD  720
RSPEYDLVFS ALSTFTKHVL QHPSIQSASV WDRKLLAREM KAYLLAHIQQ AEDSTPLSEL  780
KDVPQKTDVT RVSTSTTTFF NWVRTTSADH ISCPYSFHFV ACHLGAALSP KGSNGDCYPS  840
AGEKFLAAAV CRHLATMCRM YNDLGSAERD SDEGNLNSLD FPEFADSAGN GGIEIQKAAL  900
LRLAEFERDS YLEAFRRLQD ESNRVHGPAG GDEARLSRRR MAILEFFAQQ VDLYGQVYVI  960
RDISARIPKN EVEKKRKLDD AFN                                         983

SEQ ID NO: 56          moltype = AA  length = 881
FEATURE                Location/Qualifiers
source                 1..881
                       mol_type = protein
                       organism = Physcomitrella patens
SEQUENCE: 56
MASSTLIQNR SCGVTSSMSS FQIFRGQPLR FPGTRTPAAV QCLKKRRCLR PTESVLESSP  60
GSGSYRIVTG PSGINPSSNG HLQEGSLTHR LPIPMEKSID NFQSTLYVSD IWSETLQRTE  120
CLLQVTENVQ MNEWIEEIRM YFRNMTLGEI SMSPYDTAWV ARVPALDGSH GPQFHRSLQW  180
IIDNQLPDGD WGEPSLFLGY DRVCNTLACV IALKTWGVGA QNVERGIQFL QSNIYKMEED  240
DANHMPIGFE IVFPAMMEDA KALGLDLPYD ATILQQISAE REKKMKKIPM AMVYKYPTTL  300
LHSLEGLHRE VDWNKLLQLQ SENGSFLYSP ASTACALMYT KDVKCFDYLN QLLIKFDHAC  360
PNVYPVDLFE RLWMVDRLQR LGISRYFERE IRDCLQYVYR YWKDCGIGWA SNSSVQDVDD  420
TAMAFRLLRT HGFDVKEDCF RQFFKDGEFF CFAGQSSQAV TGMFNLSRAS QTLFPGESLL  480
KKARTFSRNF LRTKHENNEC FDKWIITKDL AGEVEYNLTF PWYASLPRLE HRTYLDQYGI  540
DDIWIGKSLY KMPAVTNEVF LKLAKADFNM CQALHKKELE QVIKWNASCQ FRDLEFARQK  600
SVECYFAGAA TMFEPEMVQA RLVWARCCVL TTVLDDYFDH GTPVEELRVF VQAVRTWNPE  660
LINGLPEQAK ILFMGLYKTV NTIAEEAFMA QKRDVHHHLK HYWDKLITSA LKEAEWAESG  720
YVPTFDEYME VAEISVALEP IVCSTLFFAG HRLDEDVLDS YDYHLVMHLV NRVGRILNDI  780
QGMKREASQG KISSVQIYME EHPSVPSEAM AIAHLQELVD NSMQQLTYEV LRFTAVPKSC  840
KRIHLNMAKI MHAFYKDTDG FSSLTAMTGF VKKVLFEPVP E                     881

SEQ ID NO: 57          moltype = AA  length = 952
FEATURE                Location/Qualifiers
source                 1..952
                       mol_type = protein
                       organism = Gibberella fujikuroi
SEQUENCE: 57
MPGKIENGTP KDLKTGNDFV SAAKSLLDRA FKSHHSYYGL CSTSCQVYDT AWVAMIPKTR  60
DNVKQWLFPE CFHYLLKTQA ADGSWGSLPT TQTAGILDTA SAVLALLCHA QEPLQILDVS  120
PDEMGLRIEH GVTSLKRQLA VWNDVEDTNH IGVEFIIPAL LSMLEKELDV PSFEFPCRSI  180
LERMHGEKLG HFDLEQVYGK PSSLLHSLEA FLGKLDFDRL SHHLYHGSMM ASPSSTAAYL  240
IGATKWDDEA EDYLRHVMRN GAGHGNGGIS GTFPTTHFEC SWIIATLLKV GFTLKQIDGD  300
GLRGLSTILL EALRDENGVI GFAPRTADVD DTAKALLALS LVNQPVSPDI MIKVFEGKDH  360
FTTFGSERDP SLTSNLHVLL SLLKQSNLSQ YHPQILKTTL FTCRWWWGSD HCVKDKWNLS  420
HLYPTMLLVE AFTEVLHLID GGELSSLFDE SFKCKIGLSI FQAVLRIILT QDNDGSWRGY  480
REQTCYAILA LVQARHVCFF THMVDRLQSC VDRGFSWLKS CSFHSQDLTW TSKTAYEVGF  540
VAEAYKLAAL QSASLEVPAA TIGHSVTSAV PSSDLEKYMR LVRKTALFSP LDEWGLMASI  600
IESSFFVPLL QAQRVEIYPR DNIKVDEDKY LSIIPFTWVG CNNRSRTFAS NRWLYDMMYL  660
SLLGYQTDEY MEAVAGPVFG DVSLLHQTID KVIDNTMGNL ARANGTVHSG NGHQHESPNI  720
GQVEDTLTRF TNSVLNHKDV LNSSSSDQDT LRREFRTFMH AHITQIEDNS RFSKQASSDA  780
FSSPEQSYFQ WVNSTGGSHV ACAYSFAFSN CLMSANLLQG KDAFPSGTQK YLISSVMRHA  840
TNMCRMYNDF GSIARDNAER NVNSIHFPEF TLCNGTSQNL DERKERLLKI ATYEQGYLDR  900
ALEALERQSR DDAGDRAGSK DMRKLKIVKL FCDVTDLYDQ LYVIKDLSSS MK         952

SEQ ID NO: 58          moltype = AA  length = 361
FEATURE                Location/Qualifiers
source                 1..361
                       mol_type = protein
                       organism = Stevia rebaudiana
SEQUENCE: 58
MALVNPTALF YGTSIRTRPT NLLNPTQKLR PVSSSSLPSF SSVSAILTEK HQSNPSENNN  60
LQTHLETPFN FDSYMLEKVN MVNEALDASV PLKDPIKIHE SMRYSLLAGG KRIRPMMCIA  120
ACEIVGGNIL NAMPAACAVE MIHTMSLVHD DLPCMDNDDF RRGKPISHKV YGEEMAVLTG  180
DALLSLSFEH IATATKGVSK DRIVRAIGEL ARSVGSEGLV AGQVVDILSE GADVGLDHLE  240
```

```
YIHIHKTAML LESSVVIGAI MGGGSDQQIE KLRKFARSIG LLFQVVDDIL DVTKSTEELG  300
KTAGKDLLTD KTTYPKLLGI EKSREFAEKL NKEAQEQLSG FDRRKAAPLI ALANYNAYRQ  360
N                                                                  361

SEQ ID NO: 59          moltype = AA  length = 342
FEATURE                Location/Qualifiers
source                 1..342
                       mol_type = protein
                       organism = Gibberella fujikuroi
SEQUENCE: 59
MAEQQISNLL SMFDASHASQ KLEITVQMMD TYHYRETPPD SSSSEGGSLS RYDERRVSLP  60
LSHNAASPDI VSQLCFSTAM SSELNHRWKS QRLKVADSPY NYILTLPSKG IRGAFIDSLN  120
VWLEVPEDET SVIKEVIGML HNSSLIIDDF QDNSPLRRGK PSTHTVFGPA QAINTATYVI  180
VKAIEKIQDI VGHDALADVT GTITTIFQGQ AMDLWWTANA IVPSIQEYLL MVNDKTGALF  240
RLSLELLALN SEASISDSAL ESLSSAVSLL GQYFQIRDDY MNLIDNKYTD QKGFCEDLDE  300
GKYSLTLIHA LQTDSSDLLT NILSMRRVQG KLTAQKRCWF WK                     342

SEQ ID NO: 60          moltype = AA  length = 300
FEATURE                Location/Qualifiers
source                 1..300
                       mol_type = protein
                       organism = Mus musculus
SEQUENCE: 60
MEKTKEKAER ILLEPYRYLL QLPGKQVRSK LSQAFNHWLK VPEDKLQIII EVTEMLHNAS  60
LLIDDIEDSS KLRRGFPVAH SIYGVPSVIN SANYVYFLGL EKVLTLDHPD AVKLFTRQLL  120
ELHQGQGLDI YWRDTYTCPT EEEYKAMVLQ KTGGLFGLAV GLMQLFSDYK EDLKPLLDTL  180
GLFFQIRDDY ANLHSKEYSE NKSFCEDLTE GKFSFPTIHA IWSRPESTQV QNILRQRTEN  240
IDIKKYCVQY LEDVGSFAYT RHTLRELEAK AYKQIEACGG NPSLVALVKH LSKMFTEENK  300

SEQ ID NO: 61          moltype = AA  length = 339
FEATURE                Location/Qualifiers
source                 1..339
                       mol_type = protein
                       organism = Thalassiosira pseudonana
SEQUENCE: 61
MARFYFLNAL LMVISLQSTT AFTPAKLAYP TTTTALNVAS AETSFSLDEY LASKIGPIES  60
ALEASVKSRI PQTDKICESM AYSLMAGGKR IRPVLCIAAC EMFGGSQDVA MPTAVALEMI  120
HTMSLIHDDL PSMDNDDLRR GKPTNHVVFG EDVAILAGDS LLSTSFEHVA RETKGVSAEK  180
IVDVIARLGK SVGAEGLAGG QVMDLECEAK PGTTLDDLKW IHIHKTATLL QVAVASGAVL  240
GGATPEEVAA CELFAMNIGL AFQVADDILD VTASSEDLGK TAGKDEATDK TTYPKLLGLE  300
ESKAYARQLI DEAKESLAPF GDRAAPLLAI ADFIIDRKN                         339

SEQ ID NO: 62          moltype = AA  length = 355
FEATURE                Location/Qualifiers
source                 1..355
                       mol_type = protein
                       organism = Streptomyces clavuligerus
SEQUENCE: 62
MHLAPRRVPR GRRSPPDRVP ERQGALGRRR GAGSTGCARA AAGVHRRRGG GEADPSAAVH  60
RGWQAGGGTG LPDEVVSTAA ALEMFHAFAL IHDDIMDDSA TRRGSPTVHR ALADRLGAAL  120
DPDQAGQLGV STAILVGDLA LTWSDELLYA PLTPPHRLAAV LPLVTAMRAE TVHGQYLDIT  180
SARRPGTDTS LALRIARYKT AAYTMERPLH IGAALAGARP ELLAGLSAYA LPAGEAFQLA  240
DDLLGVFGDP RRTGKPDLDD LRGGKHTVLV ALAREHATPE QRHTLDTLLG TPGLDRQGAS  300
RLRCVLVATG ARAEAERLIT ERRDQALTAL NALTLPPPLA EALARLTLGS TAHPA       355

SEQ ID NO: 63          moltype = AA  length = 330
FEATURE                Location/Qualifiers
source                 1..330
                       mol_type = protein
                       organism = Sulfolobus acidocaldarius
SEQUENCE: 63
MSYFDNYFNE IVNSVNDIIK SYISGDVPKL YEASYHLFTS GGKRLRPLIL TISSDLFGGQ  60
RERAYYAGAA IEVLHTFTLV HDDIMDQDNI RRGLPTVHVK YGLPLAILAG DLLHAKAFQL  120
LTQALRGLPS ETIIKAFDIF TRSIIIISEG QAVDMEFEDR IDIKEQEYLD MISRKTAALF  180
SASSSIGALI AGANDNDVRL MSDFGTNLGI AFQIVDDILG LTADEKELGK PVFSDIREGK  240
KTILVIKTLE LCKEDEKKIV LKALGNKSAS KEELMSSADI IKKYSLDYAY NLAEKYYKNA  300
IDSLNQVSSK SDIPGKALKY LAEFTIRRRK                                   330

SEQ ID NO: 64          moltype = AA  length = 297
FEATURE                Location/Qualifiers
source                 1..297
                       mol_type = protein
                       organism = Synechococcus sp.
SEQUENCE: 64
MVAQTFNLDT YLSQRQQQVE EALSAALVPA YPERIYEAMR YSLLAGGKRL RPILCLAACE  60
LAGGSVEQAM PTACALEMIH TMSLIHDDLP AMDNDDFRRG KPTNHKVFGE DIAILAGDAL  120
LAYAFEHIAS QTRGVPPQLV LQVIARIGHA VAATGLVGGQ VVDLESEGKA ISLETLEYIH  180
SHKTGALLEA SVVSGGILAG ADEELLARLS HYARDIGLAF QIVDDILDVT ATSEQLGKTA  240
GKDQAAAKAT YPSLLGLEAS RQKAEELIQS AKEALRPYGS QAEPLLALAD FITRRQH      297
```

```
SEQ ID NO: 65          moltype = AA  length = 371
FEATURE                Location/Qualifiers
source                 1..371
                       mol_type = protein
                       organism = Arabidopsis thaliana
SEQUENCE: 65
MASVTLGSWI VVHHHNHHHP SSILTKSRSR SCPITLTKPI SFRSKRTVSS SSSIVSSSVV  60
TKEDNLRQSE PSSFDFMSYI ITKAELVNKA LDSAVPLREP LKIHEAMRYS LLAGGKRVRP  120
VLCIAACELV GGEESTAMPA ACAVEMIHTM SLIHDDLPCM DNDDLRRGKP TNHKVFGEDV  180
AVLAGDALLS FAFEHLASAT SSDVVSPVRV VRAVGELAKA IGTEGLVAGQ VVDISSEGLD  240
LNDVGLEHLE FIHLHKTAAL LEASAVLGAI VGGGSDDEIE RLRKFARCIG LLFQVVDDIL  300
DVTKSSKELG KTAGKDLIAD KLTYPKIMGL EKSREFAEKL NREARDQLLG FDSDKVAPLL  360
ALANYIAYRQ N                                                       371

SEQ ID NO: 66          moltype = AA  length = 473
FEATURE                Location/Qualifiers
source                 1..473
                       mol_type = protein
                       organism = Stevia rebaudiana
SEQUENCE: 66
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG MVLKGSDCLL SKCYHEFGTQ WLPLLETLHQ  240
VPVVPVGLLP PEIPGDEKDE TWVSIKKWLD GKQKGSVVYV ALGSEALVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNARAVAID HES          473

SEQ ID NO: 67          moltype = AA  length = 459
FEATURE                Location/Qualifiers
source                 1..459
                       mol_type = protein
                       organism = Ipomoea purpurea
SEQUENCE: 67
MGSQATTYHM AMYPWFGVGH LTGFFRLANK LAGKGHRISF LIPKNTQSKL ESFNLHPHLI  60
SFVPIVVPSI PGLPPGAETT SDVPFPSTHL LMEAMDKTQN DIEIILKDLK VDVVFYDFTH  120
WLPSLARKIG IKSVFYSTIS PLMHGYALSP ERRVVGKQLT EADMMKAPAS FPDPSIKLHA  180
HEARGFTART VMKFGGDITF FDRIFTAVSE SDGLAYSTCR EIEGQFCDYI ETQFQKPVLL  240
AGPALPVPSK STMEQKWSDW LGKFKEGSVI YCAFGSECTL RKDKFQELLW GLELTGMPFF  300
AALKPPFETE SVEAAIPEEL KEKIQGRGIV HGEWVQQQLF LQHPSVGCFV SHCGWASLSE  360
ALVNDCQIVL LPQVGDQIIN ARIMSVSLKV GVEVEKGEED GVFSRESVCK AVKAVMDEKS  420
EIGREVRGNH DKLRGFLMNA DLDSKYMDSF NQKLQDLLG                         459

SEQ ID NO: 68          moltype = DNA  length = 1380
FEATURE                Location/Qualifiers
misc_feature           1..1380
                       note = Synthetic oligonucleotide
source                 1..1380
                       mol_type = other DNA
                       organism = synthetic construct
SEQUENCE: 68
atgggttctc aagctacaac ttaccatatg gccatgtatc catggtttgg ggttggacat  60
ttgactggtt tcttccgttt ggcaaacaaa ttagctggca aaggacatag aatctcattt  120
ctaattccta aaaacactca atctaagtta gaatctttca accttcatcc acacttaatc  180
tcttttgtgc ctatcgttgt cccaagtata ccaggcctgc cacctggtgc agagactaca  240
tcagatgttc ctttcccaag tacacatttg ctaatggaag caatggacaa gactcaaaac  300
gatatagaga ttatcctgaa ggatcttaaa gtagatgttg ttttctatga ttttactcac  360
tggttgcctt ctctggccag aaagattggc attaagagtg tcttttactc caccatttct  420
cctttaatgc atggatatgc tttatcacca gaaagacgtg tagttggtaa gcaattgaca  480
gaggcagata tgatgaaggc cccagcttct ttcccagacc catccattaa gctacatgca  540
catgaagcta ggggttttac agccagaacc gttatgaaat tcggtggtga catcaccttt  600
ttcgatagaa tattcacagc agtttccgaa agtgatggcc tggcctactc tacttgtaga  660
gagatcgagg gacaattctg tgattacatt gaaacacaat tccagaagcc agtcttgtta  720
gccggtccag ctttgccagt cccatccaaa tccactatgg aacaaaagtg gtcagattgg  780
ttggggaaat tcaaggaagg ctccgtcatc tactgtgctt tcgggtctga atgtacattg  840
agaaaggaca aatttcagga acttttatgg ggtttggaat tgacaggaat gcctttcttc  900
gctgctctga agccaccttt tgagactgag tctgttgagg ctgctatccc tgaggaacta  960
aaggaaaaga ttcagggaag aggtatagta catggagaat gggtacaaca acaattgttt  1020
cttcaacacc catctgtcgg gtgcttcgtt tctcactgcg gctgggcaag tttatctgaa  1080
gcccttgtta atgattgtca aatcgtgtta cttccacaag ttggcgatca gattatcaac  1140
gccagaataa tgtcagtatc acttaaagtg ggcgtggaag ttgaaaaggg tgaggaggac  1200
ggtgtctttt caagagaatc tgtgtgcaag gctgttaaag cagtaatgga tgaaaaatct  1260
gaaatcggta gagaagtcag aggtaatcat gataaactga ggggtttctt gatgaatgca  1320
gacttagatt caaagtacat ggattcattc aatcaaaagc tacaagattt gctaggttaa  1380

SEQ ID NO: 69          moltype = AA  length = 438
FEATURE                Location/Qualifiers
```

```
source                  1..438
                        mol_type = protein
                        organism = Bellis perennis
SEQUENCE: 69
MDSKIDSKTF RVVMLPWLAY SHISSFLVFA KRLTNHNFHI YICSSQTNMQ YLKNNLTSQY  60
SKSIQLIELN LPSSSELPLQ YHTTHGLPPH LTKTLSDDYQ KSGPDFETIL IKLNPHLVIY  120
DFNQLWAPEV ASTLHIPSIQ LLSGCVALYA LDAHLYTKPL DENLAKFPFP EIYPKNRDIP  180
KGGSKYIERF VDCMRRSCEI ILVRSTMELE GKYIDYLSKT LGKKVLPVGP LVQEASLLQD  240
DHIWIMKWLD KKEESSVVFV CFGSEYILSD NEIEDIAYGL ELSQVSFVWA IRAKTSALNG  300
FIDRVGDKGL VIDKWVPQAN ILSHSSTGGF ISHCGWSSTM ESIRYGVPII AMPMQFDQPY  360
NARLMETVGA GIEVGRDGEG RLKREEIAAV VRKVVVEDSG ESIREKAKEL GEIMKKNMEA  420
EVDGIVIENL VKLCEMNN                                                438

SEQ ID NO: 70           moltype = DNA  length = 1317
FEATURE                 Location/Qualifiers
misc_feature            1..1317
                        note = Synthetic oligonucleotide
source                  1..1317
                        mol_type = other DNA
                        organism = synthetic construct
SEQUENCE: 70
atggattcta aaatcgattc aaagacattc agagtcgtta tgttgccttg gcttgcatac  60
tcacacattt catcattcct agtgtttgcc aagagactaa caaatcataa cttccacatc  120
tacatttgtt cctctcaaac aaatatgcaa tacctgaaaa acaacttgac gtctcagtat  180
tcaaaatcta tacaactgat tgagttgaat cttccatcta gttccgaatt gcctctgcag  240
tatcatacta ctcacggact accaccacac cttacgaaaa cattgtctga tgattatcaa  300
aagtccggac ctgactttga aaccattttg atcaaattga acccacatct ggtaatctac  360
gactttaatc aactttgggc tccagaggtt gctagtacac ttcatattcc atccatacag  420
ttactgtctg gttgcgtcgc cttatatgcc ttagacgccc atctgtacac aaagccacta  480
gacgaaaact tggctaagtt tcctttccca gaaatctatc ctaaaaacag agatattcct  540
aagggaggta gtaaatacat cgaaaggttc gtagactgta tgagaagatc ttgtgaaatc  600
atattagtca gaagtaccat ggaacttgaa ggaaaataca ttgattactt gtctaagaca  660
ttagggaaaa aggtgttgcc agtagggcct ctggtgcaag aggcttcttt gttgcaagat  720
gatcatatat ggattatgaa gtggttagac aaaaaggagg agtcatccgt cgtgtttgtt  780
tgttttggtt ctgagtacat cttatcagac aacgaaatag aagatattgc ttatggccta  840
gagttgtccc aagtaagttt cgtttgggca ataagagcta agacttctgc cttaaatggc  900
ttcattgata gagtgggtga taaaggctta gtcatcgata aatgggttcc acaggctaac  960
atcttatctc actcttctac tggtggattc attagtcatt gcggttggtc atcaacaatg  1020
gaatctatta gatatggggt tcctattatc gccatgccaa tgcaattcga tcaaccttac  1080
aatgctaggt tgatggaaac tgttggtgca ggtatcgaag ttggcagaga tggcgaaggt  1140
agattgaaaa gagaagagat tgctgccgtg gttagaaagg tcgttgttga agattctggg  1200
gaatccataa gggagaaggc aaaggaattg ggagaaatca tgaaaaaaaa catggaggcc  1260
gaagtagatg gtatagtgat tgaaaatcta gttaagctat gtgagatgaa caattaa     1317

SEQ ID NO: 71           moltype = AA  length = 477
FEATURE                 Location/Qualifiers
source                  1..477
                        mol_type = protein
                        organism = Arabidopsis thaliana
SEQUENCE: 71
MMTLNSLSPA ESKAISFLDT SRFNPIPKLS GGFSLRRRNQ GRGFGKGVKC SVKVQQQQQP  60
PPAWPGRAVP EAPRQSWDGP KPISIVGSTG SIGTQTLDIV AENPDKFRVV ALAAGSNVTL  120
LADQVRRFKP ALVAVRNESL INELKEALAD LDYKLEIIPG EQGVIEVARH PEAVTVVTGI  180
VGCAGLKPTV AAIEAGKDIA LANKETLIAG GPFVLPLANK HNVKILPADS EHSAIFQCIQ  240
GLPEGALRKI ILTASGGAFR DWPVEKLKEV KVADALKHPN WNMGKKITVD SATLFNKGLE  300
VIEAHYLFGA EYDDIEIVIH PQSIIHSMIE TQDSSVLAQL GWPDMRLPIL YTMSWPDRVP  360
CSEVTWPRLD LCKLGSLTFK KPDNVKYPSM DLAYAAGRAG GTMTGVLSAA NEKAVEMFID  420
EKISYLDIFK VVELTCDKHR NELVTSPSLE EIVHYDLWAR EYAANVQLSS GARPVHA     477

SEQ ID NO: 72           moltype = AA  length = 440
FEATURE                 Location/Qualifiers
source                  1..440
                        mol_type = protein
                        organism = Leishmania infantum
SEQUENCE: 72
MHSTRHILRQ RAVLVTGART PFVKSFGALM KADTLELASA SVAGLLNKTS LDPRDIDHIV  60
WGNVVLQGSA HNCAREIVID LNMPKKIIGN LTSMACASGL SSLSQACMLI EGGHADVVIA  120
GGSDSVSNTE VPLPRSVTYG LMMAQRKGVM GFFKEAGYNP FKWFPGGIAL TERSTGKTMG  180
WHGDLIAELN SISRDDQEAL AVASHANAAR AEKAGYFKEE IVPVTIDKKG KKTEVTCDDV  240
MQRDTEKMKA KMPSLKPVFR KEGGTITAAT SSTLTDGGSA MLVMSEEKAK KLGYPTDVCV  300
KSWYFSGIDP YPQLLLAPVL GWGPALKKAG LTPKDIDLYE IHEAFAAQVL ATIKCLKSQE  360
FFDRYANGAK PVLTEDIDLS KLNVNGGSLA LGHPFAATGG RIVISLANEL RRSGKRHGLV  420
SICAAGGLGG VAILEHTASK                                              440

SEQ ID NO: 73           moltype = AA  length = 527
FEATURE                 Location/Qualifiers
source                  1..527
                        mol_type = protein
                        organism = Saccharomyces cerevisiae
```

```
SEQUENCE: 73
MAADQLVKTE VTKKSFTAPV QKASTPVLTN KTVISGSKVK SLSSAQSSSS GPSSSSEEDD  60
SRDIESLDKK IRPLEELEAL LSSGNTKQLK NKEVAALVIH GKLPLYALEK KLGDTTRAVA  120
VRRKALSILA EAPVLASDRL PYKNYDYDRV FGACCENVIG YMPLPVGVIG PLVIDGTSYH  180
IPMATTEGCL VASAMRGCKA INAGGGATTV LTKDGMTRGP VVRFPTLKRS GACKIWLDSE  240
EGQNAIKKAF NSTSRFARLQ HIQTCLAGDL LFMRFRTTTG DAMGMNMISK GVEYSLKQMV  300
EEYGWEDMEV VSVSGNYCTD KKPAAINWIE GRGKSVVAEA TIPGDVVRKV LKSDVSALVE  360
LNIAKNLVGS AMAGSVGGFN AHAANLVTAV FLALGQDPAQ NVESSNCITL MKEVDGDLRI  420
SVSMPSIEVG TIGGGTVLEP QGAMLDLLGV RGPHATAPGT NARQLARIVA CAVLAGELSL  480
CAALAAGHLV QSHMTHNRKP AEPTKPNNLD ATDINRLKDG SVTCIKS                527

SEQ ID NO: 74          moltype = AA  length = 1226
FEATURE                Location/Qualifiers
source                 1..1226
                       mol_type = protein
                       organism = Ganoderma lucidum
SEQUENCE: 74
MRAVLRLLST HTVFSPIETI VSVFVLATLA YFHILSGIKH SSFFASSHPP AIRPAFAHLT  60
NGEWVAVSQH DWTEAWKHPG GSLDALELQQ VVFTLDDKTQ PSAVLDASAI SQHLVSNVPA  120
LSGKAYSSLC HHPNVSGTSC FTSVSGPGAS PILTLSFKPG TRDDWLGSLR KEKTITLDGV  180
KYDVGAGKRQ ESIGDMESSK WVAYALSALV LRFWELTKAD SLDILVVLTG YILMHVTFMR  240
LFLASRALGS NFWLSAGIFS SATISFLFTL PMCRSMDIPL DPIALTEALP FLVCTVGFDK  300
PLRLARAVMA HPNILKPQDD GRMKAAGDVI LEALDRVGNM ILRDYALEIA VLFVGVNSRV  360
GGLKEFCAVA AALLAMDRLM TFTLYTAVLT IMVEVRRIKK VRDMTKARSR SSSITAVTAN  420
GTAIRGVLSR KSSKQSVTEP ETTKNLRQRA TDSAIGVKGS LLKDGGRLQE AEENPMARLK  480
LLLIASFLTL HILNFCTTLT SATANARHQR HPFRTVQEVV PIPRVDITTP AIANILSHLA  540
VAQEPMFTVV GSEPIELLVK VAAPVYVHAL PLAPALRASN TNTGEAIENF MSSWSSLVGD  600
PVVSKWIVAL LAVSVALNGY LLKGIAAGSG LAAMRAVRSQ GVRFRSRARS IVKISDEPEP  660
EPEHSIDPAP VVFFASAAPA VEAPAPAPAP EPEPPVNRPP PLTIFSRPLN LETVDKKLQD  720
ALPIRSPPPV EPITPESREV EPTQVEVRSL AECVDVFENG PRPVSVALKT LNDEEVILLC  780
QTGKIAPYAL VKMLADFDRA VRVRRALISR ASRTKTLENS LVPMKDYDYA RVMGACCENV  840
IGYMPLPLGI AGPLKIDGLM YPIPMATAEG TLVASTSRGC KALNAGGGVT TVLTADGMTR  900
GPAIDFPSIV RAAEAKAFIE SEDGYATIRE AFESTSRFAK LQKIKCALAG RTLFVRFATR  960
TGDAMGMNMI SKATEKALDV LSHEFPEMVV LALSGNYCTD KKPAAISWIE GRGKSIVAEA  1020
VIPGKVVKSV LKTTVESLCN VNTKKNLIGS AMAGSVGGFN AHAANILTAV FLATGQDPAQ  1080
NVESSNCMTL MEPTNGGEDL LMTISMPCIE VGTVGGGTIL EPQGAVLDLL GVRGAHPTNP  1140
GQNAQQLARI IASAVMAGEL SLISALAAGH LVRAHLAHNR SQLNTPMPSR PHTPGPEDVS  1200
HVQQLPTPSA SDDKGVTAQG YVVEAK                                       1226

SEQ ID NO: 75          moltype = AA  length = 888
FEATURE                Location/Qualifiers
source                 1..888
                       mol_type = protein
                       organism = Bos taurus
SEQUENCE: 75
MLSRLFRMHG LFVASHPWEV IVGTVTLTIC MMSMNMFTGN NKICGWNYEC PKLEEDVLSS  60
DIIILTITRC IAILYIYFQF QNLRQLGSKY ILGIAGLFTI FSSFVFSTVV IHFLDKELTG  120
LNEALPFFLL LVDLSRASAL AKFALSSNSQ DEVRENIARG MAILGPTFTL DALVECLVIG  180
VGTMSGVRQL EIMCCFGCMS VLANYFVFMT FFPACVSLVL ELSRESREGR PIWQLSHFAR  240
VLEEEENKPN PVTQRVKMIM SLGLVLVHAH SRWIADPSPQ NSTADNSKVS LGLDENVSKR  300
IEPSVSLWQF YLSKMISMDI EQVITLSLAL LLAVKYIFFE QAETESTLSL KNPITSPVVT  360
QKKITDDCCR RDPVLVRNDQ KFHAMEEETR KNRERKVEVI KPLLAENDTS HRATFVVGNS  420
SLLGTSLELE TQEPEMELPV EPRPNEECLQ ILENAEKGAK FLSDAEIIQL VNAKHIPAYK  480
LETLMETHER GVSIRRQLLS KKLPEPSSLQ YLPYRDYNYS LVMGACCENV IGYMPIPVGV  540
AGPLCLDGKE FQVPMATTEG CLVASTNRGC RAIGLGGGAS SRVLADGMTR GPVVRFPRAC  600
DSAEVKAWLE TPEGFTVIKE AFDSTSRVAR LQKLHMSVAG RNLYIRFQSR SGDAMGMNMI  660
SKGTEKALSK LQEYFPEMQI LAVSGNYCTD KKPAAINWIE GRGKSVVCEA VIPAKVVREV  720
LKTTTEAMIE VNINKNLVGS AMAGSIGGYN AHAANIVTAI YIACGQDAAQ NVGSSNCITL  780
MEASGPTNED LYISCTMPSI EIGTVGGGTN LLPQQACLQM LGVQGACRDN PGENARQLAR  840
IVCGTVMAGE LSLMAALAAG HLVRSHMIHN RSKINLQDLQ GTCTKKAA               888

SEQ ID NO: 76          moltype = AA  length = 567
FEATURE                Location/Qualifiers
source                 1..567
                       mol_type = protein
                       organism = Artemisia annua
SEQUENCE: 76
MDLRRKLPPK PPSSTTTKQP SHRSHSPTPI PKASDALPLP LYLTNTFFFT LFFSVAYYLL  60
HRWRDKIRSG TPLHVVTLTE LSAIVLLIAS FIYLLGFFGI DFVQSFTSRE NEQLNNDDHN  120
VVSTNNVLSD RRLVYDYGFD VTGDNDNDND DDVIVKSVVS GEVNSYSLEA SLGDCYRAAK  180
IRKRAVERIV GREVLGLGFE GFDYESILGQ CCEMPIGYVQ VPVGVAGPLL LNGGEFMVPM  240
ATTEGCLVAS TNRGCKAICL SGGATAILLK DGMTRAPVVR FATAERASQL KFYLEDGVNF  300
DTLSVVFNKS SRFARLQNIQ CSIAGKNLYI RFTCSTGDAM GMNMVSKGVQ NVLDFLQNDF  360
PDMDVIGISW KFCSDKKPTA VNWIEGRGKS VVFQAVITKK VVRKSALNPQ TCTCRTLTCL  420
RPLLVLLLLV LLVDLMHMLH IVSAVFIATG QDPAQNIESS HCITMMEAVN NGKDLHVNVT  480
MPSIEVGTVG GGTQLASQSA CLNLLGVKGA CIESPGSNAQ LLARIVAGSV LAGELSLMSA  540
ISAGQLVKSH MKYNRSSRDM SAIASKV                                      567

SEQ ID NO: 77          moltype = AA  length = 435
```

```
FEATURE                Location/Qualifiers
source                 1..435
                       mol_type = protein
                       organism = Trypanosoma cruzi
SEQUENCE: 77
MFRRAILLGC SAAKTPWSEC SNAQLVDAVK SRKISFYGLE QALEPDYRRA IEVRREVVSE  60
IASQQPEAKK KQSALHTIPF ENYDWNKVVG QNCENIIGYV PIPLGVAGPI LIDGKEYPIP  120
MATTEGALVA STHRGARAIT RSGGCKTLLL GEGMTRAPVV ELPSLEEAGR LHKYCNENFL  180
SLKEAFESTT QYGKLNSLKC VLAGRKAYLR FRATTGDAMG MNMITKGVDK ALSVLQQHFP  240
SMEILALSGN YCTDKKPSAV NWIDGRGKSV VAEATLLADV VEDTLKCTVD SLVSLNIDKN  300
LVGSAMAGSV GGFNAQAANA VAAIFIATGQ DPAQVVESSM CITTMSKVGN DLLISVTMPS  360
IEVGVVGGGT GLAAQRGCLE LIGCGGPSKE SPGTNAQLLS RVVAAGVLSA ELSLMSGLAA  420
GHLLSAHMRL NRKKK                                                   435

SEQ ID NO: 78          moltype = AA  length = 426
FEATURE                Location/Qualifiers
source                 1..426
                       mol_type = protein
                       organism = Staphylococcus aureus
SEQUENCE: 78
MQSLDKNFRH LSRQQKLQQL VDKQWLSEEQ FNILLNHPLI DEEVANSLIE NVIAQGALPV  60
GLLPNIIVDD KAYVVPMMVE EPSVVAAASY GAKLVNQTGG FKTVSSERIM IGQIVFDGVD  120
DTEKLSADIK ALEKQIHQIA DEAYPSIKAR GGGYQRIAID TFPEQQLLSL KVFVDTKDAM  180
GANMLNTILE AITAFLKNEF PQSDILMSIL SNHATASVVK VQGEIDVKDL ARGERTGEEV  240
AKRMERASVL AQVDIHRAAT HNKGVMNGIH AVVLATGNDT RGAEASAHAY ASKDGQYRGI  300
ATWRYDQERQ RLIGTIEVPM TLAIVGGGTK VLPIAKASLE LLNVESAQEL GHVVAAVGLA  360
QNFAACRALV SEGIQQGHMS LQYKSLAIVV GAKGDEIAQV AEALKQEPRA NTQVAERILQ  420
DLRSQQ                                                             426

SEQ ID NO: 79          moltype = AA  length = 481
FEATURE                Location/Qualifiers
source                 1..481
                       mol_type = protein
                       organism = Arabidopsis thaliana
SEQUENCE: 79
MHITKPHAAM FSSPGMGHVI PVIELGKRLS ANNGFHVTVF VLETDAASAQ SKFLNSTGVD  60
IVKLPSPDIY GLVDPDDHVV TKIGVIMRAA VPALRSKIAA MHQKPTALIV DLFGTDALCL  120
AKEFNMLSYV FIPTNARFLG VSIYYPNLDK DIKEEHTVQR NPLAIPGCEP VRFEDTLDAY  180
LVPDEPVYRD FVRHGLAYPK ADGILVNTWE EMEPKSLKSL LNPKLLGRVA RVPVYPIGPL  240
CRPIQSSETD HPVLDWLNEQ PNESVLYISF GSGGCLSAKQ LTELAWGLEQ SQQRFVWVVR  300
PPVDGSCCSE YVSANGGGTE DNTPEYLPEG FVSRTSDRGF VVPSWAPQAE ILSHRAVGGF  360
LTHCGWSSTL ESVVGGVPMI AWPLFAEQNM NAALLSDELG IAVRLDDPKE DISRWKIEAL  420
VRKVMTEKEG EAMRRKVKKL RDSAEMSLSI DGGGLAHESL CRVTKECQRF LERVVDLSRG  480
A                                                                  481

SEQ ID NO: 80          moltype = AA  length = 513
FEATURE                Location/Qualifiers
source                 1..513
                       mol_type = protein
                       organism = Arabidopsis thaliana
SEQUENCE: 80
MGAYETEKPT KDAAALETQS PEDFDQPSPL RKIISVASIA AGVQFGWALQ LSLLTPYVQL  60
LGIPHKWSSL IWLCGPVSGM IVQPIVGFHS DRCRSKFGRR RPFIATGAAL VAVAVFLIGY  120
AADFGYKMGD KLEEKVKVRA IGIFALGFWI LDVANNTLQG PCRAFLADLA AGDAKRTRVA  180
NAFFSFFMAV GNVLGYAAGS YTNLHKMFPF TMTKACDIYC ANLKTCFFLS ITLLLIVTVT  240
SLWYVNDKQW SPPPRNADDD EKTSSVPLFG EIFGAFKVMK RPMWMLLIVT ALNWIAWFPF  300
LLFDTDWMGR EVFGGDSDGN ERSKKLYSLG VQSGAMGLMF NSIVLGFMSL GVEWIGRKLG  360
GAKRLWGIVN FILAAGLAMT VLVTKFAEDH RKTAGDLAGP SASVKAGALS LFAVLGIPLA  420
ITFSTPFALA SIFSSCSGAG QGLSLGVLNL AIVIPQMIVS LGGGPFDALF GGGNLPAFIV  480
AAIAAAISGV LALTVLPSPP PDAPKATTMG GFH                                513

SEQ ID NO: 81          moltype = AA  length = 806
FEATURE                Location/Qualifiers
source                 1..806
                       mol_type = protein
                       organism = Coffea arabica
SEQUENCE: 81
MAERVLTRVH SLRERLDATL AAHRNDVLLF MSRLETHGKG ILKPHQLLAE FEEINKDGKQ  60
KIHDHAFEEV LKSTQEAIVL PPWVALAIRL RPGVWEYVRV NVHALVVEEL TVPEYLHFKE  120
ELVDGSKNGN FVLELDFEPF TASFPKPTLT KYIGDGVEFL NRHLSAKMFH DKESMAPLLD  180
FLRVHQYKGK TMMLNDRIKD LNTLQAVLRK AEEYLTTLSA DTPYSEFEHK FQEIGLERGW  240
GDTAERVLEM ICMLLDLLGA PDSCTLEKFL GRIPMVFNVV ILSPHGYFAQ ENVLGYPDTG  300
GQVVYILDQV PALEREMLKR IKEQGLDVKP RILIITRLLP DAPGTTCGQR LEKVYGSEYS  360
HILRVPFRTE KGVVRKWISR FEVWPYMETF TEDVAKEVTA ELQAKPDLVI GNYSEGNLVA  420
SLLAHKLGVT QCTIAHALEK TKYPDSDIYL SKFDEKYHFS CQFTADLIAM NHTDFIITST  480
FQEIAGSKDT VGQYESHMAF TMPGLYRVVH GIDVFDPKFN IVSPGADTNL YFPHTEKEKR  540
LTSFHPEIEE LLFSDVENEE HLCVLKDKKK PILFTMARLD RVKNLTGLVE LYAKNPKLRE  600
LVNLVVVGGD RRKESKDLEE QAEMKKMYSL IETYNLNGQF RWISSQMNRV RNGELYRYIA  660
DTRGAFVQPA FYEAFGLTVV EAMTCGLPTF ATNHGGPAEI IIHGKSGFHI DPYHGEQVSE  720
```

```
LLANFFERCK KEPSYWDTIS AGGLKRIQEK YTWQIYSDRL LTLAGVYGFW KCVSKLDRQE  780
IRRYLEMFYA LKYRKLAEAV PLAVDQ                                       806

SEQ ID NO: 82           moltype = DNA  length = 19
FEATURE                 Location/Qualifiers
misc_feature            1..19
                        note = Synthetic oligonucleotide
source                  1..19
                        mol_type = other DNA
                        organism = synthetic construct
SEQUENCE: 82
tgaattcgtt aacgaattc                                              19

SEQ ID NO: 83           moltype = DNA  length = 19
FEATURE                 Location/Qualifiers
misc_feature            1..19
                        note = Synthetic oligonucleotide
source                  1..19
                        mol_type = other DNA
                        organism = synthetic construct
SEQUENCE: 83
tgaattcgtt aacgaactc                                              19

SEQ ID NO: 84           moltype = DNA  length = 19
FEATURE                 Location/Qualifiers
misc_feature            1..19
                        note = Synthetic oligonucleotide
source                  1..19
                        mol_type = other DNA
                        organism = synthetic construct
SEQUENCE: 84
tgaattcgtt aacgaagtc                                              19

SEQ ID NO: 85           moltype = DNA  length = 19
FEATURE                 Location/Qualifiers
misc_feature            1..19
                        note = Synthetic oligonucleotide
source                  1..19
                        mol_type = other DNA
                        organism = synthetic construct
SEQUENCE: 85
tgaattcgtt aacgaaatt                                              19

SEQ ID NO: 86           moltype = AA  length = 473
FEATURE                 Location/Qualifiers
source                  1..473
                        mol_type = protein
                        organism = Stevia rebaudiana
SEQUENCE: 86
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG LVLKGSDCLL SKCYHEFGTQ WLPLLETLHQ  240
VPVVPVGLLP PEVPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNTRAVAID HES         473

SEQ ID NO: 87           moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 87
cggtaggtat tgattgtaat t                                           21

SEQ ID NO: 88           moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 88
cttttcggtt agagcggatg t                                           21

SEQ ID NO: 89           moltype = DNA  length = 1422
```

```
FEATURE                 Location/Qualifiers
misc_feature            1..1422
                        note = Synthetic oligonucleotide
source                  1..1422
                        mol_type = other DNA
                        organism = synthetic construct
SEQUENCE: 89
atggctacat ctgattctat tgttgatgac aggaagcagt tgcatgtggc tactttccct  60
tggcttgctt tcggtcatat actgccttac ctacaactat caaaactgat agctgaaaaa  120
ggacataaag tgtcattcct ttcaacaact agaaacattc aaagattatc ttcccacata  180
tcaccattga ttaacgtcgt tcaattgaca cttccaagag tacaggaatt accagaagat  240
gctgaagcta caacagatgt gcatcctgaa gatatccctt acttgaaaaa ggcatccgat  300
ggattacagc ctgaggtcac tagattcctt gagcaacaca gtccagattg gatcatatac  360
gactacactc actattggtt gccttcaatt gcagcatcac taggcatttc tagggcacat  420
ttcagtgtaa ccacaccttg ggccattgct tacatgggtc catccgctga tgctatgatt  480
aacggcagtg atggtagaac taccgttgaa gatttgacaa ccccaccaaa gtggtttcca  540
tttccaacta aagtctgttg gagaaaacac gacttagcaa gactggttcc atacaaggca  600
ccaggaatct cagacggcta tagaatgggt ttagtcctta aagggtctga ctgcctattg  660
tctaagtgtt accatgagtt tgggacacaa tggctaccac ttttggaaac attacaccaa  720
gttcctgtcg taccagttgg tctattacct ccagaaatcc ctggtgatga gaaggacgag  780
acttgggttt caatcaaaaa gtggttagac gggaagcaaa aaggctcagt ggtatatgtg  840
gcactgggtt ccgaagtttt agtatctcaa acagaagttg tggaacttgc cttaggtttg  900
gaactatctg gattgccatt tgtctgggcc tacagaaaac caaaaggccc tgcaaagtcc  960
gattcagttg aattgccaga cggctttgtc gagagaacta gagatagagg gttggtatgg  1020
acttcatggg ctccacaatt gagaatcctg agtcacgaat ctgtgtgcgg tttcctaaca  1080
cattgtggtt ctggttctat agttgaagga ctgatgtttg gtcatccact tatcatgttg  1140
ccaatctttg gtgaccagcc tttgaatgca cgtctgttag aagataaaca agttggaatt  1200
gaaatcccac gtaatgagga agatggatgt ttaaccaagg agtctgtggc cagatcatta  1260
cgttccgttg tcgttgaaaa ggaaggcgaa atctacaagg ccaatgcccg tgaactttca  1320
aagatctaca atgacacaaa agtagagaag gaatatgttt ctcaatttgt agattaccta  1380
gagaaaaacg ctagagccgt agctattgat catgaatcct aa                    1422

SEQ ID NO: 90           moltype = DNA  length = 1422
FEATURE                 Location/Qualifiers
misc_feature            1..1422
                        note = Synthetic oligonucleotide
source                  1..1422
                        mol_type = other DNA
                        organism = synthetic construct
SEQUENCE: 90
atggctactt ctgattccat cgttgacgat agaaagcaat tgcatgttgc tacttttcca  60
tggttggctt tcggtcatat tttgccatac ttgcaattgt ccaagttgat tgctgaaaag  120
ggtcacaagg tttcattctt gtctaccacc agaaacatcc aaagattgtc ctctcatatc  180
tccccattga tcaacgttgt tcaattgact ttgccaagag tccaagaatt gccagaagat  240
gctgaagcta ctactgatgt tcatccagaa gatatccctt acttgaaaaa ggcttccgat  300
ggtttacaac cagaagttac tagattcttg gaacaacatt ccccagattg gatcatctac  360
gattatactc attactggtt gccatccatt gctgcttcat tgggtatttc tagagcccat  420
ttctctgtta ctactccatg ggctattgct tatatgggtc catctgctga tgctatgatt  480
aacggttctg atggtagaac taccgttgaa gatttgacta ctccaccaaa gtggtttcca  540
tttccaacaa aagtctgttg gagaaaacac gatttggcta gattggttcc atacaaagct  600
ccaggtattt ctgatggtta cagaatgggt atggttttga aaggttccga ttgcttgttg  660
tctaagtgct atcatgaatt cggtactcaa tggttgcctt tgttggaaac attgcatcaa  720
gttccagttg ttccagtagg tttgttgcca ccagaaattc caggtgacga aaaagacgaa  780
acttgggttt ccatcaaaaa gtggttggat ggtaagcaaa agggttctgt tgtttatgtt  840
gctttgggtt ccgaagcttt ggtttctcaa accgaagttg ttgaattggc tttgggtttg  900
gaattgtctg gtttgccatt tgtttgggct tacagaaaac ctaaaggtcc agctaagtct  960
gattctgttg aattgccaga tggtttcgtt gaaagaacta gagatagagg tttggtttgg  1020
acttcttggg ctccacaatt gagaattttg tctcatgaat ccgtctgtgg tttcttgact  1080
cattgtggtt ctggttctat cgttgaaggt ttgatgtttg gtcacccatt gattatgttg  1140
ccaatctttg gtgaccaacc attgaacgct agattattgg aagataagca agtcggtatc  1200
gaaatcccaa gaaatgaaga agatggttgc ttgaccaaag aatctgttgc tagatctttg  1260
agatccgttg tcgttgaaaa agaaggtgaa atctacaagg ctaacgctag agaattgtcc  1320
aagatctaca acgataccaa ggtcgaaaaa gaatacgttt cccaattcgt tgactacttg  1380
gaaaagaatg ctagagctgt tgccattgat catgaatctt ga                    1422

SEQ ID NO: 91           moltype = DNA  length = 1503
FEATURE                 Location/Qualifiers
source                  1..1503
                        mol_type = other DNA
                        organism = Stevia rebaudiana
SEQUENCE: 91
atggaggctt catatctata catttccatt cttctgcttc tagcttcgta cctcttcacc  60
acccaacttc gtcgtaaatc cgccaatcta ccgccgacgg tgttcccatc catccccata  120
atcggtcatc tctacctcct caaaaaacca ctctatagaa cactagccaa aattgccgcc  180
aaatacggcc ctatcctcca actccaacta gggtaccgcc gtgtcctcgt aatctcctcc  240
ccttccgccg ccgaagaatg cttcaccaac aacgacgtta tcttcgccaa ccgtccgaag  300
acgctattcg gaaaaattgt agggggtacc agcctcgggt cgctgtcgta cggcgaccag  360
tggcgcaacc tccgccgcgt tgcatccatc gagattctat cagtccaccg gctcaacgag  420
tttcacgaca tacgtgttga cgaaaaccgg cttctgatcc gtaaactaag atccagttct  480
```

```
tctccggtga ctctgataac ggtgttttac gcactaacgt taaatgtgat tatgagaatg  540
atctccggaa agaggtattt cgactcgggt gatcgggaat tggaggagga agggaagcga  600
ttccgggaga tactcgatga gacacttttg ctcgcgggtg cttctaatgt tggggattac  660
ttgccgattc tgaattggtt gggggtgaag agcttggaga agaagctaat cgcattgcag  720
aaaaagagag atgatttctt tcagggactg atcgagcaag ttcggaaatc tagaggggct  780
aaagtgggaa aaggaaggaa gacgatgatc gagttgttgt tatccctaca agaatctgaa  840
cctgagtatt acactgacgc catgatccga tcatttgtgc tgggtttatt agcagcaggg  900
agtgatacat cggctggaac tatggaatgg gcgatgtctc ttttggtaaa ccacccgcac  960
gtattaaaaa aggcacaggc tgaaattgat cgagtcatcg gcaacaaccg tctaattgat  1020
gagtccgaca tagggaatat accttacatt ggttgcatca taaacgagac gctcagattg  1080
taccctgcgg gcccgttgct atttccccat gagtcatcag cggactgtgt tatcagcggg  1140
tacaacatcc ctcgtgggac gatgcttatt gtcaaccaat gggcgataca tcatgaccca  1200
aaggtgtggg acgaccctga gacattcaaa ccggaaagat tccaagggct tgaagggaca  1260
cgagacgggt ttaagctgat gccttttggg tccggaagga ggggttgtcc aggggaggga  1320
ttggcgattc gtttgcttgg gatgactctc gggtcggtta tccaatgctt tgattgggaa  1380
cgagtcggtg acgagatggt tgatatgacc gaaggtcttg ggtcacgtt gcctaaagct  1440
gtaccattag tcgccaagtg caagccgcgt tccgaaatga cgaatctact ctctgagcta  1500
tga                                                                1503

SEQ ID NO: 92          moltype = AA  length = 436
FEATURE                Location/Qualifiers
source                 1..436
                       mol_type = protein
                       organism = Archaeoglobus fulgidus
SEQUENCE: 92
MQVLRLDRRH YKSGKIRRAM SSRIPGFYKL SVEERLKKVA EFAGLSDEEV KAVLSQGLPL  60
DVADRMIENV IGTFELPLGI ATNFLIDGKD YLIPMAIEEP SVVAAASNAA RMARESGGFT  120
TDYTGSLMIG QIQVTKLLNP NAAKFEVLRQ KDEIIERANE CDPMLVNLGG GCKDIEARVI  180
DTIMGKMLIV HLIVDVKDAM GANAVNTMCE KVAPFIERIT GGKVYLRIIS NLAAYRLARA  240
KAVFDKDVIG GEEVVEGIML AYAFAAADPF RCATHNKGIM NGISALMIAT GNDFRAIEAG  300
AHSYAAIGGY KPLTTYEVDR KGNLVGTIEI PMAVGVIGGA TKVNPLAKIS LKILGVNTAE  360
ELARVAAALG LAQNFAALRA LATEGIQRGH MELHARNLAI MAGATGDEVD RVVEIMVRDG  420
KIRLDYAKEV LERLRS                                                  436

SEQ ID NO: 93          moltype = AA  length = 428
FEATURE                Location/Qualifiers
source                 1..428
                       mol_type = protein
                       organism = Pseudomonas mevalonii
SEQUENCE: 93
MSLDSRLPAF RNLSPAARLD HIGQLLGLSH DDVSLLANAG ALPMDIANGM IENVIGTFEL  60
PYAVASNFQI NGRDVLVPLV VEEPSIVAAA SYMAKLARAN GGFTTSSSAP LMHAQVQIVG  120
IQDPLNARLS LLRRKDEIIE LANRKDQLLN SLGGGCRDIE VHTFADTPRG PMLVAHLIVD  180
VRDAMGANTV NTMAEAVAPL MEAITGGQVR LRILSNLADL RLARAQVRIT PQQLETAEFS  240
GEAVIEGILD AYAFAAVDPY RAATHNKGIM NGIDPLIVAT GNDWRAVEAG AHAYACRSGH  300
YGSLTTWEKD NNGHLVGTLE MPMPVGLVGG ATKTHPLAQL SLRILGVKTA QALAEIAVAV  360
GLAQNLGAMR ALATEGIQRG HMALHARNIA VVAGARGDEV DWVARQLVEY HDVRADRAVA  420
LLKQKRGQ                                                           428

SEQ ID NO: 94          moltype = DNA  length = 1323
FEATURE                Location/Qualifiers
misc_feature           1..1323
                       note = Synthetic oligonucleotide
source                 1..1323
                       mol_type = other DNA
                       organism = synthetic construct
SEQUENCE: 94
atgcattcta ccagacatat cttaagacaa agggccgtcc tagttacagg cgctagaaca  60
ccattcgtga aatcatttgg ggctcttatg aaagcagata ccttggaatt ggcatcagca  120
tcagtcgctg ggttgctgaa caagacctca ctggacccta gagatatcga tcatatcgtt  180
tggggtaatg ttgtacttca aggatcagct cataactgcg ccagagaaat agttatcgac  240
cttaacatgc ctaaaaagat catcggtaat ttgacatcta tggcctgtgc ttcaggctta  300
tcttctttgt cacaagcctg tatgctaata gagggtggtc atgccgatgt cgtcattgct  360
ggcggttctg attcagtctc caacactgaa gtgcctttgc caagatccgt cacttacggt  420
ctaatgatgg cccaaaggaa gggtgttatg ggcttcttta aggaagcagg atacaaccca  480
ttcaaatggt ttccaggcgg tattgcttta accgaacgta gtacaggaaa aactatgggt  540
tggcatggag acttaattgc tgagttaaac tctatatcta gagatgacca ggaagccctg  600
gctgtggctt ctcatgcaaa tgctgctaga gcagaaaaag ctgggtactt taaggaggaa  660
attgtacctg tgacaatcga caaaaagggc aaaaagactg aagtaacatg tgatgatgtt  720
atgcaaagag atacagaaaa gatgaaggcc aagatgccat cattgaagcc tgttttcaga  780
aaagagggag gtacaataac agcagccact tccagtactc tgactgatgg tggctctgca  840
atgttggtta tgtcagagga aaaggccaaa aagttgggtt atccaactga tgtctgcgtg  900
aagtcttggt atttcagtgg tatcgatcct tacccacaac ttttgttagc accagttcta  960
ggttggggtc cagctttgaa aaaggccgga ttaacccta aagatatcga tttgtacgaa  1020
attcacgaag catttgctgc acaagttcta gccacaatta agtgtttgaa gtctcaggaa  1080
ttcttcgata ggtacgctaa cggtgcaaag ccagtattaa ctgaggatat tgatctttct  1140
aaactaaatg ttaatggcgg ttccttagca cttggccacc cattcgccgc tacaggaggt  1200
agaatcgtaa tctctctagc aaatgagttg agaagatccg gaaagagaca cgggctggtc  1260
agtatttgtg cagctggagg gttaggcgga gtagctatac ttgagcatac agcaagtaag  1320
```

```
taa                                                                   1323

SEQ ID NO: 95          moltype = DNA  length = 1584
FEATURE                Location/Qualifiers
misc_feature           1..1584
                       note = Synthetic oligonucleotide
source                 1..1584
                       mol_type = other DNA
                       organism = synthetic construct
SEQUENCE: 95
atggcagctg accaattggt gaaaactgaa gtcaccaaga agtcttttac tgctcctgta  60
caaaaggctt ctacaccagt tttaaccaat aaaacagtca tttctggatc gaaagtcaaa  120
agtttatcat ctgcgcaatc gagctcatca ggaccttcat catctagtga ggaagatgat  180
tcccgcgata ttgaaagctt ggataagaaa atacgtcctt tagaagaatt agaagcatta  240
ttaagtagtg gaaatacaaa acaattgaag aacaaagagg tcgctgcctt ggttattcac  300
ggtaagttac ctttgtacgc tttggagaaa aaattaggtg atactacgag agcggttgcg  360
gtacgtagga aggctctttc aattttggca gaagctcctg tattagcatc tgatcgttta  420
ccatataaaa attatgacta cgaccgcgta tttggcgctt gttgtgaaaa tgttataggt  480
tacatgcctt tgcccgttgg tgttataggc cccttggtta tcgatggtac atcttatcat  540
ataccaatgg caactacaga gggttgtttg gtagcttctg ccatgcgtgg ctgtaaggca  600
atcaatgctg gcggtggtgc aacaactgtt ttaactaagg atggtatgac aagaggccca  660
gtagtccgtt tcccaacttt gaaaagatct ggtgcctgta agatatggtt agactcagaa  720
gagggacaaa acgcaattaa aaaagctttt aactctacat caagatttgc acgtctgcaa  780
catattcaaa cttgtctagc aggagattta ctcttcatga gatttagaac aactactggt  840
gacgcaatgg gtatgaatat gatttctaaa ggtgtcgaat actcattaaa gcaaatggta  900
gaagagtatg gctgggaaga tatggaggtt gtctccgttt ctggtaacta ctgtaccgac  960
aaaaaaccag ctgccatcaa ctggatcgaa ggtcgtggta agagtgtcgt cgcagaagct  1020
actattcctg gtgatgttgt cagaaaagtg ttaaaaagtg atgtttccgc attggttgag  1080
ttgaacattg ctaagaattt ggttggatct gcaatggctg ggtctgttgg tggatttaac  1140
gcacatgcag ctaatttagt gacagctgtt ttcttggcat taggacaaga tcctgcacaa  1200
aatgttgaaa gttccaactg tataacattg atgaaagaag tggacggtga tttgagaatt  1260
tccgtatcca tgccatccat cgaagtaggt accatcggtg gtggtactgt tctagaacca  1320
caaggtgcca tgttggactt attaggtgta agaggcccgc atgctaccgc tcctggtacc  1380
aacgcacgtc aattagcaag aatagttgcc tgtgccgtct tggcaggtga attatcctta  1440
tgtgctgccc tagcagccgg ccatttggtt caaagtcata tgacccacaa caggaaacct  1500
gctgaaccaa caaaacctaa caatttggac gccactgata taaatcgttt gaaagatggg  1560
tccgtcacct gcattaaatc ctaa                                         1584

SEQ ID NO: 96          moltype = DNA  length = 3681
FEATURE                Location/Qualifiers
misc_feature           1..3681
                       note = Synthetic oligonucleotide
source                 1..3681
                       mol_type = other DNA
                       organism = synthetic construct
SEQUENCE: 96
atgagagctg tccttagatt gttatcaaca catactgttt tctctcctat tgaaacaatt  60
gtatctgttt tcgtgttagc tacattagct tacttccaca tcttgtccgg aatcaagcac  120
tcaagtttct ttgcatcttc tcatcctcct gctatcagac ctgcttttgc acatctgacc  180
aacggggaat gggttgccgt ctcccaacat gattggactg aagcatggaa gcatcctggc  240
ggttcacttg atgcattaga acttcaacaa gtagttttca ctttagatga caagactcaa  300
ccatctgctg tgctagatgc atccgcaatt agtcagcact tagtttccaa tgttcctgca  360
ttatctggaa aagcctactc ttcattgtgc caccatccaa atgtatcagg cacctcctgt  420
tttacatcag tttctggtcc aggagcttca ccaatcttga cactgagttt taagcctgga  480
actagagacg attggttagg atcattaagg aaggagaaaa ctatcacact agatggggtt  540
aagtacgacg ttggagccgg aaaaagacaa gagtcaatcg gcgatatgga atcatctaag  600
tgggttgctt atgcattatc agctttggta cttagatttt gggaattaac aaaggcagat  660
tccttagata tactagtggt tctaactggg tacatcctaa tgcacgtaac attcatgaga  720
ttgttcttgg catccagagc acttggcagt aacttttggt tatcagctgg catattctcc  780
tccgcaacaa tttctttcct attcacttta ccaatgtgta gatctatgga tattccactt  840
gatccaattg ccttgacaga agccctgcca ttcttggtgt gtaccgtagg ttttgacaaa  900
ccacttagat tggcaagagc tgtgatggct catcctaata tccttaaacc tcaagatgat  960
ggtaggatga aagctgccgg agatgtcatt cttgaggcac tggacagagt tggtaacatg  1020
atattgagag attacgcttt agagatcgca gttctattcg ttggcgttaa ctccagagtt  1080
ggcggtctta aggaatttgg tgctgtagct gcagcattac ttgctatgga cagattaatg  1140
acattcacac tttatacagc agtgttaacc atcatggttg aggtaaggcg tatcaaaaag  1200
gtcagagata tgactaaggc tagatctaga agttcttcta ttaccgccgt tacagccaac  1260
ggcaccgcca taagaggcgt tttgagtaga aaatcttcaa aacaatctgt gacagaacca  1320
gagacaacta aaaacctaag acaaagagcc actgattcag ccatcggtgt taagggttca  1380
ttgctgaaag atggaggcag attgcaggaa gccgaggaga atccaatggc aagattaaag  1440
ctattgttaa tcgcttcctt cttaacacta cacatcttga acttttgtac tactttgact  1500
tcagccacag ctaacgcaag acatcaaaga catcctttta gaaccgttca agaggtagta  1560
ccaattccta gagttgacat tactacccca gccatagcca atatcttgtc tcatctagct  1620
gtggctcagg aacctatgtt cactgttgtt ggcagtgaac ctatcgaact tcttgttaaa  1680
gtcgctgctc cagtctacgt ccatgctcta ccattggccc ctgctttaag agcttcaaac  1740
actaatactg gagaagctat tgaaaacttt atgagttcat ggtctagtct ggtaggtgac  1800
ccagttgtta gtaagtggat cgtagcattg ctagctgtct ctgttgcatt gaatggatac  1860
ttgttaaagg gtatagccgc aggttccggg ttggctgcca tgagagctgt tagatctcaa  1920
ggtgttcgtt tcagatctag agctagaagt atcgtaaaga tatctgatga acctgagcca  1980
```

```
gagccagaac actctatcga cccagcacca gtagtgttct tcgcttccgc agcaccagct  2040
gtagaggccc ctgctccagc tcctgcacct gaaccagaac caccagtcaa cagaccacca  2100
ccattgacta ttttctcaag accactgaac ttagaaacag tggacaaaaa gttacaagat  2160
gctctgccaa taagatcccc accacctgtt gaaccaatca ctccagaatc tagagaagtg  2220
gaaccaaccc aagtagaagt aagatctcta gctgaatgtg tggatgtgtt cgagaatggg  2280
ccaagaccag tctcagtggc tttaaagact ctgaatgatg aggaagttat cctgctttgc  2340
caaacaggta agatagctcc atatgcattg gttaagatgt tggctgattt cgatagggcc  2400
gtacgtgtca gaagagcact tattagtaga gcttcacgta caaaaacttt agaaaactca  2460
ctggttccta tgaaagatta tgattacgcc agagtcatgg gtgcctgttg tgaaaacgtt  2520
atcggataca tgccattacc actagggatt gcaggtccat tgaagattga tggcttgatg  2580
tatcctatac caatggcaac cgcagaaggt accttggttg catctacttc taggggctgt  2640
aaggccttaa atgctggtgg aggggtcaca actgtcttga cagcagatgg catgacaaga  2700
gggccagcta tagactttcc ttccatcgtc agagctgcag aggctaaggc cttcattgaa  2760
tcagaagatg gatacgctac aatcagggag gctttcgagt ctacttctag atttgccaag  2820
ttgcaaaaga tcaagtgtgc actagctggt cgtactcttt ttgtcagatt tgctactaga  2880
acaggagatg ccatgggtat gaacatgatt tctaaggcta ccgaaaaggc acttgatgtc  2940
ctgagtcacg agttccctga aatggtcgtc cttgctttgt ctggtaacta ctgcacagac  3000
aaaaagcctg cagctatttc atggatcgaa ggtaggggaa aatctattgt agcagaagca  3060
gttattcctg gtaaggtcgt taagtcagtc ctgaaaacaa cagtcgagtc tctttgcaat  3120
gtcaacacta agaaaaacct gattggttca gccatggcag gttctgttgg tggtttcaac  3180
gctcatgccg ccaacatcct aacagctgtg ttcctagcca caggtcagga tcctgctcaa  3240
aatgtcgaat cttctaattg catgacttta atggaaccaa caaacggcgg tgaggatttg  3300
ctaatgacaa tttcaatgcc atgtatagag gtaggaaccg ttggtggagg gacaattctg  3360
gaaccacaag gtgcagtttt ggatttgttg ggcgttagag ggctcaccc tactaatcct  3420
ggtcaaaacg ctcaacagtt agccagaatt atcgcatcag ctgtaatggc aggcgaattg  3480
tctttgataa gtgccttagc cgcaggtcat ttggttagag ctcatcttgc ccacaatcgt  3540
tctcaattga atacaccaat gccatccaga ccacatactc ctggccctga ggatgtctca  3600
catgtgcagc agctacctac accatctgca tctgatgata aaggtgttac agctcaaggt  3660
tacgttgtcg aagcaaaata a                                           3681
```

```
SEQ ID NO: 97           moltype = DNA  length = 2667
FEATURE                 Location/Qualifiers
misc_feature            1..2667
                        note = Synthetic oligonucleotide
source                  1..2667
                        mol_type = other DNA
                        organism = synthetic construct
SEQUENCE: 97
atgttatcaa gattgttcag aatgcatggt ctatttgttg cttctcaccc ttgggaagta  60
atagttggta ctgtaacatt aacgatctgt atgatgtcta tgaacatgtt taccggaaac  120
aacaagattt gtggttggaa ttatgagtgt cctaagctgg aagaggatgt gttgagttca  180
gacatcatca tacttactat aacaagatgc attgcaatat tgtatatcta cttccaattt  240
caaaacctta gacaattggg tagtaaatac atcctaggca tcgccggatt gttcactatt  300
ttctctagtt ttgttttctc aaccgtcgtt attcactttt tggacaaaga gttaactggt  360
ttgaacgaag ctctaccatt cttcttgctg ctggtagatt tgtccagagc ttccgcttta  420
gctaaattcg ctctgtcctc taattctcaa gatgaagtta gagagaatat agcaagggga  480
atggccatac ttggacctac tttcacactt gatgcccttg tcgaatgttt ggttattggg  540
gttggcacaa tgtccggcgt tagacagtta gaaatcatgt gttgttttgg ctgtatgagt  600
gtcttggcta actactttgt ctttatgaca ttctttccag cttgcgtttc tttggtattg  660
gagctgtcaa gagaatcaag agaaggcaga ccaatatggc aactatcaca tttcgccaga  720
gtgttagaag aggaggaaaa caaacctaat cctgtcacac agagagtgaa aatgatcatg  780
tctttgggtt tagtcctagt gcatgctcat tctagatgga tcgcagatcc atcccctcag  840
aattctacag ctgataactc taaagttagt ttaggtttag atgaaaatgt aagtaagagg  900
attgaacctt ccgtgtcttt gtggcaattc tacttatcaa aaatgatttc catggatatt  960
gaacaagtga taacgttgtc tttggcttta ttgttagccg ttaagtacat tttctttgag  1020
caagccgaaa cggaatctac attatcactg aaaaacccaa ttacatcccc agtcgttacc  1080
cagaaaaaga taactgatga ttgctgtaga agagatccag tgttggtcag gaatgatcaa  1140
aagttccacg ccatggagga ggaaactagg aaaaacagag aaaggaaagt tgaagttatc  1200
aagcctctat tagcagaaaa tgacacttca catagggcca ctttcgttgt cggcaattca  1260
tctcttttag gtacgtcatt ggagctggaa acacaggaac cagaaatgga actaccagtt  1320
gaaccaagac caaatgagga atgtttgcaa atactagaga acgctgaaaa gggagccaag  1380
ttcctatctg atgccgagat tatccagctg gtcaatgcca agcacattcc tgcctacaag  1440
ttggaaaccc ttatggagac acatgagaga ggtgtgtcta ttaggagaca attactatct  1500
aaaaagttac ctgaaccaag ttccctacaa tacctgcctt atagagatta caattactcc  1560
ttggtaatgg gagcttgttg tgaaaatgtc attgggtaca tgccaattcc agtgggtgtc  1620
gccggtccac tatgtttgga cggtaaggaa tttcaagtac ctatggcaac gactgaaggc  1680
tgcttagttg catctacaaa cagaggttgt agagccattg gattaggtgg cggtgcttct  1740
tcaagagtct tggctgacgg tatgactaga ggtcctgttg tgagatttcc tagggcctgt  1800
gactctgcag aagttaaggc ttggttggaa actccagaag gtttcaccgt aatcaaagag  1860
gcctttgatt ccacatcaag ggtggccaga ttacaaaaac tacacatgtc tgtcgctggg  1920
agaaatctgt atatcagatt tcaatccaga tccggcgacg caatgggtat gaatatgatt  1980
tcaaaaggga cagaaaaggc tttgtcaaag ctgcaggagt atttcccaga gatgcaaatc  2040
ttggccgtat ctggcaacta ttgcacagac aaaaagcctg ccgccatcaa ctggattgaa  2100
ggaagaggca aatctgtggt ttgtgaagct gtaattccag ccaaagttgt tagagaagtg  2160
ttaaagacca caacagaagc tatgattgaa gtaaacataa acaaaaactt agtagggtct  2220
gccatggctg gttcaattgg aggatacaac gctcatgctg ccaatattgt aaccgctatc  2280
tacatcgcat gtggacaaga tgctgcccaa aatgtcggtt cctcaaattg catcacattg  2340
atggaagcat ctggccctac aaacgaggat ttgtatatca gttgcacaat gccatctata  2400
gaaataggga ctgtgggagg aggaactaac ttacttccac agcaagcctg cttacaaatg  2460
```

```
ctgggtgtac aaggagcctg tagagataat ccaggggaga acgctagaca acttgccaga  2520
attgtttgtg ggacagttat ggctggtgaa cttagtctaa tggcagcttt ggctgctggg  2580
cacctggtga gatctcatat gattcataat agaagtaaga ttaaccttca agatttgcaa  2640
ggtacgtgta cgaaaaaggc tgcctaa                                       2667

SEQ ID NO: 98          moltype = DNA  length = 1704
FEATURE                Location/Qualifiers
misc_feature           1..1704
                       note = Synthetic oligonucleotide
source                 1..1704
                       mol_type = other DNA
                       organism = synthetic construct
SEQUENCE: 98
atggatttga gaaggaaatt accacctaag cctccatctt caacaacaac aaaacagcca  60
agtcataggt cccattctcc tacgccaatt ccaaaggctt cagatgcatt gcctcttcca  120
ttgtacctga ccaatacgtt tttcttcact cttttctttt ccgtagcata ttacctgttg  180
cataggtgga gagacaagat tagatccgga acacctttac acgttgtgac actgactgaa  240
ctatccgcaa ttgtactgct gattgcttcc ttcatctatc ttttaggctt tttcggtatt  300
gattttgtgc aatctttcac atcaagagaa aatgagcaac taaacaacga tgatcacaac  360
gtcgtgtcaa caaacaatgt tttatctgat agaaggttag tttacgacta tggattcgat  420
gtgacaggag acaacgataa cgataatgat gacgatgtta ttgtgaaaag tgtcgtttct  480
ggggaagtta attcttatag tttggaggct tccctaggag attgttacag agccgcaaag  540
attagaaaga gagccgtcga gagaattgtc gggagagaag tattaggctt gggtttcgag  600
ggatttgatt atgaatctat cctggggcaa tgttgtgaaa tgcctatcgg gtacgtccaa  660
gtgccagtag gtgtcgctgg acctttattg ttaaatggtg gggaattcat ggttccaatg  720
gctacaactg aaggctgtct tgtagcttcc actaatagag gttgtaaagc catatgctta  780
tcaggtggtg ccactgccat attgctaaaa gatggtatga caagagcccc agtagtgaga  840
ttcgccacag ctgagagagc ttcacaacta aagttttact tggaagatgg tgtcaatttc  900
gatacattgt ctgttgtctt taacaaaagt tcaagatttg ccagattgca aaacatccaa  960
tgctcaattg ccggtaaaaa cttgtacatt aggtttactt gctccacagg cgacgccatg  1020
ggtatgaaca tggtttcaaa aggagtacaa aatgtattag actttttaca aaatgatttt  1080
cctgatatgg acgtaattgg gatctcttgg aagttctgct ctgacaaaaa gccaacagct  1140
gtcaactgga ttgagggcag aggaaagtct gtcgttttcc aggccgtaat taccaaaaag  1200
gtggttagaa agtctgcact gaaccctcaa acttgcacat gtagaacttt gacctgttta  1260
agaccattat tggttctgct acttctggtt ttgctagtgg acttaatgca tatgcttcat  1320
atcgtgtctg ccgtgttcat cgctaccggt caagatccag ctcagaatat cgaatctagt  1380
cactgtatca ctatgatgga ggctgtcaac aatggtaagg atttgcacgt taatgttacg  1440
atgccatcta tagaagttgg cacggtggga ggtggcactc agctagcctc tcaatcagcc  1500
tgtttgaact tgcttggtgt aaagggtgcc tgtatagaat ccccaggatc aaacgcccag  1560
ttgttagcta gaatcgttgc tggttctgtt ctggcaggcg aattaagttt gatgtcagct  1620
ataagtgctg ggcaactagt taaatctcat atgaaataca ataggtctag tagagatatg  1680
tcagcaatag cttctaaggt ctaa                                          1704

SEQ ID NO: 99          moltype = DNA  length = 1308
FEATURE                Location/Qualifiers
misc_feature           1..1308
                       note = Synthetic oligonucleotide
source                 1..1308
                       mol_type = other DNA
                       organism = synthetic construct
SEQUENCE: 99
atgtttagaa gagctatact gttaggatgc tctgctgcca agacaccatg gtctgagtgt  60
tctaacgctc aattagttga tgcagttaag tctagaaaga tctcattcta cggtcttgaa  120
caagccttgg aaccagatta tagaagggct atcgaagtaa ggagagaggt tgtctctgaa  180
atcgcctcac aacagccaga agcaaaaaag aagcaatccg cattgcacac aataccattt  240
gagaattatg attggaataa ggtcgttggc caaaactgtg aaaacattat tggatacgtc  300
ccaataccac tgggcgttgc tggccctatt ttgattgatg gtaaagagta cccaatacca  360
atggctacaa cagaaggcgc tttggtcgct agtactcata gaggtgctag agctattaca  420
agatccggag gttgtaagac attgttatta ggtgaaggta tgacaagagc accagtggtt  480
gaattgcctt cattagagga agctgggcgt ttgcacaagt actgtaatga gaacttctta  540
tctttaaagg aagcatttga atcaactacc caatatggaa aacttaattc tttaaagtgc  600
gtactagctg gtagaaaagc ataccttaga ttcagagcca ctacaggcga tgctatgggc  660
atgaacatga taacaaaggg tgtagacaaa gcactgtctg ttctacagca acatttccct  720
tcaatggaaa tcctagccct aagtggtaat tactgtaccg acaaaaagcc atctgctgta  780
aattggattg atggcagagg taaatcagtg gttgcagaag ccactttatt ggctgatgtt  840
gtcgaagata ctctgaaatg tacagtcgat tctttggtat ccttgaatat cgacaaaaac  900
cttgttgggt cagctatggc tggttctgtt ggaggtttta acgcccaggc tgcaaacgct  960
gtggcagcca ttttcattgc aaccggtcaa gatcctgctc aagtggtaga aagttcaatg  1020
tgtatcacta caatgtccaa ggtaggtaac gatctattga tctctgtgac catgccttct  1080
atcgaggtcg gggtcgtggg aggagggact ggtcttgctg cccaaagagg atgcttagag  1140
ttaatagggt gcggaggccc atctaaggag tctcctggta ctaatgccca acttctaagt  1200
agagttgttg cagctggcgt tttatcagcc gaactttcct tgatgtccgg actggcagca  1260
ggtcatctat tgtcagcaca tatgagattg aacagaaaga agaaataa                1308

SEQ ID NO: 100         moltype = DNA  length = 1281
FEATURE                Location/Qualifiers
misc_feature           1..1281
                       note = Synthetic oligonucleotide
source                 1..1281
```

```
                        mol_type = other DNA
                        organism = synthetic construct
SEQUENCE: 100
atgcaatccc tggacaaaaa ctttagacac ttatcaagac aacagaagtt acaacagcta  60
gttgataaac aatggctatc agaggaacaa ttcaatattc tacttaacca cccacttatt  120
gatgaagagg tagcaaactc attgatagaa aatgtcatcg cacagggcgc actgcctgtt  180
ggtttactac caaatatcat cgttgatgac aaagcatacg tcgtgcctat gatggtggaa  240
gagccatctg ttgttgccgc tgcttcatac ggcgctaaat tggtgaacca aacaggtggt  300
ttcaaaaccg tgtcctcaga acgtatcatg ataggtcaaa tagtatttga tggagtcgat  360
gataccgaga aactgtctgc agatatcaag gctcttgaaa aacaaatcca tcagattgca  420
gatgaggctt acccttctat taaggccaga ggtggaggct atcaaaggat cgccatcgat  480
acattcccag aacaacagtt gctttcattg aaggttttcg ttgatactaa ggatgctatg  540
ggcgctaata tgttaaacac aatcctagaa gcaatcacag ccttttttgaa aaacgaattc  600
ccacaatctg atatcttgat gtctatcctt tccaaccacg caacagccag tgttgtcaag  660
gtccagggtg aaatagacgt taaggatttg gcaagaggag aacgtactgg agaagaggtc  720
gctaagagaa tggaaagagc atctgtgtta gctcaagtgg acattcatag agcagcaaca  780
cacaataagg gtgttatgaa tggcattcat gctgtagtct tggctacagg taatgatact  840
agaggtgcag aagcctctgc tcacgcttac gcttccaaag acggtcaata tagagggata  900
gctacatgga gatacgatca agagagacaa aggttaatag gaactataga agttccaatg  960
actctggcca ttgttggtgg cggtaccaag gtactgccta ttgctaaggc ctctttagaa  1020
ctgttaaacg tagaaagtgc ccaagagttg ggacatgttg tcgctgccgt tggactagct  1080
caaaacttcg ctgcatgtag agctttggtt tccgaaggta ttcaacaagg gcatatgtct  1140
ttgcaataca agtctttagc catcgtagtc ggggctaagg gcgatgaaat tgctcaggta  1200
gccgaagcac taaagcaaga gccaagagca aacactcaag ttgcagagag aattttgcaa  1260
gatttgagaa gtcaacaata a                                          1281

SEQ ID NO: 101          moltype = DNA  length = 1311
FEATURE                 Location/Qualifiers
misc_feature            1..1311
                        note = Synthetic oligonucleotide
source                  1..1311
                        mol_type = other DNA
                        organism = synthetic construct
SEQUENCE: 101
atgcaggtct taagattgga taggagacat tacaaaagtg gcaagattag aagagcaatg  60
agttctagaa ttcctggttt ctacaaattg tcagtcgagg aaagactgaa aaaggttgct  120
gaatttgcag ggttatctga tgaggaagtg aaagctgttt tgtcacaagg tttacctttg  180
gacgtagctg atagaatgat cgaaaatgtg atcggtacat ttgaattacc acttggtata  240
gcaaccaatt tccttattga tggcaaggat tatctaatcc ctatggctat agaggaacca  300
tcagtagttg cagctgcttc taacgcagct agaatggcca gagagtctgg cgggtttaca  360
actgattaca cagggtccct gatgattggt caaattcaag tcacaaaact gttgaatcca  420
aatgcagcta agttcgaagt tctacgtcaa aaagacgaaa tcatagaaag agcaaatgag  480
tgtgatccaa tgttggtgaa tttgggcggt ggatgtaaag atatagaagc aagggtgatc  540
gatacaatca tgggtaagat gctaattgtt catctgatcg ttgatgttaa agacgctatg  600
ggtgcaaatg ctgtcaacac tatgtgtgaa aaagttgctc ctttcatcga acgtattact  660
gggggaaagg tctatcttag aatcatttcc aacttggctg catatagact tgctagagca  720
aaggccgttt ttgacaaaga cgttattggc ggagaggagg ttgtagaagg gatcatgctt  780
gcatacgcct tcgctgccgc tgacccattt cgttgcgcca cccacaataa gggtatcatg  840
aatggcatat cagccttaat gatcgctaca ggaaacgact ttagagccat tgaagcagga  900
gctcattcct atgctgcaat aggtggatac aaaccactaa ctacctacga agttgataga  960
aaaggtaatc tagtaggcac aattgaaata cctatggcag taggcgtgat tggtggtgca  1020
accaaagtca acccactagc caagatctct cttaagatac taggagtgaa cactgctgaa  1080
gagttagcca gagtcgcagc cgctctaggt ttggctcaaa actttgctgc cttaagagcc  1140
ttggccacag aaggtatcca aagaggtcac atggaattac atgccaggaa cttagcaatc  1200
atggctggag ctactggaga tgaggttgac agagttgtag agattatggt gagagatggc  1260
aaaatcagat tggactacgc taaggaagta ttggagagac tgcgttccta a         1311

SEQ ID NO: 102          moltype = DNA  length = 1287
FEATURE                 Location/Qualifiers
misc_feature            1..1287
                        note = Synthetic oligonucleotide
source                  1..1287
                        mol_type = other DNA
                        organism = synthetic construct
SEQUENCE: 102
atgtccttag attcaagact gccagctttc agaaatctgt ctccagctgc aagactagat  60
cacattggcc aacttttggg actaagtcat gacgacgttt ccctttttagc aaacgccggt  120
gctttaccaa tggatatcgc taatggtatg attgaaaatg taatcgggac ctttgaactg  180
ccatatgcag tggccagtaa ctttcagatc aatggccgtg acgtcttagt accattagtt  240
gtggaggaac ctagtatcgt tgctgcagcc tcttacatgg caaagttagc tagagccaat  300
ggtgggttca ctacatcttc atctgctcca ctaatgcatg cacaagtaca aattgtcggc  360
attcaggatc cactaaacgc aagattgtct ttactgcgta gaaaggatga gatcatagaa  420
ttagccaata ggaaggacca acttctgaat tcattgggcg gtggttgcag agacatagag  480
gtgcatacat ttgccgatac tccaagagga ccaatgcttg tagcacacct tattgtcgat  540
gtgcgtgatg ccatgggagc taatactgtt aacactatgg ctgaagcagt agcacctctg  600
atggaagcca taacaggtgg ccaggtaaga ttgagaatcc tttccaattt ggctgatctt  660
agattggcca gagcccaagt gagaatcact cctcagcaat tggaaactgc cgaattctca  720
ggtgaggcag taattgaggg tatcttggac gcatatgctt ttgccgctgt ggacccttac  780
agagccgcta cccacaacaa aggcataatg aacggtatcg atcctttgat cgtcgctaca  840
```

-continued

```
ggaaatgatt ggagagctgt tgaggcagga gctcatgcat acgcttgtag atccggacat  900
tacggttcat taacaacatg ggaaaaagat aacaatggac acttggtcgg gacattggaa  960
atgcctatgc cagttggttt agttgggggt gctacaaaaa cccatcctct tgctcaattg  1020
tctttgagga tacttggtgt caaaactgct caagcactag ccgaaattgc cgttgctgtt  1080
ggtttggcac aaaacttggg tgcaatgcgt gctttagcta cagaaggcat ccaaagagga  1140
catatggctc tacacgctag aaacattgca gttgttgcag gagccagagg tgatgaggtt  1200
gattgggtgg ctagacaact tgtcgaatat catgatgtca gagcagacag ggctgtggca  1260
ttactgaaac agaagagagg tcaataa                                      1287

SEQ ID NO: 103         moltype = DNA  length = 2355
FEATURE                Location/Qualifiers
misc_feature           1..2355
                       note = Synthetic oligonucleotide
source                 1..2355
                       mol_type = other DNA
                       organism = synthetic construct
SEQUENCE: 103
atgaatttga gtttgtgtat agcatctcca ctattgacca aatctaatag accagctgct  60
ttatcagcaa ttcatacagc tagtacatcc catggtggcc aaaccaaccc tacgaatctg  120
ataatcgata cgaccaagga gagaatacaa aaacaattca aaaatgttga aatttcagtt  180
tcttcttatg atactgcgtg ggttgccatg gttccatcac ctaattctcc aaagtctcca  240
tgtttcccag aatgtttgaa ttggctgatt aacaaccagt tgaatgatgg atcttggggt  300
ttagtcaatc acacgcacaa tcacaaccat ccacttttga aagattcttt atcctcaact  360
ttggcttgca tcgtggccct aaagagatgg aacgtaggtg aggatcagat taacaagggg  420
cttagtttca ttgaatctaa cttggcttcc gcgactgaaa aatctcaacc atctccaata  480
ggattcgata tcatctttcc aggtctgtta gagtacgcca aaaatctaga tatcaactta  540
ctgtctaagc aaactgattt ctcactaatg ttacacaaga gagaattaga acaaaagaga  600
tgtcattcaa acgaaatgga tggttaccta gcttatatct ctgaaggtct tggtaatctt  660
tacgattgga atatggtgaa aaagtaccag atgaaaaatg gctcagtttt caattcccct  720
tctgcaactg cggcagcatt cattaaccat caaaatccag gatgcctgaa ctatttgaat  780
tcactactag acaaattcgg caacgcagtt ccaactgtat accctcacga tttgtttatc  840
agattgagta tggtggatac aattgaaaga cttggtatat cccaccactt tagagtcgag  900
atcaaaaatg ttttggatga gacataccgt tgttgggtgg agagagatga acaaatcttt  960
atggatgttg tgacgtgcgc gttggccttt agattgttgc gtattaacgg ttacgaagtt  1020
agtccagatc cacttgccga aattacaaac gaattagctt taaaggatga atacgccgct  1080
cttgaaacat atcatgcgtc acatatcctt taccaagagg acttatcatc tggaaaacaa  1140
attcttaaat ctgctgattt cctgaaggaa atcatatcca ctgatagtaa tagactgtcc  1200
aaactgatcc ataaagaggt tgaaaatgca cttaagttcc ctattaacac cggcttagaa  1260
cgtattaaca caagacgtaa catccagctt tacaacgtag acaatactag aatcttgaaa  1320
accacttacc attcttccaa catatcaaac actgattacc taagattagc tgttgaagat  1380
ttctacacat gtcagtctat ctatagagaa gagctgaaag gattagagag atgggtcgtt  1440
gagaataagc tagatcaatt gaaatttgcc agacaaaaga cagcttattg ttacttctca  1500
gttgccgcca ctttatcaag tccagaattg tcagatgcac gtatttcttg ggctaaaaac  1560
ggaattttga caactgttgt tgatgatttc tttgatattg gcgggacaat cgacgaattg  1620
acaaacctga ttcaatgcgt tgaaaagtgg aatgtcgatg tcgataaaga ctgttgctca  1680
gaacatgtta gaatactgtt cttggctctg aaagatgcta tctgttggat cggggatgag  1740
gctttcaaat ggcaagctag agatgtgacg tctcacgtca ttcaaacctg gctagaactg  1800
atgaactcta tgttgagaga agcaatttgg actagagatg catacgttcc tacattaaac  1860
gagtatatgg aaaacgctta tgtctccttt gctttgggtc ctatcgttaa gcctgccata  1920
tactttgtag gaccaaagct atccgaggaa atcgtcgaat catcagaata ccataacttg  1980
ttcaagttaa tgtccacaca aggcagatta cttaatgata ttcattcttt caaaagagag  2040
tttaaggaag gaaagttaaa tgctgttgct ctgcatcttt ctaatggcga aagtggtaaa  2100
gtcgaagagg aagtagttga ggaaatgatg atgatgatca aaaacaagag aaaggagttg  2160
atgaaactaa tcttcgaaga gaacggttca attgttccta gagcatgtaa ggatgcattt  2220
tggaacatgt gtcatgtgct aaactttttc tacgcaaacg acgatggttt tactgggaac  2280
acaatactag atacagtaaa agacatcata tacaaccctt tggtcttagt aaacgaaaac  2340
gaggagcaaa gataa                                                   2355

SEQ ID NO: 104         moltype = DNA  length = 2355
FEATURE                Location/Qualifiers
misc_feature           1..2355
                       note = Synthetic oligonucleotide
source                 1..2355
                       mol_type = other DNA
                       organism = synthetic construct
SEQUENCE: 104
atgaatctgt ccctttgtat agctagtcca ctgttgacaa aatcttctag accaactgct  60
ctttctgcaa ttcatactgc cagtactagt catggaggtc aaacaaaccc aacaaatttg  120
ataatcgata ctactaagga gagaatccaa aagctattca aaaatgttga aatctcagta  180
tcatcttatg acaccgcatg ggttgcaatg gtgccatcac ctaattcccc aaaaagtcca  240
tgttttccag agtgcttgaa ttggttaatc aataatcagt taaacgatgg ttcttggggt  300
ttagtcaacc acactcataa ccacaatcat ccattattga aggactcttt atcatcaaca  360
ttagcctgta ttgttgcatt gaaaagatgg aatgtaggtg aagatcaaat caacaagggt  420
ttatcattca tagaatccaa tctagcttct gctaccgaca aatcacaacc atctccaatc  480
gggttcgaca taatcttccc tggtttgctg gagtatgcca aaaaccttga tatcaactta  540
ctgtctaaac aaacagattt ctctttgatg ctacacaaaa gagagttaga gcagaaaaga  600
tgccattcta acgaaattga cgggtactta gcatatatct cagaaggttt gggtaatttg  660
tatgactgga acatggtcaa aaagtatcag atgaaaaatg gatccgtatt caattctcct  720
tctgcaactg ccgcagcatt cattaatcat caaaaccctg ggtgtcttaa ctacttgaac  780
```

```
tcactattag ataagtttgg aaatgcagtt ccaacagtct atcctttgga cttgtacatc  840
agattatcta tggttgacac tatagagaga ttaggtattt ctcatcattt cagagttgag  900
atcaaaaatg ttttggacga gacatacaga tgttgggtcg aaagagatga gcaaatcttt  960
atggatgtcg tgacctgcgc tctggctttt agattgctaa ggatacacgg atacaaagta  1020
tctcctgatc aactggctga gattacaaac gaactggctt tcaaagacga atacgccgca  1080
ttagaaacat accatgcatc ccaaatactt taccaggaag acctaagttc aggaaaacaa  1140
atcttgaagt ctgcagattt cctgaaaggc attctgtcta cagatagtaa taggttgtct  1200
aaattgatac acaaggaagt agaaaacgca ctaaagtttc ctattaacac tggtttagag  1260
agaatcaata ctaggagaaa cattcagctg tacaacgtag ataatacaag gattcttaag  1320
accacctacc atagttcaaa catttccaac acctattact taagattagc tgtcgaagac  1380
ttttacactt gtcaatcaat ctacagagag gagttaaagg gcctagaaag atgggtagtt  1440
caaaacaagt tggatcaact gaagtttgct agacagaaga cagcatactg ttatttctct  1500
gttgctgcta ccctttcatc cccagaattg tctgatgcca gaataagttg ggccaaaaat  1560
ggtattctta caactgtagt cgatgatttc tttgatattg gaggtactat tgatgaactg  1620
acaaatctta ttcaatgtgt tgaaaagtgg aacgtggatg tagataagga ttgctgcagt  1680
gaacatgtga gaatactttt cctggctcta aaagatgcaa tatgttggat tggcgacgag  1740
gccttcaagt ggcaagctag agatgttaca tctcatgtca tccaaacttg gcttgaactg  1800
atgaactcaa tgctaagaga agcaatctgg acaagagatg catacgttcc aacattgaac  1860
gaatacatgg aaaacgctta cgtctcattt gccttgggtc ctattgttaa gccagccata  1920
tactttgttg ggccaaagtt atccgaagag attgttgagt cttccgaata tcataaccta  1980
ttcaagttaa tgtcaacaca aggcagactt ctgaacgata tccactcctt caaaagagaa  2040
ttcaaggaag gtaagctaaa cgctgttgct ttgcacttgt ctaatggtga atctggcaaa  2100
gtggaagagg aagtcgttga ggaaatgatg atgatgatca aaaacaagag aaaggaattg  2160
atgaaattga ttttcgagga aaatggttca atcgtaccta gagcttgtaa agatgctttt  2220
tggaatatgt gccatgttct taacttcttt tacgctaatg atgatggctt cactggaaat  2280
acaatattgg atacagttaa agatatcatc tacaacccac ttgttttggt caatgagaac  2340
gaggaacaaa gataa                                                   2355
```

```
SEQ ID NO: 105          moltype = DNA  length = 1773
FEATURE                 Location/Qualifiers
misc_feature            1..1773
                        note = Synthetic oligonucleotide
source                  1..1773
                        mol_type = other DNA
                        organism = synthetic construct
SEQUENCE: 105
atggctatgc cagtgaagct aacacctgcg tcattatcct taaaagctgt gtgctgcaga  60
ttctcatccg gtggccatgc tttgagattc gggagtagtc tgccatgttg gagaaggacc  120
cctacccaaa gatctacttc ttcctctact actagaccag ctgccgaagt gtcatcaggt  180
aagagtaaac aacatgatca ggaagctagt gaagcgacta tcagacaaca attacaactt  240
gtggatgtcc tggagaatat gggaatatcc agacattttg ctgcagagat aaagtgcata  300
ctagacagaa cttacagatc ttggttacaa agacacgagg aaatcatgct ggacactatg  360
acatgtgcta tggcttttag aatcctaaga ttgaacggat acaacgtttc atcagatgaa  420
ctataccacg ttgtagaggc atctggtctg cataattctt tgggtgggta tcttaacgat  480
accagaacac tacttgaatt acacaaggct tcaacagtta gtatctctga ggatgaatct  540
atcttagatt caattggctc tagatccaga acattgctta gagaacaatt ggagtctggt  600
ggcgcactga gaaagccttc tttattcaaa gaggttgaac atgcactgga tggacctttt  660
tacaccacac ttgatagact tcatcatagg tggaatattg aaaacttcaa cattattgag  720
caacacatgt tggagactcc atacttatct aaccagcata catcaaggga tatcctagca  780
ttgtcaatta gagattttc ctcctcacaa ttcacttatc aacaagagct acagcatctg  840
gagagttggg ttaaggaatg tagattagat caactacagt tcgcaagaca gaaattagcg  900
tactttacc tatcagccgc aggcaccatg ttttctcctg agctttctga tgcgagaaca  960
ttatgggcca aaaacggggt gttgacaact attgttgatg atttctttga tgttgccggt  1020
tctaaagagg aattggaaaa cttagtcatg ctggtcgaaa tgtgggatga acatcacaaa  1080
gttgaattct attctgagca ggtcgaaatc atcttctctt ccatctacga ttctgtcaac  1140
caattgggtg agaaggcctc tttggttcaa gacagatcaa ttacaaaaca ccttgttgaa  1200
atatggttag acttgttaaa gtccatgatg acggaagttg aatggagact gtcaaaatac  1260
gtgcctacag aaaaggaata catgattaat gcctctctta tcttcggcct aggtccaatc  1320
gttttaccag ctttgtattt cgttggtcca aagatttcag aaagtatagt aaaggaccca  1380
gaatatgatg aattgttcaa actaatgtca acatgtggta gattgttgaa tgacgtgcaa  1440
acgttcgaaa gagaatacaa tgagggtaaa ctgaattctg tcagtctatt ggttcttcac  1500
ggaggcccaa tgtctatttc agacgcaaag aggaaattac aaaagcctat tgatacgtgt  1560
agaagagatc ttctttcttt ggtccttaga gaagagtctg tagtaccaag accatgtaag  1620
gaactattct ggaaaatgtg taaagtgtgc tatttctttt actcaacaac tgatgggttt  1680
tctagtcaag tcgaaagagc aaaagaggta gacgctgtca taaatgagcc actgaagttg  1740
caaggttctc atacactggt atctgatgtt taa                               1773
```

```
SEQ ID NO: 106          moltype = DNA  length = 2232
FEATURE                 Location/Qualifiers
misc_feature            1..2232
                        note = Synthetic oligonucleotide
source                  1..2232
                        mol_type = other DNA
                        organism = synthetic construct
SEQUENCE: 106
atgcagaact tccatggtac aaaggaaagg atcaaaaaga tgtttgacaa gattgaattg  60
tccgtttctt cttatgatac agcctgggtt gcaatggtcc catcccctga ttgcccagaa  120
acaccttgtt ttccagaatg tactaaatgg atcctagaaa atcagttggg tgatggtagt  180
tggtcacttc ctcatggcaa tccacttcta gttaaagatg cattatcttc cactcttgct  240
```

```
tgtattctgg ctcttaaaag atggggaatc ggtgaggaac agattaacaa aggactgaga  300
ttcatagaac tcaactctgc tagtgtaacc gataacgaac aacacaaacc aattggattt  360
gacattatct ttccaggtat gattgaatac gctatagact tagacctgaa tctaccacta  420
aaaccaactg acattaactc catgttgcat cgtagagccc ttgaattgac atcaggtgga  480
ggcaaaaatc tagaaggtag aagagcttac ttggcctacg tctctgaagg aatcggtaag  540
ctgcaagatt gggaaatggc tatgaaatac caacgtaaaa acggatctct gttcaatagt  600
ccatcaacaa ctgcagctgc attcatccat atacaagatg ctgaatgcct ccactatatt  660
cgttctcttc tccagaaatt tggaaacgca gtccctacaa tataccctct cgatatctat  720
gccagacttt caatggtaga tgccctggaa cgtcttggta ttgatagaca tttcagaaag  780
gagagaaagt tcgttctgga tgaaacatac agattttggt tgcaaggaga agaggagatt  840
ttctccgata acgcaacctg tgctttggcc ttcagaatat tgagacttaa tggttacgat  900
gtctctcttg aagatcactt ctctaactct ctgggcggtt acttaaagga ctcaggagca  960
gctttagaac tgtacagagc cctccaattg tcttacccag acgagtccct cctggaaaag  1020
caaaattcta gaacttctta cttcttaaaa caaggtttat ccaatgtctc cctctgtggt  1080
gacagattgc gtaaaaacat aattggagag gtgcatgatg ctttaaactt ttccgaccac  1140
gctaacttac aaagattagc tattcgtaga aggattaagc attacgctac tgacgataca  1200
aggattctaa aaacttccta cagatgctca acaatcggta accaagattt tctaaaactt  1260
gcagtggaag atttcaatat ctgtcaatca atacaaagag aggaattcaa gcatattgaa  1320
agatgggtcg ttgaaagacg tctagacaag ttaaagttcg ctagacaaaa agaggcctat  1380
tgctatttct cagccgcagc aacattgttt gcccctgaat tgtctgatgc tagaatgtct  1440
tgggccaaaa atggtgtatt gacaactgtg gttgatgatt tcttcgatgt cggaggctct  1500
gaagaggaat tagttaactt gatagaattg atcgagcgtt gggatgtgaa tggcagtgca  1560
gatttttgta gtgaggaagt tgagattatc tattctgcta tccactcaac tatctctgaa  1620
ataggtgata agtcatttgg ctggcaaggt agagatgtaa agtctcaagt tatcaagatc  1680
tggctggact tattgaaatc aatgttaact gaagctcaat ggtcttcaaa caagtctgtt  1740
cctaccctag atgagtatat gacaaccgcc catgtttcat tcgcacttgg tccaattgta  1800
cttccagcct tatacttcgt tggcccaaag ttgtcagaag aggttgcagg tcatcctgaa  1860
ctactaaacc tctacaaagt cacatctact tgtggcagac tactgaatga ttggagaagt  1920
tttaagagag aatccgagga aggtaagctc aacgctatta gtttatacat gatccactcc  1980
ggtggtgctt ctacagaaga ggaaacaatc gaacatttca aaggtttgat tgattctcag  2040
agaaggcaac tgttacaatt ggtgttgcaa gagaaggata gtatcatacc tagaccatgt  2100
aaagatctat tttggaatat gattaagtta ttacacactt tctacatgaa agatgatggc  2160
ttcacctcaa atgagatgag gaatgtagtt aaggcaatca ttaacgaacc aatctcactg  2220
gatgaattat ga                                                     2232
```

```
SEQ ID NO: 107          moltype = DNA  length = 1542
FEATURE                 Location/Qualifiers
misc_feature            1..1542
                        note = Synthetic oligonucleotide
source                  1..1542
                        mol_type = other DNA
                        organism = synthetic construct
SEQUENCE: 107
atggatgctg tgacgggttt gttaactgtc ccagcaaccg ctataactat tggtggaact  60
gctgtagcat tggcggtagc gctaatcttt tggtacctga aatcctacac atcagctaga  120
agatcccaat caaatcatct tccaagagtg cctgaagtcc caggtgttcc attgttagga  180
aatctgttac aattgaagga gaaaaagcca tacatgactt ttacgagatg ggcagcgaca  240
tatggaccta tctatagtat caaaactggg gctacaagta tggttgtggt atcatctaat  300
gagatagcca aggaggcatt ggtgaccaga ttccaatcca tatctacaag gaacttatct  360
aaagccctga aagtacttac agcagataag acaatggtcg caatgtcaga ttatgatgat  420
tatcataaaa cagttaagag acacatactg accgccgtct tgggtcctaa tgcacagaaa  480
aagcatagaa ttcacagaga tatcatgatg gataacatat ctactcaact tcatgaattc  540
gtgaaaaaca acccagaaca ggaagaggta gaccttagaa aaatctttca atctgagtta  600
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatcg atgttgattg gagagacttc tttccatacc taaagtgggt cccaaacaaa  780
aagttcgaaa atactattca acaaatgtac atcagaagag aagctgttat gaaatcttta  840
atcaaagagc acaaaaagag aatagcgtca ggcgaaaagc taaatagtta tatcgattac  900
cttttatctg aagctcaaac tttaaccgat cagcaactat tgatgtcctt gtgggaacca  960
atcattgaat cttcagatac aacaatggtc acaacagaat gggcaatgta cgaattagct  1020
aaaaacccta aattgcaaga taggttgtac agagacatta agtccgtctg tggatctgaa  1080
aagataaccg aagagcatct atcacagctg ccttacatta cagctatttt ccacgaaaca  1140
ctgagaagac actcaccagt tcctatcatt cctctaagac atgtacatga agataccgtt  1200
ctaggcggct accatgttcc tgctggcaca gaacttgccg ttaacatcta cggttgcaac  1260
atggacaaaa acgtttggga aaatccagag gaatggaacc cagaaagatt catgaaagag  1320
aatgagacaa ttgattttca aaagacgatg gccttcggtg gtggtaagag agtttgtgct  1380
ggttccttgc aagccctttt aactgcatct attgggattg ggagaatggt tcaagagttc  1440
gaatggaaac tgaaggatat gactcaagag gaagtgaaca cgataggcct aactacacaa  1500
atgttaagac cattgagagc tattatcaaa cctaggatct aa                    1542
```

```
SEQ ID NO: 108          moltype = DNA  length = 1530
FEATURE                 Location/Qualifiers
misc_feature            1..1530
                        note = Synthetic oligonucleotide
source                  1..1530
                        mol_type = other DNA
                        organism = synthetic construct
SEQUENCE: 108
atggcatttt tctctatgat ttcaattttg ttgggatttg ttatttcttc tttcatcttc  60
```

-continued

```
atctttttct tcaaaaagtt acttagtttt agtaggaaaa acatgtcaga agtttctact  120
ttgccaagtg ttccagtagt gcctggtttt ccagttattg ggaatttgtt gcaactaaag  180
gagaaaaagc ctcataaaac tttcactaga tggtcagaga tatatggacc tatctactct  240
ataaagatgg gttcttcatc tcttattgta ttgaacagta cagaaactgc taaggaagca  300
atggtcacta gattttcatc aatatctacc agaaaattgt caaacgccct aacagttcta  360
acctgcgata agtctatggt cgccacttct gattatgatg acttccacaa attagttaag  420
agatgtttgc taaatggact tcttggtgct aatgctcaaa agagaaaaag acactacaga  480
gatgctttga ttgaaaatgt gagttccaag ctacatgcac acgctagaga tcatccacaa  540
gagccagtta actttagagc aattttcgaa cacgaattgt ttggtgtagc attaaagcaa  600
gccttcggta aagacgtaga atccatatac gtcaaggagt taggcgtaac attatcaaaa  660
gatgaaatct ttaaggtgct tgtacatgat atgatggagg gtgcaattga tgtagattgg  720
agagatttct tcccatattt gaaatggatc cctaataagt cttttgaagc taggatacaa  780
caaaagcaca agagaagact agctgttatg aacgcactta tacaggacag attgaagcaa  840
aatgggtctg aatcagatga tgattgttac cttaacttct taatgtctga ggctaaaaca  900
ttgactaagg aacagatcgc aatccttgtc tgggaaacaa tcattgaaac agcagatact  960
accttagtca caactgaatg ggccatatac gagctagcca aacatccatc tgtgcaagat  1020
aggttgtgta aggagatcca gaacgtgtgt ggtggagaga aattcaagga agagcagttg  1080
tcacaagttc cttaccttaa cggcgttttc catgaaacct tgagaaaata ctcacctgca  1140
ccattagttc ctattagata cgcccacgaa gatacacaaa tcggtggcta ccatgttcca  1200
gctgggtccg aaattgctat aaacatctac gggtgcaaca tggacaaaaa gagatgggaa  1260
agaccagaag attggtggcc agaaagattc ttagatgatg gcaaatatga aacatctgat  1320
ttgcataaaa caatggcttt cggagctggc aaaagagtgt gtgccggtgc tctacaagcc  1380
tccctaatgg ctggtatcgc tattggtaga ttggtccaag agttcgaatg gaaacttaga  1440
gatggtgaag aggaaaatgt cgatacttat gggttaacat ctcaaaagtt atacccacta  1500
atggcaatca tcaatcctag aagatcctaa                                    1530

SEQ ID NO: 109          moltype = DNA  length = 1578
FEATURE                 Location/Qualifiers
misc_feature            1..1578
                        note = Synthetic oligonucleotide
source                  1..1578
                        mol_type = other DNA
                        organism = synthetic construct
SEQUENCE: 109
atgagtaagt ctaatagtat gaattctaca tcacacgaaa ccctttttca acaattggtc  60
ttgggtttgg accgtatgcc attgatggat gttcactggt tgatctacgt tgctttcggc  120
gcatggttat gttcttatgt gatacatgtt ttatcatctt cctctacagt aaaagtgcca  180
gttgttggat acaggtctgt attcgaacct acatggttgc ttagacttag attcgtctgg  240
gaaggtggct ctatcatagg tcaagggtac aataagttta aagactctat tttccaagtt  300
aggaaattgg gaactgatat tgtcattata ccacctaact atattgatga agtgagaaaa  360
ttgtcacagg acaagactag atcagttgaa cctttcatta atgattttgc aggtcaatac  420
acaagaggca tggttttctt gcaatctgac ttacaaaacc gtgttataca acaaagacta  480
actccaaaat tggtttcctt gaccaaggtc atgaaggaag agttggatta tgctttaaca  540
aaagagatgc ctgatatgaa aaatgacgaa tgggtagaag tagatatcag tagtataatg  600
gtgagattga tttccaggat ctccgccaga gtctttctag ggcctgaaca ctgtcgtaac  660
caggaatggt tgactactac agcagaatat tcagaatcac ttttcattac agggtttatc  720
ttaagagttg tacctcatat cttaagacca ttcatcgccc ctctattacc ttcatacagg  780
actctactta gaaacgtttc aagtggtaga agagtcatcg gtgacatcat aagatctcag  840
caaggggatg gtaacgaaga tatactttcc tggatgagag atgctgccac aggagaggaa  900
aagcaaatcg ataacattgc tcagagaatg ttaattcttt ctttagcatc aatccacact  960
actgcgatga ccatgacaca tgccatgtac gatctatgtg cttgccctga gtacattgaa  1020
ccattaagag atgaagttaa atctgttgtt ggggcttctg gctgggacaa gacagcgtta  1080
aacagatttc ataagttgga ctccttccta aaagagtcac aaagattcaa cccagtattc  1140
ttattgacat tcaatagaat ctaccatcaa tctatgacct tatcagatgg cactaacatt  1200
ccatctggaa cacgtattgc tgttccatca cacgcaatgt tgcaagattc tgcacatgtc  1260
ccaggtccaa ccccacctac tgaatttgat ggattcagat atagtaagat acgttctgat  1320
agtaactacg cacaaaagta cctattctcc atgaccgatt cttcaaacat ggctttcgga  1380
tacggcaagt atgcttgtcc aggtagattt tacgcgtcta atgagatgaa actaacatta  1440
gccattttgt tgctacaatt tgagttcaaa ctaccagatg gtaaaggtcg tcctagaaat  1500
atcactatcg attctgatat gattccagac ccaagagcta gactttgcgt cagaaaaaga  1560
tcacttagag atgaatga                                                 1578

SEQ ID NO: 110          moltype = DNA  length = 1500
FEATURE                 Location/Qualifiers
misc_feature            1..1500
                        note = Synthetic oligonucleotide
source                  1..1500
                        mol_type = other DNA
                        organism = synthetic construct
SEQUENCE: 110
atggaagatc ctactgtctt atatgcttgt cttgccattg cagttgcaac tttcgttgtt  60
agatggtaca gagatccatt gagatccatc ccaacagttg gtggttccga tttgcctatt  120
ctatcttaca tcggcgcact aagatggaca agacgtggca gagagatact tcaagaggga  180
tatgatggct acagaggatc tacattcaaa atcgcgatgt tagaccgttg gatcgtgatc  240
gcaaatggtc ctaaactagc tgatgaagtc agacgtagac cagatgaaga gttaaacttt  300
atggacggat taggagcatt cgtccaaact aagtacacct taggtgaagc tattcataac  360
gatccatacc atgtcgatat cataagagaa aaactaacaa gaggccttcc agccgtgctt  420
cctgatgtca ttgaagagtt gacacttgcg gttagacagt acattccaac agaaggtgat  480
gaatgggtgt ccgtaaactg ttcaaaggcc gcaagagata ttgttgctag agcttctaat  540
```

```
agagtctttg taggtttgcc tgcttgcaga aaccaaggtt acttagattt ggcaatagac  600
tttacattgt ctgttgtcaa ggatagagcc atcatcaata tgtttccaga attgttgaag  660
ccaatagttg gcagagttgt aggtaacgcc accagaaatg ttcgtagagc tgttcctttt  720
gttgctccat tggtggagga aagacgtaga cttatggaag agtacggtga agactggtct  780
gaaaaaccta atgatatgtt acagtggata atggatgaag ctgcatccag agatagttca  840
gtgaaggcaa tcgcagagag attgttaatg gtgaacttcg cggctattca tacctcatca  900
aacactatca ctcatgcttt gtaccacctt gccgaaatgc ctgaaacttt gcaaccactt  960
agagaagaga tcgaaccatt agtcaaagag gagggctgga ccaaggctgc tatgggaaaa  1020
atgtggtggt tagattcatt tctaagagaa tctcaaagat acaatggcat taacatcgta  1080
tctttaacta gaatggctga caaagatatt acattgagtg atggcacatt tttgccaaaa  1140
ggtactctag tggccgttcc agcgtattct actcatagag atgatgctgt ctacgctgat  1200
gccttagtat tcgatccttt cagattctca cgtatgagag cgagagaagg tgaaggtaca  1260
aagcaccagt tcgttaatac ttcagtcgag tacgttccat ttggtcacgg aaagcatgct  1320
tgtccaggaa gattcttcgc cgcaaacgaa ttgaaagcaa tgttggctta cattgttcta  1380
aactatgatg taaagttgcc tggtgacggt aaacgtccat tgaacatgta ttggggtcca  1440
acagttttgc ctgcaccagc aggccaagta ttgttcagaa agagacaagt tagtctataa  1500
```

```
SEQ ID NO: 111         moltype = DNA  length = 1578
FEATURE                Location/Qualifiers
misc_feature           1..1578
                       note = Synthetic oligonucleotide
source                 1..1578
                       mol_type = other DNA
                       organism = synthetic construct
SEQUENCE: 111
atgggtttgt tcccattaga ggattcctac gcgctggtct ttgaaggact agcaataaca  60
ctggctttgt actatctact gtctttcatc tacaaaacat ctaaaaagac atgtacacct  120
cctaaagcat ctggtgaaat cattccaatt acaggaatca tattgaatct gctatctggc  180
tcaagtggtc tacctattat cttagcactt gcctctttag cagacagatg tggtcctatt  240
ttcaccatta ggctgggtat taggagagtg ctagtagtat caaattggga aatcgctaag  300
gagattttca ctacccacga tttgatagtt tctaatagac caaaatactt agccgctaag  360
attcttggtt tcaattatgt ttcattctct ttcgctccat acggcccata ttgggtcgga  420
atcagaaaga ttattgctac aaaactaatg tcttcttcca gacttcagaa gttgcaattt  480
gtaagagttt ttgaactaga aaactctatg aaatctatca gagaatcatg gaaggagaaa  540
aaggatgaag agggaaaggt attagttgag atgaaaaagt ggttctggga actgaatatg  600
aacatagtgt taaggacagt tgctggtaaa caatacactg gtacagttga tgatgccgat  660
gcaaagcgta tctccgagtt attcagagaa tggtttcact acactggcag atttgtcgtt  720
ggagacgctt ttccttttct aggttggttg gacctgggcg gatacaaaaa gacaatggaa  780
ttagttgcta gtagattgga ctcaatggtc agtaaatggt tagatgagca tcgtaaaaag  840
caagctaacg atgacaaaaa ggaggatatg gatttcatgg atatcatgat ctccatgaca  900
gaagcaaatt caccacttga aggatacggc actgatacta ttatcaagac cacatgtatg  960
actttgattg tttcaggagt tgatacaacc tcaatcgtac ttacttgggc cttatcactt  1020
ttgttaaaca acagagatac tttgaaaaag gcacaagagg aattagatat gtgcgtaggt  1080
aaaggaagac aagtcaacga gtctgatctt gttaacttga tatacttgga agcagtgctt  1140
aaagaggctt taagacttta cccagcagcg ttcttaggcg gaccaagagc attcttggaa  1200
gattgtactg ttgctggtta tagaattcca aagggcacct gcttgttgat taacatgtgg  1260
aaactgcata gagatccaaa catttggagt gatccttgcg aattcaagcc agaaagattt  1320
ttgacaccta atcaaaagga tgttgatgtg atcggtatgg atttcgaatt gataccattt  1380
ggtgccggca gaagatattg tccaggtact agattggctt tacagatgtt gcatatcgta  1440
ttagcgacat tgctgcaaaa cttcgaaatg tcaacaccaa acgatgcgcc agtcgatatg  1500
actgcttctg ttggcatgac aaatgccaaa gcatcacctt tagaagtctt gctatcacct  1560
cgtgttaaat ggtcctaa                                                1578
```

```
SEQ ID NO: 112         moltype = DNA  length = 1431
FEATURE                Location/Qualifiers
misc_feature           1..1431
                       note = Synthetic oligonucleotide
source                 1..1431
                       mol_type = other DNA
                       organism = synthetic construct
SEQUENCE: 112
atgatacaag ttttaactcc aattctactc ttcctcatct tcttcgtttt ctggaaagtc  60
tacaaacatc aaaagactaa aatcaatcta ccaccaggtt ccttcggctg gccatttttg  120
ggtgaaacct tagccttact tagagcaggc tgggattctg agccagaaag attcgtaaga  180
gagcgtatca aaaagcatgg atctccactt gttttcaaga catcactatt tggagacaga  240
ttcgctgttc tttgcggtcc agctggtaat aagtttttgt tctgcaacga aaacaaatta  300
gtggcatctt ggtggccagt ccctgtaagg aagttgttcg gtaaaagttt actcacaata  360
agaggagatg aagcaaaatg gatgagaaaa atgctattgt cttacttggg tccagatgca  420
tttgccacac attatgccgt tactatggat gttgtaacac gtagacatat tgatgtccat  480
tggaggggca aggaggaagt taatgtattt caaacagtta agttgtacgc attcgaatta  540
gcttgtagat tattcatgaa cctagatgac ccaaaccaca tcgcgaaact cggtagtctt  600
ttcaacattt tcctcaaagg gatcatcgag cttcctatag acgttcctgg aactagattt  660
tactccagta aaaaggccgc agctgccatt agaattgaat tgaaaaagct cattaaagct  720
agaaaactcg aattgaagga gggtaaggcg tcttcttcac aggacttgct ttctcatcta  780
ttaacatcac ctgatgagaa tgggatgttc ttgacagaag aggaaatagt cgataacatt  840
ctacttttgt tattcgctgg tcacgatacc tctgcactat caataacact tttgatgaaa  900
accttaggtg aacacagtga tgtgtacgac aaggttttga aggaacaatt agaaatttcc  960
aaaacaaagg aggcttggga atcactaaag tgggaagata tccagaagat gaagtactca  1020
tggtcagtaa tctgtgaagt catgagattg aatcctcctg tcatagggac atacagagag  1080
```

```
gcgttggttg atatcgacta tgctggttac actatcccaa aaggatggaa gttgcattgg  1140
tcagctgttt ctactcaaag agacgaagcc aatttcgaag atgtaactag attcgatcca  1200
tccagatttg aaggggcagg ccctactcca ttcacatttg tgcctttcgg tggaggtcct  1260
agaatgtgtt taggcaaaga gtttgccagg ttagaagtgt tagcatttct ccacaacatt  1320
gttaccaact ttaagtggga tcttctaatc cctgatgaga agatcgaata tgatccaatg  1380
gctactccag ctaagggctt gccaattaga cttcatccac accaagtcta a           1431

SEQ ID NO: 113          moltype = DNA  length = 1578
FEATURE                 Location/Qualifiers
misc_feature            1..1578
                        note = Synthetic oligonucleotide
source                  1..1578
                        mol_type = other DNA
                        organism = synthetic construct
SEQUENCE: 113
atggagtctt tagtggttca tacagtaaat gctatctggt gtattgtaat cgtcgggatt  60
ttctcagttg gttatcacgt ttacggtaga gctgtggtcg aacaatggag aatgagaaga  120
tcactgaagc tacaaggtgt taaaggccca ccaccatcca tcttcaatgg taacgtctca  180
gaaatgcaac gtatccaatc cgaagctaaa cactgctctg gcgataacat tatctcacat  240
gattattctt cttcattatt cccacacttc gatcactgga gaaaacagta cggcagaatc  300
tacacatact ctactggatt aaagcaacac ttgtacatca atcatccaga aatggtgaag  360
gagctatctc agactaacac attgaacttg ggtagaatca cccatataac caaaagattg  420
aatcctatct taggtaacgg aatcataacc tctaatggtc ctcattgggc ccatcagcgt  480
agaattatcg cctacgagtt tactcatgat aagatcaagg gtatggttgg tttgatggtt  540
gagtctgcta tgcctatgtt gaataagtgg gaggagatgg taaagagagg cggagaaatg  600
ggatgcgaca taagagttga tgaggacttg aaagatgttt cagcagatgt gattgcaaaa  660
gcctgtttcg gatcctcatt ttctaaaggt aaggctattt tctctatgat aagagatttg  720
cttacagcta tcacaaagag aagtgttcta ttcagattca acggattcac tgatatggtc  780
tttgggagta aaaagcatgg tgacgttgat atagacgctt tagaaatgga attggaatca  840
tccatttggg aaactgtcaa ggaacgtgaa atagaatgta aagatactca caaaaaggat  900
ctgatgcaat tgattttgga aggggcaatg cgttcatgtg acggtaacct ttgggataaa  960
tcagcatata gaagatttgt tgtagataat tgtaaatcta tctacttcgc agggcatgat  1020
agtacagctg tctcagtgtc atggtgtttg atgttactgg ccctaaaccc atcatggcaa  1080
gttaagatcc gtgatgaaat tctgtcttct tgcaaaaatg gtattccaga tgccgaaagt  1140
atcccaaacc ttaaaacagt gactatggtt attcaagaga caatgagatt ataccctcca  1200
gcaccaatcg tcgggagaga agcctctaaa gatatcagat tgggcgatct agttgttcct  1260
aaaggcgtct gtatatggac actaatacca gctttacaca gagatcctga gatttgggga  1320
ccagatgcaa acgatttcaa accagaaaga ttttctgaag gaatttcaaa ggcttgtaag  1380
tatcctcaaa gttacattcc atttggtctg ggtcctagaa catgcgttgg taaaaacttt  1440
ggcatgatgg aagtaaaggt tcttgtttcc ctgattgtct ccaagttctc tttcactcta  1500
tctcctacct accaacatag tcctagtcac aaacttttag tagaaccaca acatggggtg  1560
gtaattagag tggtttaa                                                1578

SEQ ID NO: 114          moltype = DNA  length = 1590
FEATURE                 Location/Qualifiers
misc_feature            1..1590
                        note = Synthetic oligonucleotide
source                  1..1590
                        mol_type = other DNA
                        organism = synthetic construct
SEQUENCE: 114
atgtacttcc tactacaata cctcaacatc acaaccgttg gtgtctttgc cacattgttt  60
ctctcttatt gtttacttct ctggagaagt agagcgggta acaaaaagat tgccccagaa  120
gctgccgctg catggcctat tatcggccac ctccacttac ttgcaggtgg atcccatcaa  180
ctaccacata ttacattggg taacatggca gataagtacg gtcctgtatt cacaatcaga  240
ataggcttgc atagagctgt agttgtctca tcttgggaaa tggcaaagga atgttcaaca  300
gctaatgatc aagtgtcttc ttcaagacct gaactattag cttctaagtt gttgggttat  360
aactacgcca tgtttggttt ttcaccatac ggttcatact ggagagaaat gagaaagatc  420
atctctctcg aattactatc taattccaga ttggaactat tgaaagatgt tagagcctca  480
gaagttgtca catctattaa ggaactatac aaattgtggg cggaaaagaa gaatgagtca  540
ggattggttt ctgtcgagat gaaacaatgg ttcggagatt tgactttaaa cgtgatcttg  600
agaatggtgg ctggtaaaag atacttctcc gcgagtgacg cttcagaaaa caaacaggcc  660
cagcgttgta gaagagtctt cagagaattc ttccatctct ccggcttgtt tgtggttgct  720
gatgctatac cttttcttgg atggctcgat tggggaagac acgagaagac cttgaaaaag  780
accgccatag aaatggattc catcgcccag gagtggcttg aggaacatag acgtagaaaa  840
gattctggag atgataattc tacccaagat ttcatggacg ttatgcaatc tgtgctagat  900
ggcaaaaatc taggcggata cgatgctgat acgattaaca aggctacatg cttaactctt  960
atatcaggtg gcagtgatac tactgtagtt tctttgacat gggctcttag tcttgtgtta  1020
aacaatagag atactttgaa aaaggcacag gaagagttag acatccaagt cggtaaggaa  1080
agattggtta acgagcaaga catcagtaag ttagtttact tgcaagcaat agtaaaagag  1140
acactcagac tttatccacc aggtcctttg ggtggtttga gacaattcac tgaagattgt  1200
acactaggtg gctatcacgt ttcaaaagga actagattaa tcatgaactt atccaagatt  1260
caaaaagatc cacgtatttg gtctgatcct actgaattcc aaccagagag attccttacg  1320
actcataaag atgtcgatcc acgtggtaaa cactttgaat tcattccatt cggtgcagga  1380
agacgtgcat gtcctggtat cacattcgga ttacaagtac tacatctaac attggcatct  1440
ttcttgcatg cgtttgaatt ttcaacacca tcaaatgagc aggttaacat gagagaatca  1500
ttaggtctta cgaatatgaa atctacccca ttagaagttt tgatttctcc aagactatcc  1560
cttaattgct tcaaccttat gaaaatttga                                    1590
```

```
SEQ ID NO: 115         moltype = DNA  length = 1440
FEATURE                Location/Qualifiers
misc_feature           1..1440
                       note = Synthetic oligonucleotide
source                 1..1440
                       mol_type = other DNA
                       organism = synthetic construct
SEQUENCE: 115
atggaaccta acttttactt gtcattacta ttgttgttcg tgaccttcat ttctttaagt  60
ctgtttttca tcttttacaa acaaaagtcc ccattgaatt tgccaccagg gaaaatgggt  120
taccctatca taggtgaaag tttagaattc ctatccacag gctggaaggg acatcctgaa  180
aagttcatat ttgatagaat gcgtaagtac agtagtgagt tattcaagac ttctattgta  240
ggcgaatcca cagttgtttg ctgtggggca gctagtaaca aattcctatt ctctaacgaa  300
aacaaactgg taactgcctg gtggccagat tctgttaaca aaatcttccc aacaacttca  360
ctggattcta atttgaagga ggaatctata aagatgagaa agttgctgcc acagttcttc  420
aaaccagaag cacttcaaag atacgtcggc gttatggatg taatcgcaca aagacatttt  480
gtcactcact gggacaacaa aaatgagatc acagtttatc cacttgctaa aagatacact  540
ttcttgcttg cgtgtagact gttcatgtct gttgaggatg aaaatcatgt ggcgaaattc  600
tcagacccat tccaactaat cgctgcaggc atcatttcac ttcctatcga tcttcctggt  660
actccattca acaaggccat aaaggcttca aatttcatta gaaaagagct gataaagatt  720
atcaaacaaa gacgtgttga tctggcagag ggtacagcat ctccaaccca ggatatcttg  780
tcacatatgc tattaacatc tgatgaaaac ggtaaatcta tgaacgagtt gaacattgcc  840
gacaagattc ttggactatt gataggaggc cacgatacag cttcagtagc ttgcacattt  900
ctagtgaagt acttaggaga attaccacat atctacgata aagtctacca agagcaaatg  960
gaaattgcca agtccaaacc tgctggggaa ttgttgaatt gggatgactt gaaaaagatg  1020
aagtattcat ggaatgtggc atgtgaggta atgagattgt caccaccttt acaaggtggt  1080
tttagagagg ctataactga ctttatgttt aacggtttct ctattccaaa agggtggaag  1140
ttatactggt ccgccaactc tacacacaaa aatgcagaat gtttcccaat gcctgagaaa  1200
ttcgatccta ccagatttga aggtaatggt ccagcgcctt atacatttgt accattcggt  1260
ggaggcccta gaatgtgtcc tggaaaggaa tacgctagat tagaaatctt ggtttttcatg  1320
cataatctgg tcaaacgttt taagtgggaa aaggttattc cagacgaaaa gattattgtc  1380
gatccattcc caatcccagc taaagatctt ccaatccgtt tgtatcctca caaagcttaa  1440

SEQ ID NO: 116         moltype = DNA  length = 2133
FEATURE                Location/Qualifiers
misc_feature           1..2133
                       note = Synthetic oligonucleotide
source                 1..2133
                       mol_type = other DNA
                       organism = synthetic construct
SEQUENCE: 116
atgcaatcag attcagtcaa agtctctcca tttgatttgg tttccgctgc tatgaatggc  60
aaggcaatgg aaaagttgaa cgctagtgaa tctgaagatc caacaacatt gcctgcacta  120
aagatgctag ttgaaaatag agaattgttg acactgttca caacttcctt cgcagttctt  180
attgggtgtc ttgtatttct aatgtggaga cgttcatcct ctaaaaagct ggtacaagat  240
ccagttccac aagttatcgt tgtaaagaag aaagagaagg agtcagaggt tgatgacggg  300
aaaaagaaag tttctatttt ctacggcaca caaacaggaa ctgccgaagg ttttgctaaa  360
gcattagtcg aggaagcaaa agtgagatat gaaaagacct ctttcaaggt tatcgatcta  420
gatgactacg ctgcagatga tgatgaatat gaggaaaaac tgaaaaagga atccttagcc  480
ttcttcttct tggccacata cggtgatggt gaacctactg ataatgctgc taacttctac  540
aagtggttca cagaaggcga cgataaaggt gaatggctga aaaagttaca atacggagta  600
tttggtttag gtaacagaca atatgaacat ttcaacaaga tcgctattgt agttgatgat  660
aaacttactg aaatgggagc caaaagatta gtaccagtag gattagggga tgatgatcag  720
tgtatagaag atgacttcac cgcctggaag gaattggtat ggccagaatt ggatcaactt  780
ttaagggacg aagatgatac ttctgtgact accccataca ctgcagccgt attggagtac  840
agagtggttt accatgataa accagcagac tcatatgctg aagatcaaac ccatacaaac  900
ggtcatgttg ttcatgatgc acagcatcct tcaagatcta atgtggcttt caaaaaggaa  960
ctacacacct ctcaatcaga taggtcttgt actcacttag aattcgatat ttctcacaca  1020
ggactgtctt acgaaactgg cgatcacgtt ggcgtttatt ccgagaactt gtccgaagtt  1080
gtcgatgaag cactaaaact gttagggtta tcaccagaca catacttctc agtccatgct  1140
gataaggagg atgggacacc tatcggtggt gcttcactac caccaccttt tcctccttgc  1200
acattgagag acgctctaac cagatacgca gatgtcttat cctcacctaa aaaggtagct  1260
ttgctggcat tggctgctca tgctagtgat cctagtgaag ccgataggtt aaagttcctg  1320
gcttcaccag ccggaaaaga tgaatatgca caatggatcg tcgccaacca acgttctttg  1380
ctagaagtga tgcaaagttt tccatctgcc aagcctccat taggtgtgtt cttcgcagca  1440
gtagctccac gtttacaacc aagatactac tctatcagtt catctcctaa gatgtctcct  1500
aacagaatac atgttacatg tgctttggtg tacgagacta ctccagcagg cagaattcac  1560
agaggattgt gttcaacctg gatgaaaaat gctgtccctt taacagagtc acctgattgc  1620
tctcaagcat ccattttcgt tagaacatca aatttcagac ttccagtgga tccaaaagtt  1680
ccagtcatta tgataggacc aggcactggt cttgccccat tcaggggctt tcttcaagag  1740
agattggcct tgaaggaatc tggtacagaa ttgggttctt ctatcttttt ctttggttgc  1800
cgtaatagaa aagttgactt tatctacgag gacgagctta acaattttgt tgagacagga  1860
gcattgtcag aattgatcgt cgcattttca agagaaggga ctgccaaaga gtacgttcag  1920
cacaagatga gtcaaaaagc ctccgatata tggaaacttc taagtgaagg tgcctatctt  1980
tatgtctgtg gcgatgcaaa gggcatggcc aaggatgtcc atagaactct gcatacaatt  2040
gttcaggaac aagggagtct ggattcttcc aaggctgaat tgtacgtcaa aaacttacag  2100
atgtctggaa gatacttaag agatgtttgg taa                              2133

SEQ ID NO: 117         moltype = DNA  length = 2079
```

```
FEATURE                 Location/Qualifiers
misc_feature            1..2079
                        note = Synthetic oligonucleotide
source                  1..2079
                        mol_type = other DNA
                        organism = synthetic construct
SEQUENCE: 117
atgacttctg cactttatgc ctccgatctt ttcaaacaat tgaaaagtat catgggaacg  60
gattctttgt ccgatgatgt tgtattagtt attgctacaa cttctctggc actggttgct  120
ggtttcgttg tcttattgtg gaaaaagacc acggcagatc gttccggcga gctaaagcca  180
ctaatgatcc ctaagtctct gatggcgaaa gatgaggatg atgacttaga tctaggttct  240
ggaaaaacga gagtctctat cttcttcggc acacaaaccg gaacagccga aggattcgct  300
aaagcacttt cagaagagat caaagcaaga tacgaaaagg cggctgtaaa agtaatcgat  360
ttggatgatt acgctgccga tgatgaccaa tatgaggaaa agttgaaaaa ggaaacattg  420
gctttctttt gtgtagccac gtatggtgat ggtgaaccaa ccgataacgc cgcaagattc  480
tacaagtggt ttactgaaga gaacgaaaga gatatcaagt tgcagcaact tgcttacggc  540
gtttttgcct taggtaacag acaatacgag cactttaaca agataggtat tgtcttagat  600
gaagagttat gcaaaaaggg tgcgaagaga ttgattgaag tcggtttagg agatgatgat  660
caatctatcg aggatgactt taatgcatgg aaggaatctt tgtggtctga attagataag  720
ttacttaagg acgaagatga taaatccgtt gccactccat acacagccgt cattccagaa  780
tatagagtag ttactcatga tccaagattc acaacacaga aatcaatgga aagtaatgtg  840
gctaatggta atactaccat cgatattcat catccatgta gagtagacgt tgcagttcaa  900
aaggaattgc acactcatga atcagacaga tcttgcatac atcttgaatt tgatatatca  960
cgtactggta tcacttacga aacaggtgat cacgtgggtg tctacgctga aaaccatgtt  1020
gaaattgtag aggaagctgg aaagttgttg ggccatagtt tagatcttgt tttctcaatt  1080
catgccgata aagaggatgg ctcaccacta gaaagtgcag tgcctccacc atttccagga  1140
ccatgcaccc taggtaccgg tttagctcgt tacgcggatc tgttaaatcc tccacgtaaa  1200
tcagctctag tggccttggc tgcgtacgcc acagaacctt ctgaggcaga aaaactgaaa  1260
catctaactt caccagatgg taaggatgaa tactcacaat ggatagtagc tagtcaacgt  1320
tctttactag aagttatggc tgctttccca tccgctaaac ctcctttggg tgtttttctt  1380
gccgcaatag cgcctagact gcaaccaaga tactattcaa tttcatcctc acctagactg  1440
gcaccatcaa gagttcatgt cacatccgct ttagtgtacg gtccaactcc tactggtaga  1500
atccataagg gcgtttgttc aacatggatg aaaaacgcgg ttccagcaga gaagtctcac  1560
gaatgttctg gtgctccaat ctttatcaga gcctccaact tcaaactgcc ttccaatcct  1620
tctactccta ttgtcatggt cggtcctggt acaggtcttg ctccattcag aggtttctta  1680
caagagagaa tggccttaaa ggaggatggt gaagagttgg gatcttcttt gttgtttttc  1740
ggctgtagaa acagacaaat ggatttcatc tacgaagatg aactgaataa ctttgtagat  1800
caaggagtta tttcagagtt gataatggct tttctagag aaggtgctca gaaggagtac  1860
gtccaacaca aaatgatgga aaaggccgca caagtttggg acttaatcaa agaggaaggc  1920
tatctatatg tctgtggtga tgcaaagggt atggcaagag atgttcacag aacacttcat  1980
actatagtcc aggaacagga aggcgttagt tcttctgaag cggaagcaat tgtgaaaaag  2040
ttacaaacag agggaagata cttgagagat gtgtggtaa                          2079

SEQ ID NO: 118          moltype = DNA  length = 2142
FEATURE                 Location/Qualifiers
misc_feature            1..2142
                        note = Synthetic oligonucleotide
source                  1..2142
                        mol_type = other DNA
                        organism = synthetic construct
SEQUENCE: 118
atggcagaat tagatacact tgatatagta gtattaggtg ttatcttttt gggtactgtg  60
gcatacttta ctaagggtaa attgtggggt gttaccaagg atccatacgc taacggattc  120
gctgcaggtg gtgcttccaa gcctggcaga actagaaaca tcgtcgaagc tatggaggaa  180
tcaggtaaaa actgtgttgt tttctacggc agtcaaacag gtacagcgga ggattacgca  240
tcaagacttg caaaggaagg aaagtccaga ttcggtttga acactatgat cgccgatcta  300
gaagattatg acttcgataa cttagacact gttccatctg ataacatcgt tatgtttgta  360
ttggctactt acggtgaagg cgaaccaaca gataacgccg tggatttcta tgagttcatt  420
actggcgaag atgcctcttt caatgagggc aacgatcctc cactaggtaa cttgaattac  480
gttgcgttcg gtctgggcaa caatacctac gaacactaca actcaatggt caggaacgtt  540
aacaaggctc tagaaaagtt aggagctcat agaattggag aagcaggtga gggtgacgac  600
ggagctggaa ctatggaaga ggacttttta gcttggaaag atccaatgtg ggaagccttg  660
gctaaaaaga tgggcttgga ggaaagagaa gctgtatatg aacctatttt cgctatcaat  720
gagagagatg atttgacccc tgaagcgaat gaggtatact tgggagaacc taataagcta  780
cacttggaag gtacagcgaa aggtccattc aactcccaca acccatatat cgcaccaatt  840
gcagaatcat acgaactttt ctcagctaag gatagaaatt gtctgcatat ggaaattgat  900
atttctggta gtaatctaaa gtatgaaaca ggcgaccata tcgcgatctg gcctaccaac  960
ccaggtgaag aggtcaacaa atttcttgac attctagatc tgtctggtaa gcaacattcc  1020
gtcgtaacag tgaaagcctt agaacctaca gccaaagttc cttttccaaa tccaactacc  1080
tacgatgcta tattgagata ccatctggaa atatgcgctc cagtttctag acagtttgtc  1140
tcaactttag cagcattcgc ccctaatgat gatatcaaag ctgagatgaa ccgtttggga  1200
tcagacaaag attacttcca cgaaaagaca ggaccacatt actacaatat cgctagattt  1260
ttggcctcag tctctaaagg tgaaaaatgg acaaagatac cattttctgc tttcatagaa  1320
ggccttacaa aactacaacc aagatactat tctatctctt cctctagttt agttcagcct  1380
aaaaagatta gtattactgc tgttgtcgaa tctcagcaaa ttccaggtag agatgaccca  1440
ttcagaggtg tagcgactaa ctacttgttc gctttgaagc agaaacaaaa cggtgatcca  1500
aatccagctc cttttggcca atcatacgag ttgacaggac caaggaataa gtatgatggt  1560
atacatgttc cagtccatgt aagacattct aactttaagc taccatctga tccaggcaaa  1620
cctattatca tgatcggtcc aggtaccggt gttgcccctt ttagaggctt cgtccaagag  1680
```

```
agggcaaaac aagccagaga tggtgtagaa gttggtaaaa cactgctgtt ctttggatgt  1740
agaaagagta cagaagattt catgtatcaa aaagagtggc aagagtacaa ggaagctctt  1800
ggcgacaaat tcgaaatgat tacagctttt tcaagagaag gatctaaaaa ggtttatgtt  1860
caacacagac tgaaggaaag atcaaaggaa gtttctgatc ttctatccca aaaagcatac  1920
ttctacgttt gcggagacgc cgcacatatg gcacgtgaag tgaacactgt gttagcacag  1980
atcatagcag aaggccgtgg tgtatcagaa gccaagggtg aggaaattgt caaaaacatg  2040
agatcagcaa atcaatacca agtgtgttct gatttcgtaa ctttacactg taaagagaca  2100
acatacgcga attcagaatt gcaagaggat gtctggagtt aa                      2142
```

```
SEQ ID NO: 119          moltype = DNA  length = 2364
FEATURE                 Location/Qualifiers
misc_feature            1..2364
                        note = Synthetic oligonucleotide
source                  1..2364
                        mol_type = other DNA
                        organism = synthetic construct
SEQUENCE: 119
atgaaaaccg ggtttatctc accagcaaca gtatttcatc acagaatctc accagcgacc  60
actttcagac atcacttatc acctgctact acaaactcta caggcattgt cgccttaaga  120
gacatcaact tcagatgtaa agcagtttct aaagagtact ctgatctgtt gcagaaagat  180
gaggcttctt tcacaaaatg ggacgatgac aaggtgaaag atcatcttga taccaacaaa  240
aacttatacc caaatgatga gattaaggaa tttgttgaat cagtaaaggc tatgttcggt  300
agtatgaatg acggggagat aaacgtctct gcatacgata ctgcatgggt tgctttggtt  360
caagatgtcg atggatcagg tagtcctcag ttcccttctt ctttagaatg gattgccaac  420
aatcaattgt cagatggatc atggggagat catttgctgt tctcagctca cgatagaatc  480
atcaacacat tagcatgcgt tattgcactt acaagttgga atgttcatcc ttctaagtgt  540
gaaaaaggtt tgaattttct gagagaaaac atttgcaaat tagaagatga aaacgcagaa  600
catatgccaa ttggttttga agtaacattc ccatcactaa ttgatatcgc gaaaaagttg  660
aacattgaag tacctgagga tactccagca cttaaagaga tctacgcacg tagagatatc  720
aagttaacta agatcccaat ggaagttctt cacaaggtac ctactacttt gttacattct  780
ttggaaggaa tgcctgattt ggagtgggaa aaactgttaa agctacaatg taaagatggt  840
agtttcttgt tttccccatc tagtaccgca ttcgccctaa tgcaaacaaa agatgagaaa  900
tgcttacagt atctaacaaa tatcgtcact aagttcaacg gtggcgtgcc taatgtgtac  960
ccagtcgatt tgtttgaaca tatttgggtt gttgatagac tgcagagatt ggggattgcc  1020
agatacttca aatcagagat aaaagattgt gtagagtata tcaataagta ctggaccaaa  1080
aatggaattt gttgggctag aaatactcac gttcaagata tcgatgatac agccatggga  1140
ttcagagtgt tgagagcgca cggttatgac gtcactccag atgtttttag acaatttgaa  1200
aaagatggta aattcgtttg ctttgcaggg caatcaacac aagccgtgac aggaatgttt  1260
aacgtttaca gagcctctca aatgttgttc ccaggggaga gaattttgga agatgccaaa  1320
aagttctctt acaattactt aaaggaaaag caaagtacca acgaattgct ggataaatgg  1380
ataatcgcta aagatctacc tggtgaagtt ggttatgctc tggatatccc atggtatgct  1440
tccttaccaa gattggaaac tcgttattac cttgaacaat acggcggtga agatgatgtc  1500
tggataggca agacattata cagaatgggt tacgtgtcca ataacacata tctagaaatg  1560
gcaaagctgg attacaataa ctatgttgca gtccttcaat tagaatggta cacaatacaa  1620
caatggtacg tcgatattgg tatagagaag ttcgaatctg acaacatcaa gtcagtcctg  1680
gtttcttact acttggctgc ggcttcaata ttcgaacctg agagatctaa ggagagaatc  1740
gcttgggcaa agacaacaat cttagtcgat aagatcacat caattttcga ttcctctcag  1800
tcaagtaagg aagatattac tgcctttatt gacaagtttc gtaacaagtc ctcctctaaa  1860
aagcactcta tcaacggtga accatggcat gaagttatgg tagctttgaa aaagacctta  1920
cacggctttg ctctggatgc tcttatgact cattctcaag atatacatcc acagttacat  1980
caagcctggg aaatgtggtt gactaaacta caagacggcg tagatgttac tgctgagcta  2040
atggtccaaa tgatcaacat gactgctggc agatgggtat caaaggaatt acttactcat  2100
ccacaatatc aaagattgtc tactgtgaca aattctgtgt gtcacgatat taccaaactt  2160
cacaatttca aggagaattc caccacagtg gattcaaagg ttcaggaact agtccagttg  2220
gtttttagtg acacaccaga tgatttggat caagatatga aacaaacatt cctgacagtg  2280
atgaagacat tctactacaa ggcgtggtgt gatccaaaca ctataaacga tcatatatct  2340
aaagttttcg aaatcgtaat ttga                                          2364
```

```
SEQ ID NO: 120          moltype = DNA  length = 1584
FEATURE                 Location/Qualifiers
misc_feature            1..1584
                        note = Synthetic oligonucleotide
source                  1..1584
                        mol_type = other DNA
                        organism = synthetic construct
SEQUENCE: 120
atgcctgatg cacacgatgc tccacctcca caaataagac agagaacact agtagatgag  60
gctacccaac tgctaactga gtccgcagaa gatgcatggg gtgaagtcag tgtgtcagaa  120
tacgaaacag caaggctagt tgcccatgct acatggttag gtggacacgc cacaagagtg  180
gccttccttc tggagagaca acacgaagac gggtcatggg gtccaccagg tggatatagg  240
ttagtcccta cattatctgc tgttcacgca ttattgacat gtcttgcctc tcctgctcag  300
gatcatggcg ttccacatga tagactttta agagctgttg acgcaggctt gactgccttg  360
agaagattgg ggacatctga ctccccacct gatactatag cagttgagct ggttatccca  420
tctttgctag agggcattca acacttactg gaccctgctc atcctcatag tagaccagcc  480
ttctctcaac atagaggctc tcttgtttgt cctggtggac tagatgggag aactctagga  540
gctttgagat cacacgccgc agcaggtaca ccagtaccag gaaaagtctg gcacgcttcc  600
gagactttgg gcttgagtac cgaagctgct tctcacttgc aaccagccca aggtataatc  660
ggtggctctg ctgctgccac agcaacatgg ctaaccaggg ttgcaccatc tcaacagtca  720
gattctgcca gaagatacct tgaggaatta caacacagat actctggccc agttccttcc  780
```

```
attacccta tcacatactt cgaaagagca tggttattga acaattttgc agcagccggt  840
gttccttgtg aggctccagc tgctttgttg gattccttag aagcagcact tacaccacaa  900
ggtgctcctg ctggagcagg attgcctcca gatgctgatg atacagccgc tgtgttgctt  960
gcattggcaa cacatgggag aggtagaaga ccagaagtac tgatggatta caggactgac  1020
gggtatttcc aatgctttat tggggaaagg actccatcaa tttcaacaaa cgctcacgta  1080
ttggaaacat tagggcatca tgtggcccaa catccacaag atagagccag atacggatca  1140
gccatggata ccgcatcagc ttggctgctg gcagctcaaa agcaagatgg ctcttggtta  1200
gataaatggc atgcctcacc atactacgct actgtttgtt gcacacaagc cctagccgct  1260
catgcaagtc ctgcaactgc accagctaga cagagagctg tcagatgggt tttagccaca  1320
caaagatccg atggcggttg ggtctatggc cattcaactg ttgaagagac tgcttatgcc  1380
ttacagatct tggccccacc ttctggtggt ggcaatatcc cagtccaaca agcacttact  1440
agaggcagag caagattgtg tggagccttg ccactgactc ctttatggca tgataaggat  1500
ttgtatactc cagtaagagt agtcagagct gccagagctg ctgctctgta cactaccaga  1560
gatctattgt taccaccatt gtaa                                        1584

SEQ ID NO: 121         moltype = DNA  length = 1551
FEATURE                Location/Qualifiers
misc_feature           1..1551
                       note = Synthetic oligonucleotide
source                 1..1551
                       mol_type = other DNA
                       organism = synthetic construct
SEQUENCE: 121
atgaacgccc tatccgaaca cattttgtct gaattgagaa gattattgtc tgaaatgagt  60
gatggcggat ctgttggtcc atctgtgtat gatacggccc aggccctaag attccacggt  120
aacgtaacag gtagacaaga tgcatatgct tggttgatcg cccagcaaca agcagatgga  180
ggttggggct ctgccgactt tccactcttt agacatgctc caacatgggc tgcacttctc  240
gcattacaaa gagctgatcc acttcctggc gcagcagacg cagttcagac cgcaacaaga  300
ttcttgcaaa gacaaccaga tccatacgct catgccgttc ctgaggatgc ccctattggt  360
gctgaactga tcttgcctca gttttgtgga gaggctgctt ggttgttggg aggtgtggcc  420
ttccctagac acccagccct attaccatta agacaggctt gtttagtcaa actgggtgca  480
gtcgccatgt tgccttcagg acacccattg ctccactcct gggaggcatg gggtacttct  540
ccaacaacag cctgtccaga cgatgatggt tctataggta tctcaccagc agctacagcc  600
gcctggagag cccaggctgt gaccagaggc tcaactcctc aagtgggcag agctgacgca  660
tacttacaaa tggcttcaag agcaacgaga tcaggcatag aaggagtctt ccctaatgtt  720
tggcctataa acgtattcga accatgctgg tcactgtaca ctctccatct tgccggtctg  780
ttcgcccatc cagcactggc tgaggctgta agagttatcg ttgctcaact tgaagcaaga  840
ttgggagtgc atggcctcgg accagcttta cattttgctg ccgacgctga tgatactgca  900
gttgccttat gcgttctgca tttggctggc agagatcctg cagttgacgc attgagacat  960
tttgaaattg gtgagctctt tgttacattc ccaggagaga gaaatgctag tgtctctacg  1020
aacattcacg ctcttcatgc tttgagattg ttaggtaaac cagctgccgg agcaagtgca  1080
tacgtcgaag caaatagaaa tccacatggt ttgtgggaca acgaaaaatg gcacgtttca  1140
tggctttatc caactgcaca cgccgttgca gctctagctc aaggcaagcc tcaatggaga  1200
gatgaaagag cactagccgc tctactacaa gctcaaagag atgatggtgg ttggggagct  1260
ggtagaggat ccactttcga ggaaaccgcc tacgctcttt tcgctttaca cgttatggac  1320
ggatctgagg aagccacagg cagaagaaga atcgctcaag tcgtcgcaag agccttagaa  1380
tggatgctag ctagacatgc cgcacatgga ttaccacaaa caccactctg gattggtaag  1440
gaattgtact gtcctactag agtcgtaaga gtagctgagc tagctggcct gtggttagca  1500
ttaagatggg gtagaagagt attagctgaa ggtgctggtg ctgcacctta a          1551

SEQ ID NO: 122         moltype = DNA  length = 2952
FEATURE                Location/Qualifiers
misc_feature           1..2952
                       note = Synthetic oligonucleotide
source                 1..2952
                       mol_type = other DNA
                       organism = synthetic construct
SEQUENCE: 122
atggaatttg atgaaccatt ggttgacgaa gcaagatctt tagtgcagcg tactttacaa  60
gattatgatg acagatacgg cttcggtact atgtcatgtg ctgcttatga tacagcctgg  120
gtgtctttag ttacaaaaac agtcgatggg agaaaacaat ggcttttccc agagtgtttt  180
gaatttctac tagaaacaca atctgatgcc ggaggatggg aaatcgggaa ttcagcacca  240
atcgacggta tattgaatac agctgcatcc ttacttgctc taaaacgtca cgttcaaact  300
gagcaaatca tccaacctca acatgaccat aaggatctag caggtagagc tgaacgtgcc  360
gctgcatctt tgagagcaca attggctgca ttggatgtgt ctacaactga acacgtcggt  420
tttgagataa ttgttcctgc aatgctagac ccattagaag ccgaagatcc atctctagtt  480
ttcgattttc cagctaggaa acctttgatg aagattcatg atgctaagat gagtagattc  540
aggccagaat acttgtatgg caaacaacca atgaccgcct tacattcatt agaggctttc  600
ataggcaaaa tcgacttcga taaggtaaga caccaccgta cccatgggtc tatgatgggt  660
tctccttcat ctaccgcagc ctacttaatg cacgcttcac aatgggatgg tgactcagag  720
gcttacctta gacacgtgat taaacacgca gcagggcagg gaactggtgc tgtaccatct  780
gctttcccat caacacattt tgagtcatct tggattctta ccacattgtt tagagctgga  840
ttttcagctt ctcatcttgc ctgtgatgag ttgaacaagt tggtcgagat acttgagggc  900
tcattcgaga aggaaggtgg ggcaatcggt tacgctccag ggtttcaagc agatgttgat  960
gatactgcta aaacaataag tacattagca gtccttggaa gagatgctac accaagacaa  1020
atgatcaagg tatttgaagc taatacacat tttagaacat accctggtga aagagatcct  1080
tctttgacag ctaattgtaa tgctctatca gccttactac accaaccaga tgcagcaatg  1140
tatggatctc aaattcaaaa gattaccaaa tttgtctgtg actattggtg gaagtctgat  1200
ggtaagatta aagataagtg gaacacttgc tacttgtacc catctgtctt attagttgag  1260
```

```
gttttggttg atcttgttag tttattggag cagggtaaat tgcctgatgt tttggatcaa  1320
gagcttcaat acagagtcgc catcacattg ttccaagcat gtttaaggcc attactagac  1380
caagatgccg aaggatcatg gaacaagtct atcgaagcca cagcctacgg catccttatc  1440
ctaactgaag ctaggagagt ttgtttcttc gacagattgt ctgagccatt gaatgaggca  1500
atccgtagag gtatcgcttt cgccgactct atgtctggaa ctgaagctca gttgaactac  1560
atttggatcg aaaaggttag ttacgcacct gcattattga ctaaatccta tttgttagca  1620
gcaagatggg ctgctaagtc tcctttaggc gcttccgtag gctcttcttt gtggactcca  1680
ccaagagaag gattggataa gcatgtcaga ttattccatc aagctgagtt attcagatcc  1740
cttccagaat gggaattaag agcctccatg attgaagcag ctttgttcac accacttcta  1800
agagcacata gactagacgt tttccctaga caagatgtag gtgaagacaa atatcttgat  1860
gtagttccat tcttttggac tgccgctaac aacagagata gaacttacgc ttccactcta  1920
ttcctttacg atatgtgttt tatcgcaatg ttaaacttcc agttagacga attcatggag  1980
gccacagccg gtatcttatt cagagatcat atggatgatt tgaggcaatt gattcatgat  2040
cttttggcag agaaaacttc cccaaagagt tctggtagaa gtagtcaggg cacaaaagat  2100
gctgactcag gtatagagga agacgtgtca atgtccgatt cagcttcaga ttcccaggat  2160
agaagtccag aatacgactt ggttttcagt gcattgagta cctttacaaa acatgtcttg  2220
caacacccat ctatacaaag tgcctctgta tgggatagaa aactacttgc tagagagatg  2280
aaggcttact tacttgctca tatccaacaa gcagaagatt caactccatt gtctgaattg  2340
aaagatgtgc ctcaaaagac tgatgtaaca agagtttcta catctactac taccttcttt  2400
aactgggtta gaacaacttc cgcagaccat atatcctgcc catactcctt ccactttgta  2460
gcatgccatc taggcgcagc attgtcacct aaagggtcta acggtgattg ctatccttca  2520
gctggtgaga agttcttggc agctgcagtc tgcagacatt tggccaccat gtgtagaatg  2580
tacaacgatc ttggatcagc tgaacgtgat tctgatgaag gtaatttgaa ctccttggac  2640
ttccctgaat tcgccgattc cgcaggaaac ggagggatag aaattcagaa ggccgctcta  2700
ttaaggttag ctgagtttga gagagattca tacttagagg ccttccgtcg tttacaagat  2760
gaatccaata gagttcacgg tccagccggt ggtgatgaag ccagattgtc cagaaggaga  2820
atggcaatcc ttgaattctt cgcccagcag gtagatttgt acggtcaagt atacgtcatt  2880
agggatattt ccgctcgtat tcctaaaaac gaggttgaga aaaagagaaa attggatgat  2940
gctttcaatt ga                                                      2952

SEQ ID NO: 123          moltype = DNA  length = 2646
FEATURE                 Location/Qualifiers
misc_feature            1..2646
                        note = Synthetic oligonucleotide
source                  1..2646
                        mol_type = other DNA
                        organism = synthetic construct
SEQUENCE: 123
atggcttcta gtacacttat ccaaaacaga tcatgtggcg tcacatcatc tatgtcaagt  60
tttcaaatct tcagaggtca accactaaga tttcctggca ctagaacccc agctgcagtt  120
caatgcttga aaaagaggag atgccttagg ccaaccgaat ccgtactaga atcatctcct  180
ggctctggtt catatagaat agtaactggc ccttctggaa ttaaccctag ttctaacggg  240
cacttgcaag agggttcctt gactcacagg ttaccaatac caatggaaaa atctatcgat  300
aacttccaat ctactctata tgtgtcagat atttggtctg aaacactaca gagaactgaa  360
tgtttgctac aagtaactga aaacgtccag atgaatgagt ggattgagga aattagaatg  420
tactttagaa atatgacttt aggtgaaatt tccatgtccc cttacgacac tgcttgggtg  480
gctagagttc cagcgttgga cggttctcat gggcctcaat tccacagatc tttgcaatgg  540
attatcgaca accaattacc agatggggac tggggcgaac cttctctttt cttgggttac  600
gatagagttt gtaatacttt agcctgtgtg attgcgttga aaacatgggg tgttggggca  660
caaaacgttg aaagaggaat tcagttccta caatctaaca tatacaagat ggaggaagat  720
gacgctaatc atatgccaat aggattcgaa atcgtattcc ctgctatgat ggaagatgcc  780
aaagcattag gtttggattt gccatacgat gctactattt tgcaacagat ttcagccgaa  840
agagagaaaa agatgaaaaa gatcccaatg gcaatggtgt acaaataccc aaccacttta  900
cttcactcct tagaaggctt gcatagagaa gttgattgga ataagttgtt acaattacaa  960
tctgaaaatg gtagtttttct ttattcacct gcttcaaccg catgcgcctt aatgtacact  1020
aaggacgtta aatgttttga ttacttaaac cagttgttga tcaagttcga ccacgcatgc  1080
ccaaatgtat atccagtcga tctattcgaa agattatgga tggttgacag attgcagaga  1140
ttagggatct ccagatactt tgaaagagag attagagatt gtttacaata cgtctacaga  1200
tattggaaag attgtggaat cggatgggct tctaactctt ccgtacaaga tgttgatgat  1260
acagccatgg cgtttagact tttaaggact catggtttcg acgtaaagga agattgcttt  1320
agacagtttt tcaaggacgg agaattcttc tgcttcgcag gccaatcatc tcaagcagtt  1380
acaggcatgt ttaatctttc aagagccagt caaacattgt ttccaggaga atctttattg  1440
aaaaaggcta gaaccttctc tagaaacttc ttgagaacaa agcatgagaa caacgaatgt  1500
ttcgataaat ggatcattac taaagatttg gctggtgaag tcgagtataa cttgaccttc  1560
ccatggtatg cctctttgcc tagattagaa cataggacat acttagatca atatggaatc  1620
gatgatatct ggataggcaa atctttatac aaaatgcctg ctgttaccaa cgaagttttc  1680
ctaaagttgg caaaggcaga ctttaacatg tgtcaagctc tacacaaaaa ggaattggaa  1740
caagtgataa agtggaacgc gtcctgtcaa ttcagagatc ttgaattcgc cagacaaaaa  1800
tcagtagaat gctattttgc tggtgcagcc acaatgttcg aaccagaaat ggttcaagct  1860
agattagtct gggcaagatg ttgtgtattg acaactgtct tagacgatta ctttgaccac  1920
gggacacctg ttgaggaact tagagtgttt gttcaagctg tcagaacatg gaatccagag  1980
ttgatcaacg gtttgccaga gcaagctaaa atcttgttta tgggcttata caaaacagtt  2040
aacacaattg cagaggaagc attcatggca cagaaaagag acgtccatca tcatttgaaa  2100
cactattggg acaagttgat aacaagtgcc ctaaaggagg ccgaatgggc agagtcaggt  2160
tacgtcccaa catttgatga atacatggaa gtagctgaaa tttctgttgc tctagaacca  2220
attgtctgta gtaccttgtt ctttgcgggt catagactag atgaggatgt tctagatagt  2280
tacgattacc atctagttat gcatttggta aacagagtcg gtagaatctt gaatgatata  2340
caaggcatga agagggaggc ttcacaaggt aagatctcat cagttcaaat ctacatggag  2400
gaacatccat ctgttccatc tgaggccatg gcgatcgctc atcttcaaga gttagttgat  2460
```

```
aattcaatgc agcaattgac atacgaagtt cttaggttca ctgcggttcc aaaaagttgt  2520
aagagaatcc acttgaatat ggctaaaatc atgcatgcct tctacaagga tactgatgga  2580
ttctcatccc ttactgcaat gacaggattc gtcaaaaagg ttcttttcga acctgtgcct  2640
gagtaa                                                             2646

SEQ ID NO: 124          moltype = DNA  length = 2859
FEATURE                 Location/Qualifiers
misc_feature            1..2859
                        note = Synthetic oligonucleotide
source                  1..2859
                        mol_type = other DNA
                        organism = synthetic construct
SEQUENCE: 124
atgcctggta aaattgaaaa tggtacccca aaggacctca agactggaaa tgattttgtt  60
tctgctgcta agagtttact agatcgagct ttcaaaagtc atcattccta ctacggatta  120
tgctcaactt catgtcaagt ttatgataca gcttgggttg caatgattcc aaaaacaaga  180
gataatgtaa aacagtggtt gtttccagaa tgtttccatt acctcttaaa aacacaagcc  240
gcagatggct catggggttc attgcctaca acacagacag cgggtatcct agatacagcc  300
tcagctgtgc tggcattatt gtgccacgca caagagcctt tacaaatatt ggatgtatct  360
ccagatgaaa tggggttgag aatagaacac ggtgtcacat ccttgaaacg tcaattagca  420
gtttggaatg atgtggagga caccaaccat attggcgtcg agtttatcat accagcctta  480
ctttccatgc tagaaaagga attagatgtt ccatctttg aatttccatg taggtccatc  540
ttagagagaa tgcacgggga gaaattaggt catttcgacc tggaacaagt ttacggcaag  600
ccaagctcat tgttgcactc attggaagca tttctcggta agctagattt tgatcgacta  660
tcacatcacc tataccacgg cagtatgatg gcatctccat cttcaacggc tgcttatctt  720
attggggcta caaaatggga tgacgaagcc gaagattacc taagacatgt aatgcgtaat  780
ggtgcaggac atgggaatgg aggtatttct ggtacatttc caactactca tttcgaatgt  840
agctggatta tagcaacgtt gttaaaggtt ggctttactt tgaagcaaat tgacggcgat  900
ggcttaagag gtttatcaac catcttactt gaggcgcttc gtgatgagaa tggtgtcata  960
ggctttgccc ctagaacagc agatgtagat gacacagcca aagctctatt ggccttgtca  1020
ttggtaaacc agccagtgtc acctgatatc atgattaagg tctttgaggg caaagaccat  1080
tttaccactt ttggttcaga aagagatcca tcattgactt ccaacctgca cgtcctttta  1140
tctttactta aacaatctaa cttgtctcaa taccatcctc aaatcctcaa aacaacatta  1200
ttcacttgta gatggtggtg gggttccgat cattgtgtca aagacaaatg gaatttgagt  1260
cacctatatc caactatgtt gttggttgaa gccttcactg aagtgctcca tctcattgac  1320
ggtggtgaat tgtctagtct gtttgatgaa tcctttaagt gtaagattgg tcttagcatc  1380
tttcaagcgg tacttagaat aatcctcacc caagacaacg acggctcttg gagaggatac  1440
agagaacaga cgtgttacgc aatattggct ttagttcaag cgagacatgt atgcttttc  1500
actcacatgg ttgacagact gcaatcatgt gttgatcgag gtttctcatg gttgaaatct  1560
tgctcttttc attctcaaga cctgacttgg acctctaaaa cagcttatga agtgggtttc  1620
gtagctgaag catataaact agctgcttta caatctgctt ccctggaggt tcctgctgcc  1680
accattggac attctgtcac gtctgccgtt ccatcaagtg atcttgaaaa atacatgaga  1740
ttggtgagaa aaactgcgtt attctctcca ctggatgagt ggggtctaat ggcttctatc  1800
atcgaatctt catttttcgt accattactg caggcacaaa gagttgaaat ataccctaga  1860
gataatatca aggtggacga agataagtac ttgtctatta tcccattcac atgggtcgga  1920
tgcaataata ggtctagaac tttcgcaagt aacagatggc tatacgatat gatgtacctt  1980
tcattactcg gctatcaaac cgacgagtac atggaagctg tagctgggcc agtgtttggg  2040
gatgtttcct tgttacatca aacaattgat aaggtgattg ataatacaat gggtaacctt  2100
gcgagagcca atggaacagt acacagtggt aatggacatc agcacgaatc tcctaatata  2160
ggtcaagtcg aggacacctt gactcgtttc acaaattcag tcttgaatca caaagacgtc  2220
cttaactcta gctcatctga tcaagatact ttgagaagag agtttagaac attcatgcac  2280
gctcatataa cacaaatcga agataactca cgattcagta agcaagcctc atccgatgcg  2340
ttttcctctc ctgaacaatc ttactttcaa tgggtgaact caactggtgg ctcacatgtc  2400
gcttgcgcct attcatttgc cttctctaat tgcctcatgt ctgcaaattt gttgcagggt  2460
aaagacgcat ttccaagcgg aacgcaaaag tacttaatct cctctgttat gagacatgcc  2520
acaaacatgt gtagaatgta taacgacttt ggctctattg ccagagacaa cgctgagaga  2580
aatgttaata gtattcattt tcctgagttt actctctgta acggaacttc tcaaaaccta  2640
gatgaaagga aggaaagact tctgaaaatc gcaacttacg aacaagggta tttggataga  2700
gcactagagg ccttggaaag acagagtaga gatgatgccg gagacagagc tggatctaaa  2760
gatatgagaa agttgaaaat cgttaagtta ttctgtgatg ttacggactt atacgatcag  2820
ctctacgtta tcaaagattt gtcatcctct atgaagtaa                        2859

SEQ ID NO: 125          moltype = DNA  length = 1086
FEATURE                 Location/Qualifiers
misc_feature            1..1086
                        note = Synthetic oligonucleotide
source                  1..1086
                        mol_type = other DNA
                        organism = synthetic construct
SEQUENCE: 125
atggctttgg taaacccaac cgctcttttc tatggtacct ctatcagaac aagacctaca  60
aacttactaa atccaactca aaagctaaga ccagtttcat catcttcctt accttctttc  120
tcatcagtta gtgcgattct tactgaaaaa catcaatcta atccttctga gaacaacaat  180
ttgcaaactc atctagaaac tcctttcaac tttgatagtt atatgttgga aaaagtcaac  240
atggttaacg aggcgcttga tgcatctgtc ccactaaaag acccaatcaa aatccatgaa  300
tccatgagat actctttatt ggcaggcggt aagagaatca gaccaatgat gtgtattgca  360
gcctgcgaaa tagtcggagg taatatcctt aacgccatgc cagccgcatg tgccgtggaa  420
atgattcata ctatgtcttt ggtgcatgac gatcttccat gtatggataa tgatgacttc  480
agaagaggta aacctatttc acacaaggtc tacggggagg aaatggcagt attgaccggc  540
```

```
gatgctttac taagtttatc tttcgaacat atagctactg ctacaaaggg tgtatcaaag  600
gatagaatcg tcagagctat aggggagttg gcccgttcag ttggctccga aggtttagtg  660
gctggacaag ttgtagatat cttgtcagag ggtgctgatg ttggattaga tcacctagaa  720
tacattcaca tccacaaaac agcaatgttg cttgagtcct cagtagttat tggcgctatc  780
atgggaggag gatctgatca gcagatcgaa aagttgagaa aattcgctag atctattggt  840
ctactattcc aagttgtgga tgacattttg gatgttacaa aatctaccga agagttgggg  900
aaaacagctg gtaaggattt gttgacagat aagacaactt acccaaagtt gttaggtata  960
gaaaagtcca gagaatttgc cgaaaaactt aacaaggaag cacaagagca attaagtggc  1020
tttgatagac gtaaggcagc tcctttgatc gcgttagcca actacaatgc gtaccgtcaa  1080
aattga                                                            1086
```

```
SEQ ID NO: 126          moltype = DNA  length = 1029
FEATURE                 Location/Qualifiers
misc_feature            1..1029
                        note = Synthetic oligonucleotide
source                  1..1029
                        mol_type = other DNA
                        organism = synthetic construct
SEQUENCE: 126
atggctgagc aacaaatatc taacttgctg tctatgtttg atgcttcaca tgctagtcag  60
aaattagaaa ttactgtcca aatgatggac acataccatt acagagaaac gcctcccagat  120
tcctcatctt ctgaaggcgg ttcattgtct agatacgacg agagaagagt ctctttgcct  180
ctcagtcata atgctgcctc tccagatatt gtatcacaac tatgtttttc cactgcaatg  240
tcttcagagt tgaatcacag atggaaatct caaagattaa aggtggccga ttctccttac  300
aactatatcc taacattacc atcaaaagga attagaggtg cctttatcga ttccctgaac  360
gtatggttgg aggttccaga ggatgaaaca tcagtcatca aggaagttat tggtatgctc  420
cacaactctt cattaatcat tgatgacttc caagataatt ctccacttag aagaggaaag  480
ccatctaccc atacagtctt cggccctgcc caggctatca atactgctac ttacgttata  540
gttaaagcaa tcgaaaagat acaagacata gtgggacacg atgcattggc agatgttacg  600
ggtactatta caactatttt ccaaggtcag gccatggact tgtggtggac agcaaatgca  660
atcgttccat caatacagga atacttactt atggtaaacg ataaaaccgg tgctctcttt  720
agactgagtt tggagttgtt agctctgaat tccgaagcca gtatttctga ctctgcttta  780
gaaagtttat ctagtgctgt ttccttgcta ggtcaatact tccaaatcag agacgactat  840
atgaacttga tcgataacaa gtatacagat cagaaaggct tctgcgaaga tcttgatgaa  900
ggcaagtact cactaacact tattcatgcc ctccaaactg attcatccga tctactgacc  960
aacatccttt caatgagaag agtgcaagga aagttaacgg cacaaaagag atgttggttc  1020
tggaaatga                                                          1029
```

```
SEQ ID NO: 127          moltype = DNA  length = 903
FEATURE                 Location/Qualifiers
misc_feature            1..903
                        note = Synthetic oligonucleotide
source                  1..903
                        mol_type = other DNA
                        organism = synthetic construct
SEQUENCE: 127
atggaaaaga ctaaggagaa agcagaacgt atcttgctgg agccatacag atacttatta  60
caactaccag gaaagcaagt ccgttctaaa ctatcacaag cgttcaatca ctggttaaaa  120
gttcctgaag ataagttaca aatcattatt gaagtcacag aaatgctaca caatgcttct  180
ttactgatcg atgatataga ggattcttcc aaactgagaa gaggttttcc tgtcgctcat  240
tccatatacg gggtaccaag tgtaatcaac tcagctaatt acgtctactt cttgggattg  300
gaaaaagtat tgacattaga tcatccagac gctgtaaagc tattcaccag acaacttctt  360
gaattgcatc aaggtcaagg tttggatatc tattggagag acacttatac ttgcccaaca  420
gaagaggagt acaaagcaat ggttctacaa aagactggcg gtttgttcgg acttgccgtt  480
ggtctgatgc aacttttctc tgattacaag gaggacttaa agcctctgtt ggataccttg  540
ggcttgtttt tccagattag agatgactac gctaacttac attcaaagga atattcagaa  600
aacaaatcat tctgtgaaga tttgactgaa gggaagttta gttttccaac aatccacgcc  660
atttggtcaa gaccagaatc tactcaagtg caaaacattc tgcgtcagag aacagagaat  720
attgacatca aaaagtattg tgttcagtac ttggaagatg ttggttcttt tgcttacaca  780
agacatacac ttagagaatt agaggcaaaa gcatacaagc aaatagaagc ctgtggaggc  840
aatccttctc tagtggcatt ggttaaacat ttgtccaaaa tgttcaccga ggaaaacaag  900
taa                                                                903
```

```
SEQ ID NO: 128          moltype = DNA  length = 1020
FEATURE                 Location/Qualifiers
misc_feature            1..1020
                        note = Synthetic oligonucleotide
source                  1..1020
                        mol_type = other DNA
                        organism = synthetic construct
SEQUENCE: 128
atggcaagat tctattttct taacgcacta ttgatggtta tctcattaca atcaactaca  60
gccttcactc cagctaaact tgcttatcca acaacaacaa cagctctaaa tgtcgcctcc  120
gccgaaactt ctttcagtct agatgaatac ttggcctcta agataggacc tatagagtct  180
gccttggaag catcagtcaa atccagaatt ccacagaccg ataagatctg cgaatctatg  240
gcctactctt tgatggcagg aggcaagaga attagaccag tgttgtgtat cgctgcatgt  300
gagatgttcg gtggatccca agatgtcgct atgcctactg ctgtggcatt agaaatgata  360
cacacaatgt ctttgattca tgatgatttg ccatccatgg ataacgatga cttgagaaga  420
ggtaaaccaa caaaccatgt cgttttcggc gaagatgtag ctattcttgc aggtgactct  480
```

```
ttattgtcaa cttccttcga gcacgtcgct agagaaacaa aaggagtgtc agcagaaaag  540
atcgtggatg ttatcgctag attaggcaaa tctgttggtg ccgagggcct tgctggcggt  600
caagttatgg acttagaatg tgaagctaaa ccaggtacca cattagacga cttgaaatgg  660
attcatatcc ataaaaccgc tacattgtta caagttgctg tagcttctgg tgcagttcta  720
ggtggtgcaa ctcctgaaga ggttgctgca tgcgagttgt ttgctatgaa tataggtctt  780
gcctttcaag ttgccgacga tatccttgat gtaaccgctt catcagaaga tttgggtaaa  840
actgcaggca aagatgaagc tactgataag acaacttacc caaagttatt aggattagaa  900
gagagtaagg catacgcaag acaactaatc gatgaagcca aggaaagttt ggctcctttt  960
ggagatagag ctgccccttt attggccatt gcagatttca ttattgatag aaagaattga  1020

SEQ ID NO: 129         moltype = DNA  length = 1068
FEATURE                Location/Qualifiers
misc_feature           1..1068
                       note = Synthetic oligonucleotide
source                 1..1068
                       mol_type = other DNA
                       organism = synthetic construct
SEQUENCE: 129
atgcacttag caccacgtag agtccctaga ggtagaagat caccacctga cagagttcct  60
gaaagacaag gtgccttggg tagaagacgt ggagctggct ctactggctg tgcccgtgct  120
gctgctggtg ttcaccgtag aagaggagga ggcgaggctg atccatcagc tgctgtgcat  180
agaggctggc aagccggtgg tggcaccggt ttgcctgatg aggtggtgtc taccgcagcc  240
gccttagaaa tgtttcatgc ttttgcttta atccatgatg atatcatgga tgatagtgca  300
actagaagag gctccccaac tgttcacaga gccctagctg atcgtttagg cgctgctctg  360
gacccagatc aggccggtca actaggagtt tctactgcta tcttggttgg agatctggct  420
ttgacatggt ccgatgaatt gttatacgct ccattgactc cacatagact ggcagcagta  480
ctaccattgg taacagctat gagagctgaa accgttcatg gccaatatct tgatataact  540
agtgctagaa gacctgggac cgatacttct cttgcattga gaatagccag atataagaca  600
gcagcttaca caatggaacg tccactgcac attggtgcag ccctggctgg ggcaagacca  660
gaactattag cagggctttc agcatacgcc ttgccagctg gagaagcctt ccaattggca  720
gatgacctgc taggcgtctt cggtgatcca agacgtacag ggaaacctga cctagatgat  780
cttagaggtg gaaagcatac tgtcttagtc gccttggcaa gagaacatgc cactccagaa  840
cagagacaca cattggatac attattgggt acaccaggtc ttgatagaca aggcgcttca  900
agactaagat gcgtattggt agcaactggt gcaagagccg aagccgaaag acttattaca  960
gagagaagag atcaagcatt aactgcattg aacgcattaa cactgccacc tcctttagct  1020
gaggcattag caagattgac attagggtct acagctcatc ctgcctaa  1068

SEQ ID NO: 130         moltype = DNA  length = 993
FEATURE                Location/Qualifiers
misc_feature           1..993
                       note = Synthetic oligonucleotide
source                 1..993
                       mol_type = other DNA
                       organism = synthetic construct
SEQUENCE: 130
atgtcatatt tcgataacta cttcaatgag atagttaatt ccgtgaacga catcattaag  60
tcttacatct ctggcgacgt accaaaacta tacgaagcct cctaccattt gtttacatca  120
ggaggaaaga gactaagacc attgatcctt acaatttctt ctgatctttt cggtggacag  180
agagaaagag catactatgc tggcgcagca atcgaagttt tgcacacatt cactttggtt  240
cacgatgata tcatggatca agataacatt cgtagaggtc ttcctactgt acatgtcaag  300
tatggcctac ctttggccat tttagctggt gacttattgc atgcaaaagc ctttcaattg  360
ttgactcagg cattgagagg tctaccatct gaaactatca tcaaggcgtt tgatatcttt  420
acaagatcta tcattatcat atcagaaggt caagctgtcg atatggaatt cgaagataga  480
attgatatca aggaacaaga gtatttggat atgatatctc gtaaaaccgc tgccttattc  540
tcagcttctt cttccattgg ggcgttgata gctggagcta atgataacga tgtgagatta  600
atgtccgatt tcggtacaaa tcttgggatc gcatttcaaa ttgtagatga tatacttggt  660
ttaacagctg atgaaaaaga gctaggaaaa cctgttttca gtgatatcag agaaggtaaa  720
aagaccatat tagtcattaa gactttagaa ttgtgtaagg aagacgagaa aaagattgtg  780
ttaaaagcgc taggcaacaa gtcagcatca aaggaagagt tgatgagttc tgctgacata  840
atcaaaaagt actcattgga ttacgcctac aacttagctg agaaatacta caaaaacgcc  900
atcgattctc taaatcaagt ttcaagtaaa agtgatattc cagggaaggc attgaaatat  960
cttgctgaat tcaccatcag aagacgtaag taa  993

SEQ ID NO: 131         moltype = DNA  length = 894
FEATURE                Location/Qualifiers
misc_feature           1..894
                       note = Synthetic oligonucleotide
source                 1..894
                       mol_type = other DNA
                       organism = synthetic construct
SEQUENCE: 131
atggtcgcac aaactttcaa cctggatacc tacttatccc aaagacaaca acaagttgaa  60
gaggccctaa gtgctgctct tgtgccagct tatcctgaga gaatatacga agctatgaga  120
tactccctcc tggcaggtgg caaaagatta agacctatct tatgtttagc tgcttgcgaa  180
ttggcaggtg gttctgttga acaagccatg ccaactgcgt gtgcacttga aatgatccat  240
acaatgtcac taattcatga tgacctgcca gccatggata acgatgattt cagaagagga  300
aagccaacta atcacaaggt gttcggggaa gatatagcca tcttagcggg tgatgcgctt  360
ttagcttacg cttttgaaca tattgcttct caaacaagag gagtaccacc tcaattggtg  420
ctacaagtta ttgctagaat cggacacgcc gttgctgcaa caggcctcgt tggaggccaa  480
```

```
gtcgtagacc ttgaatctga aggtaaagct atttccttag aaacattgga gtatattcac  540
tcacataaga ctggagcctt gctggaagca tcagttgtct caggcggtat tctcgcaggg  600
gcagatgaag agcttttggc cagattgtct cattacgcta gagatatagg cttggctttt  660
caaatcgtcg atgatatcct ggatgttact gctacatctg aacagttggg gaaaaccgct  720
ggtaaagacc aggcagccgc aaaggcaact tatccaagtc tattgggttt agaagcctct  780
agacagaaag cggaagagtt gattcaatct gctaaggaag ccttaagacc ttacggttca  840
caagcagagc cactcctagc gctggcagac ttcatcacac gtcgtcagca ttaa        894

SEQ ID NO: 132          moltype = DNA  length = 1116
FEATURE                 Location/Qualifiers
misc_feature            1..1116
                        note = Synthetic oligonucleotide
source                  1..1116
                        mol_type = other DNA
                        organism = synthetic construct
SEQUENCE: 132
atggcctctg ttactttggg ttcctggatc gtcgtccacc accataacca tcaccatcca  60
tcatctatcc taactaaatc tcgttcaaga tcctgtccta ttacactaac caaaccaatc  120
tcttttcgtt caaagagaac agtttcctct agtagttcta tcgtgtcctc tagtgtcgtc  180
actaaggaag acaatctgag acagtctgaa ccttcttcct ttgatttcat gtcatatatc  240
attactaagg cagaactagt gaataaggct cttgattcag cagttccatt aagagagcca  300
ttgaaaatcc atgaagcaat gagatactct cttctagctg gcgggaagag agtcagacct  360
gtactctgca tagcagcgtg cgaattagtt ggtggcgagg aatcaaccgc tatgcctgcc  420
gcttgtgctg tagaaatgat tcatacaatg tcactgatac acgatgattt gccatgtatg  480
gataacgatg atctgagaag ggtaagccca actaaccata aggttttcgg cgaagatgtt  540
gccgtcttag ctggtgatgc tttgttatct ttcgcgttcg aacatttggc atccgcaaca  600
tcaagtgatg ttgtgtcacc agtaagagta gttagagcag ttggagaact ggctaaagct  660
attggaactg agggtttagt tgcaggtcaa gtcgtcgata tctcttccga aggtcttgat  720
ttgaatgatg taggtcttga acatctcgaa ttcatccatc ttcacaagac agctgcactt  780
ttagaagcca gtgcggttct cggcgcaatt gttggcggag ggagtgatga cgaaattgag  840
agattgagga agtttgctag atgtatagga ttactgttcc aagtagtaga cgatatacta  900
gatgtgacaa agtcttccaa agagttggga aaaacagctg gtaaagattt gattgccgac  960
aaattgacct accctaagat tatggggcta gaaaaatcaa gagaatttgc cgagaaactc  1020
aatagagagg cgcgtgatca actgttgggt ttcgattctg ataaagttgc accactctta  1080
gccttagcca actacatcgc ttacagacaa aactaa                            1116

SEQ ID NO: 133          moltype = DNA  length = 2340
FEATURE                 Location/Qualifiers
misc_feature            1..2340
                        note = Synthetic oligonucleotide
source                  1..2340
                        mol_type = other DNA
                        organism = synthetic construct
SEQUENCE: 133
gcacagcaca catcagaatc cgcagctgtc gcaaagggca gcagtttgac ccctatagtg  60
agaactgacg ctgagtcaag gagaacaaga tggccaaccg atgacgatga cgccgaacct  120
ttagtggatg agatcagggc aatgcttact tccatgtctg atggtgacat ttccgtgagc  180
gcatacgata cagcctgggt cggattggtt ccaagattag acggcggtga aggtcctcaa  240
tttccagcag ctgtgagatg gataagaaat aaccagttgc ctgacggaag ttggggcgat  300
gccgcattat tctctgccta tgacaggctt atcaataccc ttgcctgcgt tgtaactttg  360
acaaggtggt ccctagaacc agagatgaga ggtagaggac tatctttttt gggtaggaac  420
atgtggaaat tagcaactga agatgaagag tcaatgccta ttggcttcga attagcattt  480
ccatctttga tagagcttgc taagagccta ggtgtccatg acttccctta tgatcaccag  540
gccctacaag gaatctactc ttcaagagag atcaaaatga agaggattcc aaaagaagtg  600
atgcataccg ttccaacatc aatattgcac agtttggagg gtatgcctgg cctagattgg  660
gctaaactac ttaaactaca gagcagcgac ggaagttttt tgttctcacc agctgccact  720
gcatatgctt taatgaatac cggagatgac aggtgtttta gctacatcga tagaacagta  780
aagaaattca acggcggcgt ccctaatgtt tatccagtgg atctatttga acatatttgg  840
gccgttgata gacttgaaag attaggaatc tccaggtact tccaaaagga gatcgaacaa  900
tgcatggatt atgtaaacag gcattggact gaggacggta tttgttgggc aaggaactct  960
gatgtcaaag aggtggacga cacagctatg gcctttagac ttcttaggtt gcacggctac  1020
agcgtcagtc ctgatgtgtt taaaaacttc gaaaaggacg gtgaattttt cgcatttgtc  1080
ggacagtcta atcaagctgt taccggtatg tacaacttaa acagagcaag ccagatatcc  1140
ttcccaggcg aggatgtgct tcatagagct ggtgccttct catatgagtt cttgaggaga  1200
aaagaagcag agggagcttt gagggacaag tggatcattt ctaaagatct acctggtgaa  1260
gttgtgtata ctttggattt tccatggtac ggcaacttac ctagagtcga ggccagagac  1320
tacctagagc aatacggagg tggtgatgac gtttggattg gcaagacatt gtataggatg  1380
ccacttgtaa acaatgatgt atatttggaa ttggcaagaa tggatttcaa ccactgccag  1440
gctttgcatc agttagagtg gcaaggacta aaaagatggt atactgaaaa taggttgatg  1500
gactttggtg tcgcccaaga agatgccctt agagcttatt ttcttgcagc cgcatctgtt  1560
tacgagcctt gtagagctgc cgagaggctt gcatgggcta gagccgcaat actagctaac  1620
gccgtgagca cccacttaag aaatagccca tcattcagag aaaggttaga gcattctctt  1680
aggtgtagac ctagtgaaga gacagatggc tcctggttta actcctcaag tggctctgat  1740
gcagttttag taaaggctgt cttaagactt actgattcat tagccaggga agcacagcca  1800
atccatggag gtgacccaga agatattata cacaagttgt taagatctgc ttgggccgag  1860
tgggttaggg aaaaggcaga cgctgccgat agcgtgtgca atggtagttc tgcagtagaa  1920
caagagggat caagaatggt ccatgataaa cagacctgtc tattattggc tagaatgatc  1980
gaaatttctg ccggtagggc agctggtgaa gcagccagtg aggacggcga tagaagaata  2040
attcaattaa caggctccat ctgcgacagt cttaagcaaa aaatgctagt ttcacaggac  2100
```

```
cctgaaaaaa atgaagagat gatgtctcac gtggatgacg aattgaagtt gaggattaga  2160
gagttcgttc aatatttgct tagactaggt gaaaaaaaga ctggatctag cgaaaccagg  2220
caaacatttt taagtatagt gaaatcatgt tactatgctg ctcattgccc acctcatgtc  2280
gttgatagac acattagtag agtgattttc gagccagtaa gtgccgcaaa gtaaccgcgg  2340

SEQ ID NO: 134          moltype = AA  length = 777
FEATURE                 Location/Qualifiers
source                  1..777
                        mol_type = protein
                        organism = Zea mays
SEQUENCE: 134
AQHTSESAAV AKGSSLTPIV RTDAESRRTR WPTDDDDAEP LVDEIRAMLT SMSDGDISVS  60
AYDTAWVGLV PRLDGGEGPQ FPAAVRWIRN NQLPDGSWGD AALFSAYDRL INTLACVVTL  120
TRWSLEPEMR GRGLSFLGRN MWKLATEDEE SMPIGFELAF PSLIELAKSL GVHDFPYDHQ  180
ALQGIYSSRE IKMKRIPKEV MHTVPTSILH SLEGMPGLDW AKLLKLQSSD GSFLFSPAAT  240
AYALMNTGDD RCFSYIDRTV KKFNGGVPNV YPVDLFEHIW AVDRLERLGI SRYFQKEIEQ  300
CMDYVNRHWT EDGICWARNS DVKEVDDTAM AFRLLRLHGY SVSPDVFKNF EKDGEFFAFV  360
GQSNQAVTGM YNLNRASQIS FPGEDVLHRA GAFSYEFLRR KEAEGALRDK WIISKDLPGE  420
VVYTLDFPWY GNLPRVEARD YLEQYGGGDD VWIGKTLYRM PLVNNDVYLE LARMDFNHCQ  480
ALHQLEWQGL KRWYTENRLM DFGVAQEDAL RAYFLAAASV YEPCRAAERL AWARAAILAN  540
AVSTHLRNSP SFRERLEHSL RCRPSEETDG SWFNSSSGSD AVLVKAVLRL TDSLAREAQP  600
IHGGDPEDII HKLLRSAWAE WVREKADAAD SVCNGSSAVE QEGSRMVHDK QTCLLLARMI  660
EISAGRAAGE AASEDGDRRI IQLTGSICDS LKQKMLVSQD PEKNEEMMSH VDDELKLRIR  720
EFVQYLLRLG EKKTGSSETR QTFLSIVKSC YYAAHCPPHV VDRHISRVIF EPVSAAK     777

SEQ ID NO: 135          moltype = DNA  length = 1555
FEATURE                 Location/Qualifiers
misc_feature            1..1555
                        note = Synthetic oligonucleotide
source                  1..1555
                        mol_type = other DNA
                        organism = synthetic construct
SEQUENCE: 135
atggcggaac aacaaaagat caagaaatca ccacacgttc tactcatccc attcccttta  60
caaggccata taaacccttt catccagttt ggcaaacgat taatctccaa aggtgtcaaa  120
acaacacttg ttaccaccat ccacacctta aactcaaccc taaaccacag taacaccacc  180
accacctcca tcgaaatcca agcaatttcc gatggttgtg atgaaggcgg ttttatgagt  240
gcaggagaat catatttgga aacattcaaa caagttgggt ctaaatcact agctgactta  300
atcaagaagc ttcaaagtga aggaaccaca attgatgcaa tcatttatga ttctatgact  360
gaatgggttt tagatgttgc aattgagttt ggaatcgatg gtggttcgtt tttcactcaa  420
gcttgtgttg taaacagctt atattatcat gttcataagg gtttgatttc tttgccattg  480
ggtgaaactg tttcggttcc tggatttcca gtgcttcaac ggtgggagac accgttaatt  540
ttgcagaatc atgagcaaat acagagccct tggtctcaga tgttgtttgg tcagtttgct  600
aatattgatc aagcacgttg ggtcttcaca aatagttttt acaagctcga ggaagaggta  660
atagagtgga cgagaaagat atggaacttg aaggtaatcg ggccaacact tccatccatg  720
taccttgaca aacgacttga tgatgataaa gataacggat ttaatctcta caaagcaaac  780
catcatgagt gcatgaactg gttagacgat aagccaaagg aatcagttgt ttacgtagca  840
tttggtagcc tggtgaaaca tggacccgaa caagtggaag aaatcacacg ggctttaata  900
gatagtgatg tcaacttctt gtgggttatc aaacataaag aagagggaaa gctcccagaa  960
aatctttcgg aagtaataaa aaccggaaag ggtttgattg tagcatggtg caaacaattg  1020
gatgtgttag cacacgaatc agtaggatgc tttgttacac attgtgggtt caactcaact  1080
cttgaagcaa taagtcttgg agtccccgtt gttgcaatgc ctcaattttc ggatcaaact  1140
acaaatgcca agcttctaga tgaaattttg ggtgttggag ttagagttaa ggctgatgag  1200
aatgggatag tgagaagagg aaatcttgcg tcatgtatta agatgattat ggaggaggaa  1260
agaggagtaa taatccgaaa gaatgcggta aaatggaagg atttggctaa agtagccgtt  1320
catgaaggtg gtagctcaga caatgatatt gtcgaatttg taagtgagct aattaaggct  1380
taaatttttg ttgctttgta ttttatgtgt tatggttttt tgatttagat gtattcaatt  1440
aatattgaat cataactaaa ttcaagatta ttgtttgtaa tattctttgt cctaaaattt  1500
tgcgacttaa aacctttagt ttataaaaag aaattagaaa atactattgc acgga      1555

SEQ ID NO: 136          moltype = DNA  length = 2409
FEATURE                 Location/Qualifiers
misc_feature            1..2409
                        note = Synthetic oligonucleotide
source                  1..2409
                        mol_type = other DNA
                        organism = synthetic construct
SEQUENCE: 136
atgtctcttc agtatcatgt tctaaactcc attccaagta caacctttct cagttctact  60
aaaacaacaa tatcttcttc tttccttacc atctcaggat ctcctctcaa tgtcgctaga  120
gacaaatcca gaagcggttc catacattgt tcaaagcttc gaactcaaga atacattaat  180
tctcaagagg ttcaacatga tttgcctcta atacatgagt ggcaacagct tcaaggagaa  240
gatgctcctc agattagtgt tggaagtaat agtaatgcat tcaaagaagc agtgaagagt  300
gtgaaaacga tcttgagaaa cctaacggac ggggaaatta cgatatcggc ttacgataca  360
gcttgggttg cattgatcga tgccggagat aaaactccgg cgtttccctc cgccgtgaaa  420
tggatcgccg agaaccaact ttccgatggt tcttggggag atgcgtatct cttctcttat  480
catgatcgtc tcatcaatac ccttgcatgc gtcgttgctc taagatcatg gaatctcttt  540
cctcatcaat gcaacaaagg aatcacgttt ttccgggaaa atattgggaa gctagaagac  600
gaaaatgatg agcatatgcc aatcggattc gaagtagcat tcccatcgtt gcttgagata  660
```

-continued

```
gctcgaggaa taaacattga tgtaccgtac gattctccgg tcttaaaaga tatatacgcc  720
aagaaagagc taaagcttac aaggatacca aaagagataa tgcacaagat accaacaaca  780
ttgttgcata gtttggaggg gatgcgtgat ttagattggg aaaagctctt gaaacttcaa  840
tctcaagacg gatctttcct cttctctcct tcctctaccg cttttgcatt catgcagacc  900
cgagacagta actgcctcga gtatttgcga aatgccgtca aacgtttcaa tggaggagtt  960
cccaatgtct ttcccgtgga tcttttcgag cacatatgga tagtggatcg gttacaacgt  1020
ttagggatat cgagatactt tgaagaagag attaaagagt gtcttgacta tgtccacaga  1080
tattggaccg acaatggcat atgttgggct agatgttccc atgtccaaga catcgatgat  1140
acagccatgg catttaggct cttaagacaa catggatacc aagtgtccgc agatgtattc  1200
aagaactttg agaaagaggg agagtttttc tgctttgtgg ggcaatcaaa ccaagcagta  1260
accggtatgt tcaacctata ccgggcatca caattggcgt ttccaaggga agagatattg  1320
aaaaacgcca aagagtttct ttataattat ctgctagaaa aacgggagag agaggagttg  1380
attgataagt ggattataat gaaagactta cctggcgaga ttgggtttgc gttagagatt  1440
ccatggtacg caagcttgcc tcgagtagag acgagattct atattgatca atatggtgga  1500
gaaaacgacg tttggattgg caagactctt tataggatgc catacgtgaa caataatgga  1560
tatctggaat tagcaaaaca agattacaac aattgccaag ctcagcatca gctcgaatgg  1620
gacatattcc aaaagtggta tgaagaaaat aggttaagtg agtggggtgt gcgcagaagt  1680
gagcttctcg agtgttacta cttagcggct gcaactatat ttgaatcaga aaggtcacat  1740
gagagaatgg tttgggctaa gtcaagtgta ttggttaaag ccatttcttc ttcttttggg  1800
gaatcctctg actccagaag aagcttctcc gatcagtttc atgaatacat tgccaatgct  1860
cgacgaagtg atcatcactt taatgacagg aacatgagat tggaccgacc aggatcggtt  1920
caggccagtc ggcttgccgg agtgttaatc gggactttga atcaaatgtc ttttgacctt  1980
ttcatgtctc atggccgtga cgttaacaat ctcctctatc tatcgtgggg agattggatg  2040
gaaaaatgga aactatatgg agatgaagga gaaggagagc tcatggtgaa gatgataatt  2100
ctaatgaaga acaatgacct aactaacttc ttcacccaca ctcacttcgt tcgtctcgcg  2160
gaaatcatca atcgaatctg tcttcctcgc caatacttaa aggcaaggag aaacgatgag  2220
aaggagaaga caataaagag tatggagaag gagatgggga aaatggttga gttagcattg  2280
tcggagagtg acacatttcg tgacgtcagc atcacgtttc ttgatgtagc aaaagcattt  2340
tactactttg ctttatgtgg cgatcatctc caaactcaca tctccaaagt cttgtttcaa  2400
aaagtctag                                                          2409

SEQ ID NO: 137          moltype = AA  length = 400
FEATURE                 Location/Qualifiers
source                  1..400
                        mol_type = protein
                        organism = synthetic construct
SEQUENCE: 137
IILFPVPFQG HINPILQLAN VLYSKGFSIT IFHTNFNKPK TSNYPHFTFR FILDNDPQDE  60
RISNLPTHGP LAGMRIPIIN EHGADELRRE LELLMLASEE DEEVSCLITD ALWYFAQSVA  120
DSLNLRRLVL MTSSLFNFHA HVSLPQFDEL GYLDPDDKTR LEEQASGFPM LKVKDIKSAY  180
SNWQILKEIL GKMIKQTKAS SGVIWNSFKE LEESELETVI REIPAPSFLI PLPKHLTASS  240
SSLLDHDRTV FQWLDQQPPS SVLYVSFGST SEVDEKDFLE IARGLVDSKQ SFLWVVRPGF  300
VKGSTWVEPL PDGFLGERGR IVKWVPQQEV LAHGAIGAFW THSGWNSTLE SVCEGVPMIF  360
SDFGLDQPLN ARYMSDVLKV LMKGGSSYES LESLVSYISS                        400

SEQ ID NO: 138          moltype = AA  length = 446
FEATURE                 Location/Qualifiers
source                  1..446
                        mol_type = protein
                        organism = synthetic construct
SEQUENCE: 138
RRIILFPVPF QGHINPILQL ANVLYSKGFS ITIFHTNFNK PKTSNYPHFT FRFILDNDPQ  60
DERISNLPTH GPLAGMRIPI INEHGADELR RELELLMLAS EEDEEVSCLI TDALWYFAQS  120
VADSLNLRRL VLMTSSLFNF HAHVSLPQFD ELGYLDPDDK TRLEEQASGF PMLKVKDIKS  180
AYSNWQILKE ILGKMIKQTK ASSGVIWNSF KELEESELET VIREIPAPSF LIPLPKHLTA  240
SSSSLLDHDR TVFQWLDQQP PSSVLYVSFG STSEVDEKDF LEIARGLVDS KQSFLWVVRP  300
GFVKGSTWVE PLPDGFLGER GRIVKWVPQQ EVLAHGAIGA FWTHSGWNST LESVCEGVPM  360
IFSDFGLDQP LNARYMSDVL KVGVYLENGW ERGEIANAIR RVMVDEEGEY IRQNARVLKQ  420
KADVSLMKGG SSYESLESLV SYISSL                                        446
```

METHODS FOR IMPROVED PRODUCTION OF REBAUDIOSIDE D AND REBAUDIOSIDE M

CROSS-REFERENCE TO RELATED APPLICATIONS

This application is a continuation of the U.S. application Ser. No. 16/799,541, filed on Feb. 24, 2020, and issued as U.S. Pat. No. 11,530,431 on Dec. 20, 2022, which is a continuation of the U.S. application Ser. No. 15/908,214, filed on Feb. 28, 2018, and issued as the U.S. Pat. No. 10,612,066 on Apr. 7, 2020, which is a divisional of the U.S. application Ser. No. 14/761,629, filed on Jul. 17, 2015, and issued as the U.S. Pat. No. 9,957,540 on May 1, 2018, which is the U.S. National Stage Application of International Application No. PCT/EP2014/052363, filed on Feb. 6, 2014, and claims the benefit of the U.S. Provisional Application No. 61/761,490, filed on Feb. 6, 2013 and the U.S. Provisional Application No. 61/886,442, filed on Oct. 3, 2013, the disclosures of each of which are explicitly incorporated by reference herein in their entirety.

REFERENCE TO AN ELECTRONIC SEQUENCE LISTING

The instant application contains a Sequence Listing that has been submitted electronically and which is hereby incorporated by reference in its entirety. The Sequence Listing was created on Dec. 15, 2025, is named "13-1364-US-CON2_SequenceListing.xml" and is 295,827 bytes in size.

BACKGROUND OF THE INVENTION

Field of the Invention

The invention disclosed herein relates generally to the field of recombinant production of steviol glycosides. Particularly, the invention provides methods for recombinant production of steviol glycoside and compositions containing steviol glycosides.

Description of Related Art

Sweeteners are well known as ingredients used most commonly in the food, beverage, or confectionary industries. The sweetener can either be incorporated into a final food product during production or for stand-alone use, when appropriately diluted or as a tabletop sweetener. Sweeteners include natural sweeteners such as sucrose, high fructose corn syrup, molasses, maple syrup, and honey and artificial sweeteners such as aspartame, saccharine and sucralose. *Stevia* extract is a natural sweetener that can be isolated and extracted from a perennial shrub, *Stevia rebaudiana. Stevia* is commonly grown in South America and Asia for commercial production of *stevia* extract. *Stevia* extract, purified to various degrees, is used commercially as a high intensity sweetener in foods and in blends or alone as a tabletop sweetener.

Extracts of the *Stevia* plant contain Rebaudiosides and other steviol glycosides that contribute to the sweet flavor, although the amount of each glycoside often varies among different production batches. Existing commercial products are predominantly Rebaudioside A with lesser amounts of other glycosides such as Rebaudioside C, D, and F. *Stevia* extracts can also contain contaminants such as plant-derived compounds that contribute to off-flavors or have other undesirable effects. These contaminants can be more or less problematic depending on the food system or application of choice. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, beta-sitosterol, alpha- and beta-amyrin, lupeol, beta-amryin acetate, pentacyclic triterpenes, centauredin, quercitin, epi-alpha-cadinol, carophyllenes and derivatives, beta-pinene, beta-sitosterol, and gibberellin.

As recovery and purification of steviol glycosides from the *Stevia* plant have proven to be labor intensive and inefficient, there remains a need for a recombinant production system that can produce high yields of desired steviol glycosides such as Rebaudioside D and Rebaudioside M with less plant-based contaminants, including but not limited to stevioside. Steviol glycoside-producing *Saccharomyces cerevisiae* strains as well as bio-conversion and biosynthesis in vitro are described in PCT Application Nos. PCT/US2012/050021 and PCT/US2011/038967, which are incorporated herein by reference in their entirety.

In nature, the *Stevia* uridine diphosphate dependent glycosyltransferase 76G1 (UGT76G1) catalyzes several glycosylation reactions on the steviol backbone, which leads to the production of steviol glycosides. Recently, it has been shown that UGT76G1 can convert 1,2-stevioside to Rebaudioside A and 1,2-bioside to Rebaudioside B (see Richman et al., 2005, The Plant Journal 41:56-67). Thus, there is a need in the art to identify reactions directed towards producing glycosylated Rebaudiosides by UGT76G1 or other UGT enzymes. Particularly, there is a need to explore or identify other reactions catalysed by UGT76G1 as well a need to increase UGT76G1's catalytic capability in order to produce higher yields of steviol glycosides such as Rebaudioside D and Rebaudioside M.

SUMMARY OF THE INVENTION

It is against the above background that the present invention provides certain advantages and advancements over the prior art.

In particular, the invention is directed to biosynthesis of Rebaudioside D and Rebaudioside M and Rebaudioside D and Rebaudioside M preparations from genetically modified cells.

In particular embodiments, the invention is directed to Rebaudioside D and Rebaudioside M preparations from genetically modified cells having significantly improved biosynthesis rates and yields.

This disclosure relates to the production of steviol glycosides. In particular, this disclosure relates to the production of steviol glycosides including Rebaudioside M:

(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl(1R,5R,9S,13R)-13-{[(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl]oxy}-5,9-dimethyl-14-methylidenetetracyclo[11.2.1.$0^{1,10}$0.$0^{4,9}$]hexadecane-5-carboxylate and Rebaudioside D:

4,5-dihydroxy-6-(hydroxymethyl)-3-{[3,4,5-trihydroxy-6-(hydroxymethyl)oxan-2-yl]oxy}oxan-2-yl 13-{[5-hydroxy-6-(hydroxymethyl)-3,4-bis({[3,4,5-trihydroxy-6-(hydroxymethyl) oxan-2-yl]oxy})oxan-2-yl]

oxy}-5,9-dimethyl-14-methylidene tetracyclo [11.2.1.$^{01,10}$0.0$^{4,9}$]hexadecane-5-carboxylate by means not limited to in recombinant hosts such as recombinant microorganisms, through bioconversion, and in vitro.

Thus, in one aspect, the disclosure provides a recombinant host, for example, a microorganism, comprising one or more biosynthetic genes, wherein the expression of one or more biosynthetic genes results in production of steviol glycosides including Rebaudioside M and Rebaudioside D.

In particular, expression of one or more uridine 5'-diphospho (UDP) glycosyl transferases described herein, such as EUGT11, UGT74G1, UGT76G1, UGT85C2, and UGT91D2, facilitate production and accumulation of Rebaudioside M or Rebaudioside D in recombinant hosts or certain in vitro systems.

Although this invention disclosed herein is not limited to specific advantages or functionality, the invention provides a composition comprising from about 1% to about 99% w/w of Rebaudioside M, wherein the composition has a reduced level of *Stevia*-derived contaminants relative to a *stevia* extract, wherein at least one of said contaminants is a plant-derived compound. In certain instances, said plant-derived contaminating compound can, inter alia, contribute to off-flavors.

In some aspects, the composition comprising from about 1% to about 99% w/w of Rebaudioside M has less than 0.1% of *Stevia*-derived contaminants relative to a *stevia* extract, wherein at least one of said contaminants is a plant-derived compound. In certain instances, said plant-derived contaminating compound can, inter alia, contribute to off-flavors.

The invention further provides a food product comprising the composition as described above.

In some aspects, the food product is a beverage or a beverage concentrate.

The invention further provides a recombinant host cell that expresses:

(a) a recombinant gene encoding a GGPPS;

(b) a recombinant gene encoding an ent-copalyl diphosphate synthase (CDPS) polypeptide;

(c) a recombinant gene encoding a kaurene oxidase (KO) polypeptide;

(d) a recombinant gene encoding a kaurene synthase (KS) polypeptide;

(e) a recombinant gene encoding a steviol synthase (KAH) polypeptide;

(f) a recombinant gene encoding a cytochrome P450 reductase (CPR) polypeptide;

(g) a recombinant gene encoding a UGT85C2 polypeptide;

(h) a recombinant gene encoding a UGT74G1 polypeptide;

(i) a recombinant gene encoding a UGT76G1 polypeptide;

(j) a recombinant gene encoding a UGT91d2 polypeptide; and (k) a recombinant gene encoding a EUGT11 polypeptide;

wherein at least one of said genes is a recombinant gene and wherein the cell produces Rebaudioside D, Rebaudioside M, Rebaudioside Q, and/or Rebaudioside I.

The invention further provides a recombinant host cell comprising exogenous nucleic acids comprising:

(a) a recombinant gene encoding a GGPPS;

(b) a recombinant gene encoding an ent-copalyl diphosphate synthase (CDPS) polypeptide;

(c) a recombinant gene encoding a kaurene oxidase (KO) polypeptide;

(d) a recombinant gene encoding a kaurene synthase (KS) polypeptide;

(e) a recombinant gene encoding a steviol synthase (KAH) polypeptide;

(f) a recombinant gene encoding a cytochrome P450 reductase (CPR) polypeptide;

(g) a recombinant gene encoding a UGT85C2 polypeptide;

(h) a recombinant gene encoding a UGT74G1 polypeptide;

(i) a recombinant gene encoding a UGT76G1 polypeptide;

(j) a recombinant gene encoding a UGT91d2 polypeptide; and (k) a recombinant gene encoding a EUGT11 polypeptide;

wherein the cell produces Rebaudioside D, Rebaudioside M, Rebaudioside Q, and/or Rebaudioside I.

The invention further provides a recombinant host cell that expresses a GGPPS, an ent-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91d2 polypeptide, and a EUGT11 polypeptide, wherein at least one of said polypeptides is encoded by an exogenous or heterologous gene having been introduced into said cell;

wherein the cell produces a di-glycosylated steviol glycoside (13-hydroxy kaur-16-en-18-oic acid, [2-O-β-D-glucopyranosyl-β-D-glucopyranosyl]ester) or a tri-glycosylated steviol glycoside (13-hydroxy kaur-16-en-18-oic acid; [2-O-β-D-glucopyranosyl-3-O-β-D-glucopyranosyl-β-D-glucopyranosyl]ester).

In some embodiments, targeted production of individual Rebaudiosides can be accomplished by controlling the relative levels of UDP-glycosyl transferase activities (see FIG. 1).

In some aspects, targeted production of individual Rebaudiosides can be accomplished by differential copy numbers of the UGT-encoding genes (see FIG. 1) in the recombinant cell, differential promoter strengths, and/or by utilizing mutants with increased specificity/activity towards the product of interest. For example, low levels of Rebaudioside D, E, and M will be formed if EUGT11 is expressed at low levels in comparison to the other UGTs, which would favor Rebaudioside A formation. High levels of EUGT11 expression result in production of more 19-O 1,2 diglucoside that can serve as substrate for UGT76G1 to form Rebaudioside M. In certain advantageous embodiments, additional copies or mutant versions of UGT76G1 in recombinant cells of the invention can improve the rate of Rebaudioside M formation from Rebaudioside D.

In some embodiments, UGT76G1 catalyzes glycosylation of steviol and steviol glycosides at the 19-O position. Thus, in some embodiments, one or more of RebM, RebQ, RebI, di-glycosylated steviol glycoside (13-hydroxy kaur-16-en-18-oic acid, [2-O-β-D-glucopyranosyl-β-D-glucopyranosyl] ester), or tri-glycosylated steviol glycoside ((13-hydroxy kaur-16-en-18-oic acid; [2-O-β-D-glucopyranosyl-3-O-β-D-glucopyranosyl-β-D-glucopyranosyl]ester) are produced in a recombinant host expressing a recombinant gene encoding a UGT76G1 polypeptide, through bioconversion, or through catalysis by UGT76G1 in vitro. In some embodiments, UGT76G1 catalyzes the glycosylation of steviol and steviol glycosides at the 13-O position and preferentially glycosylates steviol glycoside substrates that are 1,2-diglycosylated at the 13-O position or mono-glycosylated at the 13-O position. In some embodiments, UGT76G1 does not show a preference for the glycosylation state of the 19-O position.

In some aspects, the GGPPS comprises *Synechococcus* sp. GGPPS set forth in SEQ ID NO:24.

In some aspects, the CDP polypeptide comprises a *Z. mays* CDPS polypeptide set forth in SEQ ID NO:13, wherein the polypeptide is lacking a chloroplast transit peptide.

In some aspects, the KO polypeptide comprises a KO polypeptide having 70% or greater identity to the amino acid sequence of the *S. rebaudiana* KO polypeptide set forth in SEQ ID NO:25.

In some aspects, the KS polypeptide comprises a KS polypeptide having 40% or greater identity to the amino acid sequence of the *A. thaliana* KS polypeptide set forth in SEQ ID NO:21.

In some aspects, the KAH polypeptide comprises a KAH polypeptide having 60% or greater identity to the *S. rebaudiana* KAH amino acid sequence set forth in SEQ ID NO:11.

In some aspects, the CPR polypeptide comprises a CPR polypeptide having 65% or greater identity to a *S. rebaudiana* CPR amino acid sequence set forth in SEQ ID NO:4, an *A. thaliana* CPR polypeptide of the amino acid sequence set forth in SEQ ID NO:9 or a combination thereof.

In some aspects, the UGT85C2 polypeptide comprises a UGT85C2 polypeptide having 55% or greater identity to the amino acid sequence set forth in SEQ ID NO:26.

In some aspects, the UGT74G1 polypeptide comprises a UGT74G1 polypeptide having 55% or greater identity to the amino acid sequence set forth in SEQ ID NO:19.

In some aspects, the UGT76G1 polypeptide comprises a UGT76G1 polypeptide having 50% or greater identity to the amino acid sequence set forth in SEQ ID NO:2.

In some aspects, the UGT91d2 polypeptide comprises a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof.

In some aspects, the EUGT11 polypeptide comprises a EUGT11 polypeptide having 65% or greater identity to the Os03g0702000 amino acid sequence set forth in SEQ ID NO:16.

In some aspects, the UGT76G1 polypeptide comprises one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

In some aspects, the UGT76G1 polypeptide comprises one or more of the UGT76G1 polypeptide variants comprising: Q23G, Q23H, 126F, 126W, T146A, T146G, T146P, H155R, L257P, L257W, L257T, L257G, L257A, L257R, L257E, S283G and S283N of SEQ ID NO:2.

In some aspects, the recombinant host cell is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides the cell as disclosed herein that produces Rebaudioside D.

The invention further provides the cell as disclosed herein that produces Rebaudioside M, Rebaudioside Q or Rebaudioside I.

The invention further provides the cell as disclosed herein that produces the di-glycosylated steviol glycoside (13-hydroxy kaur-16-en-18-oic acid, [2-O-β-D-glucopyranosyl-β-D-glucopyranosyl]ester) or the tri-glycosylated steviol glycoside (13-hydroxy kaur-16-en-18-oic acid; [2-O-β-D-glucopyranosyl-3-O-β-D-glucopyranosyl-3-D-glucopyranosyl]ester).

In some aspects, the Rebaudioside D is produced in the cell as disclosed herein at a concentration of between about 1,000 mg/L and about 2,900 mg/L.

In some aspects, the Rebaudioside D and Rebaudioside M are produced in the cell as disclosed herein at a ratio of between about 1:1 to about 1.7:1.

In some aspects, the Rebaudioside M is produced in the cell as disclosed herein at a concentration of between about 600 mg/L and about 2,800 mg/L.

In some aspects, the Rebaudioside M and Rebaudioside D are produced in the cell as disclosed herein at a ratio of between about 0.6:1 to about 1.1:1.

The invention further provides a method of producing Rebaudioside D, Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester), comprising:

(a) culturing a recombinant cell in a culture medium, under conditions wherein genes encoding a GGPPS; an ent-copalyl diphosphate synthase (CDPS) polypeptide; a kaurene oxidase (KO) polypeptide; a kaurene synthase (KS) polypeptide; a steviol synthase (KAH) polypeptide; a cytochrome P450 reductase (CPR) polypeptide; a UGT85C2 polypeptide; a UGT74G1 polypeptide; a UGT76G1 polypeptide; a UGT91d2 polypeptide; and a EUGT11 polypeptide are expressed, comprising inducing expression of said genes or constitutively expressing said genes; and (b) synthesizing Rebaudioside D, Rebaudioside M, Rebaudioside Q, Rebaudioside 1, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester) in the cell; and optionally (c) isolating Rebaudioside D, Rebaudioside M, Rebaudioside Q, Rebaudioside 1, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester).

In some aspects, Rebaudioside D is produced by a cell as disclosed herein.

In some aspects, Rebaudioside M, Rebaudioside Q or Rebaudioside I is produced by a cell as disclosed herein.

In some aspects, di-glycosylated steviol glycoside (13-hydroxy kaur-16-en-18-oic acid, [2-O-β-D-glucopyranosyl-β-D-glucopyranosyl]ester) or the tri-glycosylated steviol glycoside (13-hydroxy kaur-16-en-18-oic acid; [2-O-β-D-glucopyranosyl-3-O-β-D-glucopyranosyl-β-D-glucopyranosyl]ester) is produced by a cell as disclosed herein.

In some aspects, Rebaudioside D is produced at a concentration of between about 1,000 mg/L and about 2,900 mg/L.

In some aspects, Rebaudioside D and Rebaudioside M are produced at a ratio of between about 1:1 to about 1.7:1.

In some aspects, Rebaudioside M is produced at a concentration of between about 600 mg/L and about 2,800 mg/L.

In some aspects, Rebaudioside M and Rebaudioside D are produced at a ratio of between about 0.6:1 to about 1.1:1.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides methods for producing Rebaudioside D, Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester) through in vitro bioconversion of plant-derived or synthetic steviol or steviol glycosides using one or more UGT polypeptides.

In some aspects, said methods for producing Rebaudioside D or Rebaudioside M comprise using at least one UGT polypeptide that is:

- a UGT85C2 polypeptide comprising a UGT85C2 polypeptide having 55% or greater identity to the amino acid sequence set forth in SEQ ID NO:26;
- a UGT74G1 polypeptide comprising a UGT74G1 polypeptide having 55% or greater identity to the amino acid sequence set forth in SEQ ID NO:19;
- a UGT76G1 polypeptide comprising a UGT76G1 polypeptide having 50% or greater identity to the amino acid sequence set forth in SEQ ID NO:2;
- a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof; or
- a EUGT11 polypeptide comprising a EUGT11 polypeptide having 65% or greater identity to the Os03g0702000 amino acid sequence set forth in SEQ ID NO:16.

In some aspects, the steviol glycoside used for production of Rebaudioside D comprises stevioside, RebA, RebB, RebE or mixtures thereof.

In some aspects, the steviol glycoside used for production of Rebaudioside M comprises stevioside, RebA, RebB, RebE, RebD or mixtures thereof.

In some aspects, methods for producing Rebaudioside Q comprise using at least one UGT polypeptide that is:

- a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; or a UGT76G1 polypeptide comprising a UGT76G1 polypeptide having 50% or greater identity to the amino acid sequence set forth in SEQ ID NO:2.

In some aspects, the steviol glycoside used for producing Rebaudioside Q comprises rubusoside, RebG or mixtures thereof.

In some aspects, methods for producing Rebaudioside I comprise using at least one UGT polypeptide that is:

- a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15; or a combination thereof.

In some aspects, the steviol glycoside used for producing Rebaudioside I comprises 1,2-stevioside, RebA, or mixtures thereof.

In some aspects, methods for producing di-glycosylated steviol glycoside (13-hydroxy kaur-16-en-18-oic acid, [2-O-β-D-glucopyranosyl-β-D-glucopyranosyl]ester) comprise using at least one or UGT polypeptide that is:

- a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16.

In some aspects, the steviol glycoside used for producing di-glycosylated steviol glycoside (13-hydroxy kaur-16-en-18-oic acid, [2-O-β-D-glucopyranosyl-β-D-glucopyranosyl]ester) comprises steviol-19-O-glucoside.

In some aspects, methods for producing tri-glycosylated steviol glycoside (13-hydroxy kaur-16-en-18-oic acid; [2-O-β-D-glucopyranosyl-3-O-β-D-glucopyranosyl-β-D-glucopyranosyl]ester) comprise using at least one UGT polypeptide that is:

- a UGT76G1 polypeptide comprising a UGT76G1 polypeptide having 50% or greater identity to the amino acid sequence set forth in SEQ ID NO:2; a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16.

In some aspects, the steviol glycoside used for producing tri-glycosylated steviol glycoside (13-hydroxy kaur-16-en-18-oic acid; [2-O-β-D-glucopyranosyl-3-O-β-D-glucopyranosyl-β-D-glucopyranosyl]ester) comprises di-glycosylated steviol glycoside (13-hydroxy kaur-16-en-18-oic acid, [2-O-β-D-glucopyranosyl-β-D-glucopyranosyl]ester), steviol-19-O-glucoside, or mixtures thereof.

In some aspects, bioconversion methods as disclosed herein comprise enzymatic bioconversion or whole cell bioconversion.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides a recombinant host cell comprising exogenous nucleic acids comprising:

(a) a recombinant gene encoding a GGPPS;

(b) a recombinant gene encoding an ent-copalyl diphosphate synthase (CDPS) polypeptide;

(c) a recombinant gene encoding a kaurene oxidase (KO) polypeptide;

(d) a recombinant gene encoding a kaurene synthase (KS) polypeptide;

(e) a recombinant gene encoding a steviol synthase (KAH) polypeptide;

(f) a recombinant gene encoding a cytochrome P450 reductase (CPR) polypeptide; and/or (g) a one or more recombinant genes encoding a one or more UGT polypeptide;

wherein the cell produces Rebaudioside D, Rebaudioside M, Rebaudioside Q, or Rebaudioside I, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester).

In some aspects of said recombinant host cells, the GGPPS comprises *Synechococcus* sp. GGPPS set forth in SEQ ID NO:24; the CDP polypeptide comprises a *Z. mays* CDPS polypeptide set forth in SEQ ID NO:13, wherein the polypeptide is lacking a chloroplast transit peptide; the KO polypeptide comprises a KO polypeptide having 70% or greater identity to the amino acid sequence of the *S. rebaudiana* KO polypeptide set forth in SEQ ID NO:25; the KS polypeptide comprises a KS polypeptide having 40% or greater identity to the amino acid sequence of the *A. thaliana* KS polypeptide set forth in SEQ ID NO:21; the KAH polypeptide comprises a KAH polypeptide having 60% or greater identity to the *S. rebaudiana* KAH amino acid sequence set forth in SEQ ID NO:11; the CPR polypeptide comprises a CPR polypeptide having 65% or greater identity to a *S. rebaudiana* CPR amino acid sequence set forth in SEQ ID NO:4, an *A. thaliana* CPR polypeptide of the amino acid sequence set forth in SEQ ID NO:9 or a combination thereof.

In some aspects, the cell produces Rebaudioside D or Rebaudioside M, wherein the UGT polypeptide is at least one UGT polypeptide that is:

a UGT85C2 polypeptide comprising a UGT85C2 polypeptide having 55% or greater identity to the amino acid sequence set forth in SEQ ID NO:26;

a UGT74G1 polypeptide comprising a UGT74G1 polypeptide having 55% or greater identity to the amino acid sequence set forth in SEQ ID NO:19;

a UGT76G1 polypeptide comprising a UGT76G1 polypeptide having 50% or greater identity to the amino acid sequence set forth in SEQ ID NO:2;

a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof; or a EUGT11 polypeptide comprising a EUGT11 polypeptide having 65% or greater identity to the Os03g0702000 amino acid sequence set forth in SEQ ID NO:16.

In some aspects, the cell produces Rebaudioside Q, wherein the UGT polypeptide is at least one UGT polypeptide that is:

a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; or a UGT76G1 polypeptide comprising a UGT76G1 polypeptide having 50% or greater identity to the amino acid sequence set forth in SEQ ID NO:2.

In some aspects, the cell produces Rebaudioside I, wherein the UGT polypeptide is at least one UGT polypeptide that is:

a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15; or a combination thereof.

In some aspects, the cell produces di-glycosylated steviol glycoside (13-hydroxy kaur-16-en-18-oic acid, [2-O-β-D-glucopyranosyl-β-D-glucopyranosyl]ester), wherein the UGT polypeptide is at least one UGT polypeptide that is:

a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16.

In some aspects, the cell produces tri-glycosylated steviol glycoside (13-hydroxy kaur-16-en-18-oic acid; [2-O-β-D-glucopyranosyl-3-O-β-D-glucopyranosyl-β-D-glucopyranosyl]ester), wherein the UGT polypeptide is at least one UGT polypeptide that is:

a UGT76G1 polypeptide comprising a UGT76G1 polypeptide having 50% or greater identity to the amino acid sequence set forth in SEQ ID NO:2; a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16

In some aspects, the UGT76G1 polypeptide comprises one or more of the UGT76G1 polypeptide variants comprising: Q23G, Q23H, 126F, 126W, T146A, T146G, T146P, H155R, L257P, L257W, L257T, L257G, L257A, L257R, L257E, S283G and S283N of SEQ ID NO:2.

In some aspects, the UGT76G1 polypeptide comprises one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

In some aspects, the recombinant host cell is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides methods for producing Rebaudioside D by fermentation using a recombinant cell as disclosed herein.

The invention further provides methods for producing Rebaudioside M by fermentation using a recombinant cell as disclosed herein.

The invention further provides methods for producing Rebaudioside Q by fermentation using a recombinant cell as disclosed herein.

The invention further provides methods for producing Rebaudioside I by fermentation using a recombinant cell as disclosed herein.

The invention further provides methods for producing di-glycosylated steviol glycoside (13-hydroxy kaur-16-en-18-oic acid, [2-O-β-D-glucopyranosyl-β-D-glucopyranosyl] ester) by fermentation using a recombinant cell as disclosed herein.

The invention further provides methods for producing tri-glycosylated steviol glycoside (13-hydroxy kaur-16-en-18-oic acid; [2-O-β-D-glucopyranosyl-3-O-β-D-glucopyranosyl-β-D-glucopyranosyl]ester) by fermentation using a recombinant cell as disclosed herein.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides in vitro methods for producing Rebaudioside D or Rebaudioside M, comprising:

(a) adding one or more of a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof; a EUGT11 polypeptide comprising a EUGT11 polypeptide having 65% or greater identity to the Os03g0702000 amino acid sequence set forth in SEQ ID NO:16, and plant-derived or synthetic steviol or steviol glycosides to the reaction mixture; and (b) synthesizing Rebaudioside D or Rebaudioside M in the reaction mixture; and optionally (c) isolating Rebaudioside D or Rebaudioside M in the reaction mixture.

The invention further provides in vitro methods for producing Rebaudioside Q, comprising:

(a) adding one or more of a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2, and plant-derived or synthetic steviol or steviol glycosides to the reaction mixture; and (b) synthesizing Rebaudioside Q in the reaction mixture; and optionally (c) isolating Rebaudioside Q in the reaction mixture.

The invention further provides in vitro methods for producing Rebaudioside I, comprising:

(a) adding one or more of a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof, and plant-derived or synthetic steviol or steviol glycosides to the reaction mixture; and (b) synthesizing Rebaudioside I in the reaction mixture; and optionally (c) isolating Rebaudioside I in the reaction mixture.

The invention further provides in vitro methods for producing a di-glycosylated steviol glycoside (13-hydroxy kaur-16-en-18-oic acid, [2-O-β-D-glucopyranosyl-β-D-glucopyranosyl]ester), comprising:

(a) adding one or more of a UGT74G1 polypeptide comprising a UGT74G1 polypeptide having 55% or greater identity to the amino acid sequence set forth in SEQ ID NO:19; a EUGT11 polypeptide comprising a EUGT11 polypeptide having 65% or greater identity to the Os03g0702000 amino acid sequence set forth in SEQ ID NO:16, and plant-derived or synthetic steviol or steviol glycosides to the reaction mixture; and (b) synthesizing the di-glycosylated steviol glycoside (13-hydroxy kaur-16-en-18-oic acid, [2-O-β-D-glucopyranosyl-β-D-glucopyranosyl]ester) in the reaction mixture; and optionally (c) isolating di-glycosylated steviol glycoside (13-hydroxy kaur-16-en-18-oic acid, [2-O-β-D-glucopyranosyl-β-D-glucopyranosyl]ester) in the reaction mixture.

The invention further provides in vitro methods for producing a tri-glycosylated steviol glycoside (13-hydroxy kaur-16-en-18-oic acid; [2-O-β-D-glucopyranosyl-3-O-β-D-glucopyranosyl-β-D-glucopyranosyl]ester), comprising:

(a) adding one or more of a UGT76G1 polypeptide comprising a UGT76G1 polypeptide having 50% or greater identity to the amino acid sequence set forth in SEQ ID NO:2; a UGT74G1 polypeptide comprising a UGT74G1 polypeptide having 55% or greater identity to the amino acid sequence set forth in SEQ ID NO:19; a EUGT11 polypeptide comprising a EUGT11 polypeptide having 65% or greater identity to the Os03g0702000 amino acid sequence set forth in SEQ ID NO:16, and plant-derived or synthetic steviol or steviol glycosides to the reaction mixture; and (b) synthesizing tri-glycosylated steviol glycoside (13-hydroxy kaur-16-en-18-oic acid; [2-O-β-D-glucopyranosyl-3-O-β-D-glucopyranosyl-β-D-glucopyranosyl]ester) in the reaction mixture; and optionally (c) isolating tri-glycosylated steviol glycoside (13-hydroxy kaur-16-en-18-oic acid; [2-O-β-D-glucopyranosyl-3-O-β-D-glucopyranosyl-β-D-glucopyranosyl]ester) in the reaction mixture.

In some aspects, the UGT76G1 polypeptide for producing Rebaudioside D comprises one or more of the UGT76G1 polypeptide variants selected from the group consisting of: Q23G, Q23H, 126F, 126W, T146A, T146G, T146P, H155R, L257P, L257W, L257T, L257G, L257A, L257R, L257E, S283G and S283N of SEQ ID NO:2.

In some aspects, the UGT76G1 polypeptide for producing Rebaudioside M, Rebaudioside Q, Rebaudioside 1, di-glycosylated steviol glycoside and tri-glycosylated steviol glycoside comprises one or more of the UGT76G1 polypeptide variants selected from the group consisting of: T55K, T55E, S56A, Y128S, Y128E, H155L, H155R, Q198R, S285R, S285T, S253W, S253G, T284R, T284G, S285G, K337E, K337P and L379V of SEQ ID NO:2.

In some aspects, the in vitro method disclosed is enzymatic in vitro method or whole cell in vitro method.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides Rebaudioside Q produced by the methods disclosed herein.

The invention further provides Rebaudioside I produced by the methods disclosed herein.

The invention further provides a di-glycosylated steviol glycoside (13-hydroxy kaur-16-en-18-oic acid, [2-O-β-D-glucopyranosyl-β-D-glucopyranosyl]ester) produced by the methods disclosed herein.

The invention further provides a tri-glycosylated steviol glycoside (13-hydroxy kaur-16-en-18-oic acid; [2-O-β-D-glucopyranosyl-3-O-β-D-glucopyranosyl-β-D-glucopyranosyl]ester) produced by the methods disclosed herein.

The invention further provides a UGT76G1 polypeptide for producing Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester), wherein the UGT76G1 polypeptide comprises a UGT76G1 polypeptide of SEQ ID NO:2 or one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

The invention further provides a UGT76G1 polypeptide for producing Rebaudioside D, wherein the UGT76G1 polypeptide comprises a UGT76G1 polypeptide of SEQ ID NO:2 or one or more of the UGT76G1 polypeptide variants comprising: Q23G, Q23H, 126F, 126W, T146A, T146G, T146P, H155R, L257P, L257W, L257T, L257G, L257A, L257R, L257E, S283G and S283N of SEQ ID NO:2.

The invention further provides recombinant host cell comprising a recombinant gene encoding a UGT76G1 polypeptide, wherein the UGT76G1 polypeptide comprises one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

In some aspects, the recombinant host cell as disclosed herein produces Rebaudioside D.

The invention further provides a recombinant host cell comprising a recombinant gene encoding a UGT76G1 polypeptide, wherein the UGT76G1 polypeptide comprises one or more of the UGT76G1 polypeptide variants comprising: Q23G, Q23H, 126F, 126W, T146A, T146G, T146P, H155R, L257P, L257W, L257T, L257G, L257A, L257R, L257E, S283G and S283N of SEQ ID NO:2.

In some aspects, the recombinant host cell as disclosed herein produces Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl]ester) or tri-glycosylated steviol glycoside (13-hydroxy kaur-16-en-18-oic acid; [2-O-β-D-glucopyranosyl-3-O-β-D-glucopyranosyl-β-D-glucopyranosyl]ester).

In some aspects, the recombinant host cell is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a Saccharomycete.

In some aspects, the yeast cell is a cell from *Saccharomyces cerevisiae* species.

The invention further provides a composition comprising from about 1% to about 99% w/w of Rebaudioside D, wherein the composition has a reduced level of *Stevia*- derived contaminants relative to a *stevia* extract. In certain instances, the at least one of said contaminants is a plant-derived compound that inter alia contributes to off-flavors in the steviol glycoside product.

In some aspects, the composition has less than 0.1% of *Stevia*-derived contaminants relative to a *stevia* extract. In certain instances, the at least one of said contaminants is a plant-derived compound that inter alia contributes to off-flavors in the steviol glycoside product.

The invention further provides a food product comprising the composition as disclosed herein.

In some aspects, the food product is a beverage or a beverage concentrate.

Any of the hosts described herein can be a microorganism (e.g., a Saccharomycete such as *Saccharomyces cerevisiae*, or *Escherichia coli*), or a plant or plant cell (e.g., a *Stevia* such as a *Stevia rebaudiana* or *Physcomitrella*).

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 1 shows the steviol glycoside glycosylation reactions and the enzymes by which they are catalyzed.

FIG. 2 shows the chemical structure of Rebaudioside M (RebM).

FIG. 3 shows the chemical structure of Rebaudioside D (RebD).

FIG. 4 shows biochemical pathway for the production of steviol.

FIG. 8C is the structure of the NMR structure of the indicated tri-glycosylated steviol glycoside (13-hydroxy kaur-16-en-18-oic acid; [2-O-β-D-glucopyranosyl-3-O-β-D-glucopyranosyl-β-D-glucopyranosyl]ester, an isomer of RebB. The IUPAC name for tri-glycosylated steviol glycoside is (2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl (1R,4S,5R,9S,10R,13S)-13-hydroxy-5,9-dimethyl-14-methylidenetetracyclo[11.2.1.0^{1,10}0.0^{4,9}]hexadecane-5-carboxylate.

FIG. 14 shows the variance in the three homology models of UGT76G1. 76G1_1 is represented by SEQ ID NO: 137, and 76G1_2 and 76G1_3 are represented by SEQ ID NO: 138.

Figure 5:
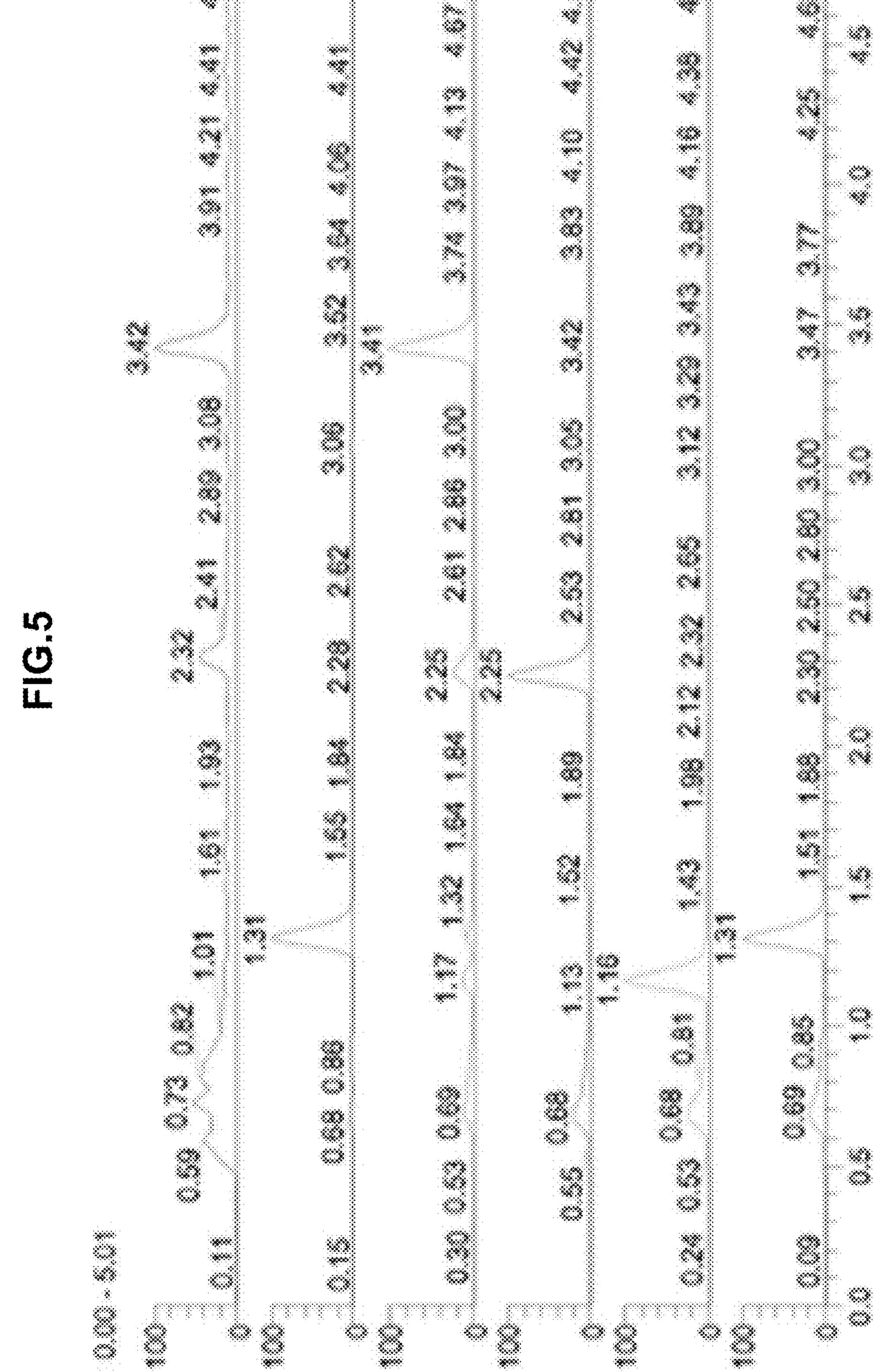
FIG. 5 is a representative chromatogram of Liquid Chromatography-Mass Spectrometry (LC-MS) analysis showing formation of a hexa-glycosylated steviol glycoside at 1.31 min retention time. The traces, from top to bottom, correspond to the m/z indicated in Table 12.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Maniatis et al., 1989, Molecular Cloning: A Laboratory Manual, Cold Spring Harbor Laboratory, New York; Ausubel et al., 1989, Current Protocols in Molecular Biology, Greene Publishing Associates and Wiley Interscience, New York, and *PCR Protocols: A Guide to Methods and Applications* (Innis et al., 1990, Academic Press, San Diego, CA).

Before describing the present invention in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the term "and/or" is utilized to describe multiple components in combination or exclusive of one another. For example, "x, y, and/or z" can refer to "x" alone, "y" alone, "z" alone, "x, y, and z," "(x and y) or z," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides, wherein one or more steviol glycosides selected from a group are produced. In some embodiments, "and/or" is used to refer to production of steviol glycosides, wherein one or more steviol glycosides are produced through one or more of the following steps: culturing a recombinant cell, synthesizing one or more steviol glycosides in a cell, and isolating one or more steviol glycosides.

Highly-glycosylated steviol glycosides can be present in trace amounts in the *Stevia* plant, but at levels so low that extraction from the plant is impractical for use of such glycosides in food and beverage systems. See, Hellfritsch et al., J. Agric. Food Chem. 60: 6782-6793 (2012); DuBois G E, Stephenson R A., J Med Chem. January; 28:93-98 (1985); and US Patent Publication 2011-0160311.

Typically, stevioside and Rebaudioside A are the primary compounds in commercially-produced *stevia* extracts. Stevioside is reported to have a more bitter and less sweet taste than Rebaudioside A. The composition of *stevia* extract can vary from lot to lot depending on the soil and climate in which the plants are grown. Depending upon the sourced plant, the climate conditions, and the extraction process, the amount of Rebaudioside A in commercial preparations is reported to vary from 20 to 97% of the total steviol glycoside content.

Other steviol glycosides are present in varying amounts in *stevia* extracts. For example, Rebaudioside B is typically present at less than 1-2%, whereas Rebaudioside C can be present at levels as high as 7-15%. Rebaudioside D is typically present in levels of 2% or less, and Rebaudioside F is typically present in compositions at 3.5% or less of the total steviol glycosides. The amount of the minor steviol glycosides, including but not limited to Rebaudioside M, can affect the flavor profile of a *Stevia* extract.

In addition, Rebaudioside D and other higher glycosylated steviol glycosides are thought to be higher quality sweeteners than Rebaudioside A. As such, the recombinant hosts and methods described herein are particularly useful for producing steviol glycoside compositions having an increased amount of Rebaudioside D for use, for example, as a non-caloric sweetener with functional and sensory properties superior to those of many high-potency sweeteners.

Rebaudioside M, a hexa-glycosylated steviol glycoside has been reported to be present in the *Stevia* plant and has an IUPAC name of (2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl(1R,5R,9S,13R)-13-{[(2S,3R,4S,5R,6R)-5-hydroxy-6-(hydroxymethyl)-3,4-bis({[(2S,3R,4S,5S,6R)-3,4,5-tri hydroxy-6-(hydroxymethyl)oxan-2-yl]oxy})oxan-2-yl]oxy}-5,9-dimethyl-14-methylidenetetracyclo[11.2.1.01,10.04,9]hexadecane-5-carboxylate. See, Ohta et al., MassBank record: FU000341, FU000342, FU000343 (2010) and Ohta et al (J. Applied Glycosides, 57(3):199-209, 2010). Rebaudioside M has been given a CAS number of 1220616-44-3. See FIG. 2 for the structure of Rebaudioside M.

Rebaudioside D, a penta-glycosylated steviol glycoside, has also been reported to be present in the *Stevia* plant and has an IUPAC name of 4,5-dihydroxy-6-(hydroxymethyl)-3-{[3,4,5-trihydroxy-6-(hydroxymethyl)oxan-2-yl]oxy}oxan-2-yl 13-{[5-hydroxy-6-(hydroxymethyl)-3,4-bis({[3,4,5-trihydroxy-6-(hydroxymethyl)oxan-2-yl]oxy})oxan-2-yl]oxy}-5,9-dimethyl-14-methylidenetetracyclo[11.2.1.$^{01,10}$0.0$^{4,9}$]hexadecane-5-carboxylate. Rebaudioside D has been given a CAS number of 64849-39-4. See FIG. 3 for the structure of Rebaudioside D.

Provided herein are recombinant hosts such as microorganisms that express polypeptides useful for de novo biosynthesis of Rebaudioside M or Rebaurdioside D. Hosts described herein express one or more uridine 5'-diphospho (UDP) glycosyl transferases suitable for producing steviol glycosides. Expression of these biosynthetic polypeptides in various microbial systems allows steviol glycosides to be produced in a consistent, reproducible manner from energy and carbon sources such as sugars, glycerol, $CO_2$, $H_2$, and sunlight. The proportion of each steviol glycoside produced by a recombinant host can be tailored by incorporating preselected biosynthetic enzymes into the hosts and expressing them at appropriate levels, to produce a sweetener composition with a consistent taste profile. Furthermore, the concentrations of steviol glycosides produced by recombinant hosts are expected to be higher than the levels of steviol glycosides produced in the *Stevia* plant, which improves the efficiency of the downstream purification. Such sweetener compositions advantageously contain little or no plant based contaminants, relative to the amount of contaminants present in *Stevia* extracts.

The practice of the methods and recombinant host cells as disclosed are provided wherein at least one of the genes encoding a UGT85C2 polypeptide; a UGT74G1 polypeptide; a UGT76G1 polypeptide; or a UGT91d2 polypeptide is a recombinant gene, the particular recombinant gene(s) depending on the species or strain selected for use. Additional genes or biosynthetic modules can be included in order to increase steviol glycoside yield, improve efficiency with which energy and carbon sources are converted to steviol and its glycosides, and/or to enhance productivity from the cell culture. As used herein, "biosynthetic modules" refer to a collection of genes that are part of a common biosynthetic pathway and thus are often co-expressed in a recombinant organism. As used herein, such additional biosynthetic modules include genes involved in the synthesis of the terpenoid precursors, isopentenyl diphosphate and dimethylallyl diphosphate. Additional biosynthetic modules include terpene synthase and terpene cyclase genes, such as genes encoding geranylgeranyl diphosphate synthase and copalyl diphosphate synthase; these genes can be endogenous genes or recombinant genes.

I. Steviol and Steviol Glycoside Biosynthesis Polypeptides

A. Steviol Biosynthesis Polypeptides

Figure 4:
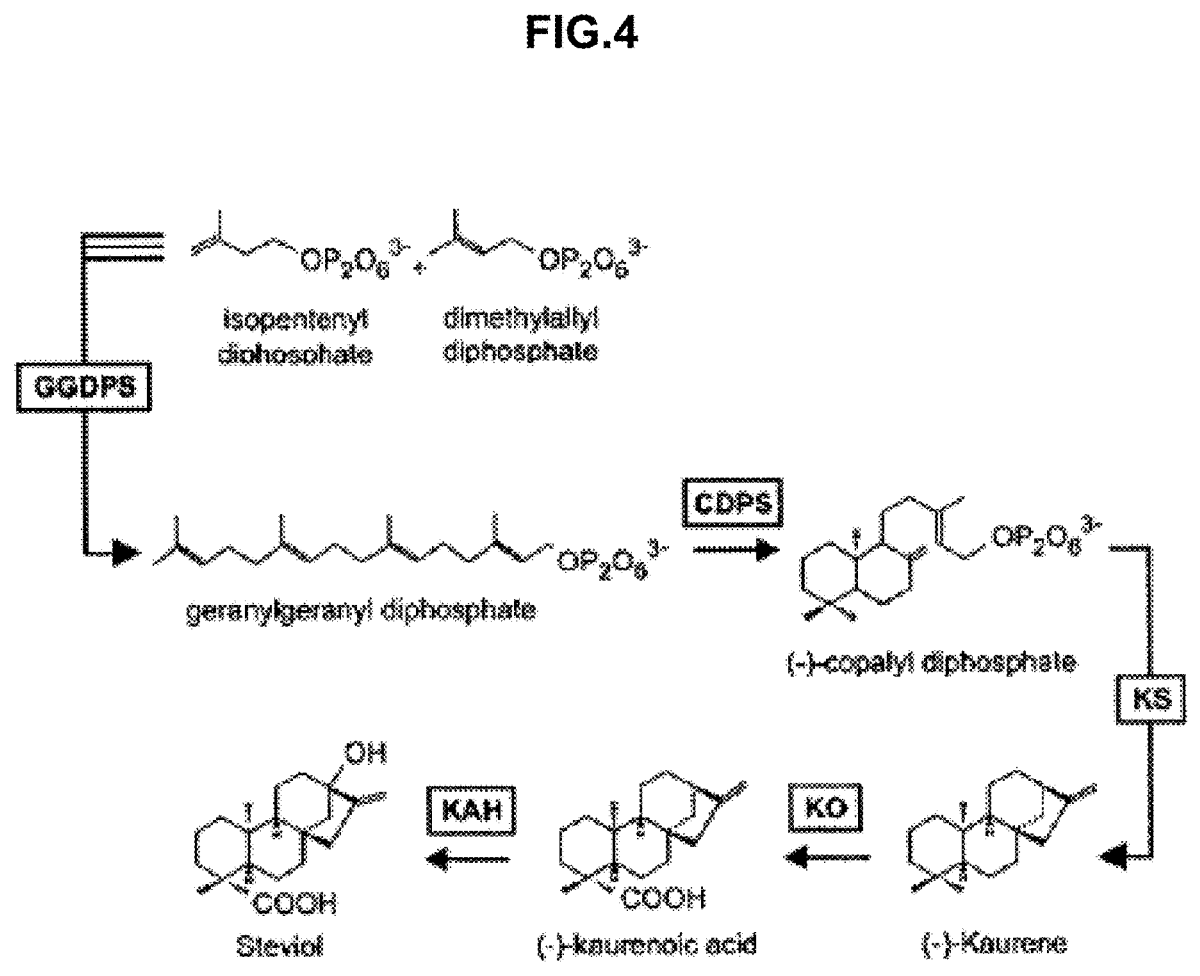

The biochemical pathway to produce steviol involves formation of the precursor, geranylgeranyl diphosphate (catalyzed by GGDPS), cyclization to (−) copalyl diphosphate (catalyzed by CDPS), followed by formation of (−)-kaurene (catalyzed by KS), followed by oxidation (catalyzed by KO), and hydroxylation (catalyzed by KAH) to form steviol. See FIG. 4. Thus, conversion of geranylgeranyl diphosphate to steviol in a recombinant microorganism involves the expression of a gene encoding a kaurene synthase (KS), a gene encoding a kaurene oxidase (KO), and a gene encoding a steviol synthetase (KAH). Steviol synthetase also is known as kaurenoic acid 13-hydroxylase.

Suitable KS polypeptides are known. For example, suitable KS enzymes include those made by *Stevia rebaudiana, Zea mays, Populus trichocarpa*, and *Arabidopsis thaliana*. See, Table 2 and PCT Application Nos. PCT/US2012/050021 and PCT/US2011/038967, which are incorporated herein by reference in their entirety. The nucleotide sequence encoding the *A. thaliana* KS polypeptide is set forth in SEQ ID NO:6, and the amino acid sequence of the *A. thaliana* KS polypeptide is set forth in SEQ ID NO:21.

TABLE 2

Kaurene synthase (KS) clones.

| Enzyme Source Organism | gi Number | Accession Number | Construct Name | Length (nts) |
|---|---|---|---|---|
| *Stevia rebaudiana* | 4959241 | AAD34295 (amino acid SEQ ID NO: 27) | MM-12 | 2355 (nt SEQ ID NO: 103) |
| *Stevia rebaudiana* | 4959239 | AAD34294 (amino acid SEQ ID NO: 28) | MM-13 | 2355 (nt SEQ ID NO: 104) |
| *Zea mays* | 162458963 | NP_001105097 (amino acid SEQ ID NO: 29) | MM-14 | 1773 (nt SEQ ID NO: 105) |
| *Populus trichocarpa* | 224098838 | XP_002311286 (amino acid SEQ ID NO: 30) | MM-15 | 2232 (nt SEQ ID NO: 106) |
| *Arabidopsis thaliana* | 3056724 | AF034774 (amino acid SEQ ID NO: 32) | EV-70 | 2358 (nt SEQ ID NO: 31) |

Suitable KO polypeptides are known. For example, suitable KO enzymes include those made by *Stevia rebaudiana, Arabidopsis thaliana, Gibberella fujikoroi* and *Trametes versicolor*. See, e.g., Table 3 and POT Application Nos. PCT/US2012/050021 and PCT/US2011/038967, which are incorporated herein by reference in their entirety.

TABLE 3

Kaurene oxidase (KO) clones.

| Enzyme Source Organism | gi Number | Accession Number | Construct Name | Length (nts) |
|---|---|---|---|---|
| *Stevia rebaudiana* | 76446107 | ABA42921 (amino acid SEQ ID NO: 33) | MM-18 | 1542 (nt SEQ ID NO: 107) |
| *Arabidopsis thaliana* | 3342249 | AAC39505 (amino acid SEQ ID NO: 34) | MM-19 | 1530 (nt SEQ ID NO: 108) |
| *Gibberella fujikoroi* | 4127832 | CAA76703 (amino acid SEQ ID NO: 35) | MM-20 | 1578 (nt SEQ ID NO: 109) |
| *Trametes versicolor* | 14278967 | BAB59027 (amino acid SEQ ID NO: 36) | MM-21 | 1500 (nt SEQ ID NO: 110) |

Suitable KAH polypeptides are known. For example, suitable KAH enzymes include those made by *Stevia rebaudiana, Arabidopsis thaliana, Vitis vinifera* and *Medicago trunculata*. See, e.g., Table 4, POT Application Nos. PCT/US2012/050021 and PCT/US2011/038967, U.S. Patent Publication Nos. 2008/0271205 and 2008/0064063, and Genbank Accession No. gi 189098312 (SEQ ID NO: 37) and GenBank Accession ABD60225; GI:89242710 (SEQ ID NO: 38), which are incorporated herein by reference in their entirety. The steviol synthetase from *A. thaliana* is classified as a CYP714A2.

TABLE 4

Steviol synthetase (KAH) clones.

| Enzyme Source Organism | gi Number | Accession Number | Plasmid Name | Construct Name | Length (nts) |
|---|---|---|---|---|---|
| *Stevia rebaudiana* | * | (amino acid SEQ ID NO: 43) | pMUS35 | MM-22 | 1578 (nt SEQ ID NO: 111) |
| *Stevia rebaudiana* | 189418962 | ACD93722 (amino acid SEQ ID NO: 39) | pMUS36 | MM-23 | 1431 (nt SEQ ID NO: 112) |
| *Arabidopsis thaliana* | 15238644 | NP_197872 (amino acid SEQ ID NO: 40) | pMUS37 | MM-24 | 1578 (nt SEQ ID NO: 113) |
| *Vitis vinifera* | 225458454 | XP_002282091 (amino acid SEQ ID NO: 41) | pMUS38 | MM-25 | 1590 (nt SEQ ID NO: 114) |
| *Medicago trunculata* | 84514135 | ABC59076 (amino acid SEQ ID NO: 42) | pMUS39 | MM-26 | 1440 (nt SEQ ID NO: 115) |

* = Sequence is identified with sequence identifier number 2 as shown in U.S. Patent Publication No. 2008-0064063.

In addition, a KAH polypeptide from *Stevia rebaudiana* that was identified as described in PCT Application No. PCT/US2012/050021, which is incorporated herein by reference in its entirety, is particularly useful in a recombinant host. The nucleotide sequence encoding the *S. rebaudiana* KAH (SrKAHe1) is set forth in SEQ ID NO:91. A nucleotide sequence encoding the *S. rebaudiana* KAH that has been codon-optimized for expression in yeast is set forth in SEQ ID NO:8, and the amino acid sequence of the *S. rebaudiana* KAH polypeptide is set forth in SEQ ID NO:11. When expressed in *S. cerevisiae*, the *S. rebaudiana* KAH (SEQ ID NO:11) shows significantly higher steviol synthase activity as compared to the *A. thaliana* ent-kaurenoic acid hydroxylase described by Yamaguchi et al. (U.S. Patent Publication No. 2008/0271205 A1) and other *S. rebaudiana* KAH enzymes described in U.S. Patent Publication No. 2008/0064063 as well as the protein sequence deposited in GenBank as ACD93722. The *S. rebaudiana* KAH polypeptide (SEQ ID NO:11) has less than 20% identity to the KAH from U.S. Patent Publication No. 2008/0271205 and less than 35% identity to the KAH from U.S. Patent Publication No. 2008/0064063.

For example, the steviol synthase encoded by SrKAHe1 is activated by the *S. cerevisiae* CPR encoded by gene NCP1 (YHR042W). Greater activation levels of the steviol synthase encoded by SrKAHe1 is observed when the *A. thaliana* CPR encoded by the gene ATR2 (SEQ ID NO: 10) and the *S. rebaudiana* CPR encoded by the gene CPR8 (SEQ ID NO:5) are co-expressed. The amino acid sequence of the *A. thaliana* ATR2 is set forth in SEQ ID NO:9, and the amino acid sequence for *S. rebaudiana* CPR8 polypeptides is set forth in SEQ ID NO:4.

In some embodiments, a recombinant microorganism contains a recombinant gene encoding a KO, KS, and a KAH polypeptide. Such microorganisms also typically contain a recombinant gene encoding a cytochrome P450 reductase (CPR) polypeptide, since certain combinations of KO and/or KAH polypeptides require expression of an exogenous CPR polypeptide. In particular, the activity of a KO and/or a KAH polypeptide of plant origin can be significantly increased by the inclusion of a recombinant gene encoding an exogenous CPR polypeptide. Suitable CPR polypeptides are known. For example, suitable CPR enzymes include those made by *S. rebaudiana* and *A. thaliana*. See, e.g., Table 5 and POT Application Nos. PCT/US2012/050021 and PCT/US2011/038967, which are incorporated herein by reference in their entirety.

TABLE 5

Cytochrome P450 reductase (CPR) Clones.

| Enzyme Source Organism | gi Number | Accession Number | Plasmid Name | Construct Name | Length (nts) |
|---|---|---|---|---|---|
| *Stevia rebaudiana* | 93211213 | ABB88839 (amino acid SEQ ID NO: 44) | pMUS40 | MM-27 | 2133 (nt SEQ ID NO: 116) |
| *Arabidopsis thaliana* | 15233853 | NP_194183 (amino acid SEQ ID NO: 45) | pMUS41 | MM-28 | 2079 (nt SEQ ID NO: 117) |
| *Giberella fujikuroi* | 32562989 | CAE09055 (amino acid SEQ ID NO: 46) | pMUS42 | MM-29 | 2142 (nt SEQ ID NO: 118) |

The yeast gene DPP1 and/or the yeast gene LPP1 can reduce the yield of steviol by converting the GGPP and FPP precursors by these enzymes. These genes can be disrupted or deleted such that the degradation of farnesyl pyrophosphate (FPP) to farnesol is reduced and the degradation of geranylgeranylpyrophosphate (GGPP) to geranylgeraniol (GGOH) is reduced. Alternatively, the promoter or enhancer elements of an endogenous gene encoding a phosphatase can be altered such that the expression of their encoded proteins is altered. Homologous recombination can be used to disrupt an endogenous gene. For example, a "gene replacement" vector can be constructed in such a way to include a selectable marker gene. The selectable marker gene can be operably linked, at both 5' and 3' end, to portions of the gene of sufficient length to mediate homologous recombination using methods known to those skilled in the art.

A selectable marker can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, Southern blot analysis. Subsequent to its use in selection, a selectable marker can be removed from the genome of the host cell by, e.g., Cre-loxP systems (see, e.g., Gossen et al., 2002, *Ann. Rev. Genetics* 36:153-173 and U.S. Application Publication No. 20060014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Expression in a recombinant microorganism of these genes can result in the conversion of geranylgeranyl diphosphate to steviol.

B. Steviol Glycoside Biosynthesis Polypeptides

Recombinant host cells are described herein that can convert steviol to a steviol glycoside. Such hosts (e.g., microorganisms) contains genes encoding one or more UDP Glycosyl Transferases, also known as UGTs. UGTs transfer a monosaccharide unit from an activated nucleotide sugar to an acceptor moiety, in this case, an —OH or —COOH moiety on steviol or steviol derivative or an —OH moiety on a glucose already attached to the steviol backbone. UGTs have been classified into families and subfamilies based on sequence homology. See Li et al., 2001, J. Biol. Chem. 276:4338-4343.

Rubusoside Biosynthesis Polypeptides

Biosynthesis of rubusoside involves glycosylation of the 13-OH and the 19-COOH of steviol. See FIG. 1. Conversion of steviol to rubusoside in a recombinant host such as a microorganism can be accomplished by expression of gene (s) encoding UGTs 85C2 and 74G1, which transfer a glucose unit to the 13-OH or the 19-COOH, respectively, of steviol.

A suitable UGT85C2 functions as a uridine 5'-diphospho-glucosyl:steviol 13-OH transferase, and a uridine 5'-diphosphoglucosyl:steviol-19-O-glucoside 13-OH transferase. Exemplary reactions for UGT85C2 include conversion of steviol and UDP-glucose to Steviol-13-0-glucoside or conversion of Steviol-19-O-glucoside and UDP-glucose to Rubusoside. See FIG. 1. Functional UGT85C2 polypeptides also can catalyze glucosyl transferase reactions that utilize steviol glycoside substrates other than steviol and steviol-19-O-glucoside.

A suitable UGT74G1 polypeptide functions as a uridine 5'-diphospho glucosyl: steviol 19-COOH transferase and a uridine 5'-diphospho glucosyl: steviol-13-O-glucoside 19-COOH transferase. Exemplary reactions of 74G1 include conversion of steviol to steviol-19-O-glucoside and conversion of steviol-13-O-glucoside to Rubusoside. See FIG. 19 for these and other non-limiting examples of UGT74G1 reactions. Functional UGT74G1 polypeptides also can catalyze glycosyl transferase reactions that utilize steviol glycoside substrates other than steviol and steviol-13-O-glucoside, or that transfer sugar moieties from donors other than uridine diphosphate glucose.

A recombinant microorganism expressing a functional UGT74G1 and a functional UGT85C2 can make rubusoside and both steviol monosides (i.e., steviol 13-O-monoglucoside and steviol 19-O-monoglucoside) when steviol is used as a feedstock in the medium. Typically, however, genes encoding UGT74G1 and UGT85C2 are recombinant genes that have been transformed into a host (e.g., microorganism) that does not naturally possess them.

As used herein, the term "recombinant host" is intended to refer to (including but not limited to) a host cell, the genome of which has been augmented by at least one incorporated DNA sequence; extrachromosomal examples, like plasmids in bacteria and episomes comprising the 2-micron circle in yeast. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Generally, the introduced DNA is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, mammalian cells, insect cells, fungal cells, plant cells, and plants.

The term "recombinant gene" refers to a gene or DNA sequence that is introduced into a recipient host, regardless of whether the same or a similar gene or DNA sequence can already be present in such a host. "Introduced," or "augmented" in this context, is known in the art to mean introduced or augmented by the hand of man. Thus, a recombinant gene can be a DNA sequence from another species, or can be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified (including but not limited to regulated or inducible) expression of the gene product of that DNA.

Suitable UGT74G1 and UGT85C2 polypeptides include those made by *S. rebaudiana*. Genes encoding functional UGT74G1 and UGT85C2 polypeptides from *Stevia* are reported in Richman et al., 2005, Plant J. 41: 56-67. Amino acid sequences of *S. rebaudiana* UGT74G1 (SEQ ID NO: 19) and UGT85C2 (SEQ ID NO: 26) polypeptides are set forth in SEQ ID NOs: 1 and 3, respectively, of PCT Application No. PCT/US2012/050021, as are nucleotide sequences that encode UGT74G1 and UGT85C2 that have been optimized for expression in yeast and DNA 2.0 codon-optimized sequence for UGTs 85C2, 91D2e, 74G1 and 76G1. The Gene Art codon optimized nucleotide sequence encoding a *S. rebaudiana* UGT85C2 is set forth in SEQ ID NO:3. See also, the UGT85C2 and UGT74G1 variants described below in the "Functional Homolog" section. For example, a UGT85C2 polypeptide can contain substitutions at any one of the positions 65, 71, 270, 289, and 389 (e.g., A65S, E71Q, T270M, Q289H, and A389V) or a combination thereof.

In some embodiments, the recombinant host is a microorganism. Recombinant microorganism can be grown on media containing steviol in order to produce rubusoside. In other embodiments, however, the recombinant microorganism expresses genes involved in steviol biosynthesis, e.g., a CDPS gene, a KS gene, a KO gene, and a KAH gene. Suitable CDPS polypeptides are known. For example, suitable CDPS enzymes include those made by *S. rebaudiana, Streptomyces clavuligerus, Bradyrhizobium japonicum, Zea mays*, and *Arabidopsis* sp. See, e.g., Table 6 and PCT Application Nos. PCT/US2012/050021 and PCT/US2011/038967, which are incorporated herein by reference in their entirety.

In some embodiments, CDPS polypeptides that lack a chloroplast transit peptide at the amino terminus of the unmodified polypeptide can be used. For example, the first 150 nucleotides from the 5' end of the *Zea mays* CDPS coding sequence (SEQ ID NO:12) can be removed, the truncated nucleotide sequence is shown in SEQ ID NO:133. Doing so removes the amino terminal 50 residues of the amino acid sequence shown in SEQ ID NO:13, which encode a chloroplast transit peptide; the truncated amino acid sequence is shown in SEQ ID NO:134. The truncated CDPS gene can be fitted with a new ATG translation start site and operably linked to a promoter, typically a constitutive or highly expressing promoter. When a plurality of copies, including but not limited to, one copy, two copies or three copies of the truncated coding sequence are introduced into a microorganism, expression of the CDPS polypeptide from the promoter results in an increased carbon flux towards ent-kaurene biosynthesis.

TABLE 6

CDPS Clones.

| Enzyme Source Organism | gi Number | Accession Number | Plasmid Name | Construct Name | Length (nts) |
|---|---|---|---|---|---|
| *Stevia rebaudiana* | 2642661 | AAB87091 (amino acid SEQ ID NO: 48) | pMUS22 | MM-9 | 2364 (nt SEQ ID NO: 119) |
| *Streptomyces clavuligerus* | 197705855 | EDY51667 (amino acid SEQ ID NO: 49) | pMUS23 | MM-10 | 1584 (nt SEQ ID NO: 120) |
| *Bradyrhizobium japonicum* | 529968 | AAC28895.1 (amino acid SEQ ID NO: 50) | pMUS24 | MM-11 | 1551 (nt SEQ ID NO: 121) |
| *Zea mays* | 50082774 | AY562490 (amino acid SEQ ID NO: 52) | | EV65 | 2484 (nt SEQ ID NO: 51) |
| *Arabidopsis thaliana* | 18412041 | NM_116512 (SEQ ID NO: 54) | | EV64 | 2409 (nt SEQ ID NO: 53) |

CDPS-KS bifunctional proteins also can be used. Nucleotide sequences encoding the COPS-KS bifunctional enzymes shown in Table 7 were modified for expression in yeast (see POT Application No. PCT/US2012/050021, which is incorporated herein by reference in its entirety). A bifunctional enzyme from *Gibberella fujikuroi* also can be used.

TABLE 7

CDPS-KS Clones.

| Enzyme Source Organism | gi Number | Accession Number | Construct Name | Length (nts) |
|---|---|---|---|---|
| *Phomopsis amygdali* | 186704306 | BAG30962 (amino acid SEQ ID NO: 55) | MM-16 | 2952 (nt SEQ ID NO: 122) |

TABLE 7-continued

| CDPS-KS Clones. | | | | |
|---|---|---|---|---|
| Enzyme Source Organism | gi Number | Accession Number | Construct Name | Length (nts) |
| *Physcomitrella patens* | 146325986 | BAF61135 (amino acid SEQ ID NO: 56) | MM-17 | 2646 (nt SEQ ID NO: 123) |
| *Gibberella fujikuroi* | 62900107 | Q9UVY5.1 (amino acid SEQ ID NO: 57) | | 2859 (nt SEQ ID NO: 124) |

Thus, a microorganism containing a COPS gene, a KS gene, a KO gene and a KAH gene in addition to a UGT74G1 and a UGT85C2 gene is capable of producing both steviol monosides and rubusoside without the necessity for using steviol as a feedstock.

In some embodiments, the recombinant microorganism further expresses a recombinant gene encoding a geranylgeranyl diphosphate synthase (GGPPS). Suitable GGPPS polypeptides are known. For example, suitable GGPPS enzymes include those made by *S. rebaudiana, Gibberella fujikuroi, Mus musculus, Thalassiosira pseudonana, Streptomyces clavuligerus, Sulfulobus acidocaldarius, Synechoccus* sp. and *A. thaliana*. See, Table 8 and POT Application Nos. PCT/US2012/050021 and PCT/US2011/038967, which are incorporated herein by reference in their entirety.

TABLE 8

| GGPPS Clones. | | | | | |
|---|---|---|---|---|---|
| Enzyme Source Organism | gi Number | Accession Number | Plasmid Name | Construct Name | Length (nts) |
| *Stevia rebaudiana* | 90289577 | ABD92926 (amino acid SEQ ID NO: 58) | pMUS14 | MM-1 | 1086 (nt SEQ ID NO: 125) |
| *Gibberella fujikuroi* | 3549881 | CAA75568 (amino acid SEQ ID NO: 59) | pMUS15 | MM-2 | 1029 (nt SEQ ID NO: 126) |
| *Mus musculus* | 47124116 | AAH69913 (amino acid SEQ ID NO: 60) | pMUS16 | MM-3 | 903 (nt SEQ ID NO: 127) |
| *Thalassiosira pseudonana* | 223997332 | XP_002288339 (amino acid SEQ ID NO: 61) | pMUS17 | MM-4 | 1020 (nt SEQ ID NO: 128) |
| *Streptomyces clavuligerus* | 254389342 | ZP_05004570 (amino acid SEQ ID NO: 62) | pMUS18 | MM-5 | 1068 (nt SEQ ID NO: 129) |
| *Sulfulobus acidocaldarius* | 506371 | BAA43200 (amino acid SEQ ID NO: 63) | pMUS19 | MM-6 | 993 (nt SEQ ID NO: 130) |
| *Synechococcus* sp. | 86553638 | ABC98596 (amino acid SEQ ID NO: 64) | pMUS20 | MM-7 | 894 (nt SEQ ID NO: 131) |
| *Arabidopsis thaliana* | 15234534 | NP_195399 (amino acid SEQ ID NO: 63) | pMUS21 | MM-8 | 1113 (nt SEQ ID NO: 132) |

In some aspects, the KAH gene encoding the KAH polypeptide set forth in SEQ ID NO: 11, comprising a recombinant cell of the invention is overexpressed. In some aspects, the KAH gene can be present in (including but not limited to) one, two or three copies. In some aspects, the KS gene encoding the KS polypeptide, set forth in SEQ ID NO:21, comprising a recombinant cell of the invention is overexpressed. In some aspects, the KS gene can be present in (including but not limited to) one, two or three copies.

In some embodiments, the recombinant microorganism further can express recombinant genes involved in diterpene biosynthesis or production of terpenoid precursors, e.g., genes in the methylerythritol 4-phosphate (MEP) pathway or genes in the mevalonate (MEV) pathway discussed below, have reduced phosphatase activity, and/or express a sucrose synthase (SUS) as discussed herein.

Rebaudioside A, Rebaudioside 0, and Rebaudioside E Biosynthesis Polypeptides

Biosynthesis of Rebaudioside A involves glucosylation of the aglycone steviol. Specifically, Rebaudioside A can be formed by glucosylation of the 13-OH of steviol which forms the 13-O-steviolmonoside, glucosylation of the C-2' of the 13-O-glucose of steviolmonoside which forms steviol-1,2-bioside, glucosylation of the C-19 carboxyl of steviol-1,2-bioside which forms stevioside, and glucosylation of the C-3' of the C-13-O-glucose of stevioside to produce Reb A. The order in which each glucosylation reaction occurs can vary. See FIG. 1.

Biosynthesis of Rebaudioside E and/or Rebaudioside D involves glucosylation of the aglycone steviol. Specifically, Rebaudioside E can be formed by glucosylation of the 13-OH of steviol which forms steviol-13-O-glucoside, glucosylation of the C-2' of the 13-O-glucose of steviol-13-O-glucoside which forms the steviol-1,2-bioside, glucosylation of the C-19 carboxyl of the 1,2-bioside to form 1,2-stevioside, and glucosylation of the C-2' of the 19-O-glucose of the 1,2-stevioside to form Rebaudioside E. Rebaudioside D can be formed by glucosylation of the C-3' of the C-13-O-glucose of Rebaudioside E. The order in which each glycosylation reaction occurs can vary. For example, the glucosylation of the C-2' of the 19-O-glucose can be the last step in the pathway, wherein Rebaudioside A is an intermediate in the pathway. See FIG. 1.

Rebaudioside M Polypeptides

As provided herein, conversion of steviol to Rebaudioside M in a recombinant host can be accomplished by expressing combinations of the following functional UGTs: 91D2, EUGT11, 74G1, 85C2, and 76G1. See FIG. 1. It is particularly useful to express EUGT11 at high levels using a high copy number plasmid, or using a strong promoter, or multiple integrated copies of the gene, or episome under selection for high copy number of the gene. Thus, a recombinant microorganism expressing combinations of these UGTs can make Rebaudioside A (85C2; 76G1; 74G1; 91D2e), Rebaudioside D (85C2; 76G1; 74G1; 91D2e; EUGT11), Rebaudioside E (85C2; 74G1; 91D2e; EUGT11), or Rebaudioside M (85C2; 76G1; 74G1; 91D2e; EUGT11). See FIG. 1. Typically, one or more of these genes are recombinant genes that have been transformed into a microorganism that does not naturally possess them. It has also been discovered that UGTs designated herein as SM12UGT can be substituted for UGT91D2.

Targeted production of individual Rebaudiosides can be accomplished by differential copy numbers of the UGT-encoding genes (see FIG. 1) in the recombinant cell, differential promoter strengths, and/or by utilizing mutants with increased specificity/activity towards the product of interest. For example, low levels of Rebaudioside D, E, and M will be formed if EUGT11 is expressed at low levels in comparison to the other UGTs, which would favor Rebaudioside A formation. High levels of EUGT11 expression result in production of more 19-O 1,2 diglucoside that can serve as substrate for UGT76G1 to form Rebaudioside M. In certain advantageous embodiments, additional copies or mutant versions of UGT76G1 in recombinant cells of the invention can improve the rate of Rebaudioside M formation from Rebaudioside D.

In some embodiments, UGT76G1 catalyzes glycosylation of steviol and steviol glycosides at the 19-O position. Thus, in some embodiments, one or more of RebM, RebQ, RebI, di-glycosylated steviol glycoside (13-hydroxy kaur-16-en-18-oic acid, [2-O-β-D-glucopyranosyl-β-D-glucopyranosyl] ester), or tri-glycosylated steviol glycoside ((13-hydroxy kaur-16-en-18-oic acid; [2-O-β-D-glucopyranosyl-3-O-β-D-glucopyranosyl-β-D-glucopyranosyl]ester) are produced in a recombinant host expressing a recombinant gene encoding a UGT76G1 polypeptide, through bioconversion, or through catalysis by UGT76G1 in vitro. In some embodiments, UGT76G1 catalyzes the glycosylation of steviol and steviol glycosides at the 13-O position and preferentially glycosylates steviol glycoside substrates that are 1,2-di-glycosylated at the 13-O position or mono-glycosylated at the 13-O position. In some embodiments, UGT76G1 does not show a preference for the glycosylation state of the 19-O position.

In some aspects, a recombinant host cell of the invention comprises the gene encoding the UGT76G1 polypeptide set forth in SEQ ID NO:2. In some aspects, the gene encoding the UGT76G1 polypeptide set forth in SEQ ID NO:2, comprising a recombinant cell of the invention is overexpressed. In some aspects, the gene can be present in (including but not limited to) two or three copies.

Figure 12:
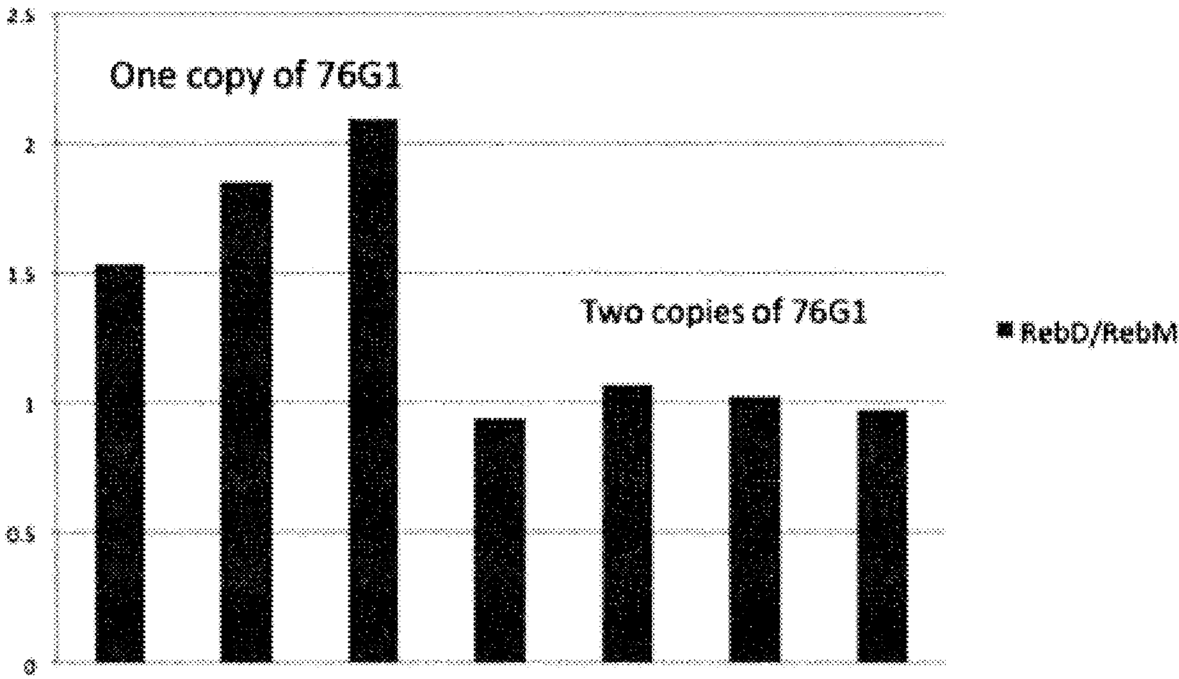
FIG. 12 compares RebD/RebM produced with one or two copies of UGT76G1.

In some embodiments, the gene encoding the UGT76G1 polypeptide set forth in SEQ ID NO:2 is present in one copy. As shown in FIG. 12 (Example 9), a lower copy number (one copy) of the gene encoding the UGT76G1 polypeptide results in lower UGT76G1 expression and increases the Rebaudioside D/Rebaudioside M ratio.

In some embodiments, less than five (e.g., one, two, three, or four) UGTs are expressed in a host. For example, a recombinant microorganism expressing a functional EUGT11 can make Rebaudioside D when Rebaudioside A is used as a feedstock. A recombinant microorganism expressing a functional UGT76G1 can make Rebaudioside M when Rebaudioside D or Rebaudioside E is used as a feedstock. Rebaudioside M can be formed from either Rebaudioside D or Rebaudioside E by glucosylation of the C-3' of the 19-O-glucose of Rebaudioside D or Rebuadioside E; in the case of Rebaudioside E a second glucosylation is required, of the 13-O-glucose to produce Rebaudioside M.

A recombinant microorganism expressing EUGT11, 74G1 or 76G1, and 91D2 can make Rebaudioside D or Rebaudioside M when rubusoside or 1,2-stevioside is used as a feedstock. As another alternative, a recombinant microorganism expressing EUGT11, 74G1, 76G1, and 91D2 can make Rebaudioside D or Rebaudioside M when the monoside, steviol-13-0-glucoside are added to the medium. Similarly, conversion of steviol-19-O-glucoside to Rebaudioside D in a recombinant microorganism can be accomplished by expressing in the cell genes encoding UGTs EUGT11, 85C2, 76G1, and 91D2e, when fed steviol-19-O-glucoside.

Suitable UGT74G1 and UGT85C2 polypeptides include those discussed above. A suitable UGT76G1 adds a glucose moiety to the C-3' of the C-13-O-glucose of the acceptor molecule, a steviol 1,2 glycoside. UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides can also catalyze glucosyl transferase reactions that utilize steviol glycoside substrates that contain sugars other than glucose, e.g., steviol rhamnosides and steviol xylosides. See, FIG. 1. Suitable UGT76G1 polypeptides include those made by *S. rebaudiana* and reported in Richman et al., 2005, Plant J. 41: 56-67. A nucleotide sequence encoding the *S. rebaudiana* UGT76G1 polypeptide optimized for expression in yeast is set forth in SEQ ID NO:14. See also the UGT76G1 variants set forth in the "Functional Homolog" section.

A suitable EUGT11 or UGT91D2 polypeptide functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside.

A suitable EUGT11 or UGT91 D2 polypeptide also functions as a uridine 5'-diphospho glucosyl: rubusoside transferase transferring a glucose moiety to the C-2' of the 13-O-glucose of the acceptor molecule, rubusoside, to produce stevioside. EUGT11 polypeptides also can transfer a glucose moiety to the C-2' of the 19-O-glucose of the acceptor molecule, rubusoside, to produce a 19-O-1,2-diglycosylated rubusoside (see FIG. 1).

Functional EUGT11 or UGT91 D2 polypeptides also can catalyze reactions that utilize steviol glycoside substrates other than steviol-13-O-glucoside and rubusoside. For example, a functional EUGT11 polypeptide can utilize stevioside as a substrate, transferring a glucose moiety to the C-2' of the 19-O-glucose residue to produce Rebaudioside E (see FIG. 1). Functional EUGT11 and UGT91 D2 polypeptides can also utilize Rebaudioside A as a substrate, transferring a glucose moiety to the C-2' of the 19-O-glucose residue of Rebaudioside A to produce Rebaudioside D. EUGT11 can convert Rebaudioside A to Rebaudioside D at a rate that is least 20 times faster (e.g., as least 25 times or at least 30 times faster) than the corresponding rate of wildtype UGT91D2e (SEQ ID NO: 15) when the reactions are performed under similar conditions, i.e., similar time, temperature, purity, and substrate concentration. As such, EUGT11 produces greater amounts of RebD than UGT91D2e under similar conditions in cells or in vitro, under conditions where the temperature-sensitive EUGT11 is stable.

In addition, a functional EUGT11 exhibits significant C-2' 19-O-diglycosylation activity with rubusoside or stevioside as substrates, whereas UGT91D2e has no detectable diglycosylation activity with these substrates under some conditions. Thus, a functional EUGT11 can be distinguished from UGT91 D2e by the differences in steviol glycoside substrate-specificity.

A functional EUGT11 or UGT91D2 polypeptide does not transfer a glucose moiety to steviol compounds having a 1,3-bound glucose at the C-13 position, i.e., transfer of a glucose moiety to steviol-1,3-bioside and 1,3-stevioside (RebG) does not occur.

Functional EUGT11 and UGT91 D2 polypeptides can transfer sugar moieties from donors other than uridine diphosphate glucose. For example, a functional EUGT11 or UGT91D2 polypeptide can act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a functional EUGT11 or UGT91 D2 polypeptide can act as a uridine 5'-diphospho L-rhamnosyl: steviol-13-O-glucoside transferase, transferring a rhamnose moiety to the C-2' of the 13-O-glucose of the acceptor molecule, steviol-13-O-glucoside.

Suitable EUGT11 polypeptides are described herein and can include the EUGT11 polypeptide from *Oryza sativa* (GenBank Accession No. AC133334; SEQ ID NO:16). For example, an EUGT11 polypeptide can have an amino acid sequence with at least 70% sequence identity (e.g., at least 75, 80, 85, 90, 95, 96, 97, 98, or 99% sequence identity) to the amino acid sequence set forth in SEQ ID NO:16. The nucleotide sequence encoding the amino acid sequence of EUGT11 also is set forth in SEQ ID NO:17, as is a codon optimized nucleotide sequence for expression in yeast (SEQ ID NO:18).

Suitable functional UGT91 D2 polypeptides include, e.g., the polypeptides designated UGT91D2e and UGT91D2m and functional homologs as described herein. The amino acid sequence of an exemplary UGT91D2e polypeptide from *S. rebaudiana* is set forth in SEQ ID NO:15, as is the nucleotide sequence encoding the UGT91D2e polypeptide that has been codon optimized for expression in yeast (SEQ ID NO:89). The amino acid sequences of exemplary UGT91 D2m (SEQ ID NO:86) polypeptides from *S. rebaudiana* are set forth as SEQ ID NO: 10 in PCT Application No. PCT/US2012/050021, which is incorporated herein by reference in its entirety. In addition, UGT91 D2 variants containing a substitution at amino acid residues 206, 207, and 343 can be used. For example, the amino acid sequence having G206R, Y207C, and W343R mutations with respect to wild-type UGT91D2e can be used. In addition, a UGT91D2 variant containing substitutions at amino acid residues 211 and 286 can be used. For example, a UGT91 D2 variant can include a substitution of a methionine for leucine at position 211 and a substitution of an alanine for valine at position 286 (referred to as UGT91 D2e-b). These variants, L211M and V286A, are variants of SEQ ID NO: 5 from PCT/US2012/050021, which is disclosed herein as SEQ ID NO: 66. Additional variants can include variants (except T144S, M152L, L213F, S364P, and G384C variants) described in Table 12 and Example 11 of the PCT/US2012/050021, which is incorporated herein by reference in its entirety.

As indicated above, UGTs designated herein as SM12UGT can be substituted for UGT91 D2. Suitable functional SM12UGT polypeptides include those made by *Ipomoea purpurea* (Japanese morning glory) and described in Morita et al., 2005, Plant J. 42, 353-363. The amino acid sequence encoding the *I. purpurea* IP3GGT (SEQ ID NO: 67) (which is set forth in PCT Application No. PCT/US2012/050021, which is incorporated herein by reference in its entirety) as a nucleotide sequence (SEQ ID NO: 68) that encodes the polypeptide and that has been codon optimized for expression in yeast. Another suitable SM12UGT polypeptide is a UGT94B1 polypeptide having an R25S mutation (Bp94B1 polypeptide). See Osmani et al., 2008, Plant Phys. 148: 1295-1308 and Sawada et al., 2005, J. Biol. Chem. 280:899-906. The amino acid sequence of the *Bellis perennis* (red daisy) UGT94B1 (SEQ ID NO: 69) and the nucleotide sequence that has been codon optimized for expression in yeast (SEQ ID NO: 70) are set forth in PCT Application No. PCT/US2012/050021, which is incorporated herein by reference in its entirety.

In some embodiments, the recombinant microorganism is grown on media containing steviol-13-O-glucoside or steviol-19-O-glucoside in order to produce Rebaudioside M. In such embodiments, the microorganism contains and expresses genes encoding a functional EUGT11, a functional UGT74G1, a functional UGT85C2, a functional UGT76G1, and a functional UGT91 D2, and is capable of accumulating Rebaudioside A, Rebaudioside D, Rebaudioside M or a combination thereof, depending on the relative levels of UDP-glycosyl transferase activities, when steviol, one or both of the steviolmonosides, or rubusoside is used as feedstock.

In other embodiments, the recombinant microorganism is grown on media containing rubusoside in order to produce Rebaudioside A, D, or M. In such embodiments, the microorganism contains and expresses genes encoding a functional EUGT11, a functional UGT76G1, and a functional UGT91D2, and is capable of producing Rebaudioside A, D, M or a combination thereof, depending on the relative levels of UDP-glycosyl transferase activities, when rubusoside is used as feedstock.

In other embodiments the recombinant microorganism expresses genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a EUGT11, a UGT74G1, a UGT85C2, a UGT76G1, and a functional UGT91D2 (e.g., UGT91D2e), is capable of producing Rebaudioside A, D, E, and/or M without the necessity of including steviol in the culture media.

In some embodiments, the recombinant host further contains and expresses a recombinant GGPPS gene in order to provide increased levels of the diterpene precursor geranylgeranyl diphosphate, for increased flux through the steviol biosynthetic pathway.

In some embodiments, the recombinant host further contains a construct to silence expression of non-steviol pathways consuming geranylgeranyl diphosphate, ent-Kaurenoic acid or farnesyl pyrophosphate, thereby providing increased flux through the steviol and steviol glycosides biosynthetic pathways. As discussed below, flux to sterol production pathways such as ergosterol can be reduced by downregulation of the ERG9 gene. In cells that produce gibberellins, gibberellin synthesis can be downregulated to increase flux of ent-kaurenoic acid to steviol. In carotenoid-producing organisms, flux to steviol can be increased by downregulation of one or more carotenoid biosynthetic genes. In some embodiments, the recombinant microorganism further can express recombinant genes involved in diterpene biosynthesis or production of terpenoid precursors, e.g., genes in the MEP or MEV pathways discussed below, have reduced phosphatase activity, and/or express a SUS as discussed herein.

One with skill in the art will recognize that by modulating relative expression levels of different UGT genes, a recombinant host can be tailored to specifically produce steviol glycoside products in a desired proportion. Transcriptional regulation of steviol biosynthesis genes and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside. One with skill in the art will recognize that a higher proportion of Rebaudioside D or M, or more efficient conversion to Rebaudioside D or M can be obtained with a diglycosylation enzyme that has a higher activity for the 19-O-glucoside reaction as compared to the 13-O-glucoside reaction (substrates Rebaudioside A and stevioside).

In some embodiments, a recombinant host such as a microorganism produces Rebaudioside M-enriched steviol glycoside compositions that have greater than at least 3% Rebaudioside M by weight total steviol glycosides, e.g., at least 4% Rebaudioside M, at least 5% Rebaudioside M, at least 10-20% Rebaudioside M, at least 20-30% Rebaudioside M, at least 30-40% Rebaudioside M, at least 40-50% Rebaudioside M, at least 50-60% Rebaudioside M, at least 60-70% Rebaudioside M, or at least 70-80% Rebaudioside M. Other steviol glycosides present can include those depicted in FIG. 1 such as steviol monosides, steviol glucobiosides, Rebaudioside A, Rebaudioside D, Rebaudioside E, and stevioside. In some embodiments, the Rebaudioside M-enriched composition produced by the host (e.g., microorganism) can be further purified and the Rebaudioside M so purified can then be mixed with other steviol glycosides, flavors, or sweeteners to obtain a desired flavor system or sweetening composition. For instance, a Rebaudioside M-enriched composition produced by a recombinant host can be combined with a Rebaudioside A, C, D, or E-enriched composition produced by a different recombinant host, with Rebaudioside A, C, D, or E purified from a *Stevia* extract, or with Rebaudioside A, C, D, or E produced in vitro.

In some embodiments, Rebaudioside M can be produced using in vitro methods while supplying the appropriate UDP-sugar and/or a cell-free system for regeneration of UDP-sugars. In some embodiments, sucrose and a sucrose synthase can be provided in the reaction vessel in order to regenerate UDP-glucose from the UDP generated during glycosylation reactions. The sucrose synthase can be from any suitable organism. For example, a sucrose synthase coding sequence from *A. thaliana, S. rebaudiana*, or *Coffea arabica* can be cloned into an expression plasmid under control of a suitable promoter, and expressed in a host such as a microorganism or a plant.

Conversions requiring multiple reactions can be carried out together, or stepwise. For example, Rebaudioside M can be produced from Rebaudioside D or Rebaudioside E that is commercially available as an enriched extract or produced via biosynthesis, with the addition of stoichiometric or excess amounts of UDP-glucose and UGT76G1. As an alternative, Rebaudioside D and Rebaudioside M can be produced from steviol glycoside extracts that are enriched for stevioside and Rebaudioside A, using EUGT11 and a suitable UGT76G1 enzyme. In some embodiments, phosphatases are used to remove secondary products and improve reaction yields. UGTs and other enzymes for in vitro reactions can be provided in soluble forms or in immobilized forms.

In some embodiments, Rebaudioside M can be produced using whole cells that are fed raw materials that contain precursor molecules such as steviol and/or steviol glycosides, including mixtures of steviol glycosides derived from plant extracts. The raw materials can be fed during cell growth or after cell growth. The whole cells can be in suspension or immobilized. The whole cells can be entrapped in beads, for example calcium or sodium alginate beads. The whole cells can be linked to a hollow fiber tube reactor system. The whole cells can be concentrated and entrapped within a membrane reactor system. The whole cells can be in fermentation broth or in a reaction buffer. Similar methodology can be applied to fermentation of recombinant cells.

In some embodiments, a permeabilizing agent is utilized for efficient transfer of substrate into the cells. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. The cells can contain one recombinant UGT or multiple recombinant UGTs. For example, the cells can contain UGT76G1, 91D2e, 85C2, 74G1 and EUGT11 such that mixtures of steviol and/or steviol glycosides are efficiently converted to Rebaudioside M. In some embodiments, the whole cells are the host cells described below. In some embodiments, the whole cells are a Gram-negative bacterium such as *E. coli*. In some embodiments, the whole cell is a Gram-positive bacterium such as *Bacillus*. In some embodiments, the whole cell is a fungal species such as *Aspergillus*, or yeast such as *Saccharomyces*. In some embodiments, the term "whole cell biocatalysis" is used to refer to the process in which the whole cells are grown as described above (e.g., in a medium and optionally permeabilized) and a substrate such as Rebaudioside D, Rebaudioside E, or stevioside is provided and converted to the end product using the enzymes from the cells. The cells can or cannot be viable, and can or cannot be growing during the bioconversion reactions. In contrast, in fermentation, the cells are cultured in a growth medium and fed a carbon and energy source such as glucose and the end product is produced with viable cells.

C. Other Polypeptides

Genes for additional polypeptides whose expression facilitates more efficient or larger scale production of steviol or a steviol glycoside can also be introduced into a recombinant host. For example, a recombinant microorganism, plant, or plant cell can also contain one or more genes encoding a geranylgeranyl diphosphate synthase (GGPPS, also referred to as GGDPS). As another example, the recombinant host can contain one or more genes encoding a rhamnose synthetase, or one or more genes encoding a UDP-glucose dehydrogenase and/or a UDP-glucuronic acid decarboxylase. As another example, a recombinant host can also contain one or more genes encoding a cytochrome P450 reductase (CPR). Expression of a recombinant CPR facilitates the cycling of NADP+ to regenerate NADPH, which is utilized as a cofactor for terpenoid biosynthesis. Other methods can be used to regenerate NADHP levels as well. In circumstances where NADPH becomes limiting, for example, strains can be further modified to include exogenous transhydrogenase genes. See, e.g., Sauer et al., 2004, J. Biol. Chem. 279: 6613-6619. Other methods are known to those with skill in the art to reduce or otherwise modify the ratio of NADH/NADPH such that the desired cofactor level is increased.

As another example the recombinant host can contain one or more genes encoding a sucrose synthase, and additionally can contain sucrose uptake genes if desired. The sucrose synthase reaction can be used to increase the UDP-glucose pool in a fermentation host, or in a whole cell bioconversion process. This regenerates UDP-glucose from UDP produced during glycosylation and sucrose, allowing for efficient glycosylation. In some organisms, disruption of the endogenous invertase is advantageous to prevent degradation of sucrose. For example, the *S. cerevisiae* SUC2 invertase can be disrupted. The sucrose synthase (SUS) can be from any suitable organism. For example, a sucrose synthase coding sequence from, without limitation, *A. thaliana, S. rebaudiana*, or *C. arabica* can be cloned into an expression plasmid under control of a suitable promoter, and expressed in a host (e.g., a microorganism or a plant). The sucrose synthase can be expressed in such a strain in combination with a sucrose transporter (e.g., the *A. thaliana* SUC1 transporter or a functional homolog thereof) and one or more UGTs (e.g., UGT85C2, UGT74G1, UGT76G1, and UGT91D2e, EUGT11 or functional homologs thereof). Culturing the host in a medium that contains sucrose can promote production of UDP-glucose, as well as one or more glucosides (e.g., steviol glycosides).

Expression of the ERG9 gene, which encodes squalene synthase (SQS), also can be reduced in recombinant hosts such that there is a build-up of precursors to squalene synthase in the recombinant host. SQS is classified under EC 2.5.1.21 and is the first committed enzyme of the biosynthesis pathway that leads to the production of sterols. It catalyzes the synthesis of squalene from farnesyl pyrophosphate via the intermediate presqualene pyrophosphate, wherein two units of farnesyl pyrophosphate are converted into squalene. This enzyme is a branch point enzyme in the biosynthesis of terpenoids/isoprenoids and is thought to regulate the flux of isoprene intermediates through the sterol pathway. The enzyme is sometimes referred to as farnesyl-diphosphate farnesyltransferase (FDFT1). In addition, a recombinant host can have reduced phosphatase activity as discussed herein.

MEP Biosynthesis Polypeptides

As another example, the recombinant host can contain one or more genes encoding one or more enzymes in the MEP pathway or the mevalonate pathway. Such genes are useful because they can increase the flux of carbon into the diterpene biosynthesis pathway, producing geranylgeranyl diphosphate from isopentenyl diphosphate and dimethylallyl diphosphate generated by the pathway. The geranylgeranyl diphosphate so produced can be directed towards steviol and steviol glycoside biosynthesis due to expression of steviol biosynthesis polypeptides and steviol glycoside biosynthesis polypeptides. See, e.g., Brandle et al., 2007, Phytochemistry 68:1855-1863.

In some embodiments, a recombinant host contains one or more genes encoding enzymes involved in the methylerythritol 4-phosphate (MEP) pathway for isoprenoid biosynthesis. Enzymes in the MEP pathway include deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS) and 1-hydroxy-2-methyl-2(E)-butenyl 4-diphosphate reductase (HDR). One or more DXS genes, DXR genes, CMS genes, CMK genes, MCS genes, HDS genes and/or HDR genes can be incorporated into a recombinant microorganism. See, Rodríguez-Concepción and Boronat, Plant Phys. 130: 1079-1089 (2002).

Suitable genes encoding DXS, DXR, CMS, CMK, MCS, HDS and/or HDR polypeptides include those made by *E. coli, A. thaliana* and *Synechococcus leopoliensis*. Nucleotide sequences encoding DXR polypeptides (e.g., SEQ ID NO: 71) are described, for example, in U.S. Pat. No. 7,335,815.

Mevalonate Biosynthesis Polypeptides

*S. cerevisiae* contains endogenous genes encoding the enzymes of a functional mevalonate pathway for isoprenoid synthesis. In some embodiments, a recombinant host also contains one or more heterologous genes encoding enzymes involved in the mevalonate pathway. Genes suitable for transformation into a host encode enzymes in the mevalonate pathway such as a truncated 3-hydroxy-3-methyl-glutaryl (HMG)-CoA reductase (tHMG), and/or a gene encoding a mevalonate kinase (MK), and/or a gene encoding a phosphomevalonate kinase (PMK), and/or a gene encoding a mevalonate pyrophosphate decarboxylase (MPPD). Thus, one or more HMG-CoA reductase genes, MK genes, PMK genes, and/or MPPD genes can be incorporated into a recombinant host such as a microorganism.

Suitable genes encoding mevalonate pathway polypeptides are known. For example, suitable polypeptides include those made by *E. coli, Paracoccus denitrificans, S. cerevisiae, A. thaliana, Kitasatospora griseola, Homo sapiens, Drosophila melanogaster, Gallus gallus, Streptomyces* sp. KO-3988, *Nicotiana attenuata, Kitasatospora griseola, Hevea brasiliensis, Enterococcus faecium* and *Haematococcus pluvialis*. See, e.g., Table 9, U.S. Pat. Nos. 7,183,089, 5,460,949, and 5,306,862, and POT Application Nos. PCT/US2012/050021 and PCT/US2011/038967, which are incorporated herein by reference in their entirety.

TABLE 9

Sources of HMG CoA Reductases and other Mevalonate Genes

| Accession# | Organism | Enzyme | Size (nt) | Gene name |
|---|---|---|---|---|
| XM_001467423 (amino acid SEQ ID NO: 72) | *Leishmania infantum* | Acetyl-CoA C-acetyl-transferase | 1323 (nt SEQ ID NO: 94) | MEV-4 |
| YML075C (amino acid SEQ ID NO: 73) | *Saccharomyces cerevisiae* | Truncated HMG (tHMG1) | 1584 (nt SEQ ID NO: 95) | tHMG1 |

TABLE 9-continued

| Sources of HMG CoA Reductases and other Mevalonate Genes | | | | |
|---|---|---|---|---|
| Accession# | Organism | Enzyme | Size (nt) | Gene name |
| EU263989 (amino acid SEQ ID NO: 74) | *Ganoderma lucidum* | 3-HMG-CoA reductase | 3681 (nt SEQ ID NO: 96) | MEV-11 |
| BC153262 (amino acid SEQ ID NO: 75) | *Bos taurus* | 3-HMG-CoA reductase | 2667 (nt SEQ ID NO: 97) | MEV-12 |
| AAD47596 (amino acid SEQ ID NO: 76) | *Artemisia annua* | 3-HMG-CoA reductase | 1704 (nt SEQ ID NO: 98) | MEV-13 |
| AAB62280 (amiono acid SEQ ID NO: 77) | *Trypanosoma cruzi* | 3-HMG-CoA reductase | 1308 (nt SEQ ID NO: 99) | MEV-14 |
| CAG41604 (amino acid SEQ ID NO: 78) | *Staph aureus* | 3-HMG-CoA reductase | 1281 (nt SEQ ID NO: 100) | MEV-15 |
| DNA2.0 sequence (amino acid SEQ ID NO: 92) | *Archaeoglobus fulgidus* | 3-HMG-CoA reductase | 1311 (nt SEQ ID NO: 101) | HMG re-ductase |
| DNA2.0 sequence (amino acid SEQ ID NO: 93) | *Pseudomonas mevalonii* | 3-HMG-CoA reductase | 1287 (nt SEQ ID NO: 102) | HMG re-ductase |

Sucrose Synthase Polypeptides

Sucrose synthase (SUS) can be used as a tool for generating UDP-sugar, in particular UDP-glucose. SUS (EC 2.4.1.13) catalyzes the formation of UDP-glucose and fructose from sucrose and UDP. UDP generated by the reaction of UGTs thus can be converted by SUS into UDP-glucose in the presence of sucrose. See, e.g., Chen et al., 2001, J. Am. Chem. Soc. 123:8866-8867; Shao et al., 2003, Appl. Env. Microbiol. 69:5238-5242; Masada et al., 2007, FEBS Lett. 581:2562-2566; and Son et al., 2009, J. Microbiol. Biotechnol. 19:709-712.

Sucrose synthases can be used to generate UDP-glucose and remove UDP, facilitating efficient glycosylation of compounds in various systems. For example, yeast deficient in the ability to utilize sucrose can be made to grow on sucrose by introducing a sucrose transporter and a SUS. For example, *S. cerevisiae* does not have an efficient sucrose uptake system, and relies on extracellular SUC2 to utilize sucrose. The combination of disrupting the endogenous *S. cerevisiae* SUC2 invertase and expressing recombinant SUS resulted in a yeast strain that was able to metabolize intracellular but not extracellular sucrose (Riesmeier et al., 1992, EMBO J. 11:4705-4713). The strain was used to isolate sucrose transporters by transformation with a cDNA expression library and selection of transformants that had gained the ability to take up sucrose.

The combined expression of recombinant sucrose synthase and a sucrose transporter in vivo can lead to increased UDP-glucose availability and removal of unwanted UDP. For example, functional expression of a recombinant sucrose synthase, a sucrose transporter, and a glycosyltransferase, in combination with knockout of the natural sucrose degradation system (SUC2 in the case of *S. cerevisiae*) can be used to generate a cell that is capable of producing increased amounts of glycosylated compounds such as steviol glycosides. This higher glycosylation capability is due to at least (a) a higher capacity for producing UDP-glucose in a more energy efficient manner, and (b) removal of UDP from growth medium, as UDP can inhibit glycosylation reactions.

The sucrose synthase can be from any suitable organism. For example, a sucrose synthase coding sequence from, without limitation, *A. thaliana* (e.g. SEQ ID NO: 79 or 80), or *C. arabica* (e.g., SEQ ID NO: 81) (see e.g., SEQ ID NOs: 178, 179, and 180 of PCT/US2012/050021, which is incorporated herein by reference in its entirety) includes the amino acid sequence of the sucrose transporter SUC1 from *A. thaliana* (SEQ ID NO: 80), and the amino acid sequence of the sucrose synthase from coffee (SEQ ID NO: 81).

The sucrose synthase can be from any suitable organism. For example, a sucrose synthase coding sequence from, without limitation, *A. thaliana, S. rebaudiana*, or *C. arabica* (see e.g., SEQ ID NOs: 79-81) can be cloned into an expression plasmid under control of a suitable promoter, and expressed in a host (e.g., a microorganism or a plant). A SUS coding sequence can be expressed in a SUC2 (sucrose hydrolyzing enzyme) deficient *S. cerevisiae* strain, so as to avoid degradation of extracellular sucrose by the yeast.

The sucrose synthase can be expressed in such a strain in combination with a sucrose transporter (e.g., the *A. thaliana* SUC1 transporter or a functional homolog thereof) and one or more UGTs (e.g., UGT85C2, UGT74G1, UGT76G1, EUGT11, and UGT91D2e, or functional homologs thereof). Culturing the host in a medium that contains sucrose can promote production of UDP-glucose, as well as one or more glucosides (e.g., steviol glucoside). It is to be noted that in some cases, a sucrose synthase and a sucrose transporter can be expressed along with a UGT in a host cell that also is recombinant for production of a particular compound (e.g., steviol).

Modulating Expression of ERG9 Gene

Expression of the endogenous ERG9 gene can be altered in a recombinant host described herein using a nucleic acid construct. The construct can include two regions that are homologous to parts of the genome sequence within the ERG9 promoter or 5' end of the ERG9 open reading frame (ORF), respectively. The construct can further include a promoter, such as either the wild type ScKex2 or wild type ScCyc1, and the promoter further can include a heterologous insert such as a hairpin at its 3'-end. The polypeptide encoded by the ORF advantageously has at least 70% identity to a squalene synthase (EC 2.5.1.21) or a biologically active fragment thereof, said fragment having at least 70% sequence identity to said squalene synthase in a range of overlap of at least 100 amino acids. See, for example, PCT/US2012/050021 (incorporated herein for all purposes in its entirety).

The heterologous insert can adapt the secondary structure element of a hairpin with a hairpin loop. The heterologous insert sequence has the general formula (1):

-X1-X2-X3-X4-X5, wherein

X2 comprises at least 4 consecutive nucleotides being complementary to, and forming a hairpin secondary structure element with at least 4 consecutive nucleotides of X4, and X3 is optional and if present comprises nucleotides involved in forming a hairpin loop between X2 and X4, and X1 and X5 individually and optionally comprise one or more nucleotides, and X2 and X4 can individually consist of any suitable number of nucleotides, so long as a consecutive sequence of at least 4 nucleotides of X2 is complementary to a consecutive sequence of at least 4 nucleotides of X4. In some embodiments, X2 and X4 consist of the same number of nucleotides.

The heterologous insert is long enough to allow a hairpin to be completed, but short enough to allow limited translation of an ORF that is present in-frame and immediately 3' to the heterologous insert. Typically, the heterologous insert is from 10-50 nucleotides in length, e.g., 10-30 nucleotides, 15-25 nucleotides, 17-22 nucleotides, 18-21 nucleotides, 18-20 nucleotides, or 19 nucleotides in length. As provided herein:

X2 can for example consist of in the range of 4 to 25 nucleotides, such as in the range of 4 to 20, 4 to 15, 6 to 12, 8 to 12, or 9 to 11 nucleotides.

X4 can for example consist of in the range of 4 to 25 nucleotides, such as in the range of 4 to 20, 4 to 15, 6 to 12, 8 to 12, or 9 to 11 nucleotides.

In some embodiments, X2 consists of a nucleotide sequence that is complementary to the nucleotide sequence of X4, all nucleotides of X2 are complementary to the nucleotide sequence of X4.

X3 can be absent, i.e., X3 can consist of zero nucleotides. It is also possible that X3 consists of in the range of 1 to 5 nucleotides, such as in the range of 1 to 3 nucleotides.

X1 can be absent, i.e., X1 can consist of zero nucleotides. It is also possible that X1 consists of in the range of 1 to 25 nucleotides, such as in the range of 1 to 20, 1 to 15, 1 to 10, 1 to 5, or 1 to 3 nucleotides.

X5 can be absent, i.e., X5 can consist of zero nucleotides. It is also possible that X5 can consist of in the range 1 to 5 nucleotides, such as in the range of 1 to 3 nucleotides.

The heterologous insert can be any suitable sequence fulfilling the requirements defined herein. For example, the heterologous insert can comprise tgaattcgttaacgaattc (SEQ ID NO: 82), tgaattcgttaacgaactc (SEQ ID NO: 83), tgaattcgttaacgaagtc (SEQ ID NO: 84), or tgaattcgttaacgaaatt (SEQ ID NO: 85).

Without being bound to a particular mechanism, ERG9 expression can be decreased by at least partly, sterically hindering binding of the ribosome to the RNA thus reducing the translation of squalene synthase. Thus, the translation rate of a functional squalene synthase (EC 2.5.1.21) can be reduced, for example. Using such a construct also can decrease turnover of farnesyl-pyrophosphate to squalene and/or enhance accumulation of a compound selected from the group consisting of farnesyl-pyrophosphate, isopentenyl-pyrophosphate, dimethylallyl-pyrophosphate, geranyl-pyrophosphate and geranylgeranyl-pyrophosphate.

In some instances it can be advantageous to include a squalene synthase inhibitor when culturing recombinant hosts described herein. Chemical inhibition of squalene synthase, e.g., by lapaquistat, is known in the art. Other squalene synthase inhibitors include Zaragozic acid and RPR 107393. Thus, in one embodiment the culturing step of the method(s) defined herein are performed in the presence of a squalene synthase inhibitor.

In some embodiments, the recombinant hosts described herein contain a mutation in the ERG9 open reading frame.

In some embodiments, the recombinant hosts described herein contain an ERG9[Delta]::HIS3 deletion/insertion allele.

D. Functional Homologs

Functional homologs of the polypeptides described above are also suitable for use in producing steviol or steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be natural occurring polypeptides, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional UGT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol or steviol glycoside biosynthesis polypeptides. Sequence analysis can involve BLAST, Reciprocal BLAST, or PSI-BLAST analysis of nonredundant databases using a GGPPS, a CDPS, a KS, a KO or a KAH amino acid sequence as the reference sequence. Amino acid sequence is, in some instances, deduced from the nucleotide sequence. Those polypeptides in the database that have greater than 40% sequence identity are candidates for further evaluation for suitability as a steviol or steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol biosynthesis polypeptides, e.g., conserved functional domains.

Conserved regions can be identified by locating a region within the primary amino acid sequence of a steviol or a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol glycosides in a recombinant host include functional homologs of EUGT11 (SEQ ID NO: 16), UGT91D2e (SEQ ID NO: 15), UGT91D2m (SEQ ID NO: 86), UGT85C (SEQ ID NO: 26), and UGT76G (SEQ ID NO:2). Such homologs have greater than 90% (e.g., at least 95% or 99%) sequence identity to the amino acid sequence of EUGT11, UGT91D2e, UGT91D2m, UGT85C, or UGT76G disclosed herein or in PCT Application No. PCT/US2012/050021, which is incorporated herein by reference in its entirety. Variants of EUGT11, UGT91 D2, UGT85C, and UGT76G polypeptides typically have 10 or fewer amino acid substitutions within the primary amino acid sequence, e.g., 7 or fewer amino acid substitutions, 5 or conservative amino acid substitutions, or between 1 and 5 substitutions. However, in some embodiments, variants of EUGT11, UGT91D2, UGT85C, and UGT76G polypeptides can have 10 or more amino acid substitutions (e.g., 10, 15, 20, 25, 30, 35, 10-20, 10-35, 20-30, or 25-35 amino acid substitutions). The substitutions can be conservative, or in some embodiments, non-conservative. Non-limiting examples of non-conservative changes in UGT91D2e polypeptides include glycine to arginine and tryptophan to arginine. Non-limiting examples of non-conservative substitutions in UGT76G polypeptides include valine to glutamic acid, glycine to glutamic acid, glutamine to alanine, and serine to proline. Non-limiting examples of changes to UGT85C polypeptides include histidine to aspartic acid, proline to serine, lysine to threonine, and threonine to arginine.

In some embodiments, a useful UGT91D2 homolog can have amino acid substitutions (e.g., conservative amino acid substitutions) in regions of the polypeptide that are outside of predicted loops, e.g., residues 20-26, 39-43, 88-95, 121-124, 142-158, 185-198, and 203-214 are predicted loops in the N-terminal domain and residues 381-386 are predicted loops in the C-terminal domain of 91D2e (see SEQ ID NO:15). For example, a useful UGT91D2 homolog can include at least one amino acid substitution at residues 1-19, 27-38, 44-87, 96-120, 125-141, 159-184, 199-202, 215-380, or 387-473. In some embodiments, a UGT91D2 homolog can have an amino acid substitution at one or more residues selected from the group consisting of residues 30, 93, 99, 122, 140, 142, 148, 153, 156, 195, 196, 199, 206, 207, 211, 221, 286, 343, 427, and 438. For example, a UGT91D2 functional homolog can have an amino acid substitution at one or more of residues 206, 207, and 343, such as an arginine at residue 206, a cysteine at residue 207, and an arginine at residue 343. Other functional homologs of UGT91 D2 can have one or more of the following: a tyrosine or phenylalanine at residue 30, a proline or glutamine at residue 93, a serine or valine at residue 99, a tyrosine or a phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, a lysine or asparagine at residue 427, an alanine at residue 438, and either an alanine or threonine at residue 462. In another embodiment, a UGT91 D2 functional homolog contains a methionine at residue 211 and an alanine at residue 286.

In some embodiments, a useful UGT85C homolog can have one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471. Non-limiting examples of useful UGT85C homologs include polypeptides having substitutions (with respect to SEQ ID NO: 26) at residue 65 (e.g., a serine at residue 65), at residue 65 in combination with residue 15 (a leucine at residue 15), 270 (e.g., a methionine, arginine, or alanine at residue 270), 418 (e.g., a valine at residue 418), 440 (e.g., an aspartic acid at residue at residue 440), or 441 (e.g., an asparagine at residue 441); residues 13 (e.g., a phenylalanine at residue 13), 15, 60 (e.g., an aspartic acid at residue 60), 270, 289 (e.g., a histidine at residue 289), and 418; substitutions at residues 13, 60, and 270; substitutions at residues 60 and 87 (e.g., a phenylalanine at residue 87); substitutions at residues 65, 71 (e.g., a glutamine at residue 71), 220 (e.g., a threonine at residue 220), 243 (e.g., a tryptophan at residue 243), and 270; substitutions at residues 65, 71, 220, 243, 270, and 441; substitutions at residues 65, 71, 220, 389 (e.g., a valine at residue 389), and 394 (e.g., a valine at residue 394); substitutions at residues 65, 71, 270, and 289; substitutions at residues 220, 243, 270, and 334 (e.g., a serine at residue 334); or substitutions at residues 270 and 289. The following amino acid mutations did not result in a loss of activity in 85C2 polypeptides: V13F, F15L, H60D, A65S, E71Q, 187F, K220T, R243W, T270M, T270R, Q289H, L334S, A389V, 1394V, P397S, E418V, G440D, and H441N. Additional mutations that were seen in active clones include K9E, K10R, Q21H, M27V, L91P, Y298C, K350T, H368R, G420R, L431P, R444G, and M471T. In some embodiments, an UGT85C2 contains substitutions at positions 65 (e.g., a serine), 71 (a glutamine), 270 (a methionine), 289 (a histidine), and 389 (a valine).

In some embodiments, a useful UGT76G1 homolog (SEQ ID NO: 2) can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 (see TABLE 10). Non-limiting examples of useful UGT76G1 homologs include polypeptides having substitutions at residues 74, 87, 91, 116, 123, 125, 126, 130, 145, 192, 193, 194, 196, 198, 199, 200, 203, 204, 205, 206, 207, 208, and 291; residues 74, 87, 91, 116, 123, 125, 126, 130, 145, 192, 193, 194, 196, 198, 199, 200, 203, 204, 205, 206, 207, 208, 266, 273, 274, 284, 285, and 291; or residues 74, 87, 91, 116,123,125,126, 130,145,192,193, 194,196, 198, 199, 200, 203, 204, 205, 206, 207, 208, 266, 273, 274, 284, 285, 291, 330, 331, and 346. See, Table 10.

TABLE 10

| Clone | Variants |
|---|---|
| 76G_G7 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion, L330V, G331A, L346I |
| 76G_H12 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion |
| 76G_C4 | M29I, V74E, V87G, L91P, G116E, A123T, Q125A, I126L, T130A, V145M, C192S, S193A, F194Y, M196N, K198Q, |

TABLE 10-continued

| Clone | Variants |
|---|---|
| | K199I, Y200L, Y203I, F204L, E205G, N206K, I207M, T208I |

Methods to modify the substrate specificity of, for example, EUGT11 or UGT91 D2e, are known to those skilled in the art, and include without limitation site-directed/rational mutagenesis approaches, random directed evolution approaches and combinations in which random mutagenesis/saturation techniques are performed near the active site of the enzyme. For example see Sarah A. Osmani, et al., Phytochemistry 70 (2009) 325-347.

A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A functional homolog polypeptide typically has a length that is from 95 percent to 105 percent of the length of the reference sequence, e.g., 90, 93, 95, 97, 99, 100, 105, 110, 115, or 120 percent of the length of the reference sequence, or any range between. A percent identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGTs can include additional amino acids that are not involved in glucosylation or other enzymatic activities carried out by the enzyme, and thus such a polypeptide can be longer than would otherwise be the case. For example, a EUGT11 polypeptide can include a purification tag (e.g., HIS tag or GST tag), a chloroplast transit peptide, a mitochondrial transit peptide, an amyloplast peptide, signal peptide, or a secretion tag added to the amino or carboxy terminus. In some embodiments, a EUGT11 polypeptide includes an amino acid sequence that functions as a reporter, e.g., a green fluorescent protein or yellow fluorescent protein.

II. Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it can be desirable to downregulate synthesis of sterols in a yeast strain in order to further increase steviol or steviol glycoside production, e.g., by downregulating squalene epoxidase. As another example, it can be desirable to inhibit degradative functions of certain endogenous gene products, e.g., glycohydrolases that remove glucose moieties from secondary metabolites or phosphatases as discussed herein. As another example, expression of membrane transporters involved in transport of steviol glycosides can be inhibited, such that secretion of glycosylated steviosides is inhibited. Such regulation can be beneficial in that secretion of steviol glycosides can be inhibited for a desired period of time during culture of the microorganism, thereby increasing the yield of glycoside product(s) at harvest. In such cases, a nucleic acid that inhibits expression of the polypeptide or gene product can be included in a recombinant construct that is transformed into the strain. Alternatively, mutagenesis can be used to generate mutants in genes for which it is desired to inhibit function.

III. Hosts

Microorganisms

Recombinant hosts can be used to express polypeptides for the production of steviol glycosides, including mammalian, insect, and plant cells. A number of prokaryotes and eukaryotes are also suitable for use in constructing the recombinant microorganisms described herein, e.g., gram-negative bacteria, yeast and fungi. A species and strain selected for use as a steviol or steviol glycoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species can be suitable. For example, suitable species can be in a genus selected from the group consisting of *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis, Candida glabrata, Candida albicans*, and *Yarrowia lipolytica*. In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *Saccharomyces cerevisiae*. In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of steviol glycosides.

*Saccharomyces cerevisiae*

*Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

A steviol biosynthesis gene cluster can be expressed in yeast using any of a number of known promoters. Strains that overproduce terpenes are known and can be used to increase the amount of geranylgeranyl diphosphate available for steviol and steviol glycoside production.

*Aspergillus* spp.

*Aspergillus* species such as *A. oryzae, A. niger* and *A. sojae* are widely used microorganisms in food production, and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients such as steviol and steviol glycosides.

*Escherichia coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of gibberellin in culture. Thus, the terpene precursors for producing large amounts of steviol and steviol glycosides are already produced by endogenous genes. Thus, modules containing recombinant genes for steviol or steviol glycoside biosynthesis polypeptides can be introduced into species from such genera without the necessity of introducing mevalonate or MEP pathway genes.

*Arxula adeninivorans* (*Blastobotrys adeninivorans*)

*Arxula adeninivorans* is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is a dimorphic yeast (see *Arxula adeninivorans*) that can grow on a wide range of substrates. It has a high potential for industrial applications but there are no recombinant products commercially available yet.

*Rhodobacter* spp.

*Rhodobacter* can be used as the recombinant microorganism platform. Similar to *E. coli*, there are libraries of mutants available as well as suitable plasmid vectors, allowing for rational design of various modules to enhance product yield. Isoprenoid pathways have been engineered in membranous bacterial species of *Rhodobacter* for increased production of carotenoid and CoQ10. See, U.S. Patent Publication Nos. 20050003474 and 20040078846. Methods similar to those described above for *E. coli* can be used to make recombinant *Rhodobacter* microorganisms.

*Candida boidinii*

*Candida boidinii* is a methylotrophic yeast (it can grow on methanol). Like other methylotrophic species such as *Hansenula polymorpha* and *Pichia pastoris*, it provides an excellent platform for the production of heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH.

*Hansenula polymorpha* (*Pichia angusta*)

*Hansenula polymorpha* is another methylotrophic yeast (see *Candida boidinii*). It can furthermore grow on a wide range of other substrates; it is thermo-tolerant and can assimilate nitrate (see also *Kluyveromyces lactis*). It has been applied to the production of hepatitis B vaccines, insulin and interferon alpha-2a for the treatment of hepatitis C, furthermore to a range of technical enzymes.

*Kluyveromyces lactis*

*Kluyveromyces lactis* is yeast regularly applied to the production of kefir. It can grow on several sugars, most importantly on lactose which is present in milk and whey. It has successfully been applied among others to the production of chymosin (an enzyme that is usually present in the stomach of calves) for the production of cheese. Production takes place in fermenters on a 40,000 L scale.

*Pichia pastoris*

*Pichia pastoris* is a methylotrophic yeast (see *Candida boidinii* and *Hansenula polymorpha*). It provides an efficient platform for the production of foreign proteins. Platform elements are available as a kit and it is worldwide used in academia for the production of proteins. Strains have been engineered that can produce complex human N-glycan (yeast glycans are similar but not identical to those found in humans).

*Physcomitrella* spp.

*Physcomitrella* mosses, when grown in suspension culture, have characteristics similar to yeast or other fungal cultures. This genera is becoming an important type of cell for production of plant secondary metabolites, which can be difficult to produce in other types of cells.

IV. Methods of Producing Steviol Glycosides

Recombinant hosts described herein can be used in methods to produce steviol glycosides such as Rebaudioside M. For example, if the recombinant host is a microorganism, the method can include growing the recombinant microorganism in a culture medium under conditions in which steviol and/or steviol glycoside biosynthesis genes are expressed. The recombinant microorganism can be grown in a fed batch or continuous process. Typically, the recombinant microorganism is grown in a fermentor at a defined temperature(s) for a desired period of time. In certain embodiments, microorganisms include, but are not limited to *S. cerevisiae, A. niger, A. oryzae, E. coli, L. lactis* and *B. subtilis*. The constructed and genetically engineered microorganisms provided by the invention can be cultivated using conventional fermentation processes, including, inter alia, chemostat, batch, fed-batch cultivations, continuous perfusion fermentation, and continuous perfusion cell culture.

Depending on the particular microorganism used in the method, other recombinant genes such as isopentenyl biosynthesis genes and terpene synthase and cyclase genes can also be present and expressed. Levels of substrates and intermediates, e.g., isopentenyl diphosphate, dimethylallyl diphosphate, geranylgeranyl diphosphate, kaurene and kaurenoic acid, can be determined by extracting samples from culture media for analysis according to published methods.

After the recombinant microorganism has been grown in culture for the desired period of time, steviol and/or one or more steviol glycosides can then be recovered from the culture using various techniques known in the art. In some embodiments, a permeabilizing agent can be added to aid the feedstock entering into the host and product getting out. If the recombinant host is a plant or plant cells, steviol or steviol glycosides can be extracted from the plant tissue using various techniques known in the art. For example, a crude lysate of the cultured microorganism or plant tissue can be centrifuged to obtain a supernatant. The resulting supernatant can then be applied to a chromatography column, e.g., a C18 column such as Aqua® C18 column from Phenomenex or a Synergi™ Hydro RP 80 Å column, and washed with water to remove hydrophilic compounds, followed by elution of the compound(s) of interest with a solvent such as acetonitrile or methanol. The compound(s) can then be further purified by preparative HPLC. See also WO 2009/140394.

The amount of steviol glycoside (e.g., Rebaudioside M) produced can be from about 1 mg/L to about 2800 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing steviol while a second microorganism comprises steviol glycoside biosynthesis genes. Alternatively, the two or more microorganisms each can be grown in a separate culture medium and the product of the first culture medium, e.g., steviol, can be introduced into second culture medium to be converted into a subsequent intermediate, or into an end product such as Rebaudioside A. The product produced by the second, or final microorganism is then recovered. It will also be appreciated that in some embodiments, a recombinant microorganism is grown using nutrient sources other than a culture medium and utilizing a system other than a fermentor.

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., Rebaudioside M) and have a consistent taste profile. Thus, the recombinant microorganisms, plants, and plant cells described herein can facilitate the production of compositions that are tailored to meet the sweetening profile desired for a given food product and that have a proportion of each steviol glycoside that is consistent from batch to batch. Microorganisms described herein do not produce the undesired plant byproducts found in *Stevia* extracts. Thus, steviol glycoside compositions produced by the recombinant microorganisms described herein are distinguishable from compositions derived from *Stevia* plants.

V. Food Products

The steviol glycosides obtained by the methods disclosed herein can be used to make food and beverage products, dietary supplements and sweetener compositions. For example, substantially pure steviol glycoside such as Rebaudioside M can be included in food products such as ice cream, carbonated beverages, fruit juices, yogurts, baked goods, chewing gums, hard and soft candies, and sauces. Substantially pure steviol glycoside also can be included in non-food products such as pharmaceutical products, medicinal products, dietary supplements and nutritional supplements. Substantially pure steviol glycosides can also be included in animal feed products for both the agriculture industry and the companion animal industry. Alternatively, a mixture of steviol glycosides can be made by culturing recombinant microorganisms separately or growing different plants/plant cells, each producing a specific steviol or steviol glycoside, recovering the steviol or steviol glycoside in substantially pure form from each microorganism or plant/plant cells and then combining the compounds to obtain a mixture containing each compound in the desired proportion (e.g., Rebaudioside M with one or more other steviol glycosides). The recombinant microorganisms, plants, and plant cells described herein permit more precise and consistent mixtures to be obtained compared to current *Stevia* products. In another alternative, a substantially pure steviol glycoside can be incorporated into a food product along with other sweeteners, e.g. saccharin, dextrose, sucrose, fructose, erythritol, aspartame, sucralose, monatin, or acesulfame potassium. The weight ratio of steviol glycoside relative to other sweeteners can be varied as desired to achieve a satisfactory taste in the final food product. See, e.g., U.S. Patent Publication No. 2007/0128311. In some embodiments, the steviol glycoside can be provided with a flavor (e.g., citrus) as a flavor modulator.

Compositions produced by a recombinant microorganism, plant, or plant cell described herein can be incorporated into food products. For example, a steviol glycoside composition produced by a recombinant microorganism, plant, or plant cell can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism, plant, or plant cell can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism, plant, or plant cell can be incorporated into a baked good (e.g., a biscuit) such that the food product has a maximum of 300 mg steviol glycoside/kg food on a dry weight basis. A steviol glycoside composition produced by a recombinant microorganism, plant, or plant cell can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism, plant, or plant cell can be incorporated into bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for Rebaudioside M can be package in a sachet, for example, at from 10,000 to 30,000 mg steviol glycoside/kg product on a dry weight basis, for tabletop use.

The invention will be further described in the following examples, which do not limit the scope of the invention described in the claims.

EXAMPLES

The Examples that follow are illustrative of specific embodiments of the invention and various uses thereof. They are set forth for explanatory purposes only and are not to be taken as limiting the invention.

Example 1: Strain Engineering and Fermentation of EFSC 3044

Yeast strain EFSC 3044 was derived from a wild type *Saccharomyces cerevisiae* strain containing three auxotrophic modifications, namely the deletions of URA3, LEU2 and HIS3. The strain can be manipulated using standard genetic methods and can be used as a regular diploid or haploid yeast strain. The strain was converted to steviol glycosides-producing yeast by genomic-integration of five DNA constructs. Each construct contained multiple genes and was introduced into the yeast genome by homologous recombination. Furthermore, the first, second, and fifth construct were assembled by homologous recombination in yeast.

The first construct contained eight genes and was inserted in the DPP1 locus and disrupted and partially deleted DPP1 (phosphatase). The DNA inserted contained: the *Ashbya gossypii* TEF1 promoter expressing the natMX gene (selectable marker) followed by the TEF1 terminator from *A. gossypii*; Gene Art codon optimized *Stevia rebaudiana* UGT85C2 (GenBank AAR06916.1; SEQ ID NO:3) expressed from the native yeast GPD1 promoter and followed by the native yeast CYC1 terminator; *S. rebaudiana* CPR-8 (SEQ ID NO:5) expressed using the native yeast TP11 promoter followed by the native yeast TDH1 terminator; *Arabidopsis thaliana* kaurene synthase (SEQ ID NO:6, similar to GenBank AEE36246.1) expressed from the native yeast PDC1 promoter and followed by the native yeast FBA1 terminator; synthetic *Synechococcus* sp. GGPPS (SEQ ID NO: 22, GenBank ABC98596.1) expressed using the native yeast TEF2 promoter and followed by the native yeast PGI1 terminator; DNA2.0 codon-optimized *S. rebaudiana* KAHe1 (SEQ ID NO:8) expressed from the native yeast TEF1 promoter and followed by the native yeast ENO2 terminator; synthetic *S. rebaudiana* KO-1 (SEQ ID NO: 23, GenBank ABA42921.1) expressed using the native yeast FBA1 promoter and followed by the native yeast TDH2 terminator; and *Zea mays* truncated CDPS (SEQ ID NO:133) expressed using the native yeast PGK1 promoter and followed by the native yeast ADH2 terminator.

The second construct was inserted at the YPRCA15 locus and contained: the TEF1 promoter from *A. gossypii* in front of the kanMX gene (selectable marker) followed by the TEF1 terminator from *A. gossypii*; the Gene Art codon optimized *A. thaliana* ATR2 (SEQ ID NO: 10) expressed from the native yeast PGK1 promoter followed by the native yeast ADH2 terminator; *S. rebaudiana* UGT74G1 (SEQ ID NO:135, GenBank AAR06920.1) expressed from the native yeast TP11 promoter followed by the native yeast TDH1 terminator; Gene Art codon-optimized *S. rebaudiana* UGT76G1 (SEQ ID NO:14, encodes GenBankAAR06912) expressed from the native yeast TEF1 promoter followed by the native yeast ENO2 terminator; and GeneArt codon-optimized sequence encoding a *S. rebaudiana* UGT91D2e-b with the amino acid modifications L211M and V286A (SEQ ID NO:15 for UGT91D2e amino acid sequence for the wild type sequence; codon optimized nucleotide sequence is set forth in SEQ ID NO:90) and expressed from the native yeast GPD1 promoter and followed by the native yeast CYC1 terminator. UGT91D2e-b is disclosed herein as SEQ ID NO: 66 with mutations at methionine residue at residue 211 and an alanine residue at residue 286.

The first and the second construct were combined in the same spore clone by mating and dissection. This yeast strain was subsequently transformed with construct three and four in two successive events.

Construct three was integrated between genes PRP5 and YBR238C and contained the *Kluyveromyces lactis* leu2 promoter expressing the *K. lactis* leu2 gene followed by the leu2 terminator from *K. lactis*, the native yeast GPD1 promoter expressing the DNA2.0-optimized *S. rebaudiana* KAHe1 (SEQ ID NO:8) followed by the native yeast CYC1 terminator, and the native yeast TPI1 promoter expressing the *Zea mays* truncated CDPS (SEQ ID NO: 133) followed by the native yeast TP11 terminator.

Construct four was integrated in the genome between genes ECM3 and YOR093C with an expression cassette containing the TEF1 promoter from *A. gossypii* expressing the *K. pneumoniae* hphMX gene followed by the TEF1 terminator from *A. gossypii, Synechococcus* sp. GGPPS (SEQ ID NO: 22) expressed from the native yeast GPD1 promoter followed by the native yeast CYC1 terminator, and the native yeast TP11 promoter expressing the *A. thaliana* KS (SEQ ID NO: 6) followed by the native yeast TP11 terminator.

The four introduced selectable markers natMX, kanMX, *K. lactis* LEU2 and *K. pneumoniae* hphMX and the promoters preceding and terminators succeeding the selectable marker genes were then removed by recombination.

In this yeast strain, the fifth construct was inserted and assembled by yeast transformation and homologue recombination. The fifth construct contained seven genes and was inserted at the YORWΔ22 locus. The DNA inserted contained: the *A. gossypii* TEF1 promoter expressing the *Schizosaccharomyces Pombe* HIS5 gene (selectable marker) followed by the TEF1 terminator from *A. gossypii; S. rebaudiana* KO-1 (SEQ ID NO: 23, GenBank ABA42921.1) expressed from the native yeast GPD1 promoter and followed by the native yeast CYC1 terminator; *S. rebaudiana* CPR-8 (SEQ ID NO: 5) expressed using the native yeastTP11 promoter followed by the native yeast TH1 terminator; *Arabidopsis thaliana* kaurene synthase (SEQ ID NO: 6, similar to GenBank AEE36246.1) expressed from the native yeast POC1 promoter and followed by the native yeast FBA1 terminator, a codon optimized version of the rice gene Os03g0702000 (SEQ ID NO:18, encoding EUGT11) expressed using the native yeast TEF2 promoter and followed by the native yeast PG1 terminator; DNA2.0 codon-optimized *S. rebaudiana* KAHe1 (SEQ ID NO: 8) expressed from the native yeast TEF promoter and followed by the native yeast EN2 terminator; and *Zea mays* truncated COPS (SEQ ID NO:133) expressed using the native yeast PGK1 promoter and followed by the native yeast ADH2 terminator.

The described yeast strain was made prototrophic by introduction of the two plasmids, EPC2182 and EPC2308. EPSC2182 was derived from a p415TEF CEN/ARS shuttle plasmid with a LEU2 marker and contains another copy of *S. rebaudiana* KAHe1 expressed from the native yeast TEF1 promoter and succeeded by the native yeast CYC2 terminator. EPSC2308 was a p416TEF-based CEN/ARS shuttle plasmid with the URA3 marker wherein the EUGT11 gene was cloned and expressed from the native yeast TEF1 promoter and succeeded by the native yeast CYC1 terminator. This yeast strain was then designated EFSC 3044.

TABLE 11

List of Recombinant Genes in Strain EFSC 3044.

| Gene Designation | Yeast Location | Construct No. |
|---|---|---|
| UGT85C2 | Genomic | 1 |
| *S. rebaudiana* CPR-8 | Genomic | 1 |
| *A thaliana* Kaurene synthase | Genomic | 1 |
| *Synechococcus* sp. GGPPS | Genomic | 1 |
| *S. rebaudiana* KAHe1 | Genomic | 1 |
| *S. rebaudiana* KO-1 | Genomic | 1 |
| *Zea mays* truncated CDPS | Genomic | 1 |
| *A. thaliana* ATR2 | Genomic | 2 |
| *S. rebaudiana* UGT74G1 | Genomic | 2 |
| *S. rebaudiana* UGT76G1 | Genomic | 2 |
| *Stevia* UGT91D2e-b altered | Genomic | 2 |
| *S. rebaudiana* KAHe1 | Genomic | 3 |
| *Zea mays* truncated CDPS | Genomic | 3 |
| *Synechococcus* sp. GGPPS | Genomic | 4 |
| *A. thaliana* Kaurene synthase | Genomic | 4 |
| *S. rebaudiana* KO-1 | Genomic | 5 |
| *S. rebaudiana* CPR-8 | Genomic | 5 |
| *A thaliana* Kaurene synthase | Genomic | 5 |
| Os03g0702000 (EUGT11) | Genomic | 5 |
| *S. rebaudiana* KAHe1 | Genomic | 5 |
| *Zea mays* truncated CDPS | Genomic | 5 |
| *S. rebaudiana* KAHe1 | Plasmid | 6 |
| EUGT11 | Plasmid | 7 |

Fed-batch fermentation was carried out aerobically in 2 L (working volume) fermenters which included a ~16 hour growth phase in the base medium (Synthetic Complete media) followed by ~100 hours of feeding with glucose utilized as the carbon and energy source combined with trace metals, vitamins, salts, and Yeast Nitrogen Base (YNB) and/or amino acid supplementation. The pH was kept near pH 5, and the temperature setpoint was 30° C. The feed rate was controlled to prevent oxygen depletion and to minimize ethanol formation (glucose-limited conditions). Whole culture samples (without cell removal) were taken and boiled in an equal volume of DMSO for total glycosides levels.

The following methodology was used to analyze steviol glycosides and steviol pathway intermediates, unless otherwise indicated. LC-MS analyses were performed using an UltiMate® 3000 UPLC system (Dionex, Sunnyvale, CA) fitted with an Acquity UPLCO BEH C18 column (100×2.1 mm, 1.7 μm particles; Waters, Milford, MA) connected to a TSQ Quantum Access (ThermoFisher Scientific) triple quadropole mass spectrometer with a heated electrospray ion (HESI) source. Elution was carried out using a mobile phase of eluent B (MeCN with 0.1% Formic acid) and eluent A (water with 0.1% Formic acid) by increasing the gradient from 29→48% B from min 0.0 to 4.0, increasing 48→100% B in min 4.0 to 4.2, holding 100% B from min 4.2 to 6.2, and re-equilibrating with 29% eluent B. The flow rate was 0.4 ml/min and the column temperature was kept at 55° C. Steviol glycosides were detected using SIM (Single Ion Monitoring) in positive mode with the following m/z-traces in Table 12.

TABLE 12

Summary of Analytical Compounds Detected by LC/MS.

| Description | Exact Mass | m/z trace | Compound (typical $t_R$ in min) |
|---|---|---|---|
| Steviol + 1 Glucose | $[M + H]^+$ 481.2796 | 481.2 ± 0.5 | 19-SMG (4.15), 13-SMG (4.38) |
| | $[M + Na]^+$ 503.2615 | 503.1 ± 0.5 | |
| Steviol + 2 Glucose | $[M + Na]^+$ 665.3149 | 665 ± 0.5 | Rubusoside (3.04) Steviol-1,2-bioside (3.48) Steviol-1,3-bioside (4.05) |
| Steviol + 3 Glucose | $[M + Na]^+$ 827.3677 | 827.4 ± 0.5 | 1,2-Stevioside (2.28) 1,3-Stevioside (2.82) Rebaudioside B (3.9) |
| Steviol + 4 Glucose | $[M + Na]^+$ 989.4200 | 989.4 ± 0.5 | Rebaudioside A (2.23) |
| Steviol + 5 Glucose | $[M + Na]^+$ 1151.4728 | 1151.4 ± 0.5 | Rebaudioside D (1.19) |
| Steviol + 6 Glucose | $[M + Na]^+$ 1313.5257 | 1313.5 ± 0.5 | Rebaudioside M (1.31) |

The level of steviol glycosides were quantified by comparing with calibration curves obtained with authentic standards from LGC Standards. For example, standard solutions of 0.5 to 100 μM Rebaudioside A (RebA) were typically utilized to construct a calibration curve. FIG. contains representative mass spectra of fermentations that resulted in the formation of a hexaglycosylated steviol glycoside (retention time 1.31, mass traces corresponding to a hexa-glucose steviol glycoside and stevioside).

A modified LC-MS methodology (using a BEH RPshield C18 HPLC column (50×2.1 mm, 1.7 μm particles; Waters, Milford, MA) was used to analyze compounds described in Example 5 and in vitro experiment to determine relative rates for UGT76G1. The elution was carried out using a mobile phase of eluent B (MeCN with 0.1% formic acid) and eluent A (water with 0.1% formic acid) by increasing the gradient from 25→47% B from min 0.0 to 4.0, increasing 47→100% B in min 4.0 to 5.0, holding 100% B from min 5.0 to 6.5, and finally re-equilibrating with 25% B. The flow rate was 0.4 ml/min and the column temperature was kept at 35° C. A modified LC-MS methodology resulted in shorter retention time for the compounds shown in Table 12. Typical retention times using the modified LC-MS methodology ($t_R$ in min) were: 3.34 for 19-SMG; 3.54 for 13-SMG; 2.55 for Rubusoside; 2.95 for Steviol-1,2-bioside; 3.31 for Steviol-1,3-bioside; 2.04 for 1,2-Stevioside; 2.42 for 1,3-Stevioside; 2.91 for Rebaudioside B; 2.03 for Rebaudioside A; 1.1 for Rebaudioside D; and 1.32 for Rebaudioside M.

Example 2: In Vitro Characterization of Reactions that Produce a Hexa-Qlycosylated Steviol Glycoside As described in Example 1, a hexa-glucosyl steviol glycoside was observed when EUGT11 was expressed at high levels in steviol-glycoside producing yeast strains. To characterize the reactions that were occurring to produce this molecule, further in vitro work was done with individual UGTs.

UGT76G1 (SEQ ID NO: 1) was cloned into the pET30a plasmid (EMD Millipore). The resulting vector was transformed into an appropriate DE3 *E. coli* strain and transformants were grown and induced according to manufacturer's protocols. The corresponding fusion protein (6×HIS-tagged) was purified by immobilized metal affinity chromatography using standard methods.

Approximately 0.08 μg of purified UGT76G1 per μL of reaction was incubated with 100 μM RebD, 300 μM UDP-glucose, and 10 U/mL Alkaline Phosphatase (Fermentas/Thermo Fisher, Waltham, MA). The reactions were performed at 30° C. in 20 mM Hepes-NaOH, pH 7.6, for 24 hours. Prior to LC-MS analysis, one volume of 100% DMSO was added to each reaction and vortexed, and samples were centrifuged at 16,000×g for 1 minute.

A new peak appeared during the reaction at a mass corresponding to steviol+6 glucose moieties, eluting at 1.31 min and corresponding to a trace of one of the hexaglucosyl steviol glycosides found upon the overexpression of EUGT11 in vivo. This result suggested that UGT76G1 can further glycosylate RebD, resulting in a hexaglycoside. It was hypothesized that UGT76G1, in addition to making a 1,3-glucose linkage with the primary glucose at C13 of the steviol backbone, has a secondary activity of adding a 1,3-bound glucose to the primary glucose at C19. It is likely that the only glycosylation site available in RebD available for UGT76G1 is the glucose at C19, which would result in the production of a hexaglycoside designated RebM. The hexaglycoside detected was isolated and determined to be Rebaudioside M, as shown in Examples 3 and 4.

Example 3: Isolation of the Hexa-Glycosylated Molecule

Figure 6:
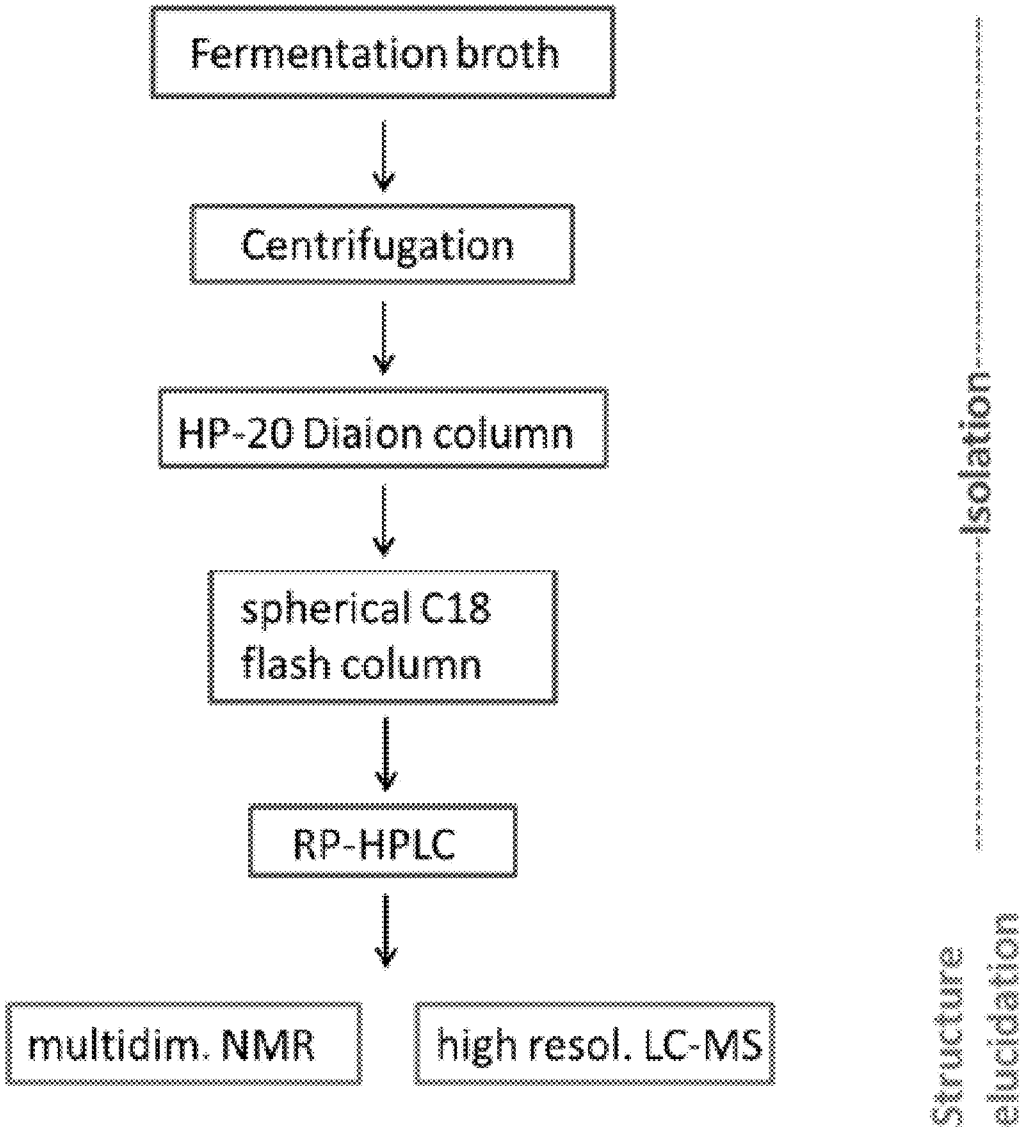
FIG. 6 is a schematic of the methods for isolating hexa-glycosylated steviol glycosides.

The hexa-glucosyl steviol glycoside product was isolated from a fermentation similar to that described in Example 1 for structural analysis following the scheme outlined in FIG. 6.

Figure 7A:
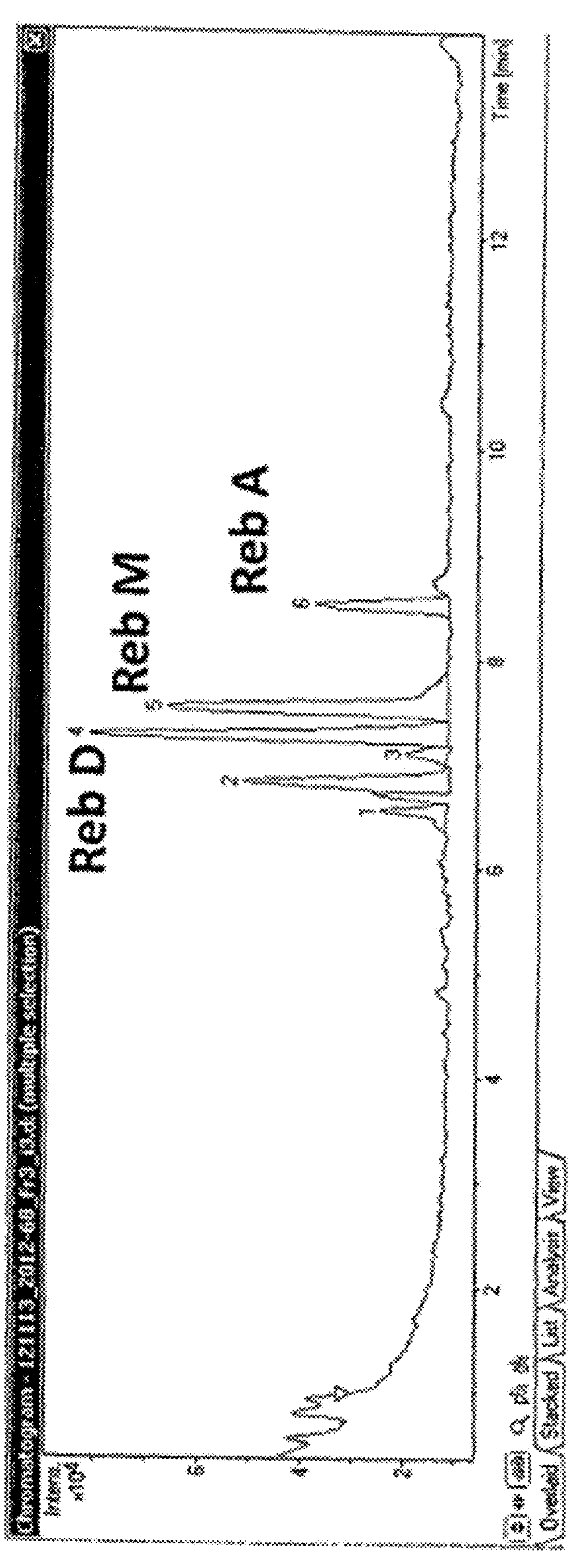
FIG. 7A is a representative chromatogram of the semi-purified hexa-glycosylated steviol glycoside after flash chromatography.
Figure 7B:
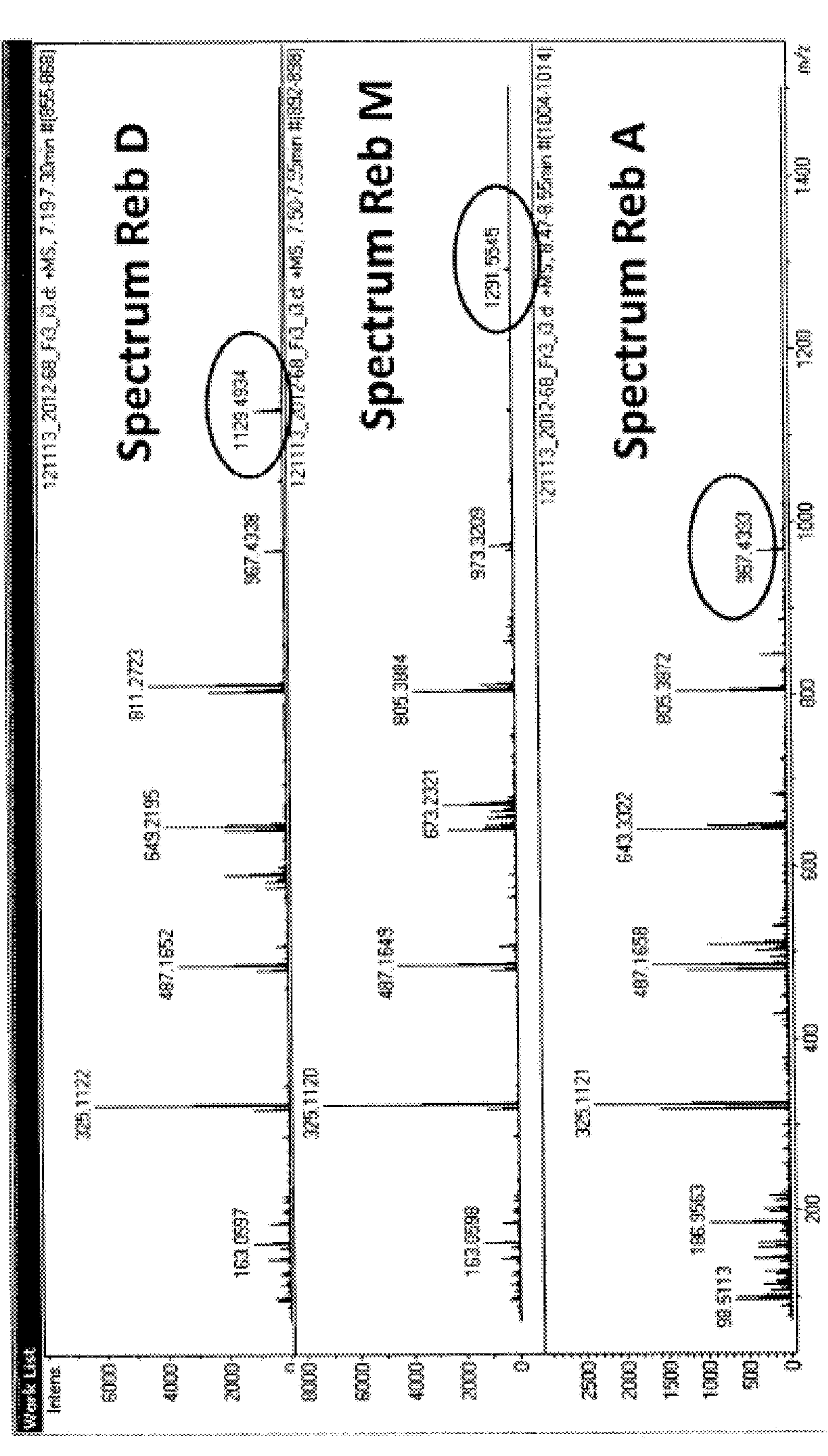
FIG. 7B is a representative mass spectrum from a liquid chromatography-quadrupole time-of-flight (LC-QTOF) analysis of the semi-purified hexa-glycosylated steviol glycoside after flash chromatography.

After the fermentation, the culture broth was centrifuged for 30 min at 7000 rpm at 4° C. and the supernatant was purified as follows: A glass column was filled with 150 mL HP20 Diaion® resin (Supelco), and an aliquot of 300 mL supernatant was loaded on to the column and washed with 2×250 mL MilliQ water. The glycoside product was eluted by stepwise incremental increases in the methanol concentration in MilliQ water (in 250 mL portions—starting with 0%→10%→40%→60%→80%→100% MeOH). The levels of steviol glycosides in each fraction were analyzed by LC-MS. The most promising fractions (60-80% MeOH) were combined and reduced to total of 10 mL using a vacuum evaporator. A glass column filled with 600 mL spherical C18 bonded flash silica gel (45-70 um, 70 Å/Supelco) was equilibrated with 5% aqueous acetonitrile (Acetronitrile: HPLC grade—Water: MilliQ). The concentrated residue from the HP20 purification was loaded on the column and eluted by stepwise increases in the acetonitrile contribution. The starting eluent was 5% acetonitrile in water. The level of acetonitrile was raised by 5% per step (each 400 mL). After reaching 50% acetonitrile 10% steps were made. All fractions were analyzed by LC-MS, pooled according to their steviol glycoside composition, and dried under vacuum. Table 13 contains a summary of the glycosides found in each of the fractions. FIG. 7 contains a chromatogram and mass spectra from LC-QTOF analysis of the semi-purified hexa-glycosylated compound after flash chromatography.

TABLE 13

Summary of Fractionation of Steviol Glycosides.

| mg | Fraction | Description |
|---|---|---|
| 321.1 | 2-11 | RebD and some 6X glycosylated steviol glycoside |
| 138.3 | 12-20 | RebD and some 6X glycosylated steviol glycoside |
| 357.4 | 21-27 | Bulk of 6X glycosylated steviol glycoside |
| 98.9 | 28-30 | RebA |
| 68.4 | 31-36 | Rubusoside, steviol-1,2-bioside |
| 14.8 | 34-45 | Mostly 13-SMG |
| 852.8 | Wash | Acetonitrile wash |

Example 4: NMR Confirmation of Structure

To produce a pure sample for NMR, approximately 50 mg of the hexa-glycosylated enriched residue obtained in Example 3 were further purified on a semi-preparative HPLC system. The system was equipped with an Aqua® C18 column (Phenomenex: Dimension 250×21.2 mm, 5 micron). Elution was carried out using a mobile phase of eluent B (MeCN with 0.1% trifluoroacetic acid) and eluent A (water with 0.1% triflouroacidic acid) by increasing the gradient from 1%→50% B from min 0.0 to 21, 50→100% min 21.0 to 27.0 and finally washing with 100% B and re-equilibration. The flow rate was 14 mL/min at room temperature. The fractions were collected by time and analyzed by LC-QTOF-MS for the presence of steviol glycosides. The system used was a UPLC (Waters) coupled to a MicrOTOFII Mass Spectrometer (Bruker). The column used was Acquity UPLC® BEH C18, 100×2.1 mm, 1.7 μm (Waters). Mobile phases were A: 0.1% Formic Acid in water and B: 0.1% Formic Acid in Acetonitrile. The gradient applied was from 1% B to 50% B in 12 minutes and then to 100% B in 3 minutes. The flow rate was 0.4 ml/min.

Fraction 93 was utilized for NMR analysis. All NMR experiments were performed in DMSO-d6 at 25C using a Bruker Avance III 600 MHz NMR spectrometer equipped with a 1.7 mm cryogenic TCI probe.

The structures were solved by means of standard homo- and heteronuclear multipulse NMR experiments, namely $^1$H, $^1$H-COSY, $^1$H, $^{13}$C-HSQC and $^1$H, $^{13}$C-HMBC experiments. The NMR data obtained was as follows:

1H NMR (600 MHz, DMSO-d6) δ ppm 0.78 (br. s., 1H) 0.83 (s, 3H) 0.92 (d, J=7.39 Hz, 2H) 0.97-1.04 (m, 1H) 1.17 (s, 3H) 1.30-1.54 (m, 6H) 1.67 (d, J=10.40 Hz, 1H) 1.72-1.86 (m, 4H) 1.92 (d, J=6.49 Hz, 1H) 1.96-2.05 (m, 2H) 2.08 (d, J=10.82 Hz, 1H) 2.32 (d, J=12.71 Hz, 1H) 2.91 (t, J=8.82 Hz, 1H) 2.95-3.01 (m, 1H) 3.02-3.27 (m, 14H) 3.31-3.55 (m, 10H) 3.57-3.86 (m, 10H) 4.47 (d, J=7.86 Hz, 1H) 4.51 (d, J=8.00 Hz, 1H) 4.53 (d, J=7.62 Hz, 1H) 4.66 (d, J=7.81 Hz, 1H) 4.73 (br. s., 1H) 4.80 (d, J=7.86 Hz, 1H) 5.11 (br. s., 1H) 5.53 (d, J=8.19 Hz, 1H)

13C NMR (150.91 MHz, DMSO-d6) δ ppm 16.4, 19.4, 19.9, 21.8, 28.3, 36.7, 37.2, 39.3, 40.3, 41.5, 41.6, 43.2, 43.7, 47.0, 47.2, 53.2, 57.0, 60.7, 61.2, 61.4, 61.8, 62.0, 62.1, 68.5, 68.9, 70.4 (3C), 71.2, 71.6, 74.1-74.3 (4C), 74.8, 75.8, 76.9-77.1 (6C), 77.6, 79.6, 85.8, 86.8, 87.1, 92.1, 96.2, 102.1, 102.8, 103.2, 103.3, 104.5, 153.1, 175.1

The confirmed structure of RebM (systematic name: 13-[β-D-glucopyranosyl-(1→3)-[β-D-glucopyranosyl-(1→2)]-□β-D-glucopyranosyl-1-oxy]kaur-16-en-18-oic acid, 18-[β-D-glucopyranosyl-(1→3)-[β-D-glucopyranosyl-(1→2))]-□β-D-glucopyranosyl-1-ester]) is shown in FIG. 2.

Example 5: Isolation and Determination of Additional Fermentation Products of EFSC 3044

Figure 8A:
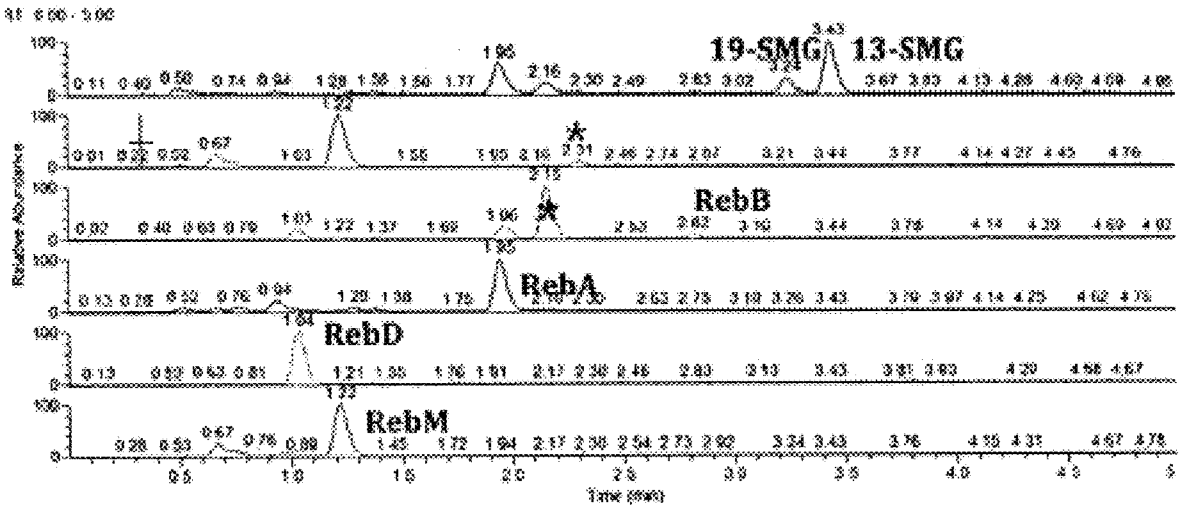
FIG. 8A is a chromatogram indicating compounds produced by fermentation of yeast strain EFSC 3044.
Figure 8B:
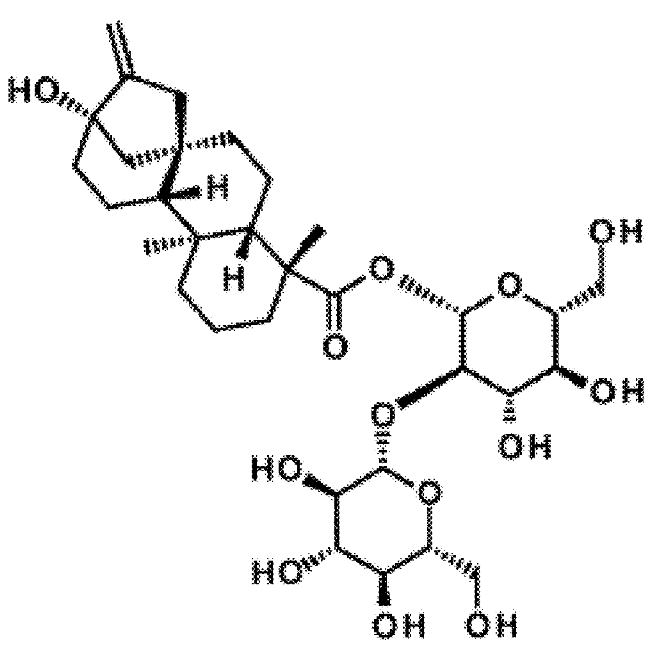
FIG. 8B is the NMR structure of the indicated di-glycosylated steviol glycoside (13-hydroxy kaur-16-en-18-oic acid, [2-O-β-D-glucopyranosyl-β-D-glucopyranosyl]ester), an analog of steviol-1,2-bioside. The IUPAC name for di-glycosylated steviol glycoside is (2S,3R,4S,5S,6R)-4,5-dihydroxy-6-(hydroxymethyl)-3-{[(2S,3R,4S,5S,6R)-3,4,5-trihydroxy-6-(hydroxymethyl)oxan-2-yl]oxy}oxan-2-yl(1R,4S,5R,9S,10R,13S)-13-hydroxy-5,9-dimethyl-14-methylidenetetracyclo[11.2.1.0^{1,10}0.0^{4,9}]hexadecane-5-carboxylate.
Figure 8C:
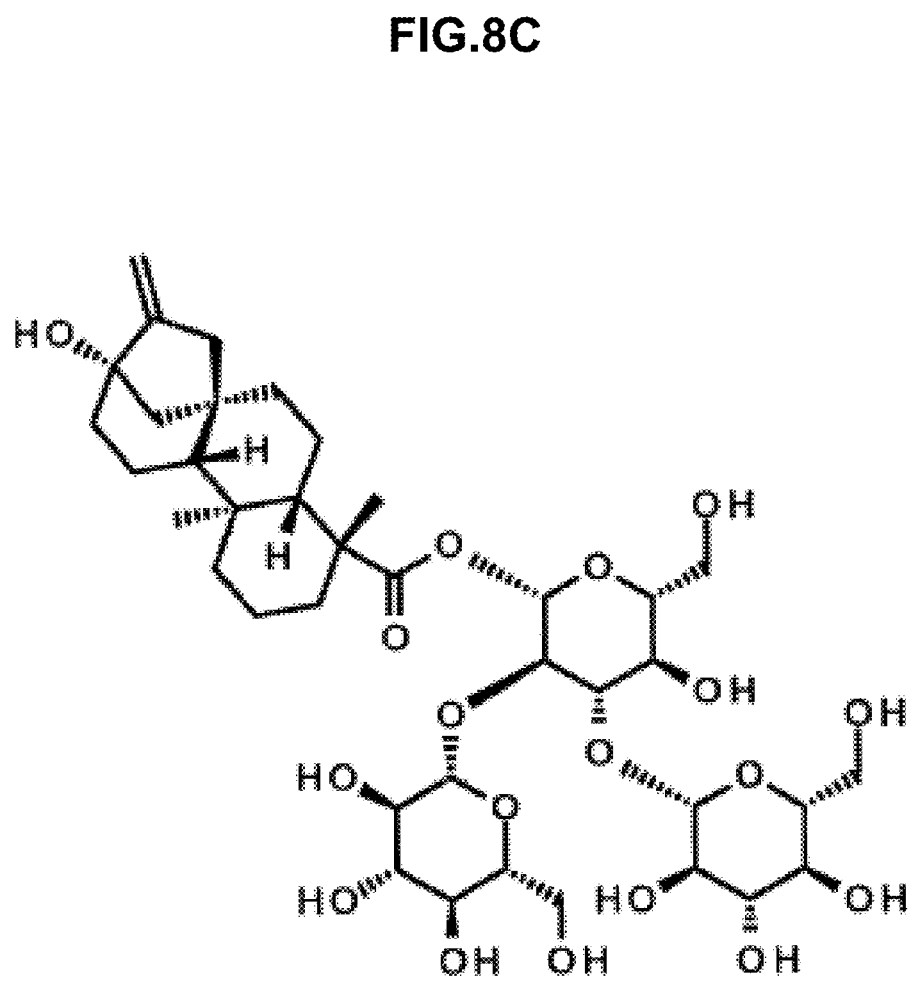

In addition to RebM, fermentation of EFSC 3044 resulted in formation of a di-glycosylated steviol glycoside (13- hydroxy kaur-16-en-18-oic acid, [2-O-β-D-glucopyranosyl-□β-D-glucopyranosyl]ester) with a retention time of 2.31 (FIG. 8B) and a tri-glycosylated steviol glycoside (13-hydroxy kaur-16-en-18-oic acid; [2-O-β-D-glucopyranosyl-3-O-□β-D-glucopyranosyl-β-D-glucopyranosyl]ester) with a retention time of 2.15 (FIG. 8C).

These compounds were isolated according to the following method. After the fermentation, the culture broth was centrifuged for 10 min at 5000 rpm at 4° C. and the supernatant was purified as follows: A glass column was filled with 300 mL HP20 Diaion® resin (Supelco), and an aliquot of 1700 mL supernatant was loaded on to the column and washed with 3.5 Litres of ddH2O. The compounds were eluted by using 2 L MeOH and fractions of 500 mL each collected. After LC-MS analysis, the fractions containing the majority of the target compounds were pooled and evaporated on a rotary evaporation system (Rotavap, Buchi, Switzerland) yielding 1.85 grams of dark grey material. The crude extract was re-dissolved in 3.5 mL of DMSO and injected in aliquots of 0.7 mL in a semi-preparative LC-MS for further purification. The column used was a XBridge C18, 19×250 mm, 5 um (Waters Corporation). Mobile phases were A: 0.1% TFA in water and B: 0.1% TFA in Acetonitrile. Elution was done by a linear gradient from 1% B to 60% B in 44 min. Fractions of 2.1 mL were continuously collected during the run. Fractions collected were analysed by LC-MS in order to evaluate the presence and purity of target analytes. Fractions containing compounds identified as 'Peak 8' and 'Peak 9' were neutralized by adding 0.8 mL of NH3 (aq.), pooled and dried by Genevac centrifugal evaporation system.

Structures of these compounds were determined by NMR with the method of Example 4.

The NMR data obtained for the di-glycosylated steviol glycoside are as follows:

1H NMR (600 MHz, DMSO-$d_6$) δ ppm 0.72-0.79 (m, 1H) 0.81 (s, 3H) 0.93 (d, J=8.07 Hz, 1H) 0.98-1.05 (m, 1H) 1.17 (s, 3H) 1.20 (d, J=11.37 Hz, 1H) 1.36 (d, J=4.03 Hz, 2H) 1.40-1.52 (m, 1H) 1.55-1.70 (m, 1H) 1.77 (d, J=9.54 Hz, 3H) 1.84-1.90 (m, 1H) 2.03 (d, J=8.07 Hz, 1H) 2.31-2.41 (m, 1H) 2.79-2.87 (m, 1H) 2.89-2.96 (m, 1H) 3.08 (s, 2H) 3.12-3.18 (m, 3H) 3.19-3.24 (m, 1H) 3.34 (d, J=4.77 Hz, 2H) 3.41-3.45 (m, 2H) 3.46-3.55 (m, 1H) 3.65 (d, J=11.37 Hz, 1H) 3.73 (dd, J=15.41, 8.44 Hz, 4H) 4.26-4.40 (m, 1H) 4.48 (d, J=7.70 Hz, 1H) 4.52-4.62 (m, 1H) 4.69 (br.s., 1H) 4.81 (d, J=7.70 Hz, 1H) 4.88 (br.s., 1H) 4.91-5.03 (m, 1H) 5.05-5.26 (m, 2H) 5.51 (d, J=7.70 Hz, 1H) 5.55 (br.s., 1H; the formula is C32H50013; formula weight is 642.7316).

The NMR data obtained for the tri-glycosylated steviol glycoside are as follows:

1H NMR (600 MHz, DMSO-$d_6$) b ppm 0.73-0.79 (m, 1H) 0.81 (s, 3H) 0.89-0.97 (m, 2H) 0.99-1.05 (m, 1H) 1.17 (s, 3H) 1.19 (d, J=11.37 Hz, 1H) 1.24 (s, 2H) 1.31-1.40 (m, 4H) 1.40-1.51 (m, 3H) 1.55-1.63 (m, 1H) 1.67 (dd, J=14.12, 5.32 Hz, 1H) 1.71-1.82 (m, 5H) 1.88 (d, J=11.00 Hz, 1H) 1.98-2.08 (m, 2H) 2.23-2.30 (m, 1H) 2.94 (t, J=8.44 Hz, 1H) 3.01-3.11 (m, 3H) 3.12-3.17 (m, 1H) 3.19-3.28 (m, 3H) 3.44-3.52 (m, 5H) 3.54-3.60 (m, 1H) 3.61-3.71 (m, 3H) 4.36 (br. s., 1H) 4.49 (br. s., 1H) 4.55 (d, J=7.70 Hz, 1H) 4.69 (s, 1H) 4.73 (br. s., 1H) 4.88 (br. s., 1H) 4.91-5.05 (m, 2H) 5.17 (br.s., 1H) 5.31 (br.s., 1H) 5.44 (d, J=8.07 Hz, 1H) 5.55 (br. s., 1H; the formula is C38H60018; formula weight is 804.8722).

The di-glycosylated steviol glycoside ester was determined to be an analog of steviol-1,2-bioside (FIG. 8B), and the tri-glycosylated steviol glycoside was determined to be an isomer of RebB, both of which are glycosylated at the 19-O position (FIG. 8C) instead of the 13-0 position of their respective isomers. This data suggests that these compounds form when the activity of UGT85C is low compared to the activity of EUGT11, UGT76G1, or UGT74G1.

Example 6: Engineering and Fermentation of EFSC 3261

The wild type *Saccharomyces* strain utilized in Example 1 was modified to contain the heterologous genes in Table 14 involved in steviol glycoside production. The genes were all integrated into the chromosome of the host strain using similar methods described in Example 1.

TABLE 14

List of Recombinant Genes and Promoters Used in Strain EFSC 3261.

| Heterologous pathway gene | Number of copies | Promoter(s) used |
|---|---|---|
| GGPPS7 (*Synechococcus* sp) synthetic gene | 2 | TEF2, GPD1 |
| CDPS (truncated, *Zea mays*) native gene | 3 | PGK1 (X2), TPI1 |
| KS5 (*A. thaliana*) native gene | 3 | TPI1, PDC1 (X2) |
| KO (*S. rebaudiana* KO1) synthetic gene | 2 | FBA1, GPD1 |
| ATR2 synthetic gene | 1 | PGK1 |
| KAH (*S. rebaudiana* KAHe1) synthetic gene | 3 | GPD1, TEF1 (X2) |
| *S. rebaudiana* CPR 8 native gene | 2 | TPI1 (X2) |
| 85C2 (*S. rebaudiana*) synthetic | 1 | GPD1 |
| 74G1 native (*S. rebaudiana*) | 1 | TPI1 |
| 76G1 synthetic (*S. rebaudiana*) | 1 | TEF1 |
| 91d2e-b 2X mutant from *S. rebaudiana* | 1 | GPD1 |
| EUGT11 synthetic (*Oryza sativa*) | 1 | TEF2 |

Fed-batch fermentation was carried out aerobically in 2 L (working volume) fermenters which included a ~16 hour growth phase in the base medium (minimal medium containing glucose, ammonium sulfate, trace metals, vitamins, salts, and buffer) followed by ~100 hours of feeding with a glucose-containing defined feed medium. Glucose was utilized as the carbon and energy source and combined with trace metals, vitamins, and salts. The pH was kept near pH 5 and the temperature setpoint was 30° C. The feed rate was controlled to prevent oxygen depletion and to minimize ethanol formation (glucose-limited conditions). Whole culture samples (without cell removal) were taken and boiled in an equal volume of DMSO for total glycosides levels.

Figure 9:
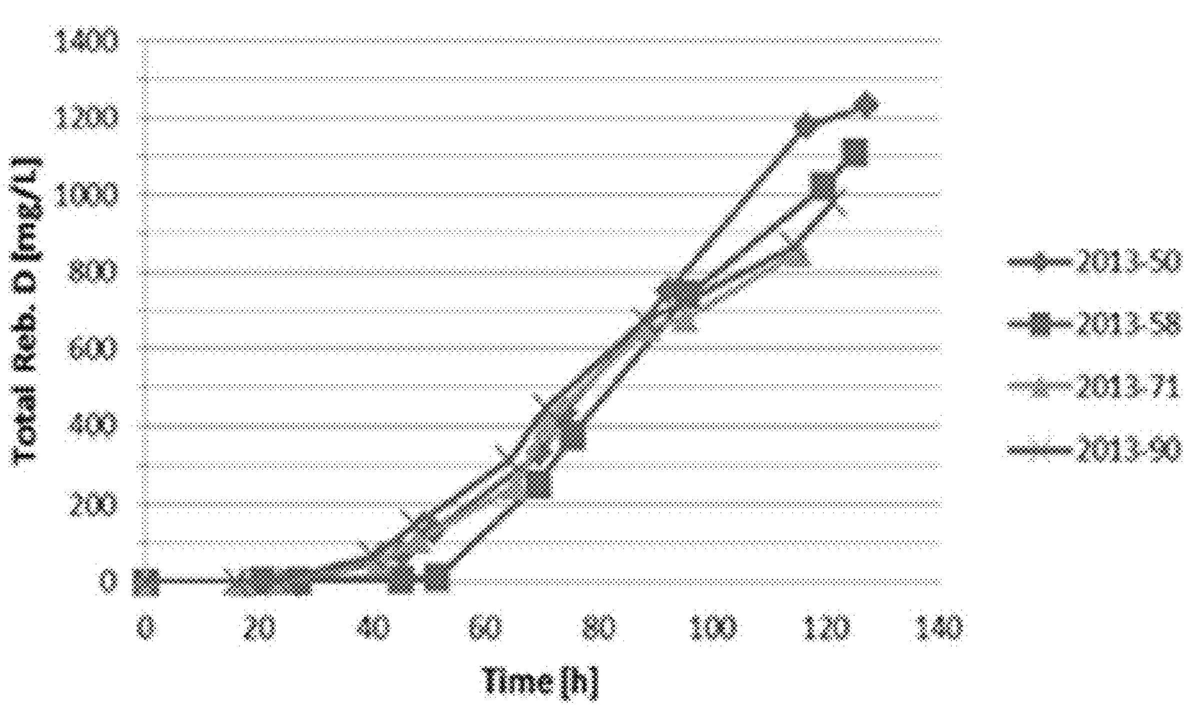
FIG. 9 shows RebD production by the EFSC 3261 yeast strain. Four fermentations of the EFSC 3261 yeast strain in minimal medium (MM) are shown.

FIG. 9 shows production of RebD by EFSC 3261 in four separate trials. Total production (intracellular and extracellular combined) averaged titer were between 800-1200 mg/L. For fermentation run 58, the final total titer at 123 hours was 1109 mg/L RebD, 695 mg/L RebM; the ratio of D:M on a mass basis was 1.6. 394 mg/L RebA were also produced.

Example 7: Strain Engineering and Fermentation of EFSC 3297 for Increased Production of RebD and RebM The same wild type *Saccharomyces* strain utilized in Example 1 was modified to contain the heterologous genes in Table 15 involved in steviol glycoside production. The genes were all integrated into the chromosome of the host strain using similar methods described in Example 1.

Although the genes used are identical to those in Example 1, increased copy numbers of bottleneck enzymes in the steviol pathway allowed for increased production of RebD and RebM. Fermentation of strain 3297 was carried out in a manner similar to that described above for strain 3261.

TABLE 15

List of Recombinant Genes and Promoters Used in Strain EFSC 3297.

| Heterologous pathway gene | Number of copies | Promoter(s) used |
|---|---|---|
| GGPPS7 (*Synechococcus* sp) synthetic gene | 3 | TEF2 (X2), GPD1 |
| CDPS (truncated, *Zea mays*) native gene | 4 | PGK1 (X3), TPI1 |
| KS5 (*A. thaliana*) native gene | 4 | TPI1, PDC1 (X3) |
| KO (*S. rebaudiana* KO1) synthetic gene | 2 | FBA1, GPD1 |
| ATR2 synthetic gene | 1 | PGK1 |
| KAH (*S. rebaudiana* KAHe1) synthetic gene | 4 | GPD1 (X2), TEF1 (X2) |
| *S. rebaudiana* CPR 8 native gene | 3 | TPI1 (X3) |
| 85C2 (*S. rebaudiana*) synthetic | 1 | GPD1 |
| 74G1 native (*S. rebaudiana*) | 1 | TPI1 |
| 76G1 synthetic (*S. rebaudiana*) | 1 | TEF1 |
| 91d2e-b 2X mutant from *S. rebaudiana* | 1 | GPD1 |
| EUGT11 synthetic (*Oryza sativa*) | 2 | TEF2 (X2) |

Figure 10:
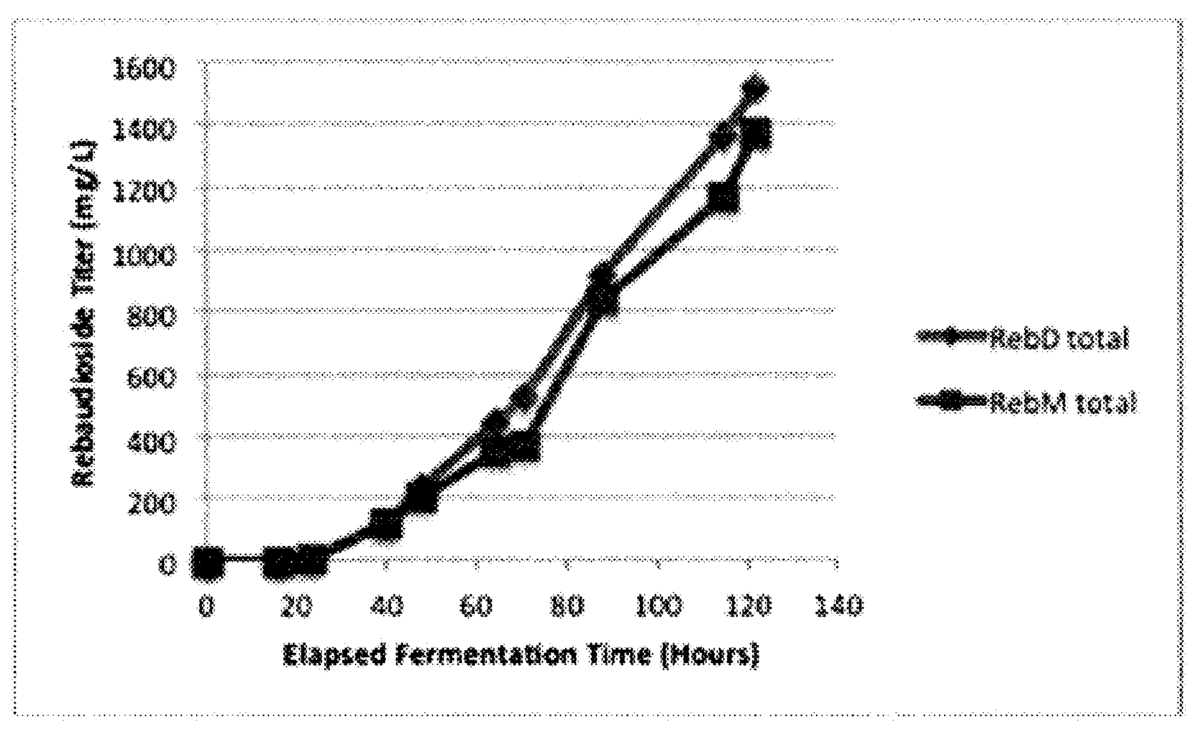
FIG. 10 shows RebD and RebM production by the EFSC 3297 yeast strain.

Production of RebD and RebM by EFSC 3297 is shown in FIG. 10. The ratio of D:M on a mass basis was 1.1. 1517 mg/L RebD was produced at the end of the fermentation (total, intracellular plus extracellular) and 1375 mg/L of RebM was produced.

Example 8: Strain Engineering and Fermentation of EFSC 3841 with Two Copies of the UGT76G1 Gene The wild type *Saccharomyces* strain utilized in Example 1 was modified to contain the heterologous genes in Table 16 involved in steviol glycoside production. The genes were all integrated into the chromosome of the host strain using similar methods described in Example 1. Fermentation conditions for 3841 were similar to those described above for strain 3261.

TABLE 16

List of Recombinant Genes and Promoters Used in Strain EFSC 3841.

| Heterologous pathway gene | Number of copies | Promoter(s) used |
|---|---|---|
| GGPPS7 (*Synechococcus* sp) synthetic gene | 3 | TEF2 (X3) |
| CDPS (truncated, *Zea mays*) native gene | 4 | PGK1 (X4) |
| KS5 (*A. thaliana*) native gene | 4 | PDC1 (X4) |
| KO (*S. rebaudiana* KO1) synthetic gene | 3 | FBA1, GPD1, TPI1 |
| ATR2 synthetic gene | 2 | PGK1 (X2) |
| KAH (*S. rebaudiana* KAHe1) synthetic gene | 4 | GPD1, TEF1 (X3) |
| *S. rebaudiana* CPR 8 native gene | 3 | TPI1 (X3) |
| 85C2 (*S. rebaudiana*) synthetic | 2 | GPD1 (X2) |
| 74G1 native (*S. rebaudiana*) | 2 | TPI1 (X2) |
| 76G1 synthetic (*S. rebaudiana*) | 2 | TEF1 (X2) |
| 91d2e-b 2X mutant from *S. rebaudiana* | 2 | GPD1 (X2) |
| EUGT11 synthetic (*Oryza sativa*) | 2 | TEF2, TEF1 |

Figure 11:
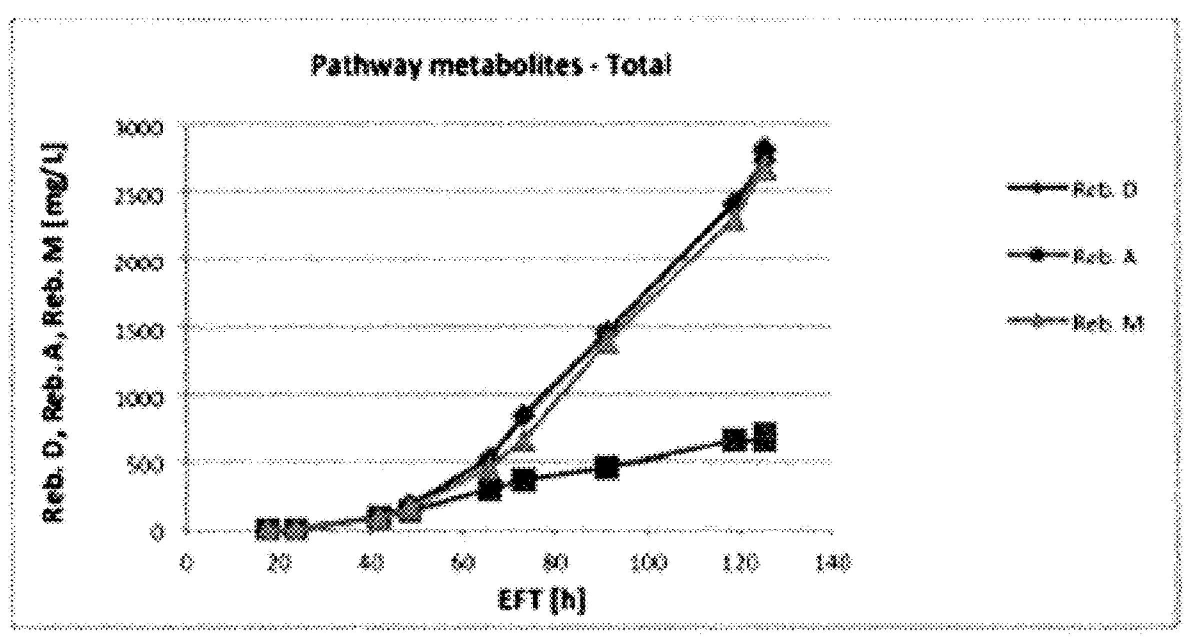
FIG. 11 shows RebD, RebM, and RebA production by the EFSC 3841 yeast strain.

Production of RebD, RebM, and RebA by EFSC 3841 is shown in FIG. 11. Here, the total amount of RebD produced was 2786 mg/L, and the total amount of RebM produced was 2673 mg/L for a ratio of 1.04 D:M (g per g). 703.7 mg/L RebA was also produced.

Example 9: Knockdown of One UGT76G1 Gene from EFSC 3841 and Decreased Production of RebD and RebM An auxotrophic (leu2, ura3) version of strain EFSC 3841 described above, designated EFSC 3643, was further modified to delete one of the wild type 76G1 UGT genes. The performance of 3 colonies containing one copy of UGT 76G1 was tested versus 4 colonies of the unmodified strain which contains 2 copies of UGT 76G1. PCR was used to verify that the new strain only harbored one copy of the 76G1. Briefly, the disruption of one copy of UGT76G1 was verified by two PCR reactions amplifying a region upstream of the insertion site with part of the integration cassette and a region downstream of the insertion site with part of the integration cassette used for disruption. PCR primers designed for the wildtype 76G1 confirmed that wildtype 76G1 was still intact and present in the strain. The colonies were grown in 96 deep-well plates for 96 hours at 30° C. and 400 RPM. The total amounts of RebD and RebM were determined by LC/MS analysis.

From FIG. 12, it can be seen that the copy number of 76G1 significantly changes the RebD/RebM ratio. The ratio of RebD to RebM was plotted for the 3 colonies containing only one 76G1 copy (bars on the left-hand side of the graph), versus 4 colonies of the parent strain that contained 2 copies of the 76G1 UGT (right-hand bars of the graph).

Example 10: Determination of Relative Rates of RebD and RebM Production p416GPD containing WT-76G1 was expressed in the protease deficient yeast strain DSY6 for 48 h in SC-ura media. 100 μL of cells were then reinoculated in 3 mL of SC-ura media for 16 h. The cells were lysed with 200 μL CelLytic™ Y according to manufacturer's description. 6 μL of the lysate were added to 24 μL of the reaction mixture consisting of 20 mM Tris-buffer (pH 8.0), 0.3 μMUDPG, and 0.1 μM Reb D or Reb E. The reactions were incubated at 30° C. and stopped at 0, 1, 2, and 18 h by transferring 25 μL of the 30 μL reaction mixture to 25 μL DMSO. Amounts of RebD, RebE, and RebM were analyzed by LC-MS and assessed by peak integration during data processing as "area under the curve."

Figure 13A:
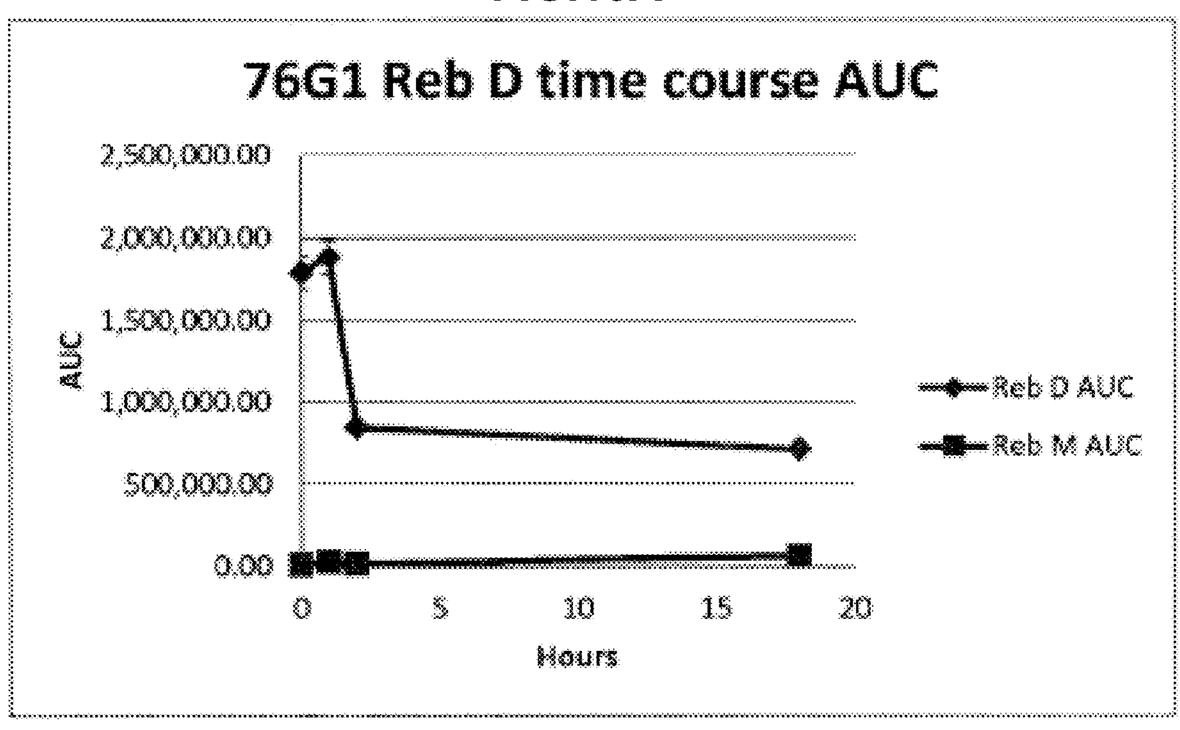
FIG. 13A shows the relative rates of consumption of RebD and production of RebM by UGT76G1.
Figure 13B:
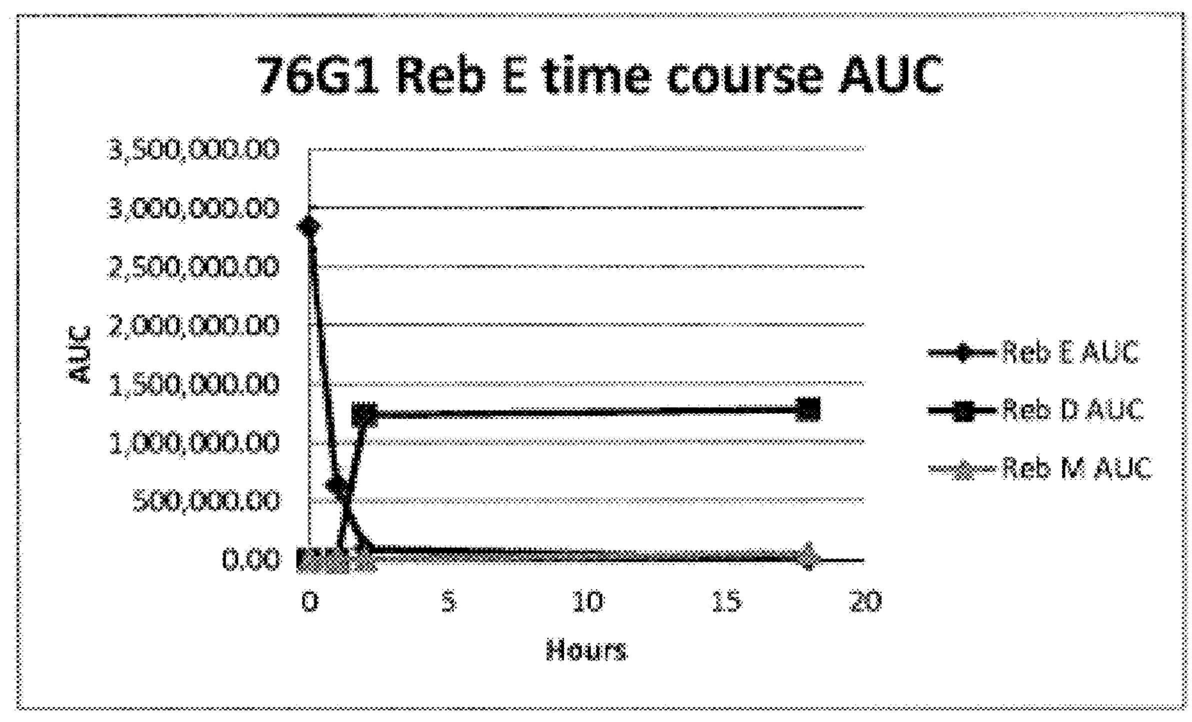
FIG. 13B shows the relative rates of consumption of RebE and production of RebD and RebM by UGT76G1.

FIG. 13 shows that a large portion of RebD is consumed without generating a corresponding amount of RebM. It is also shown that RebE is consumed within 2 h and converted to RebD. This finding confirms an alternative glycosylation route from steviol to RebM through RebE instead of RebA is possible, which is first observed at the 18 h time point.

Example 11: Prediction of Amino Acids Involved in RebM and RebD Binding in UGT76G1

As a means for identifying UGT76G1 variants with increased activity and regioselectivity towards RebM or RebD, homology modeling and docking studies were performed. Three homology models were generated using standard setting in the SybylX program with a combination of the following PDB-files 2PQ6 (% ID=31), 2C1X (% ID=28), 3HBF (% ID=28), 2VCE (% ID=35) as templates. The ligands present in PDB2VCE were used during the generation of main- and side-chains but removed prior to energy minimization. To yield the highest quality structures, models were energy minimized using an AMBER FF99 forcefield with either the standard settings or a gradient termination with a threshold of 0.1 kJ, a cutoff radius of 10 Å, and a maximum iteration of 5000 cycles. Statistics for the models are shown in Table 17, and variance between the models can be found in FIG. 14.

TABLE 17

Summary of UGT76G1 homology models.

| Statistic | Model 1 | Model 2 | Model 3 | Goal |
|---|---|---|---|---|
| Clashscore, all atoms | 1.1 (99$^{th}$ percentile) | 0.42 (99$^{th}$ percentile) | 3.38 (97$^{th}$ percentile) | |
| Poor rotamers | 16 (4.47%) | 6 (1.52%) | 8 (2.02%) | <1% |
| Ramachandran outliers | 5 (1.26%) | 12 (2.70%) | 6 (1.35%) | <0.05% |
| Ramachandran favored | 354 (88.94%) | 375 (84.27%) | 404 (90.79%) | >98% |
| MolProbity score | 1.89 (81$^{st}$ percentile) | 1.46 (96$^{th}$ percentile) | 1.89 (81$^{st}$ percentile) | |
| Deviations >0.25 Å | 3 (0.80%) | 1 (0.24%) | 5 (1.20%) | 0 |
| Bad backbone bonds | 0/1599 (0%) | 0/1780 (0%) | 0/1780 (0%) | 0% |
| Bad backbone angles | 0/1996 (0%) | 1/2224 (0.04%) | 0/2224 (0%) | <0.1% |

After model generation, substrates were docked into the active site of the enzyme using the Surflex Dock suite in SybylX to predict the amino acids forming the binding pocket. The UDPG portion of the UGT76G1 binding groove was located by aligning the 76G1 models with PDB2VCE and importing the ligand, UDPF2G, directly from the template. To dock the acceptor substrates, a protocol was generated using standard values covering the remaining part of the binding site. The dockings were performed using the GeomX settings on a ligand library containing steviol glycosides allowed with protein flexibility (model 1) or no flexibility (model 2). The docking results were analyzed using a combination of the scoring functions in SybylX using top 3 docking results in base mode and top 1 docking result with protein flexibility.

All UGT76G1 amino acids are shown in Table 18 below. The sites for the saturation library were determined by selecting all residues found to be within 5 Å of RebD and RebM in the docking analysis on two or more models (shown as bold "x"). Furthermore, all residues found to be within 5 Å of the RebM and RebD 19-O-glucose moiety, which were positioned in the binding site for the RebD→RebM reaction, were selected. Residues completely conserved between similar enzymes, which are shown in bold and with a "!," were omitted from the screen.

TABLE 18

Prediction of amino acids involved in RebM and RebD binding in UGT76G1.

| | | Enzyme UGT76G1 | | | | | | | | |
|---|---|---|---|---|---|---|---|---|---|---|
| | | Top3 (base) | Top3 (Base) | Top1 (PF) | Top1 (PF) | Top1 (Base) | | | | |
| | | Model no. | | | | | Model | | | |
| | | 2 | 1 | 1 | 1 | 1 | 1 + 2 minus | Unique 5 Å: | Unique | Total |
| | | Substrate: | | | | | | | | |
| | | RebM | RebM | RebM | RebM 19Glcs | RebD 19Glcs Å: | cons. AAs: | RebM 19G1c: | RebD 19Glcs: | screened residues: |
| | | 5 | 5 | 5 | 5 | 5 | 5 | 5 | 5 | **5** |
| | | No. of res in group: | | | | | | | | |
| Residue | | 73 | 58 | 42 | 15 | 11 | 23 | 12 | 3 | **38** |
| VAL | 20 | 20 | 20 | 20 | | | X | | | **x** |
| **PRO** | **21!** | **21** | **21** | **21** | **21** | **21** | | | | |
| PHE | 22 | 22 | 22 | 22 | 22 | 22 | X | | | **x** |
| GLN | 23 | | 23 | 23 | 23 | 23 | | x | | **x** |
| GLY | 24 | 24 | 24 | 24 | | 24 | X | | | **x** |
| **HIS** | **25!** | **25** | **25** | **25** | | | | | | |
| ILE | 26 | | 26 | 26 | | 26 | | | x | **x** |
| ASN | 27 | | 27 | 27 | | | | | | |
| THR | 48 | | 48 | | | | | | | |
| ASN | 49 | | 49 | 49 | 49 | 49 | | x | | **x** |
| PHE | 50 | | 50 | 50 | 50 | 50 | | x | | **x** |
| ASN | 51 | | 51 | 51 | 51 | 51 | | x | | **x** |
| PRO | 53 | | 53 | 53 | 53 | | | x | | **x** |
| LYS | 54 | | 54 | 54 | 54 | 54 | | x | | **x** |

TABLE 18-continued

Prediction of amino acids involved in RebM and RebD binding in UGT76G1.

| | Enzyme UGT76G1 | | | | | | | | |
|---|---|---|---|---|---|---|---|---|---|
| | Top3 (base) | Top3 (Base) | Top1 (PF) | Top1 (PF) | Top1 (Base) | | | | |
| | Model no. | | | | | Model | | | |
| | 2 | 1 | 1 | 1 | 1 | 1 + 2 minus | Unique 5 Å: | Unique | Total |
| | Substrate: | | | | | | | | |
| | RebM | RebM | RebM | RebM 19Glcs | RebD 19Glcs Å: | cons. AAs: | RebM 19G1c: | RebD 19Glcs: | screened residues: |
| | 5 | 5 | 5 | 5 | 5 | 5 | 5 | 5 | **5** |
| | No. of res in group: | | | | | | | | |
| Residue | 73 | 58 | 42 | 15 | 11 | 23 | 12 | 3 | **38** |
| THR 55 | | 55 | 55 | 55 | 55 | | x | | **x** |
| SER 56 | | 56 | 56 | 56 | 56 | | x | | **x** |
| PRO 80 | 80 | | | | | | | | |
| THR 81 | 81 | | | | | | | | |
| HIS 82 | 82 | | | | | | | | |
| GLY 83 | 83 | | | | | | | | |
| PRO 84 | 84 | | | | | | | | |
| LEU 85 | 85 | 85 | | | | X | | | **x** |
| MET 88 | 88 | | | | | | | | |
| ARG 89 | 89 | | | | | | | | |
| ILE 92 | | 92 | | | | | | | |
| GLU 95 | | 95 | 95 | | | | | | |
| HIS 96 | | 96 | 96 | | | | | | |
| ASP 99 | | 99 | 99 | | | | | | |
| ARG 103 | | 103 | 103 | | | | | | |
| THR 123 | 123 | | | | | | | | |
| **ASP 124!** | **124** | **124** | | | | | | | |
| ALA 125 | 125 | | | | | | | | |
| LEU 126 | 126 | 126 | 126 | | | X | | | **x** |
| TRP 127 | 127 | 127 | 127 | | | X | | | **x** |
| TYR 128 | 128 | 128 | | | | X | | | **x** |
| VAL 143 | 143 | | | | | | | | |
| LEU 144 | 144 | | | | | | | | |
| MET 145 | 145 | 145 | | | | X | | | **x** |
| THR 146 | 146 | 146 | 146 | | | X | | | **x** |
| SER 147 | 147 | 147 | 147 | | | X | | | **x** |
| SER 148 | 148 | | | | | | | | |
| PHE 150 | 150 | | | | | | | | |
| ASN 151 | 151 | 151 | 151 | | | X | | | **x** |
| PHE 152 | 152 | | | | | | | | |
| ALA 154 | 154 | | | | | | | | |
| HIS 155 | 155 | 155 | 155 | | | X | | | **x** |
| VAL 156 | 156 | | | | | | | | |
| SER 157 | 157 | | | | | | | | |
| LEU 158 | 158 | | | | | | | | |
| PRO 159 | 159 | | | | | | | | |
| GLN 160 | 160 | | | | | | | | |
| PHE 161 | 161 | | | | | | | | |
| ASP 162 | 162 | | | | | | | | |
| GLU 163 | 163 | | | | | | | | |
| GLY 165 | 165 | | | | | | | | |
| TYR 166 | 166 | | | | | | | | |
| LEU 167 | 167 | | | | | | | | |
| ASP 168 | 168 | | | | | | | | |
| ASP 189 | 189 | | | | | | | | |
| ILE 190 | 190 | | | | | | | | |
| LYS 191 | 191 | 191 | 191 | | | X | | | **x** |
| SER 192 | 192 | | | | | | | | |
| ALA 193 | 193 | | | | | | | | |
| TYR 194 | 194 | | | | | | | | |
| SER 195 | 195 | 195 | 195 | | | X | | | **x** |
| ASN 196 | 196 | | | | | | | | |
| TRP 197 | 197 | | | | | | | | |
| GLN 198 | 198 | 198 | 198 | | | X | | | **x** |
| ILE 199 | 199 | 199 | | | | X | | | **x** |
| LEU 200 | 200 | 200 | 200 | | | X | | | **x** |
| LYS 201 | 201 | | | | | | | | |
| GLU 202 | 202 | | | | | | | | |
| ILE 203 | 203 | 203 | 203 | | | X | | | **x** |
| LEU 204 | 204 | 204 | 204 | | | X | | | **x** |
| GLY 205 | 205 | | | | | | | | |

TABLE 18-continued

Prediction of amino acids involved in RebM and RebD binding in UGT76G1.

| Residue | | Enzyme UGT76G1 Top3 (base) | Top3 (Base) | Top1 (PF) | Top1 (PF) | Top1 (Base) | Model | Unique | Unique | Total |
|---|---|---|---|---|---|---|---|---|---|---|
| | | Model no. | | | | | | | | |
| | | 2 | 1 | 1 | 1 | 1 | 1 + 2 minus | 5 Å: | | |
| | | Substrate: | | | | | | | | |
| | | RebM | RebM | RebM | RebM 19Glcs | RebD 19Glcs Å: | cons. AAs: | RebM 19G1c: | RebD 19Glcs: | screened residues: |
| | | 5 | 5 | 5 | 5 | 5 | 5 | 5 | 5 | **5** |
| | | No. of res in group: | | | | | | | | |
| | | 73 | 58 | 42 | 15 | 11 | 23 | 12 | 3 | **38** |
| LYS | 206 | 206 | | | | | | | | |
| MET | 207 | 207 | 207 | | | | | | | |
| ILE | 208 | 208 | | | | | | | | |
| LYS | 209 | 209 | | | | | | | | |
| SER | 253 | | 253 | 253 | 253 | 253 | | x | | **x** |
| LEU | 257 | | 257 | 257 | 257 | | | x | | **x** |
| **PHE** | **281!** | | | | | **281** | | | | |
| **GLY** | **282!** | | **282** | **282** | | **282** | | | | |
| SER | 283 | | 283 | 283 | 283 | 283 | | x | | **x** |
| THR | 284 | 284 | 284 | 284 | | 284 | X | | | **x** |
| SER | 285 | | 285 | 285 | | 285 | | | x | **x** |
| GLU | 286 | | 286 | | | | | | | |
| VAL | 309 | | 309 | | | | | | | |
| **ARG** | **311!** | | **311** | | | | | | | |
| PHE | 314 | | 314 | 314 | 314 | 314 | | x | | **x** |
| LYS | 337 | | 337 | | | 337 | | | x | **x** |
| **TRP** | **338!** | | **338** | **338** | **338** | **338** | | | | |
| **HIS** | **356!** | | | | | **356** | | | | |
| **GLY** | **358!** | **358** | | | | | | | | |
| **TRP** | **359!** | **359** | **359** | | | | | | | |
| **ASN** | **360!** | | **360** | | | | | | | |
| PHE | 377 | | 377 | | | | | | | |
| GLY | 378 | 378 | 378 | | | | X | | | **x** |
| LEU | 379 | 379 | 379 | 379 | | | X | | | **x** |
| ASP | 380 | 380 | 380 | 380 | | | X | | | **x** |
| **GLN** | **381!** | **381** | **381** | **381** | | | | | | |
| PRO | 382 | 382 | | | | | | | | |
| LEU | 383 | 383 | | | | | | | | |
| ASN | 384 | 384 | | | | | | | | |

Bold indicates complete conservation in amino acid.

Bold "!" indicates amino acid residues that are completely conserved between similar enzymes and were omitted from the screen.

Example 12: UGT76G1 Site Saturation Library Prescreen

Prior to performing the UGT76G1 site saturation library screening as described herein, culture growth and production of RebM and RebD were monitored in 96 and 4×24 deep-well plates. Using the standard lithium acetate protocol, the EFSC 3385 strain was transformed with p416GPD containing WT-76G1, and the transformants were plated on SC-URA plates. EFSC 3385 is a strain that is deficient in UGT76G1 and thus will make RebE until transformed with a plasmid containing an active UGT76G1. The strain contained a disruption in the UGT76G1 coding region, which was replaced with the spHIS5 marker, and also contained integrated copies of the UGT91 D2e-2X mutant, UGT74G1, ATR2, UGT85C2, *S. rebaudiana* CPR8 (2 copies), *A. thaliana* KS5 (2 copies), *Synechococcus* GGPPS7, codon optimized *S. rebaudiana* KAHe1 (2 copies), *S. rebaudiana* KO (two copies), the truncated *Zea mays* CDPS5 (2 copies), and EUGT11.

For the 96 deep-well plate condition, 96 colonies were transferred to a plate containing 1 mL SC-URA, and the plate was incubated at 30° C. and 400 RPM for 96 h. For the 4×24 deep-well plate condition, 96 colonies were transferred to a plate containing 3 mL SC-URA. The plate was incubated at 300C and 320 RPM for 96 h, and 200 μL were then transferred from each well to a 96 deep-well plate.

50 μL of the cultures from each plate were transferred to 96 well polymerase chain reaction (PCR) plates and diluted 1:1 with 100% dimethyl sulfoxide (DMSO). The plates were heat sealed, incubated at 80° C. for 10 min, and subsequently cooled to 25° C. The plates were spun at 4000 RPM for 10 min, and 50 μL of the culture mixtures were transferred to a new plate for LC-MS analysis.

Figure 15A:
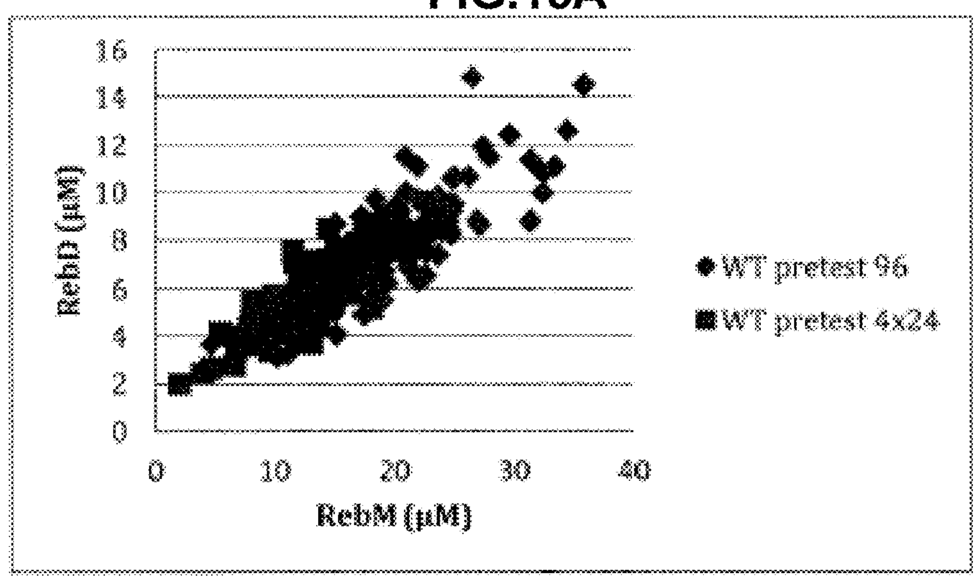
FIG. 15A is a scatter-plot of production of RebD and RebM in 96 and 4×24 deep-well plates.
Figure 15B:
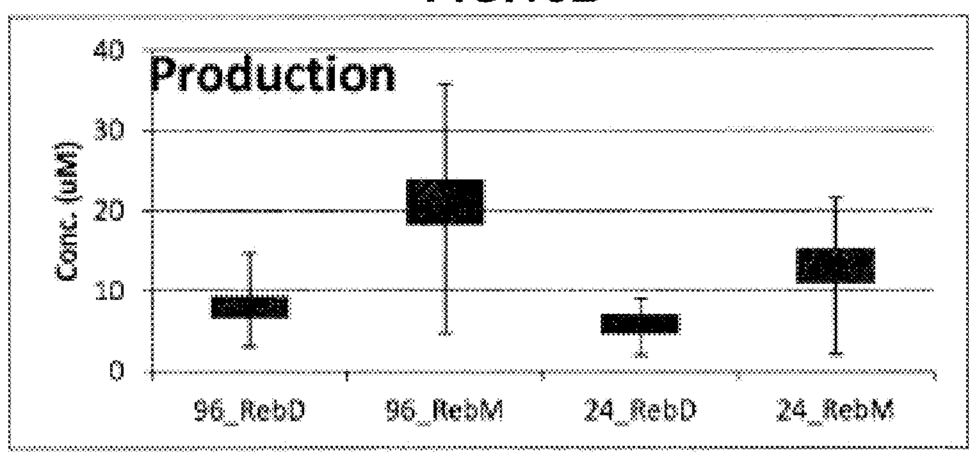
FIG. 15B is a box-plot of RebD and RebM production in 96 and 4×24 deep-well plates.
Figure 15C:
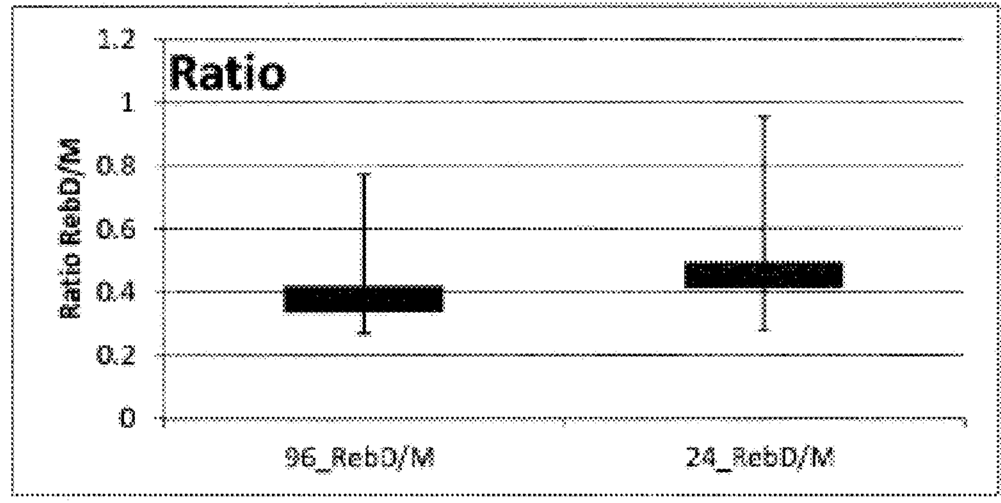
FIG. 15C is a box-plot of RebD/RebM production in 96 and 4×24 deep-well plates.

Results of the UGT76G1 site saturation library prescreen can be found in FIG. 15. Variance in RebD and RebM production can be explained by evaporation, particularly in the wells located at the edges of the plate, over the course of the 96 h incubation period. The higher concentrations of RebM and RebD produced by colonies grown in 96 deep-well plates suggest that these plates are better suited for LC-MS analysis, as compared to 4×24 deep-well plate, and were thus selected for use in the UGT76G1 site saturation library screen.

Example 13: UGT76G1 Site Saturation Library Screen

Through the company, Baseclear, UGT76G1 was subcloned from EPSC2060 (p423GPD) to EPSB492 (p416GPD) using the SpeI and XhoI restriction sites, and the site saturation libraries were created using degenerate NNS-primers. Using the standard lithium acetate protocol, the EFSC3385 strain was transformed with the library or with control plasmid containing WT-76G1, and the transformants were plated on SC-URA plates.

1 mL of SC-URA media was added to 96 deep-well plates, and colonies from each of the 38 site saturation library residues identified in Example 9 were picked and incubated in the 96 deep-well plates at 30° C. and 400 RPM for 96 h. 50 μL of each culture samples were then transferred to 96 well PCR plates containing 50 μL 100% DMSO. The plates were then heat sealed, incubated at 80° C. for 10 min, subsequently cooled to 12° C., and spun at 4000 RPM for 10 min. 70 μL of each supernatant were transferred to a new plate for LC-MS analysis.

Figure 16:
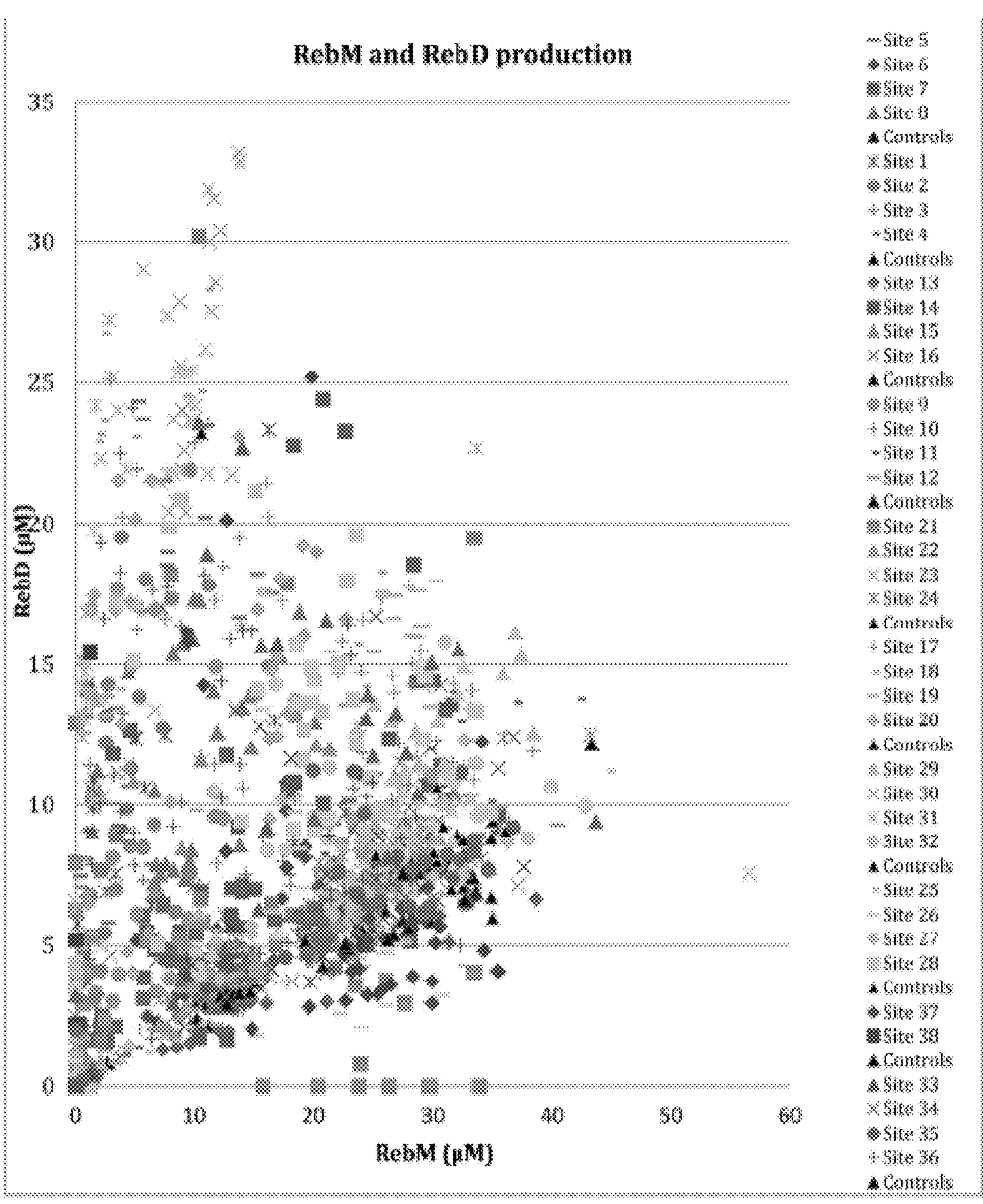
FIG. 16 shows all data points of the initial UGT76G1 site saturation screen with wild type production shown as black triangles.

FIG. 16 shows all data points of the UGT76G1 site saturation library screen, with wild type production depicted with black triangles. The variant numbering system can be found in Table 19.

TABLE 19

Numbering for UGT76G1 site saturation library variants.

| Number | Residue |
|---|---|
| 1 | VAL 20 |
| 2 | PHE 22 |
| 3 | GLN 23 |
| 4 | GLY 24 |
| 5 | ILE 26 |
| 6 | ASN 49 |
| 7 | PHE 50 |
| 8 | ASN 51 |
| 9 | PRO 53 |
| 10 | LYS 54 |
| 11 | THR 55 |
| 12 | SER 56 |
| 13 | LEU 85 |
| 14 | LEU 126 |
| 15 | TRP 127 |
| 16 | TYR 128 |
| 17 | MET 145 |
| 18 | THR 146 |
| 19 | SER 147 |
| 20 | ASN 151 |
| 21 | HIS 155 |
| 22 | LYS 191 |
| 23 | SER 195 |
| 24 | GLN 198 |
| 25 | ILE 199 |
| 26 | LEU 200 |
| 27 | GLU 202 |
| 28 | ILE 203 |
| 29 | SER 253 |
| 30 | LEU 257 |
| 31 | SER 283 |
| 32 | THR 284 |
| 33 | SER 285 |
| 34 | PHE 314 |
| 35 | LYS 337 |
| 36 | GLY 378 |
| 37 | LEU 379 |
| 38 | ASP 380 |

Figure 17:
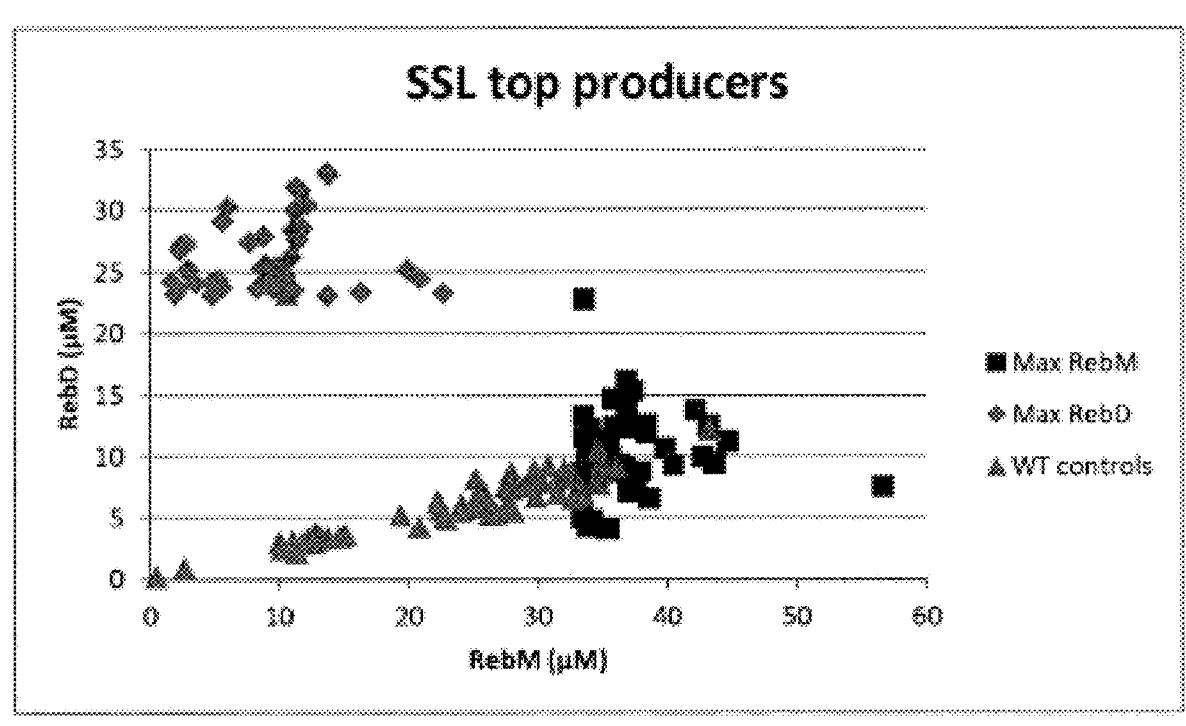
FIG. 17 shows the top RebD and RebM producing colonies selected for further study.
Figure 18:
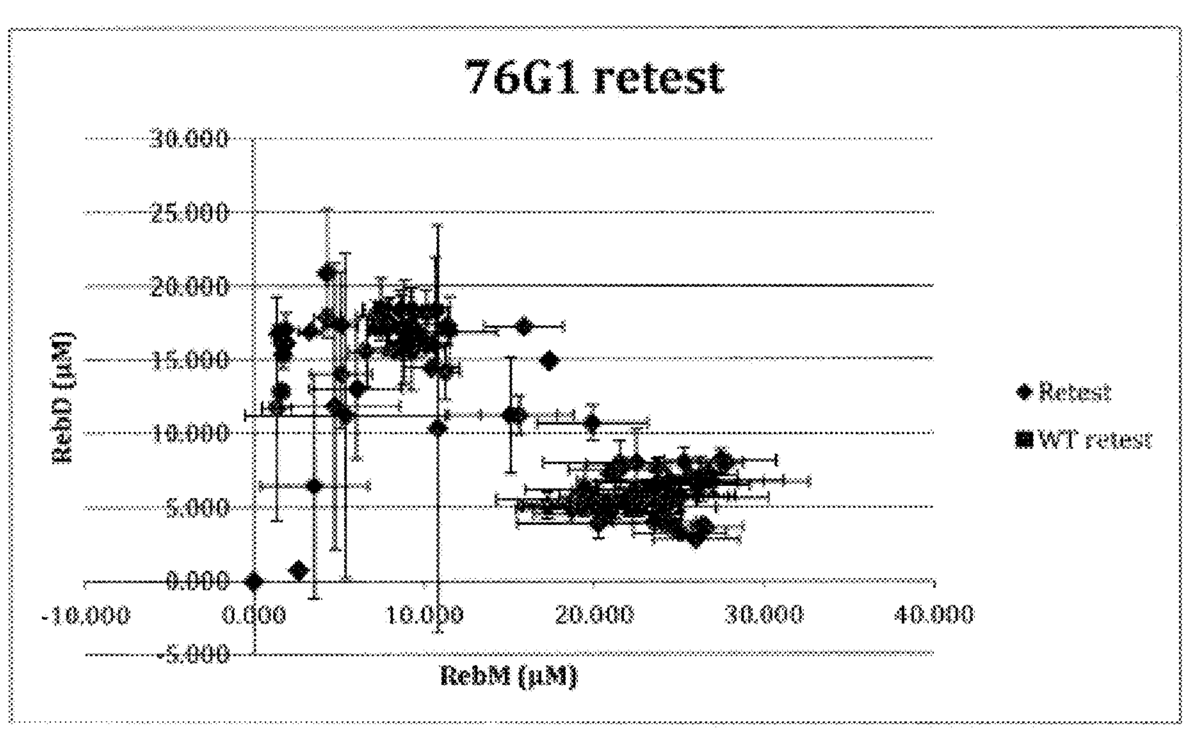
FIG. 18 shows a rescreen of UGT76G1 RebD and RebM top producers (as shown in FIG. 17) run in triplicate showing the same trends as the initial screen.

Table 20 and FIG. 17 show the UGT76G1 variant colonies with the highest selectivity towards production of either RebM or RebD, which were selected for further study. In FIG. 17, all data points with the "WT" prefix indicate RebM and RebD production of the wild type enzyme. It is shown that selected enzyme variants exhibited an inhibited RebD to RebM activity or an increased production of RebM, as compared to wild type controls.

TABLE 20

Top RebM- and RebD-producing colonies.

| Colony | RebM (μM) | RebD (μM) |
|---|---|---|
| A1 | 16.28 | 23.35 |
| A2 | 4.83 | 24.12 |
| A3 | 2.92 | 25.13 |
| A4 | 34.07 | 12.24 |
| A5 | 5.66 | 23.72 |
| A6 | 11.08 | 23.50 |
| A7 | 5.33 | 24.35 |
| A8 | 38.36 | 11.90 |
| A9 | 42.18 | 13.76 |
| A10 | 33.80 | 8.95 |
| A11 | 34.66 | 10.13 |
| A12 | 40.44 | 9.30 |
| B1 | 36.86 | 13.64 |
| B2 | 34.88 | 9.05 |
| B3 | 38.61 | 6.64 |
| B4 | 20.84 | 24.42 |
| B5 | 22.70 | 23.28 |
| B6 | 35.49 | 9.63 |
| B7 | 34.55 | 8.71 |
| B8 | 35.47 | 11.31 |
| B9 | 35.62 | 9.17 |
| B10 | 37.59 | 7.80 |
| B11 | 36.76 | 12.41 |
| B12 | 2.31 | 26.75 |
| C1 | 2.21 | 23.66 |
| C2 | 9.24 | 24.56 |
| C3 | 1.93 | 23.18 |
| C4 | 10.47 | 24.70 |
| C5 | 4.91 | 23.09 |
| C6 | 2.38 | 27.11 |
| C7 | 11.06 | 28.32 |
| C8 | 13.77 | 23.07 |
| C9 | 35.58 | 9.92 |
| C10 | 33.51 | 5.02 |
| C11 | 33.87 | 4.24 |
| C12 | 6.04 | 30.20 |
| D1 | 33.51 | 4.93 |
| D2 | 43.18 | 12.50 |
| D3 | 34.04 | 8.06 |
| D4 | 35.92 | 12.38 |
| D5 | 37.11 | 7.14 |
| D6 | 44.66 | 11.19 |
| D7 | 33.61 | 13.36 |
| D8 | 36.19 | 8.68 |
| D9 | 36.88 | 16.12 |
| D10 | 11.25 | 30.00 |
| D11 | 11.68 | 31.55 |
| E1 | 56.60 | 7.58 |
| E2 | 12.18 | 30.41 |
| E3 | 13.75 | 33.16 |
| E4 | 8.79 | 27.90 |
| E5 | 8.69 | 25.33 |
| E6 | 11.78 | 28.56 |
| E7 | 8.31 | 23.67 |
| E8 | 9.19 | 25.35 |
| E9 | 7.77 | 27.41 |
| E10 | 8.96 | 24.06 |
| E11 | 11.25 | 31.88 |
| E12 | 10.18 | 24.20 |
| F1 | 9.94 | 23.65 |
| F2 | 38.36 | 12.57 |
| F3 | 37.37 | 15.35 |
| F4 | 8.89 | 25.59 |
| F5 | 10.78 | 23.51 |
| F6 | 11.41 | 27.57 |
| F7 | 10.96 | 26.18 |
| F8 | 35.86 | 14.67 |
| F9 | 5.69 | 29.07 |
| F10 | 13.84 | 32.85 |
| F11 | 2.81 | 27.27 |

TABLE 20-continued

Top RebM- and RebD-producing colonies.

| Colony | RebM (μM) | RebD (μM) |
|---|---|---|
| F12 | 39.86 | 10.64 |
| G1 | 37.94 | 8.80 |
| G2 | 9.56 | 23.64 |
| G3 | 33.80 | 9.62 |
| G4 | 3.01 | 25.15 |
| G5 | 9.81 | 25.41 |
| G6 | 42.71 | 9.96 |
| G7 | 1.65 | 24.20 |
| G8 | 9.63 | 24.28 |
| G9 | 33.65 | 22.69 |
| G10 | 34.87 | 9.69 |
| G11 | 33.66 | 11.49 |
| G12 | 3.58 | 24.04 |
| H1 | 33.94 | 9.84 |
| H2 | 10.39 | 23.59 |
| H3 | 43.64 | 9.40 |
| H4 | 33.50 | 8.73 |
| H5 | 36.32 | 9.39 |
| H6 | 34.61 | 7.69 |
| H7 | 36.73 | 9.20 |
| H8 | 35.49 | 4.09 |
| H9 | 34.25 | 4.82 |
| H10 | 35.36 | 4.10 |
| H11 | 19.87 | 25.19 |

Example 14: UGT76G1 Site Saturation Library Rescreen and Variant Sequencing

Figure 19A:
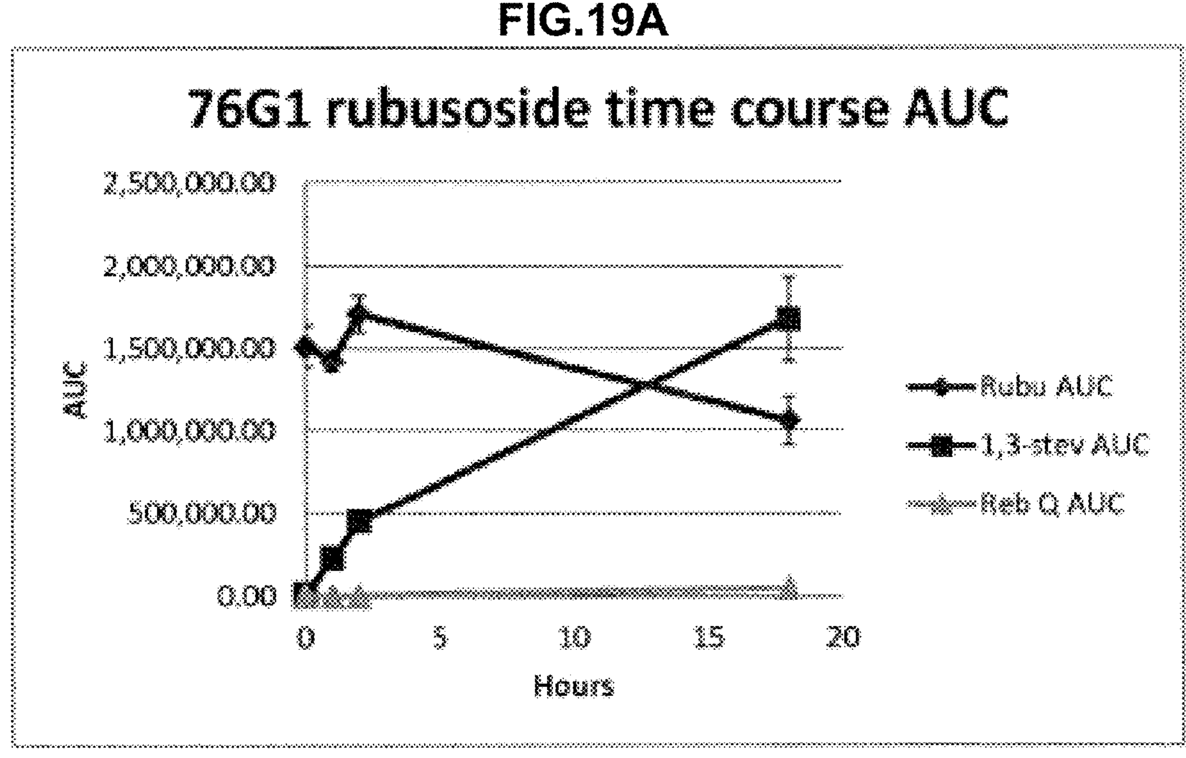
FIG. 19A shows the relative rates of consumption of Rubusoside and production of 1,3-stevioside (RebG) and Rebaudioside Q ("RebQ") by UGT76G1.
Figure 19B:
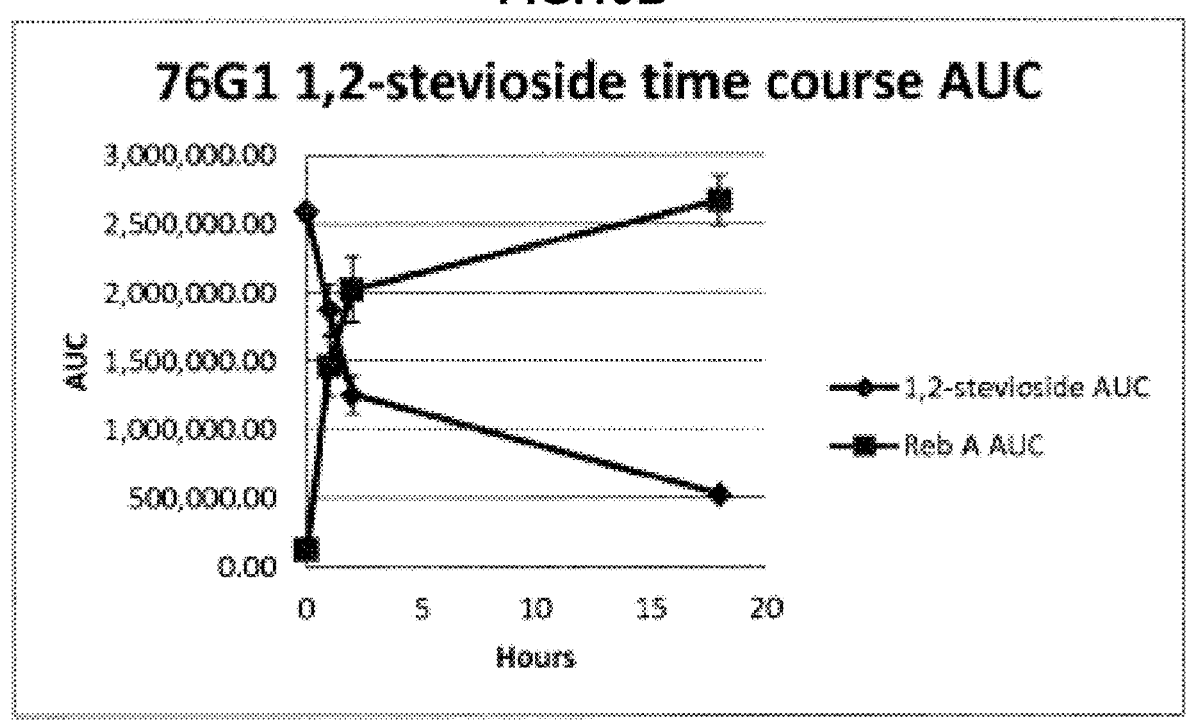
FIG. 19B shows the relative rates of consumption of 1,2-stevioside and production of RebA by UGT76G1.
Figure 19C:
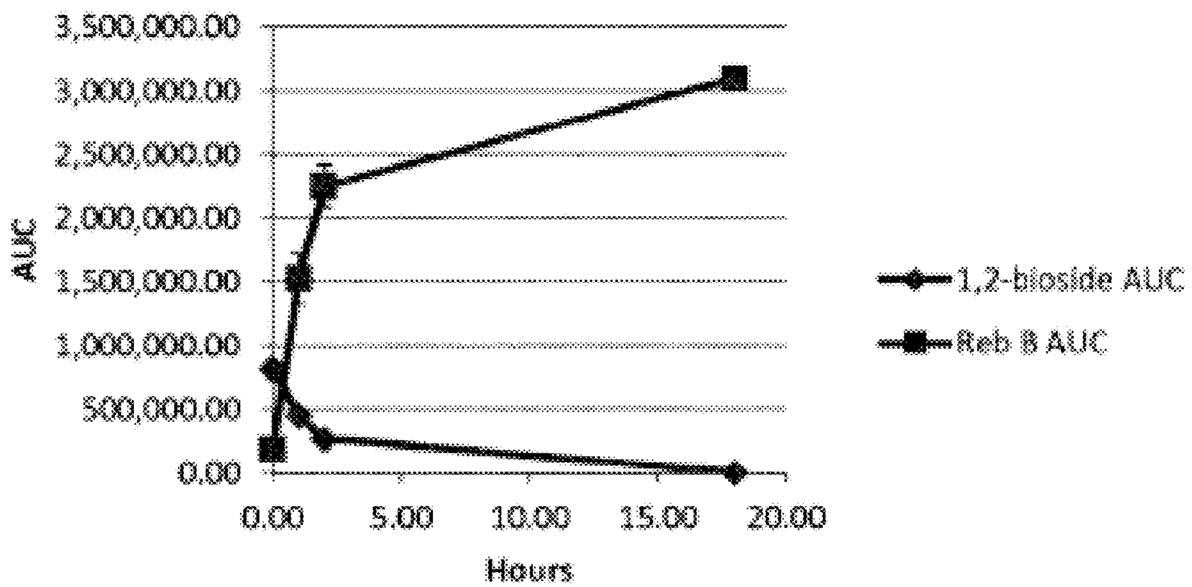
FIG. 19C shows the relative rates of consumption of 1,2-bioside and production of RebB by UGT76G1.

A rescreen of the 47 UGT76G1 variant colonies producing either the highest amounts of RebD or RebM was done in triplicate and showed the same trends as the initial screen (FIG. 19). The colonies to be sequenced were selected by compiling the results from the screen and rescreen. As the production levels of the screen and rescreen could not be directly compared, the colonies were ranked from highest producers to lowest producers of RebD and RebM, respectively, and the ranks from the screen and rescreen were averaged. From the averages, the top 16 RebD-, top 16 RebM-, and top 16 RebD/M-producing colonies (a total of 48 colonies) were identified. As some of the top RebD and top RebD/M producers were found to be the same colonies, duplicate colonies were counted only once, and additional colonies were chosen to reach the 48 total colonies to be sequenced. These colonies were then sequenced in duplicate with the GPDseq_fwd and CYC1seq-rev primers, shown below.

```
GPDseq_fwd primer seq:
                                    (SEQ ID NO: 88)
CGG TAG GTA TTG ATT GTA ATT

CYC1seq_rev primer seq:
                                    (SEQ ID NO: 89)
CTT TTC GGT TAG AGC GGA TGT
```

Tables 21-23 show the amounts and rankings of RebD, RebM, and RebD/RebM produced by the indicated variants, and Table 24 summarizes the mutations that selectively increase either RebD or RebM production. Amounts of RebM, RebD, RebA, Rubusoside, and RebB produced by wild type and UGT76G1 variant colonies are shown in Table 25.

TABLE 21

Identities of top RebD-producing UGT76G1 variants.

| | Screen | | Rescreen Sample 1 | | Rescreen Sample 2 | | Rescreen Sample 3 | | Average | | |
|---|---|---|---|---|---|---|---|---|---|---|---|
| Colony | RebD (μM) | Rank | RebD (μM) | Rank | RebD (μM) | Rank | RebD (μM) | Rank | RebD (μM) | RANK | Mutation |
| E2 | 25.33 | 21 | 17.00 | 21 | 18.99 | 7 | 19.35 | 3 | 20.17 | 13 | L257A |
| E5 | 33.16 | 1 | 17.51 | 15 | 15.34 | 29 | 18.49 | 8 | 21.13 | 13 | L257G |
| F9 | 29.07 | 8 | 21.05 | 3 | 17.23 | 15 | 13.89 | 28 | 20.31 | 14 | L257T |
| G5 | 25.15 | 23 | 21.53 | 2 | 19.07 | 4 | 14.50 | 25 | 20.06 | 14 | S283G |
| E3 | 28.56 | 9 | 16.42 | 22 | — | — | 18.28 | 10 | 21.09 | 14 | L257W |
| C7 | 27.11 | 15 | 18.64 | 8 | 14.64 | 32 | 18.97 | 4 | 19.84 | 15 | T146A |
| F6 | 25.59 | 18 | 18.17 | 11 | 15.55 | 25 | 18.87 | 5 | 19.55 | 15 | L257R, (S389F) |
| C5 | 28.32 | 10 | — | — | — | — | 16.03 | 20 | 22.18 | 15 | T146A |
| D11 | 30.00 | 7 | — | — | 15.58 | 24 | — | — | 22.79 | 16 | L257R |
| A5 | 23.72 | 35 | 18.52 | 10 | 16.76 | 19 | 18.66 | 6 | 19.42 | 18 | I26F |
| F1 | 24.06 | 33 | 19.91 | 4 | 16.90 | 17 | — | — | 20.29 | 18 | L257G |
| B12 | 24.56 | 26 | 18.11 | 12 | 17.29 | 14 | 15.98 | 21 | 18.99 | 18 | T146G |
| E4 | 30.41 | 5 | 16.30 | 23 | 17.46 | 11 | 12.88 | 34 | 19.26 | 18 | L257P |
| E10 | 23.65 | 38 | — | — | 19.31 | 3 | 17.12 | 15 | 20.03 | 19 | L257G |
| F4 | 12.57 | 55 | 19.36 | 5 | 17.43 | 13 | 18.55 | 7 | 16.98 | 20 | L257E |
| E9 | 24.20 | 31 | 17.49 | 16 | 16.93 | 16 | — | — | 19.54 | 21 | L257G |
| E7 | 23.67 | 36 | 19.24 | 6 | 15.51 | 26 | 16.74 | 17 | 18.79 | 21 | L257G |
| H2 | 23.59 | 40 | 15.85 | 26 | 17.95 | 8 | 17.63 | 12 | 18.75 | 22 | S285R |
| G7 | 24.20 | 30 | — | — | 16.34 | 21 | 17.22 | 14 | 19.26 | 22 | S283N |
| C12 | 30.20 | 6 | — | — | 14.50 | 33 | 14.36 | 27 | 19.68 | 22 | H155R |
| C1 | 26.75 | 16 | 15.32 | 27 | 16.30 | 22 | 14.43 | 26 | 18.20 | 23 | T146G |
| A6 | 23.50 | 42 | 14.96 | 29 | 19.59 | 2 | 16.25 | 19 | 18.57 | 23 | I26W |
| C4 | 24.70 | 25 | — | — | — | — | 15.94 | 22 | 20.32 | 24 | T146P |

TABLE 22

Identities of the top RebM-producing UGT76G1 variants.

| | Screen | | Rescreen Sample 1 | | Rescreen Sample 2 | | Rescreen Sample 3 | | Rescreen Average | | |
|---|---|---|---|---|---|---|---|---|---|---|---|
| Colony | RebD (μM) | Rank | RebD (μM) | Rank | RebD (μM) | Rank | RebD (μM) | Rank | RebD (μM) | RANK | Mutation |
| G1 | 37.94 | 12 | — | — | 26.68 | 7 | 26.77 | 6 | 30.46 | 8 | T284G |
| H7 | 36.73 | 19 | — | — | 29.81 | 1 | 25.11 | 12 | 30.55 | 11 | K337P |
| B1 | 36.86 | 17 | — | — | — | — | 27.82 | 5 | 32.34 | 11 | T55K |
| D2 | 43.18 | 4 | 21.39 | 30 | 27.28 | 4 | — | — | 30.62 | 13 | Q198R |
| H3 | 43.64 | 3 | 23.32 | 21 | 24.67 | 14 | 22.03 | 23 | 28.42 | 15 | S285T |
| C11 | 33.87 | 39 | 28.92 | 3 | 26.07 | 8 | 24.21 | 14 | 28.27 | 16 | H155L |
| A10 | 33.80 | 41 | 25.52 | 10 | 23.48 | 15 | 29.50 | 1 | 28.08 | 17 | S56A |
| B11 | 36.76 | 18 | 25.28 | 12 | 20.88 | 28 | 24.69 | 13 | 26.90 | 18 | Y128S |
| H04 | 33.50 | 47 | 25.34 | 11 | 24.98 | 13 | 28.71 | 3 | 28.13 | 19 | K337E |
| B02 | 34.88 | 30 | 28.40 | 4 | — | — | 20.65 | 27 | 27.98 | 20 | T55E |
| D09 | 56.60 | 1 | 21.14 | 32 | 20.84 | 29 | — | — | 32.86 | 21 | S253G |
| D01 | 33.51 | 45 | 23.48 | 20 | 25.27 | 11 | 25.33 | 10 | 26.89 | 22 | H155L |
| H09 | 34.25 | 35 | — | — | 21.90 | 21 | 25.28 | 11 | 27.14 | 22 | L379V |
| G11 | 33.65 | 43 | 22.95 | 22 | 27.77 | 3 | — | — | 28.12 | 23 | T284R |
| B8 | 35.47 | 28 | 25.66 | 9 | 21.01 | 26 | 20.13 | 28 | 25.57 | 23 | Y128E |
| F2 | 11.41 | 58 | 31.01 | 1 | 21.06 | 25 | 26.62 | 7 | 22.53 | 23 | S253W |
| C10 | 33.51 | 46 | 22.04 | 28 | 25.54 | 10 | 25.42 | 8 | 26.63 | 23 | H155L |

TABLE 23

Identities of the top RebD/M-producing UGT76G1 variants.

| Colony | Average RebD (μM) | Average Rank RebD | Average RebM (μM) | Average Rank RebM | Rank RebD + Rank (96-M) | Mutation |
|---|---|---|---|---|---|---|
| G7 | 19.26 | 22 | 1.51 | 84 | 34 | S283N |
| F9 | 20.31 | 14 | 5.27 | 71 | 38 | L257T |
| C1 | 18.20 | 23 | 1.90 | 79 | 40 | T146G |
| B12 | 18.99 | 18 | 3.74 | 74 | 41 | T146G |
| A5 | 19.42 | 18 | 6.76 | 68 | 46 | I26F |
| F6 | 19.55 | 15 | 8.23 | 63 | 48 | L257R + S389F |
| C6 | 17.74 | 29 | 2.59 | 77 | 48 | T146G |
| F1 | 20.29 | 18 | 7.98 | 65 | 49 | L257G |
| E2 | 20.17 | 13 | 8.64 | 60 | 49 | L257A |
| C7 | 19.84 | 15 | 7.52 | 61 | 50 | T146A |
| C3 | 16.30 | 37 | 1.74 | 83 | 50 | T146G |
| E11 | 17.80 | 25 | 6.48 | 69 | 52 | L257G |
| A2 | 15.34 | 32 | 4.48 | 76 | 52 | Q23H |
| E5 | 21.13 | 13 | 9.32 | 57 | 52 | L257G |
| E4 | 19.26 | 18 | 8.00 | 61 | 54 | L257P |
| G5 | 20.06 | 14 | 8.79 | 56 | 54 | S283G |
| D11 | 22.79 | 16 | 9.75 | 58 | 54 | L257R |
| C5 | 22.18 | 15 | 10.81 | 57 | 54 | T146A |
| E9 | 19.54 | 21 | 8.21 | 62 | 55 | L257G |
| E7 | 18.79 | 21 | 8.00 | 62 | 55 | L257G |
| C2 | 18.29 | 26 | 6.95 | 67 | 55 | T146A |
| A3 | 15.25 | 35 | 3.19 | 76 | 56 | Q23G |
| E12 | 17.28 | 25 | 7.26 | 65 | 56 | L257W |
| E10 | 20.03 | 19 | 10.10 | 57 | 57 | L257G |

TABLE 24

Summary of UGT76G1 variants for RebD production and RebM production.

| | |
|---|---|
| RebD | Q23G, Q23H, I26F, I26W, T146A, T146G, T146P, H155R, L257P, L257W, L257T, L257G, L257A, L257R, L257E, S283G and S283N |
| RebM | T55K, T55E, S56A, Y128S, Y128E, H155L, H155R, Q198R, S285R, S285T, S253W, S253G, T284R, T284G, S285G, K337E, K337P and L379V |

TABLE 25

Production of steviol glycosides by UGT76G1 variants.

| Mutation | RebM | RebD | RebA | Rubu | RebB | Total RebA-->RebM SUM |
|---|---|---|---|---|---|---|
| | | | AVG (μM) | | | |
| WT | 22.35 | 4.98 | 7.03 | 0.65 | 2.54 | 34.37 |
| WT | 24.01 | 5.14 | 5.68 | 0.77 | 2.43 | 34.83 |
| RebD-optimizing mutations | | | | | | |
| L257W | 9.35 | 18.46 | 4.70 | | 2.03 | 32.52 |
| L257A | 8.62 | 18.45 | 4.75 | | 1.97 | 31.82 |
| L257E | 8.72 | 18.44 | 3.70 | | 1.54 | 30.87 |
| L257G | 7.49 | 18.40 | 4.44 | 0.18 | 1.80 | 30.34 |
| S283G | 10.71 | 18.37 | 3.77 | | 1.58 | 32.85 |
| L257G | 10.18 | 18.22 | 4.47 | 0.20 | 1.87 | 32.86 |
| I26F | 7.13 | 17.98 | 3.81 | | 1.64 | 28.92 |
| Q23H | 4.30 | 17.88 | 3.04 | | 1.38 | 25.22 |
| L257R, S389F | 8.01 | 17.53 | 4.21 | | 1.92 | 29.75 |
| T146A | 9.24 | 17.41 | 4.16 | 0.18 | 1.72 | 30.82 |
| L257T | 5.13 | 17.39 | 2.73 | 0.25 | 1.29 | 25.24 |
| L257W | 11.40 | 17.35 | 4.28 | | 1.94 | 33.04 |
| L257G | 7.23 | 17.21 | 4.19 | 0.45 | 1.81 | 28.62 |
| L257G | 7.90 | 17.16 | 4.16 | | 1.73 | 29.22 |
| S285R | 8.66 | 17.14 | 3.44 | | 1.70 | 29.25 |
| T146G | 1.91 | 17.13 | 1.69 | | 0.74 | 20.73 |
| L257G | 7.84 | 17.12 | 3.93 | | 1.80 | 28.88 |
| I26W | 11.51 | 16.93 | 5.22 | | 1.93 | 33.67 |
| S283N | 1.45 | 16.78 | 1.48 | | 0.67 | 19.70 |
| T146A | 10.57 | 16.03 | 4.07 | | 1.86 | 30.68 |
| T146G | 1.82 | 15.95 | 1.75 | 0.22 | 0.72 | 19.52 |
| T146P | 10.12 | 15.94 | 4.05 | | 1.96 | 30.11 |
| T146A | 9.31 | 15.60 | 4.34 | | 1.91 | 29.25 |
| L257R | 8.26 | 15.58 | 3.60 | 0.17 | 1.88 | 27.44 |
| L257P | 6.61 | 15.55 | 3.62 | 0.15 | 1.59 | 25.78 |
| T146G | 1.76 | 15.35 | 1.81 | 0.24 | 0.68 | 18.92 |
| H155R | 10.49 | 14.43 | 4.46 | 0.25 | 1.78 | 29.38 |
| L257G | 5.12 | 14.03 | 3.63 | | 0.95 | 22.78 |
| T146G | 1.64 | 12.86 | 1.65 | 0.21 | 0.67 | 16.14 |
| Q23G | 3.33 | 11.96 | 1.71 | 0.16 | 0.80 | 17.00 |
| RebM-optimizing mutations | | | | | | |
| T55K | 27.82 | 7.96 | 6.28 | 0.40 | 2.31 | 42.06 |
| K337P | 27.46 | 8.14 | 5.83 | 0.41 | 2.18 | 41.43 |
| T284G | 26.72 | 7.29 | 7.27 | 0.34 | 2.72 | 41.28 |
| H155L | 26.40 | 3.70 | 6.79 | 0.30 | 2.50 | 36.89 |
| K337E | 26.34 | 7.14 | 6.35 | 0.39 | 2.66 | 39.83 |

TABLE 25-continued

| Production of steviol glycosides by UGT76G1 variants. | | | | | | |
|---|---|---|---|---|---|---|
| Mutation | RebM | RebD | RebA AVG (μM) | Rubu | RebB | Total RebA-->RebM SUM |
| S253W | 26.23 | 6.83 | 5.82 | 0.37 | 2.26 | 38.89 |
| S56A | 26.17 | 6.50 | 6.94 | 0.66 | 2.46 | 39.61 |
| T284R | 25.36 | 7.99 | 6.24 | 0.24 | 2.56 | 39.58 |
| H155L | 24.69 | 3.65 | 7.38 | 0.39 | 2.66 | 35.72 |
| T55E | 24.52 | 6.73 | 5.84 | 0.46 | 2.09 | 37.09 |
| Q198R | 24.33 | 6.61 | 6.37 | 0.60 | 2.33 | 37.32 |
| H155L | 24.33 | 4.00 | 7.43 | 0.29 | 2.53 | 35.76 |
| Y128S | 23.62 | 6.20 | 6.48 | 0.43 | 2.29 | 36.29 |
| L379V | 23.59 | 4.01 | 7.09 | 0.28 | 2.72 | 34.69 |
| S285T | 23.34 | 5.90 | 5.73 | 0.44 | 2.30 | 34.97 |
| Y128E | 22.27 | 5.04 | 5.78 | 0.41 | 2.17 | 33.09 |
| S253G | 20.99 | 7.26 | 5.78 | 0.27 | 2.42 | 34.04 |

Example 15: Determination of Relative Rates of UGT76G1 Glycosylation Reactions UGT76G1 was only known in the literature to catalyze the 1,3-glycosylation of 1,2-stevioside to convert it into RebA and converting 1,2-bioside to RebB. The inventors have newly discovered that the reactions shown in Table 26 are catalyzed by UGT76G1.

TABLE 26

| Newly discovered UGT76G1 reactions. | |
|---|---|
| Substrate | Product |
| Rebaudioside D | Rebaudioside M |
| Rubusoside | "Rebaudioside Q" (1,3-O-glycoside linkages on both the 13- and 19-O-glucose position) |
| Steviol 1,2 bioside isomer (19-O) | Rebaudioside B isomer (19-O) |

Similar to Example 9, p416GPD containing WT-76G1 was expressed in the protease deficient yeast strain DSY6 for 48 h in SC-ura media. 100 μL of cells were then reinoculated in 3 mL of SC-ura media for 16 h. The cells were lysed with 200 μL CelLytic™ Y according to manufacturer's description. 6 μL of the lysate were added to 24 μL of the reaction mixture consisting of 20 mM Tris-buffer (pH 8.0), 0.3 μMUDPG, and either 0.1 μM rubusoside, 0.2 μM 1,2-bioside, 0.2 μM 1,2-stevioside, 0.2 μM RebA, or 0.1 μM RebE. The reactions were incubated at 30° C. and stopped at 0, 1, 2, and 18 h by transferring 25 μL of the 30 μL reaction mixture to 25 μL DMSO. Amounts of steviol glycosides were analyzed by LC-MS and assessed by peak integration during data processing as "area under the curve."

In FIG. 19, it is shown that an approximately 50% decrease in the "area under the curve" for rubusoside resulted in considerable production of 1,3-stevioside (RebG) over 18 h. RebQ, newly discovered by the inventors, was first detected at 18 h. Additionally, FIG. 19 shows that 1,2-stevioside was not completely consumed over the 18 h period for the production of RebA as 1,2-bioside was for the production of RebB.

Figure 20:
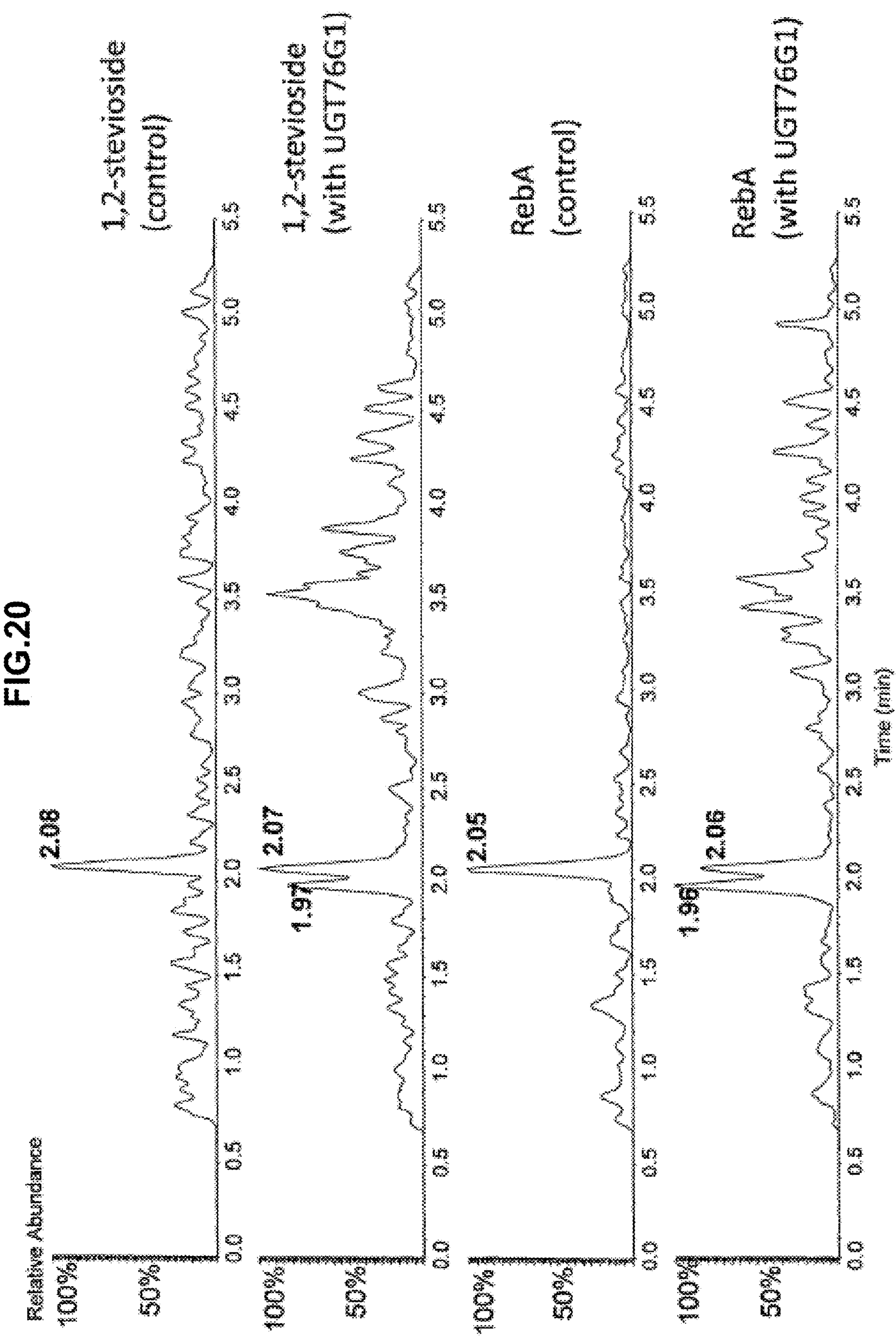
FIG. 20 shows chromatograms of 1,2-stevioside and RebA with or without UGT76G1 peaks indicating production of RebI.

Furthermore, using either 1,2-stevioside or RebA as a substrate, a peak eluting at 1.96 min on the steviol+5 glucose chromatogram appeared (FIG. 20). Because RebD elutes at 1.11 min and UGT76G1 only catalyzes 1,3-glycosylation reactions, the peak eluting at 1.96 min appeared to be RebI. However, it was not possible to integrate the RebI peak because it was situated in a substrate artifact peak (FIG. 20).

These results collectively indicated that UGT76G1 preferentially catalyzed glycosylation of steviol glycoside substrates that are 1,2-di-glycosylated on the 13-O-position, followed by steviol glycoside substrates that are mono-glycosylated at the 13-O-position. There appeared to be little preference arising from the glycosylation state of the 19-O-position. FIG. 1 summarizes steviol glycoside glycosylation reactions and the enzymes by which they are known to be catalyzed.

Example 16: Production of Steviol Glycosides by UGT76G1 Variants

Quantitative standards are not commercially available for each steviol glycoside, which prevented some concentration measurements. Therefore, production of additional steviol glycosides by the enzyme variants, as compared to the wild type enzyme, was assessed by peak integration during data processing. The "area under the curve" data for each variant was normalized to the wild type UGT76G1 and is shown in Table 27. These data were in agreement with previous examples but also showed that some of the variants did not produce 1,3-stevioside (RebG), rubusoside, "Reb Q," and/or a steviol-tetraglycoside eluting at 1.43 min, as the wild type controls did. Increases in RebM and RebD production can be explained by this observation.

TABLE 27

"Area under the curve" data as a measure of the production of steviol glycosides by UGT76G1 variants relative to wildtype UGT76G1 production.

| Variant | Reb M | Reb D | RebA | 1,2 Stev | 1,3 Stev | RebB | Rubu | 1,2-Bios | 1,3-Bios | 19-SMG | 13-SMG | Stev | 0.95 min Stv4Glc (suspect RebE) | 1.43 min Stv4Glc | 1,3 at 13 and 19Pos "Reb Q" |
|---|---|---|---|---|---|---|---|---|---|---|---|---|---|---|---|
| Q23H | 0.2 | 2.6 | 0.4 | 2.5 | — | 0.5 | — | — | — | — | 1.0 | — | 3.7 | 0.5 | — |
| Q23G | 0.2 | 2.5 | 0.3 | 2.0 | — | 0.3 | 0.3 | — | — | — | 0.6 | — | 2.8 | 0.4 | — |
| I26F | 0.3 | 3.8 | 0.6 | 2.2 | — | 0.7 | — | — | — | — | 1.1 | — | 3.0 | 0.5 | — |
| I26W | 0.5 | 3.6 | 0.9 | 1.8 | — | 0.8 | — | — | — | — | 0.6 | — | 2.5 | 0.4 | — |
| S56A | 1.2 | 1.4 | 1.2 | 1.2 | 0.7 | 1.0 | 1.0 | — | — | — | 1.2 | — | 1.4 | 0.3 | 0.7 |
| T55K | 1.3 | 1.7 | 1.0 | 1.0 | — | 1.0 | 0.6 | — | — | — | 1.0 | — | 1.1 | 0.9 | — |
| T55E | 1.2 | 1.4 | 1.0 | 1.3 | 0.8 | 0.9 | 0.7 | — | — | — | 0.9 | — | 1.7 | 0.3 | 0.9 |
| Y128E | 1.1 | 1.1 | 1.0 | 1.1 | — | 0.9 | 0.6 | — | — | — | 1.0 | — | 1.0 | 0.7 | 0.4 |
| Y128S | 1.1 | 1.3 | 1.1 | 1.2 | 0.6 | 1.0 | 0.7 | — | — | — | 1.0 | — | 1.3 | 1.0 | 0.6 |
| T146G | 0.1 | 3.6 | 0.3 | 3.7 | — | 0.3 | — | — | — | — | 1.0 | — | 7.6 | 0.9 | — |
| T146G | 0.1 | 3.3 | 0.3 | 4.0 | — | 0.3 | 0.4 | — | — | — | 1.4 | — | 7.3 | 1.0 | — |
| T146A | 0.4 | 3.3 | 0.7 | 2.1 | — | 0.8 | — | — | — | — | 0.9 | — | 3.2 | 0.5 | — |
| T146G | 0.1 | 2.7 | 0.3 | 3.8 | — | 0.3 | 0.3 | — | — | — | 1.2 | — | 6.2 | 0.9 | — |

TABLE 27-continued

"Area under the curve" data as a measure of the production of steviol glycosides by UGT76G1 variants relative to wildtype UGT76G1 production.

| Variant | Reb M | Reb D | RebA | 1,2 Stev | 1,3 Stev | RebB | Rubu | 1,2-Bios | 1,3-Bios | 19-SMG | 13-SMG | Stev | 0.95 min Stv4Glc (suspect RebE) | 1.43 min Stv4Glc | 1,3 at 13 and 19Pos "Reb Q" |
|---|---|---|---|---|---|---|---|---|---|---|---|---|---|---|---|
| T146P | 0.5 | 3.4 | 0.7 | 2.2 | — | 0.8 | — | — | — | — | 0.9 | — | 3.0 | 0.5 | — |
| T146A | 0.5 | 3.4 | 0.7 | 2.2 | — | 0.8 | — | — | — | — | 0.8 | — | 3.3 | 0.5 | — |
| T146G | 0.1 | 3.4 | 0.3 | 3.7 | — | 0.3 | 0.3 | — | — | — | 1.2 | — | 6.6 | 0.9 | — |
| T146A | 0.4 | 3.7 | 0.7 | 2.2 | — | 0.7 | 0.3 | — | — | — | 1.1 | — | 3.8 | 0.5 | — |
| H155L | 1.2 | 0.8 | 1.2 | 1.0 | — | 1.1 | 0.4 | — | — | — | 1.0 | — | 0.6 | — | 0.4 |
| H155L | 1.3 | 0.8 | 1.1 | 0.8 | — | 1.1 | 0.5 | — | — | — | 1.0 | — | 0.5 | — | 0.3 |
| H155R | 0.5 | 3.1 | 0.7 | 2.2 | — | 0.8 | 0.4 | — | — | — | 0.9 | — | 2.8 | 0.6 | — |
| H155L | 1.2 | 0.8 | 1.2 | 1.0 | — | 1.1 | 0.6 | — | — | — | 1.1 | — | 0.8 | 0.5 | 0.5 |
| Q198R | 1.2 | 1.4 | 1.1 | 1.3 | 0.8 | 1.0 | 0.9 | — | — | — | 1.1 | — | 1.6 | — | 0.6 |
| S253G | 1.0 | 1.5 | 1.0 | 1.1 | — | 1.0 | 0.4 | — | — | — | 1.2 | — | 1.2 | 0.2 | — |
| L257R | 0.4 | 3.3 | 0.6 | 2.4 | — | 0.8 | 0.3 | — | — | — | 1.1 | — | 2.8 | 0.6 | — |
| L257A | 0.4 | 3.9 | 0.8 | 2.8 | — | 0.8 | — | — | — | — | 1.3 | — | 4.3 | 0.7 | — |
| L257W | 0.5 | 3.7 | 0.7 | 2.5 | — | 0.8 | — | — | — | — | 0.9 | — | 3.8 | 0.6 | — |
| L257P | 0.3 | 3.3 | 0.6 | 2.3 | — | 0.7 | 0.2 | — | — | — | 0.9 | — | 3.1 | 0.5 | — |
| L257G | 0.4 | 3.6 | 0.7 | 2.4 | — | 0.8 | — | — | — | — | 1.2 | — | 3.3 | 0.5 | — |
| L257G | 0.4 | 3.6 | 0.7 | 2.4 | — | 0.7 | — | — | — | — | 1.2 | — | 3.6 | 0.6 | — |
| L257G | 0.3 | 3.6 | 0.7 | 3.7 | — | 0.8 | 0.7 | — | — | — | 1.2 | — | 7.9 | 0.9 | — |
| L257G | 0.5 | 3.9 | 0.7 | 2.6 | — | 0.8 | 0.3 | — | — | — | 1.1 | — | 3.2 | 0.7 | — |
| L257G | 0.2 | 3.0 | 0.6 | 2.2 | — | 0.4 | — | — | — | — | 1.0 | — | 3.0 | 0.5 | — |
| L257W | 0.3 | 2.9 | 1.8 | 4.1 | — | 1.8 | 0.8 | — | — | — | 1.3 | — | 4.0 | 0.5 | — |
| L257G | 0.4 | 3.9 | 0.7 | 2.6 | — | 0.8 | 0.3 | — | — | — | 1.4 | — | 4.1 | 0.7 | — |
| S353W | 1.3 | 1.4 | 1.0 | 1.3 | — | 1.0 | 0.6 | — | — | — | 0.9 | — | 1.4 | 0.7 | 0.4 |
| L257E | 0.4 | 3.9 | 0.6 | 2.4 | — | 0.7 | — | — | — | — | 0.9 | — | 3.9 | 0.6 | — |
| L257R, S389F | 0.4 | 3.7 | 0.7 | 2.5 | — | 0.8 | — | — | — | — | 1.1 | — | 3.5 | 0.5 | — |
| L257T | 0.2 | 3.7 | 0.5 | 2.6 | — | 0.5 | 0.4 | — | — | — | 0.8 | — | 4.0 | 0.6 | — |
| T284G | 1.3 | 1.5 | 1.2 | 1.3 | — | 1.2 | 0.5 | — | — | — | 1.1 | — | 2.2 | 0.7 | — |
| S283G | 0.5 | 3.9 | 0.6 | 1.9 | — | 0.7 | — | — | — | — | 1.1 | — | 3.5 | 0.4 | — |
| S283N | 0.1 | 3.6 | 0.2 | 3.9 | — | 0.3 | — | — | — | — | 1.1 | — | 6.8 | 1.0 | — |
| T284R | 1.2 | 1.7 | 1.0 | 1.4 | — | 1.1 | 0.4 | — | — | — | 1.0 | — | 2.2 | 0.4 | — |
| S285R | 0.4 | 3.6 | 0.6 | 2.6 | — | 0.7 | — | — | — | — | 1.3 | — | 4.4 | 0.6 | — |
| S285T | 1.1 | 1.3 | 1.0 | 1.0 | — | 1.0 | 0.7 | — | — | — | 1.0 | — | 1.2 | 0.9 | 0.3 |
| K337E | 1.3 | 1.5 | 1.1 | 1.1 | — | 1.1 | 0.6 | — | — | — | 1.2 | — | 1.2 | 0.7 | — |
| K337P | 1.3 | 1.7 | 1.0 | 1.3 | — | 0.9 | 0.6 | — | — | — | 1.1 | — | 1.6 | 1.1 | 0.4 |
| L379V | 1.1 | 0.9 | 1.2 | 1.2 | — | 1.2 | 0.4 | — | — | — | 1.1 | — | 1.1 | 0.4 | — |

Table 28 summarizes trends in steviol glycoside production through RebD-optimizing and RebM-optimizing mutations, compared to the normalized production of wild type controls. The variants with increased RebD production appeared to primarily be the result of inhibiting the RebD→RebM reaction. Additional RebD production can stem from inhibition of the Rubu→RebG→RebQ steviol glycosylation branch as well as a reduction in RebB and of a tetraglucoside eluting at 1.43 min. The four-fold increase in 1,2-Stevioside and seven-fold increase in RebE were unexpected, but the RebE increase could be a seven-fold increase in a very small amount of side product found in the wild type controls. Nevertheless, this finding indicated that the Stevioside→RebA reaction had also been partially inhibited by the RebD-optimizing mutations, which was seen as a reduction in RebA intermediate.

TABLE 28

Steviol glycoside production by the UGT76G1 wild type or RebD and RebM-optimizing mutations.

| | RebM | RebD | RebA | 1,2 Stev | 1,3 Stev | RebB | Rubu | 1,2 Bios | 1,3 Bios | 19-SMG | 13-SMG | Stev | 0.95 min Stv4Glc (RebE) | 1.43 min Stv4Glc (UNK) | 1,3 at 13 and 19 Pos ("RebQ") |
|---|---|---|---|---|---|---|---|---|---|---|---|---|---|---|---|
| RebD | 0.1-0.5x | 2.5-3.9x | 0.3-0.8x | 1.8-4.0x | 0.0x | 0.3-0.8x | 0.0-0.4x | — | — | — | 0.9-1.3x | — | 3.0-7.0x | 0.4-0.9x | 0.0x |
| RebM | 1.0-1.3x | 0.8-1.7x | 1.0-1.2x | 0.8-1.3x | 0.0-0.8x | 0.9-1.1x | 0.4-1.0x | — | — | — | 0.9-1.2x | — | 0.5-2.0x | 0.0-0.9x | 0.0-0.8x |
| WT | 23.2 μM | 5.1 μM | 6.4 μM | AUC | AUC | 2.5 μM | 0.7 μM | — | — | — | AUC | — | AUC | AUC | AUC |

The mutation resulting in the highest RebD levels, L257G, produced nearly four-fold the RebD of the wild type and was found in six colonies sequenced. Other L257 mutations demonstrated nearly the same productivity. Mutants 126W and S283G showed the highest RebD/stevioside ratio, indicating that these mutations lead to the greatest inhibition of the RebD→M reaction without mitigating the Stev→RebA reaction. These two mutations also completely abolished the Rubu→RebG→RebQ pathway and reduced the amount of the tetraglucoside eluting at 1.43 min while minimally affecting RebB production. The best RebD/RebM ratios were found with T146G and S283N mutants, which showed a 40-50-fold increase over the wild type. The S389Fmutation found with L257R demonstrated higher RebD production than L257R alone.

Generally, increases in RebM also resulted in increases in RebD, while decreasing or completely blocking the Rubu→RebG→RebQ glycosylation pathway and the tetraglucoside eluting at 1.43 min. Yet, the remaining steviol glycosides studied appeared unaffected. The top RebM producers, T55K and K337P, each increased RebM by 1.3-fold and decreased rubusoside by 0.6-fold, compared to the wild type. Since rubusoside was only present at 0.7 μM in the wild type, this observed decrease was insufficient to explain the increase in RebM. The Rubu→RebG→RebQ pathway was almost removed, with no 1,3-stevioside (RebG) produced by these mutants. As well, the variant with the K337P mutation produced 0.6-fold the levels of RebQ with the wild type. The mutations H155L and L379V each produced more RebM to RebD, with the wild type UGT76G1 producing approximately 4.58 RebM per RebD, and H155L and L379 producing approximately 6.66 and 5.88 RebM per RebD, respectively. Through the data uncovered by this study, UGT76G1 enzymes can be screened to identify species having improved kinetics towards RebD and RebM and that minimize side products, thereby increasing the flux towards the desired steviol glycosides.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

REFERENCES

1. Critical Reviews in Food Science and Nutrition, 52:11, 988-998, DOI:10.1080/10408398.2010.519447.
2. J Nat Prod. 2013 Jun. 28; 76(6):1201-28. doi: 10.1021/np400203b. Epub 2013 May 28.
3. Plant Physiology and Biochemistry 63 (2013) 245e253.
4. Praveen Guleria and Sudesh Kumar Yadav, 2013. Insights into Steviol Glycoside Biosynthesis Pathway Enzymes Through Structural Homology Modelling. American Journal of Biochemistry and Molecular Biology, 3: 1-19.
5. The Plant Journal (2005) 41, 56-67 doi: 10.1111/j.1365-313X.2004.02275.
6. Madhav et al., "Functional and structural variation of uridine diphosphate glycosyltransferase (UGT) gene of *Stevia rebaudianae* UGTSr involved in the synthesis of rebaudioside A" Plant Physiology and Biochemistry 63 (2013) 245e253.
7. Jewett M C, et al., Molecular Systems Biology, Vol. 4, article 220 (2008).
8. Masada S et al., FEBS Letters, Vol. 581, 2562-2566 (2007).

The invention claimed is:

1. Rebaudioside M (RebM) or a steviol glycoside composition comprising RebM produced by a whole cell in vitro method, wherein the method comprises:

(a) providing a whole cell comprising:

(i) a first uridine 5'-diphospho (UDP) glycosyl transferase polypeptide capable of beta 1,2 glycosylation of a C2' of the 13-O-glucose, the 19-O-glucose, or both the 13-O-glucose and the 19-O-glucose of the steviol glycoside and having 65% or greater sequence identity to the amino acid sequence set forth in SEQ ID NO:16; and (ii) a uridine 5'-diphospho (UDP) glycosyl transferase polypeptide capable of beta 1,3 glycosylation of the C3' of the 13-O-glucose, the 19-O-glucose, or both the 13-O-glucose and the 19-O-glucose of the steviol glycoside and having 90% or greater sequence identity to the amino acid sequence set forth in SEQ ID NO:2; and (b) providing the whole cell with:

(i) composition comprising a steviol glycoside having a 13-O-glucose, a 19-O-glucose, or both a 13-O-glucose and a 19-0-glucose, wherein the steviol glycoside is selected from the group consisting of rubusoside, stevioside, Rebaudioside A (RebA), and isomers thereof; and (ii) UDP-sugars, wherein the UDP glycosyl transferase of (a)(i) and (a)(ii) transfer the sugar moieties from the UDP-sugars of (b)(ii) to the steviol glycoside of (b)(i), thereby producing RebM or the steviol glycoside composition comprising RebM;

wherein the first 5'-UDP glycosyl transferase polypeptide of (a)(i) is capable of converting RebA to Rebaudioside D (RebD) at a rate that is at least 20 times faster than the rate at which a UDP glycosyl transferase polypeptide having the amino acid sequence set forth in SEQ ID NO:15 or SEQ ID NO:86 is capable of converting RebA to RebD under corresponding reaction conditions; and/or wherein the first 5'-UDP glycosyl transferase polypeptide of (a)(i) is capable of converting higher amounts of RebA to RebD compared to the UDP glycosyl transferase polypeptide having the amino acid sequence set forth in SEQ ID NO:15 or SEQ ID NO:86 under corresponding reaction conditions.

2. The Rebaudioside M (RebM) or the steviol glycoside composition comprising RebM of claim 1, wherein the whole cell is a recombinant host cell that is a fungal cell, an algal cell, or a bacterial cell.

3. The Rebaudioside M (RebM) or the steviol glycoside composition comprising RebM of claim 2, wherein both the first 5'-UDP glycosyl transferase polypeptide of (a)(i) and the 5'-UDP glycosyl transferase polypeptide of (a)(ii) are expressed in the recombinant host cell.

4. The Rebaudioside M (RebM) or the steviol glycoside composition comprising RebM of claim 3, wherein the recombinant host cell is fed with rubusoside, stevioside, RebA, or a mixture thereof.

5. The Rebaudioside M (RebM) or the steviol glycoside composition comprising RebM of claim 4, wherein the recombinant host cell is fed with steviol-13-O-glucoside and the recombinant host cell further expresses:

(a) a second 5'-UDP glycosyl transferase polypeptide capable of beta 1,2 glycosylation of the C2' of the 13-O-glucose, 19-O-glucose, or both 13-O-glucose and 19-O-glucose of the steviol glycoside of (b)(i); and (b) a 5'-UDP glycosyl transferase polypeptide capable of glycosylating the steviol glycoside of (b)(i) at its C-19 carboxyl group.

6. Rebaudioside M (RebM) or a steviol glycoside composition comprising RebM produced by an enzymatic in vitro method, wherein the method comprises:

(a) providing a composition comprising a steviol glycoside having a 13-O-glucose, a 19-O-glucose, or both a 13-O-glucose, wherein the steviol glycoside is selected from the group consisting of rubusoside, stevioside, Rebaudioside A (RebA), or isomers thereof;

(b) contacting the composition with:

(i) a first uridine 5'-diphospho (UDP) glycosyl transferase polypeptide capable of beta 1,2 glycosylation of a C2' of the 13-O-glucose, the 19-O-glucose, or both the 13-O-glucose and the 19-O-glucose of the steviol glycoside and having 65% or greater sequence identity to the amino acid sequence set forth in SEQ ID NO:16, (ii) a uridine 5'-diphospho (UDP) glycosyl transferase polypeptide capable of beta 1,3 glycosylation of the C3' of the 13-O-glucose, the 19-O-glucose, or both the 13-O-glucose and the 19-O-glucose of the steviol glycoside and having 90% or greater sequence identity to the amino acid sequence set forth in SEQ ID NO:2; and (iii) UDP-sugars, wherein the UDP glycosyl transferase of (b)(i) and of (b)(ii) transfer the sugar moieties from the UDP-sugars to the steviol glycoside of (a), thereby producing RebM or the steviol glycoside composition comprising RebM;

wherein the first 5'-UDP glycosyl transferase polypeptide is capable of converting RebA to Rebaudioside D (RebD) at a rate that is at least 20 times faster than the rate at which a UDP glycosyl transferase polypeptide having the amino acid sequence set forth in SEQ ID NO:15 or SEQ ID NO:86 is capable of converting RebA to RebD under corresponding reaction conditions; and/or wherein the first 5'-UDP glycosyl transferase polypeptide is capable of converting higher amounts of RebA to RebD compared to the UDP glycosyl transferase polypeptide having the amino acid sequence set forth in SEQ ID NO:15 or SEQ ID NO:86 under corresponding reaction conditions.

7. Rebaudioside M (RebM) or a steviol glycoside composition comprising RebM produced by a reaction mixture, wherein the reaction mixture comprises:

(a) a first uridine 5'-diphospho (UDP) glycosyl transferase polypeptide capable of beta 1,2 glycosylation of a C2' of the 13-O-glucose, the 19-O-glucose, or both the 13-O-glucose and the 19-O-glucose of the steviol glycoside and having 65% or greater sequence identity to the amino acid sequence set forth in SEQ ID NO:16;

(b) a uridine 5'-diphospho (UDP) glycosyl transferase polypeptide capable of beta 1,3 glycosylation of the C3' of the 13-O-glucose, the 19-O-glucose, or both the 13-O-glucose and the 19-O-glucose of the steviol glycoside and having 90% or greater sequence identity to the amino acid sequence set forth in SEQ ID NO:2;

(c) composition comprising a steviol glycoside having a 13-O-glucose, a 19-O-glucose, or both a 13-O-glucose and a 19-O-glucose, wherein the steviol glycoside is selected from the group consisting of rubusoside, stevioside, Rebaudioside A (RebA), and isomers thereof; and (d) UDP-sugars;

wherein the UDP glycosyl transferase of (a) and (a) transfer the sugar moieties from the UDP-sugars of (d) to the steviol glycoside of (c), thereby producing RebM or the steviol glycoside composition comprising RebM;

wherein the first 5'-UDP glycosyl transferase polypeptide of (a) is capable of converting RebA to Rebaudioside D (RebD) at a rate that is at least 20 times faster than the rate at which a UDP glycosyl transferase polypeptide having the amino acid sequence set forth in SEQ ID NO:15 or SEQ ID NO:86 is capable of converting RebA to RebD under corresponding reaction conditions; and/or wherein the first 5'-UDP glycosyl transferase polypeptide of (a) is capable of converting higher amounts of RebA to RebD compared to the UDP glycosyl transferase polypeptide having the amino acid sequence set forth in SEQ ID NO:15 or SEQ ID NO:86 under corresponding reaction conditions.

8. Rebaudioside M (RebM) or a steviol glycoside composition comprising RebM produced by a recombinant host cell capable of producing Rebaudioside M (RebM) or a steviol glycoside composition comprising RebM in a whole-cell bioconversion of a plant-derived or a synthetic steviol glycoside in a cell culture of the host cell, wherein the host cell comprises:

(a) a first recombinant gene encoding a first polypeptide capable of beta 1,2 glycosylation of the C2' of the 13-O-glucose, 19-O-glucose, or both 13-O-glucose and 19-O-glucose of the steviol glycoside and having 65% or greater sequence identity to the amino acid sequence set forth in SEQ ID NO:16; and (b) a gene encoding a polypeptide capable of beta 1,3 glycosylation of the C3' of the 13-O-glucose, 19-O-glucose, or both 13-O-glucose and 19-O-glucose of the steviol glycoside and having 90% or greater sequence identity to the amino acid sequence set forth in SEQ ID NO:2;

wherein at least one of the polypeptides is a recombinant polypeptide expressed in the host cell;

wherein the steviol glycoside is rubusoside, stevioside, Rebaudioside A, Rebaudioside E, or a combination thereof; and wherein the recombinant host cell is capable of producing at least 600 mg/L of Rebaudioside M alone or in the composition comprising RebM when grown in the cell culture.

9. The Rebaudioside M (RebM) or the steviol glycoside composition comprising RebM of claim 8, wherein the polypeptide capable of beta 1,3 glycosylation of the C3' of the 13-O-glucose, 19-O-glucose, or both 13-O-glucose and 19-O-glucose of the steviol glycoside comprises a polypeptide having 90% or greater sequence identity to the amino acid sequence set forth in SEQ ID NO:2.

10. The Rebaudioside M (RebM) or the steviol glycoside composition comprising RebM of claim 8, wherein the polypeptide capable of beta 1,3 glycosylation of the C3' of the 13-O-glucose, 19-O-glucose, or both 13-O-glucose and 19-O-glucose of the steviol glycoside comprises at least one amino acid substitution of SEQ ID NO:2 that is Q23G, Q23H, T55K, T55E, S56A, 126F, 126W, Y128S, Y128E, T146A, T146G, T146P, H155L, H155R, Q198R, S285R, S285T, S253W, S253G, L257P, L257W, L257T, L257G, L257A, L257R, L257E, S283N, T284R, T284G, S285G, K337E, K337P, L379A, L379G, or L379V.

11. The Rebaudioside M (RebM) or the steviol glycoside composition comprising RebM of claim 8, wherein the recombinant host cell is a fungal cell, an algal cell, or a bacterial cell.

12. The Rebaudioside M (RebM) or the steviol glycoside composition comprising RebM of claim 8, wherein the cell culture comprises:

(a) the Rebaudioside M (RebM) or the steviol glycoside composition comprising RebM that is produced in the whole-cell bioconversion in the cell culture of the host cell, (b) glucose, uridine diphosphate (UDP)-glucose, UDP-rhamnose, UDP-xylose, fructose, and/or N-acetyl-glucosamine; and (c) supplemental nutrients comprising trace metals, vitamins, salts, yeast nitrogen base (YNB) and/or amino acids.

* * * * *